(12) United States Patent
Bhanot et al.

(10) Patent No.: US 7,732,590 B2
(45) Date of Patent: Jun. 8, 2010

(54) MODULATION OF DIACYLGLYCEROL ACYLTRANSFERASE 2 EXPRESSION

(75) Inventors: Sanjay Bhanot, Carlsbad, CA (US); Kenneth W. Dobie, Del Mar, CA (US); Xing-Xian Yu, San Diego, CA (US); Brett P. Monia, Encinitas, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 23 days.

(21) Appl. No.: 11/066,725

(22) Filed: Feb. 24, 2005

(65) Prior Publication Data

US 2005/0272680 A1  Dec. 8, 2005

Related U.S. Application Data

(63) Continuation of application No. PCT/US2004/024384, filed on Aug. 18, 2004.

(51) Int. Cl.
C07H 21/04 (2006.01)
(52) U.S. Cl. ............... 536/24.5; 536/24.1; 536/24.31; 514/44; 435/6; 435/325; 435/375
(58) Field of Classification Search ................. None
See application file for complete search history.

(56) References Cited

U.S. PATENT DOCUMENTS

| 5,801,154 A * | 9/1998 | Baracchini et al. ............ 514/44 |
| 5,837,542 A * | 11/1998 | Grimm et al. ............... 435/366 |
| 5,998,148 A * | 12/1999 | Bennett et al. ................ 435/6 |
| 6,083,695 A | 7/2000 | Hardin et al. |
| 6,100,077 A | 8/2000 | Sturley et al. |
| 6,127,533 A * | 10/2000 | Cook et al. ................ 536/23.1 |
| 6,284,538 B1 | 9/2001 | Monia et al. |
| 6,344,548 B1 | 2/2002 | Farese, Jr. et al. |
| 6,444,427 B1 | 9/2002 | Ludwig et al. |
| 6,512,099 B2 | 1/2003 | Omura et al. |
| 6,582,908 B2 | 6/2003 | Fodor et al. |
| 6,605,451 B1 | 8/2003 | Marmaro et al. |
| 6,607,893 B2 | 8/2003 | Ramharack et al. |
| 6,822,141 B2 | 11/2004 | Lardizabal et al. |
| 7,250,496 B2 * | 7/2007 | Bentwich ................... 536/23.1 |
| 2001/0053519 A1 | 12/2001 | Fodor et al. |
| 2002/0119138 A1 | 8/2002 | Cases et al. |
| 2002/0127627 A1 | 9/2002 | Ramharack et al. |
| 2002/0193315 A1 | 12/2002 | Omura et al. |
| 2003/0028923 A1 | 2/2003 | Lardizabal et al. |
| 2003/0073103 A1 | 4/2003 | Ludwig et al. |
| 2003/0100480 A1 | 5/2003 | Smith et al. |
| 2003/0104414 A1 | 6/2003 | Attersand |
| 2003/0115632 A1 | 6/2003 | Lardizabal et al. |
| 2003/0124126 A1 | 7/2003 | Cases et al. |
| 2003/0152574 A1 | 8/2003 | Logan et al. |
| 2003/0161831 A1 | 8/2003 | Cases et al. |
| 2003/0170691 A1 | 9/2003 | Gimeno et al. |
| 2003/0200563 A1 | 10/2003 | Butler et al. |
| 2003/0202968 A1 | 10/2003 | Cases et al. |
| 2003/0228597 A1 | 12/2003 | Cowsert et al. |
| 2004/0054177 A1 | 3/2004 | Otake et al. |
| 2004/0058820 A1 | 3/2004 | Hagmann et al. |
| 2004/0097459 A1 * | 5/2004 | Dobie et al. .................. 514/44 |
| 2004/0122033 A1 | 6/2004 | Nargund et al. |
| 2004/0259247 A1 * | 12/2004 | Tuschl et al. ................ 435/375 |

FOREIGN PATENT DOCUMENTS

| EP | 1 308 459 A3 | 5/2003 |
| WO | WO 00/78961 | 12/2000 |
| WO | WO 01/68848 | 9/2001 |
| WO | WO 01/77389 | 10/2001 |
| WO | WO 01/92512 | * 12/2001 |
| WO | WO 02/08260 | 1/2002 |
| WO | WO/02/068595 | 9/2002 |
| WO | WO/03/053363 | 7/2003 |

OTHER PUBLICATIONS

Chin, Andrew "On the Preparation and Utilization of Isolated and Purified Oligonucleotides." Document purportedly located on a CD-ROM and contributed to the public collection of the Katherine R. Everett Law Library of the University of North Carolina on Mar. 14, 2002.

Desai, U. J. et al., "Phenotypic Correction of Diabetic Mice by Adenovirus-Mediated Glucokinase Expression," *Diabetes* (2001) 50:2287-2295.

Guo, S. et al., "*par-1*, a Gene Required for Establishing Polarity in *C. elegans* Embryos, Encodes a Putative Ser/Thr Kinase That is Asymmetrically Distributed," *Cell* (1995) 81:611-620.

Montgomery, M. K. et al., "RNA as a target of double-stranded RNA-mediated genetic interference in *Caenorhabditis elegans*," *Proc. Natl. Acad. Sci. USA* (1998)95:15502-15507.

Stone, S. J. et al., "Lipopenia and Skin Barrier Abnormalities in DGAT2-deficient Mice," *J. Biol. Chem.* (2004) 279(12):11767-11776.

Tijsterman, M. et al., "RNA Helicase MUT-14-Dependent Gene Silencing Triggered in *C. elegans* by Short Antisense RNAs," *Science* (2002) 295:694-697.

(Continued)

*Primary Examiner*—Kimberly Chong

(57) ABSTRACT

Compounds, compositions and methods are provided for modulating the expression of diacylglycerol acyltransferase 2. The compositions comprise oligonucleotides, targeted to nucleic acid encoding diacylglycerol acyltransferase 2. Methods of using these compounds for modulation of diacylglycerol acyltransferase 2 expression and for diagnosis and treatment of diseases and conditions associated with expression of diacylglycerol acyltransferase 2 are provided.

31 Claims, No Drawings

OTHER PUBLICATIONS

Yu, X. X. et al., "Antisense Oligonucleotide Inhibition of DGAT2 Expression Reduced Hepatic Steatosis and Hyperlipidemia in Diet-Induced Obese Mice," *Obesity Res.* (2003) NAASO's 2003 Annual Meeting, Oct. 11-15, 11:A48.

Yu, X. X. et al., "Antisense Oligonucleotide Reduction of DGAT2 Expression Improves Hepatic Steatosis and Hyperlipidemia in Obese Mice," *Hepatology* (2005) 42:362-371.

The European Supplementary European Search Report dated Jul. 4, 2008 (EP 04 77 9444).

Cheng et al., "Human acyl-CoA: diacylglycerol acyltransferase is a tetrameric protein", *Biochem. J.* Nov. 1, 2001 359 (pt 3) :707-714.

Ludwig et al., "DGAT1 promoter polymorphism associated with alterations in body mass index, high density lipoprotein levels and blood pressure in Turkish women", *Clin. Genet.* Jul. 2002 62 (1) : 687-73.

Tabata et al., "Xanthohumols, diacylglycerol acyltransferase inhibitors, from Humulus lupulus", *Phytochemistry* Oct. 1997 46 (4) : 683-687.

Tomoda et al., "Roselipins, inhibitors of diacylglycerol acyltransferase, produced by Gliocladium roseum KF-1040", *J. Antibiot.* (Tokyo) Aug. 1999 52 (8) :689-694.

Yu et al., "Posttranscriptional control of the expression and function of diacylglycerol acyltransferase-1 in mouse adipocytes", *J. Biol. Chem.* Dec. 27, 2002 277 (52) :50876-50884.

Branch et al., "A good antisense molecule is hard to find" TIBS (1998) 23:45-50.

Buhman et al., "DGAT1 is not essential for intestinal triacylglycerol absorption or chylomicron synthesis" J. Biol. Chem. (2002) 277:25474-25479.

Cases et al., "Identification of a gene encoding an acyl CoA: diacylglycerol acyltransferase, a key enzyme in triacylglycerol synthesis" Proc. Natl. Acad. Sci. (1998) 95:13018-13023.

Cases et al., "Cloning of DGAT2, a second mammalian diacylglycerol acyltransferase, and related family members" J. Biol. Chem. (2001) 276:38870-38876.

Chen et al., "Increased insulin and leptin sensitivity in mice lacking acyl CoA:diacylglycerol acyltransferase 1" J. Clin. Invest. (2002) 109:1049-1055.

Chen et al., "Leptin modulates the effects of acyl CoA: diacylglycerol acyltransferase deficiency on murine fur and sebaceuous glands" J. Clin. Invest. (2002) 109:175-181.

Cheng et al., "Human acyl-CoA: diacylglycerol acyltransferase is a tetrameric protein" Biochem. J. (2001) 359:707-714.

Crooke et al., "Basic Principles of Antisense Therapeutics" Antisense Research and Application (1998) Chapter 1:1-50.

Farese et al., "Triglyceride synthesis: insights from the cloning of diacylglycerol acyltransferase" Curr. Opin. Lipidol. (2000) 11:229-234.

Final Rejection for U.S. Appl. No. 10/643,801 dated Apr. 18, 2008.

International Search Report for Int. Application No. PCT/US04/24384 dated Mar. 23, 2006.

Lardizabal et al., "DGAT2 is a new diacylglycerol acyltransferase gene family: purification, cloning, and expression in insect cells of two polypeptides from Mortierella ramanniana with diacylglycerol acyltransferase activity" J. Biol. Chem. (2001) 276:38862-38869.

Ludwig et al., "DGAT1 promotor polymorphism associated with alterations in body mass index, high density lipoprotein levels and blood pressure in Turkish women" Clin. Genet. (2002) 62:68-73.

Meegalla et al., "Concerted elevation of acyl-coenzyme A:diacylglycerol acyltransferase (DGAT) activity through independent stimulation of mRNA expression of DGAT1 and DGAT2 by carbohydrate and insulin" Biochem. Biophys. Res. Comm. (2002) 298:317-323.

Melo et al., Trends in Molecular Medicine, 2005, 11:240-250.

New England Biolabs 1998/1999 Catalog, cover page, pp. 121 and 284.

Oelkers et al., "Characterization of two human genes encoding acyl coenzyme A: cholesterol acyltransferase-related enzymes" J. Biol. Chem. (1998) 273:26765-26771.

Office Action for U.S. Appl. No. 10/643,801 dated Sep. 19, 2005.

Office Action for U.S. Appl. No. 10/643,801 dated Aug. 28, 2006.

Office Action for U.S. Appl. No. 10/643,801 dated Jan. 21, 2009.

Smith et al., "Obesity resistance and multiple mechanisms of triglyceride synthesis in mice lacking Dgat" Nat. Genet. (2000) 25:87-90.

Tabata et al., "Xanthohumols, diacylglycerol acyltransferase inhibitors, from Humulus lupulus" Phytochemistry (1997) 46:683-687.

Tomoda et al., "Roselipins, inhibitors of diacylglycerol acyltransferase, produced by Gliocladium roseum KF-1040" J. Antibiot. Tokyo (1999) 52:689-694.

Vaughan et al., Current Opinions in Cardiology, 2001, 16:195-200.

Waterman et al., "Distinct ontogenic patterns of overt and latent DGAT activities of rat liver microsomes" J. Lipid Res. (2002) 43:1555-1562.

Yu et al., "Posttranscriptional control of the expression and function of diacylglycerol acyltransferase-1 in mouse adipocytes" J. Biol. Chem. (2002) 277:50876-50884.

Reynolds et al., "Rational siRNA design for RNA interference" Nature Biotechnology (2004) 22(3):326-330.

Sanghvi et al., "Heterocyclic Base Modifications in Nucleic Acids and Their Applications in Antisense Oligonucleotides" Antisense Research and Applications (1993) pp. 273-288.

\* cited by examiner

SEQUENCE LISTING

<160> NUMBER OF SEQ ID NOS: 492

<210> SEQ ID NO 1
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 1
tccgtcatcg ctcctcaggg                                           20

<210> SEQ ID NO 2
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 2
gtgcgcgcga gcccgaaatc                                           20

<210> SEQ ID NO 3
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 3
atgcattctg cccccaagga                                           20

<210> SEQ ID NO 4
<211> LENGTH: 2439
<212> TYPE: DNA
<213> ORGANISM: H. sapiens
<220> FEATURE:
<220> FEATURE:
<221> NAME/KEY: CDS
<222> LOCATION: (231)...(1397)

<400> SEQUENCE: 4
ctccgggaac gccagcgccg cggctgccgc ctctgctggg gtctaggctg tttctctcgc     60
gccaccactg gccgccggcc gcagctccag gtgtcctagc cgcccagcct cgacgccgtc    120
ccgggacccc tgtgctctgc gcgaagccct ggccccgggg gccggggcat gggcaggggg    180
cgcggggtga agcggcttcc cgcggggccg tgactgggcg ggcttcagcc atg aag      236
                                                       Met Lys
                                                         1 acc ctc ata gcc gcc tac tcc ggg gtc ctg cgc ggc gag cgt cag gcc     284
Thr Leu Ile Ala Ala Tyr Ser Gly Val Leu Arg Gly Glu Arg Gln Ala
         5                  10                  15 gag gct gac cgg agc cag cgc tct cac gga gga cct gcg ctg tcg cgc     332
Glu Ala Asp Arg Ser Gln Arg Ser His Gly Gly Pro Ala Leu Ser Arg
     20                  25                  30 gag ggg tct ggg aga tgg ggc act gga tcc agc atc ctc tcc gcc ctc     380
Glu Gly Ser Gly Arg Trp Gly Thr Gly Ser Ser Ile Leu Ser Ala Leu
 35                  40                  45                  50 cag gac ctc ttc tct gtc acc tgg ctc aat agg tcc aag gtg gaa aag     428
Gln Asp Leu Phe Ser Val Thr Trp Leu Asn Arg Ser Lys Val Glu Lys
                 55                  60                  65 cag cta cag gtc atc tca gtg ctc cag tgg gtc ctg tcc ttc ctt gta     476

```
                Gln Leu Gln Val Ile Ser Val Leu Gln Trp Val Leu Ser Phe Leu Val
                                70                  75                  80 ctg gga gtg gcc tgc agt gcc atc ctc atg tac ata ttc tgc act gat          524
Leu Gly Val Ala Cys Ser Ala Ile Leu Met Tyr Ile Phe Cys Thr Asp
                85                  90                  95 tgc tgg ctc atc gct gtg ctc tac ttc act tgg ctg gtg ttt gac tgg          572
Cys Trp Leu Ile Ala Val Leu Tyr Phe Thr Trp Leu Val Phe Asp Trp
        100                 105                 110 aac aca ccc aag aaa ggt ggc agg agg tca cag tgg gtc cga aac tgg          620
Asn Thr Pro Lys Lys Gly Gly Arg Arg Ser Gln Trp Val Arg Asn Trp
115                 120                 125                 130 gct gtg tgg cgc tac ttt cga gac tac ttt ccc atc cag ctg gtg aag          668
Ala Val Trp Arg Tyr Phe Arg Asp Tyr Phe Pro Ile Gln Leu Val Lys
                135                 140                 145 aca cac aac ctg ctg acc acc agg aac tat atc ttt gga tac cac ccc          716
Thr His Asn Leu Leu Thr Thr Arg Asn Tyr Ile Phe Gly Tyr His Pro
        150                 155                 160 cat ggt atc atg ggc ctg ggt gcc ttc tgc aac ttc agc aca gag gcc          764
His Gly Ile Met Gly Leu Gly Ala Phe Cys Asn Phe Ser Thr Glu Ala
165                 170                 175 aca gaa gtg agc aag aag ttc cca ggc ata cgg cct tac ctg gct aca          812
Thr Glu Val Ser Lys Lys Phe Pro Gly Ile Arg Pro Tyr Leu Ala Thr
        180                 185                 190 ctg gca ggc aac ttc cga atg cct gtg ttg agg gag tac ctg atg tct          860
Leu Ala Gly Asn Phe Arg Met Pro Val Leu Arg Glu Tyr Leu Met Ser
195                 200                 205                 210 gga ggt atc tgc cct gtc agc cgg gac acc ata gac tat ttg ctt tca          908
Gly Gly Ile Cys Pro Val Ser Arg Asp Thr Ile Asp Tyr Leu Leu Ser
                215                 220                 225 aag aat ggg agt ggc aat gct atc atc atc gtg gtc ggg ggt gcg gct          956
Lys Asn Gly Ser Gly Asn Ala Ile Ile Ile Val Val Gly Gly Ala Ala
        230                 235                 240 gag tct ctg agc tcc atg cct ggc aag aat gca gtc acc ctg cgg aac         1004
Glu Ser Leu Ser Ser Met Pro Gly Lys Asn Ala Val Thr Leu Arg Asn
245                 250                 255 cgc aag ggc ttt gtg aaa ctg gcc ctg cgt cat gga gct gac ctg gtt         1052
Arg Lys Gly Phe Val Lys Leu Ala Leu Arg His Gly Ala Asp Leu Val
        260                 265                 270 ccc atc tac tcc ttt gga gag aat gaa gtg tac aag cag gtg atc ttc         1100
Pro Ile Tyr Ser Phe Gly Glu Asn Glu Val Tyr Lys Gln Val Ile Phe
275                 280                 285                 290 gag gag ggc tcc tgg ggc cga tgg gtc cag aag aag ttc cag aaa tac         1148
Glu Glu Gly Ser Trp Gly Arg Trp Val Gln Lys Lys Phe Gln Lys Tyr
                295                 300                 305 att ggt ttc gcc cca tgc atc ttc cat ggt cga ggc ctc ttc tcc tcc         1196
Ile Gly Phe Ala Pro Cys Ile Phe His Gly Arg Gly Leu Phe Ser Ser
        310                 315                 320 gac acc tgg ggg ctg gtg ccc tac tcc aag ccc atc acc act gtt gtg         1244
Asp Thr Trp Gly Leu Val Pro Tyr Ser Lys Pro Ile Thr Thr Val Val
325                 330                 335 gga gag ccc atc acc atc ccc aag ctg gag cac cca acc cag caa gac         1292
Gly Glu Pro Ile Thr Ile Pro Lys Leu Glu His Pro Thr Gln Gln Asp
                340                 345                 350 atc gac ctg tac cac acc atg tac atg gag gcc ctg gtg aag ctc ttc         1340
Ile Asp Leu Tyr His Thr Met Tyr Met Glu Ala Leu Val Lys Leu Phe
        355                 360                 365                 370 gac aag cac aag acc aag ttc ggc ctc ccg gag act gag gtc ctg gag         1388
Asp Lys His Lys Thr Lys Phe Gly Leu Pro Glu Thr Glu Val Leu Glu
                375                 380                 385
```

```
gtg aac tga gccagccttc ggggccaact ccctggagga accagctgca aatcactttt   1447
Val Asn ttgctctgta aatttggaag tgtcatgggt gtctgtgggt tatttaaaag aaattataac   1507
aattttgcta aaccattaca atgttaggtc tttttttaaga aggaaaaagt cagtatttca   1567
agttctttca cttccagctt gccctgttct aggtggtggc taaatctggg cctaatctgg   1627
gtggctcagc taacctctct tcttcccttc ctgaagtgac aaaggaaact cagtcttctt   1687
ggggaagaag gattgccatt agtgacttgg accagttaga tgattcactt tttgcccta   1747 gggatgagag gcgaaagcca cttctcatac aagccccttt attgccacta ccccacgctc   1807
gtctagtcct gaaactgcag gaccagtttc tctgccaagg ggaggagttg gagagcacag   1867
ttgccccgtt gtgtgagggc agtagtaggc atctggaatg ctccagtttg atctcccttc   1927
tgccacccct acctcacccc tagtcactca tatcggagcc tggactggcc tccaggatga   1987
ggatgggggt ggcaatgaca ccctgcaggg gaaaggactg cccccatgc accattgcag    2047 ggaggatgcc gccaccatga gctaggtgga gtaactggtt tttcttgggt ggctgatgac   2107
atggatgcag cacagactca gccttggcct ggagcacatg cttactgtg gcctcagttt    2167 accttcccca gatcctagat tctggatgtg aggaagagat ccctcttcag aaggggcctg   2227
gccttctgag cagcagatta gttccaaagc aggtggcccc cgaacccaag cctcactttt   2287
ctgtgccttc ctgaggggt tgggccgggg aggaaaccca accctctcct gtgtgttctg    2347
ttatctcttg atgagatcat tgcaccatgt cagacttttg tatatgcctt gaaaataaat   2407
gaaagtgaga atccaaaaaa aaaaaaaaaa aa                                  2439

<210> SEQ ID NO 5
<211> LENGTH: 22
<212> TYPE: DNA
<213> ORGANISM: Artificial Sequence
<220> FEATURE:
<223> OTHER INFORMATION: PCR Primer

<400> SEQUENCE: 5
catacggcct tacctggcta ca                                              22

<210> SEQ ID NO 6
<211> LENGTH: 24
<212> TYPE: DNA
<213> ORGANISM: Artificial Sequence
<220> FEATURE:
<223> OTHER INFORMATION: PCR Primer

<400> SEQUENCE: 6
cagacatcag gtactccctc aaca                                            24

<210> SEQ ID NO 7
<211> LENGTH: 22
<212> TYPE: DNA
<213> ORGANISM: Artificial Sequence
<220> FEATURE:
<223> OTHER INFORMATION: PCR Probe

<400> SEQUENCE: 7
tggcaggcaa cttccgaatg cc                                              22

<210> SEQ ID NO 8
<211> LENGTH: 19
<212> TYPE: DNA
<213> ORGANISM: Artificial Sequence
<220> FEATURE:
```

<223> OTHER INFORMATION: PCR Primer

<400> SEQUENCE: 8
gaaggtgaag gtcggagtc                                                                19

<210> SEQ ID NO 9
<211> LENGTH: 20
<212> TYPE: DNA
<213> ORGANISM: Artificial Sequence
<220> FEATURE:
<223> OTHER INFORMATION: PCR Primer

<400> SEQUENCE: 9
gaagatggtg atgggatttc                                                               20

<210> SEQ ID NO 10
<211> LENGTH: 20
<212> TYPE: DNA
<213> ORGANISM: Artificial Sequence
<220> FEATURE:
<223> OTHER INFORMATION: PCR Probe

<400> SEQUENCE: 10
caagcttccc gttctcagcc                                                               20

<210> SEQ ID NO 11
<211> LENGTH: 2262
<212> TYPE: DNA
<213> ORGANISM: M. musculus
<220> FEATURE:
<220> FEATURE:
<221> NAME/KEY: CDS
<222> LOCATION: (207)...(1373)

<400> SEQUENCE: 11

```
ggtggccgcg cttcgctggc tttctgctca tctagggtgg cagcggctac ctacctcagc        60
tctcgccctg ctgccgccac ggcctgggcg ctgtccctca gctcccggag ctcagcgcga       120
agccctggcc ccggcggccg gggcatgggt caggggcgcg gcgtgaggcg gctttctgca       180
cggccgtgac gtgcattggc ttcagc atg aag acc ctc atc gcc gcc tac tcc       233
                             Met Lys Thr Leu Ile Ala Ala Tyr Ser
                               1               5 ggg gtc ctg cgg ggt gag cgt cgg gcg gaa gct gcc cgc agc gaa aac        281
Gly Val Leu Arg Gly Glu Arg Arg Ala Glu Ala Ala Arg Ser Glu Asn
 10              15                  20                  25 aag aat aaa gga tct gcc ctg tca cgc gag ggg tct ggg cga tgg ggc        329
Lys Asn Lys Gly Ser Ala Leu Ser Arg Glu Gly Ser Gly Arg Trp Gly
             30                  35                  40 act ggc tcc agc atc ctc tca gcc ctc caa gac atc ttc tct gtc acc        377
Thr Gly Ser Ser Ile Leu Ser Ala Leu Gln Asp Ile Phe Ser Val Thr
         45                  50                  55 tgg ctc aac aga tct aag gtg gaa aaa cag ctg cag gtc atc tca gta        425
Trp Leu Asn Arg Ser Lys Val Glu Lys Gln Leu Gln Val Ile Ser Val
     60                  65                  70 cta caa tgg gtc cta tcc ttc ctg gtg cta gga gtg gcc tgc agt gtc        473
Leu Gln Trp Val Leu Ser Phe Leu Val Leu Gly Val Ala Cys Ser Val
 75                  80                  85 atc ctc atg tac acc ttc tgc aca gac tgc tgg ctg ata gct gtg ctc        521
Ile Leu Met Tyr Thr Phe Cys Thr Asp Cys Trp Leu Ile Ala Val Leu
 90                  95                 100                 105 tac ttc acc tgg ctg gca ttt gac tgg aac acg ccc aag aaa ggt ggc        569
Tyr Phe Thr Trp Leu Ala Phe Asp Trp Asn Thr Pro Lys Lys Gly Gly
            110                 115                 120
```

-continued

| | |
|---|---|
| agg aga tcg cag tgg gtg cga aac tgg gcc gtg tgg cgc tac ttc cga<br>Arg Arg Ser Gln Trp Val Arg Asn Trp Ala Val Trp Arg Tyr Phe Arg<br>125 130 135 | 617 |
| gac tac ttt ccc atc cag ctg gtg aag aca cac aac ctg ctg acc acc<br>Asp Tyr Phe Pro Ile Gln Leu Val Lys Thr His Asn Leu Leu Thr Thr<br>140 145 150 | 665 |
| agg aac tat atc ttt gga tac cac ccc cat ggc atc atg ggc ctg ggt<br>Arg Asn Tyr Ile Phe Gly Tyr His Pro His Gly Ile Met Gly Leu Gly<br>155 160 165 | 713 |
| gcc ttc tgt aac ttc agc aca gag gct act gaa gtc agc aag aag ttt<br>Ala Phe Cys Asn Phe Ser Thr Glu Ala Thr Glu Val Ser Lys Lys Phe<br>170 175 180 185 | 761 |
| cct ggc ata agg ccc tat ttg gct acg ttg gct ggt aac ttc cgg atg<br>Pro Gly Ile Arg Pro Tyr Leu Ala Thr Leu Ala Gly Asn Phe Arg Met<br>190 195 200 | 809 |
| cct gtg ctt cgc gag tac ctg atg tct gga ggc atc tgc cct gtc aac<br>Pro Val Leu Arg Glu Tyr Leu Met Ser Gly Gly Ile Cys Pro Val Asn<br>205 210 215 | 857 |
| cga gac acc ata gac tac ttg ctc tcc aag aat ggg agt ggc aat gct<br>Arg Asp Thr Ile Asp Tyr Leu Leu Ser Lys Asn Gly Ser Gly Asn Ala<br>220 225 230 | 905 |
| atc atc atc gtg gtg gga ggt gca gct gag tcc ctg agc tcc atg cct<br>Ile Ile Ile Val Val Gly Gly Ala Ala Glu Ser Leu Ser Ser Met Pro<br>235 240 245 | 953 |
| ggc aag aac gca gtc acc ctg aag aac cgc aaa ggc ttt gtg aag ctg<br>Gly Lys Asn Ala Val Thr Leu Lys Asn Arg Lys Gly Phe Val Lys Leu<br>250 255 260 265 | 1001 |
| gcc ctg cgc cat gga gct gat ctg gtt ccc act tat tcc ttt gga gag<br>Ala Leu Arg His Gly Ala Asp Leu Val Pro Thr Tyr Ser Phe Gly Glu<br>270 275 280 | 1049 |
| aat gag gta tac aag cag gtg atc ttt gag gag ggt tcc tgg ggc cga<br>Asn Glu Val Tyr Lys Gln Val Ile Phe Glu Glu Gly Ser Trp Gly Arg<br>285 290 295 | 1097 |
| tgg gtc cag aag aag ttc cag aag tat att ggt ttc gcc ccc tgc atc<br>Trp Val Gln Lys Lys Phe Gln Lys Tyr Ile Gly Phe Ala Pro Cys Ile<br>300 305 310 | 1145 |
| ttc cat ggc cga ggc ctc ttc tcc tct gac acc tgg ggg ctg gtg ccc<br>Phe His Gly Arg Gly Leu Phe Ser Ser Asp Thr Trp Gly Leu Val Pro<br>315 320 325 | 1193 |
| tac tcc aag ccc atc acc acc gtc gtg ggg gag ccc atc act gtc ccc<br>Tyr Ser Lys Pro Ile Thr Thr Val Val Gly Glu Pro Ile Thr Val Pro<br>330 335 340 345 | 1241 |
| aag ctg gag cac ccg acc cag aaa gac atc gac ctg tac cat gcc atg<br>Lys Leu Glu His Pro Thr Gln Lys Asp Ile Asp Leu Tyr His Ala Met<br>350 355 360 | 1289 |
| tac atg gag gcc ctg gtg aag ctc ttt gac aat cac aag acc aaa ttt<br>Tyr Met Glu Ala Leu Val Lys Leu Phe Asp Asn His Lys Thr Lys Phe<br>365 370 375 | 1337 |
| ggc ctt cca gag act gag gtg ctg gag gtg aac tga cccagccctc<br>Gly Leu Pro Glu Thr Glu Val Leu Glu Val Asn<br>380 385 | 1383 |
| gcgtgccagc tcctgggagg gacgactgca gatcctttc taccgagttc ttgagtgcat | 1443 |
| tttgttctgt aaatttggaa gcgtcatggg tgtctgtggg ttatttaaaa gaaattataa | 1503 |
| tgtgttaaac cattgcaatg ttagatgttt ttttaagaag ggaagagtca gtattttaag | 1563 |
| ctcacttcta gtgtgtcctg ctcaaggtgg aggctgatat ttatgggcct tggtggtttc | 1623 |
| ttacccaccc cttctagcgt tccccagacg acagacactt ggccctggct agctgggcaa | 1683 |

-continued

```
gggcagtcct tagtgactcc agggattctt gagaggcaga ggccatgtcc cacccgtggc    1743
tgcaggtcgg gttcctcgta ccaaggggag gctgagggca cagctggccc cacttgggga    1803
gggtagataa catctggact gcccggcttg ggtctctgct cctcacccta gccctcttct    1863
ccaatctgag cctaccctgg cctcctgtct cctggctagg acacggctg tcccacaggt     1923 gccgtcttgg gttatctcgc tgctgttggc tggtttcact ctggaggttg gcaccatgga    1983
cacagctcag cgttgctctg gcgcatatcc tcctgagcca caccccaagt ctggtgtgag    2043
gaagggcttc tcttctcttc acagaggtgc ctggcttcct gtgcagcaca ctgggtccag    2103
gacaggaggc ccccccccca aaccaagcct cacgtgtgtg cctttatgag gcgttgggag    2163
aaagctaccc tcctgtgtat tctgttttct ccatgagatt gttgtgccat gtcacacttt    2223
tgtatattcc tagactaata aatggaaaca agaacagcc                            2262
```

```
<210> SEQ ID NO 12
<211> LENGTH: 20
<212> TYPE: DNA
<213> ORGANISM: Artificial Sequence
<220> FEATURE:
<223> OTHER INFORMATION: PCR Primer

<400> SEQUENCE: 12
actctggagg ttggcaccat                                                 20

<210> SEQ ID NO 13
<211> LENGTH: 19
<212> TYPE: DNA
<213> ORGANISM: Artificial Sequence
<220> FEATURE:
<223> OTHER INFORMATION: PCR Primer

<400> SEQUENCE: 13
gggtgtggct caggaggat                                                  19

<210> SEQ ID NO 14
<211> LENGTH: 18
<212> TYPE: DNA
<213> ORGANISM: Artificial Sequence
<220> FEATURE:
<223> OTHER INFORMATION: PCR Probe

<400> SEQUENCE: 14
cagcgttgct ctggcgca                                                   18

<210> SEQ ID NO 15
<211> LENGTH: 20
<212> TYPE: DNA
<213> ORGANISM: Artificial Sequence
<220> FEATURE:
<223> OTHER INFORMATION: PCR Primer

<400> SEQUENCE: 15
ggcaaattca acggcacagt                                                 20

<210> SEQ ID NO 16
<211> LENGTH: 20
<212> TYPE: DNA
<213> ORGANISM: Artificial Sequence
<220> FEATURE:
<223> OTHER INFORMATION: PCR Primer

<400> SEQUENCE: 16
gggtctcgct cctggaagat                                                 20
```

-continued

```
<210> SEQ ID NO 17
<211> LENGTH: 27
<212> TYPE: DNA
<213> ORGANISM: Artificial Sequence
<220> FEATURE:
<223> OTHER INFORMATION: PCR Probe

<400> SEQUENCE: 17
aaggccgaga atgggaagct tgtcatc                                        27

<210> SEQ ID NO 18
<211> LENGTH: 42823
<212> TYPE: DNA
<213> ORGANISM: H. sapiens
<220> FEATURE:

<400> SEQUENCE: 18
gcagcagaag tgttaaagtt taagtgaaag ttttaaaaag gggtatgtgt ggttgtaaag      60
aaggcttctt ggaggaagat gcatcaagac aggacagatg gacagggtgt gaaaaagggg    120
gagcttgggg aagggcttga gctcaagagc acagtgtggg cagggaccca gaggtggaaa    180
agcacgttca ggggcagggc aagtgacctg atgggcctag ggagctggac ccacattaga    240
gcatggcggt gggagaggag tggaggcggc tggagagagt ggcaggagca ggatgatgtg    300
aggccttgaa tgccaagtta aggagctggg gcctcatcct aagaactatg gggagccacg    360
agaaacaatg gttgggttct gtgttctgaa gctcattctg gaatctgga dacaggggac     420 cagtgaagag gatagtacag ctgtctatgc aaggtggcat ggcccaaggc agaagagaga    480
aggagagaac tgtttcctgg ttgttgggca tagaggtatc agtgtgaatg ttttttgtatg    540 tgtccatgag cacaagtaat cttcctcaga gagtcagcct aaaaaaaaaa aaaaacccaa    600
ccctattcag tttcatgacc cagcataccc agcagcctgg gggaggccaa agttaccaaa    660
gaaagaggct gagagacatt cagttaaagc ctgactttat agttcttcct catcaacacc    720
atcctgcaaa ttcacattca tctacaggct ttcagggtgt tttaatccca gttatctcac    780
ccaaaatatt tgcttttccg cctttctttg tgtttcctgt atgcctcatg tcagcatcct    840
tgttcaggtc acttacttaa aaaaaaaaaa aaatccataa ggccgggctg aggtggagcc    900
tggagtgacc aggaaaccac tctagaatga actcctacct gaggcagctc ctcctccctta   960 gcagagccca cactggcctg ctgatcacct ccctgctcag gactctgctg ataccataga    1020
cctagtccta ggccagtttg ggaatctaga gaggccattg aaaagaaaac tgatatatgg    1080
ataccacccc tcctcggtga ctcaatcgta gctcctgaca actcagggtt ttgttttttt    1140
gtttgtttgt ttttctctt gagggttaca gagcatcatt tatagaatgc agtttataca    1200
actgacctca gaatatggcc aggattttgc agctattata gagcatggtc tctggagcca    1260
gaccatctca gcttaaatcc tggctctgcc acttcctaag ctgtgtgacc ttgggcaatt    1320
ttttttaacc tctttgtgtc tcaatttctc catctgaaaa atggactcat atagtatcta    1380
ctccaaaggg ttgttgtgag gcttaactaa atccacccat gtaaggaacc tagaatagta    1440
actggcagac agtaaatact cactgaagtt taacacctgt tatattgcct gttatagttc    1500
atgaaaactg ttgcttctcc ttttggaaaa atcaggatgg cactagccca cctccagtct    1560
cccaacgctt ctccagctga acagcatttc ctagagatta cagattctgt aatctgcagg    1620
ttctctgaga tgcagttgga acaattaat acagcagagc agtcccatgc tccactgtag    1680
tctcactgca aaacagttca gcagcggttc tcaaaatgtg ggcttcaaac tagcagtatc    1740
```

```
agcatgtcct gggaacttgt tagaaatgca cattctcagc ctcactccag aacctactga    1800
atcagaaact ctgggggtgg aacccagaaa gctatatttt aaccagccct ctgctaatgt    1860
ttgaaaactg ccacagcata ttatagcaca gtggtttatt taggtagata tggcgcagtt    1920
cattgcccac tccttctcca caaagtgttc ctgattcccc cagaaccctc ttttactaac    1980
agctctaact tcctccctgt attactgttg tccatgctca aaagtgctca atcccctg      2040 gattacaggt tacctgagag cagtgttggg tcttacacat ctctgcactg ggcagcccag    2100
gggctgccac agggaccttt gcttaggaaa gacatgctga gtcaagcgtg caacatttcc    2160
agtttcctct gactaaggct actattactg agcctctgct ccttccagga cccttgctca    2220
tactgcattt tccttttgtga attgtggtca tctcctatgc taagatgcct ggttctttgt   2280
catttctagt atcctccagt tccactgcct tctcaggcat tttactcttc tccctccctt    2340 tatgttttgtt caaagccctt tggagaaggt gtcagagctc caggcaaacc tgtcacccta   2400
atccttattt tcaatcataa tacttctact ggtaacaatt tgtcaagtac tatatgccag    2460
gccctgtact gggcatttta cattcattca ttcattcact tagagacagg gtgtctctct    2520
gctgcccagg ctgcagcgca gtgacacgat catagctcac tgcggcctct aactcctgga    2580
ctcaagcaat cctcccctcc ccctaccttg gcctcctacg tagctgggac tacagacaca    2640
tgccaccatg cctaggtaat ttttttttt tgggtagaga tggggtctgt ctgtgttgcc     2700
caggctggtc ttcaactcct gggctcaaat gatcctcatg cctcagcatc ccaaagtact    2760
gagattacag gcatgagcca ttgtgcccat atggcacttt acatttatta ttttagtctt    2820
tacaacaacc ctaggaggaa gatacctatt cccatttgga tggagcacag ggaaactgag    2880
gctcaaacac agtaagcaac attaacatgt ggcaaggtgg gggcttattc agtctggggc    2940
caagtcaggg tctgggtgga tggaccagga gaagggcctt gtctaggcat atgtattcat    3000
ataaaaatga tccaccaaca aacctgtcca gtgcccttgc tcaggaagat gggtctgacc    3060
aggtgccagc ccaccagggt gcctttccac agtgtgcagg gggcatccac ctgaatgccc    3120
gtcttcagtg catcccctgg ccctgcactt gctattctgt gcagcaggag tttcaaactg    3180
tgttccacag agccctggag ataggtgtg tgggctgggc aagtgagaga caaaccctga    3240
ggaactgtgg gaccacccca gcagcctgtc atccctgtca cttcttgggc tctcaaggtt    3300
gtatttgaag aaatgatttc agctgggcgc ggtggctcac gcctgtaatc ccagcgcttt    3360
gggaggttga gatgggcgga tcacgaggtc aggagcttga gaccatcttg ctaacatgg     3420 caaaacctcg tctctaaaaa tacaaaaaaa aaattagctg gatgtggtgg cgggcgcctg    3480
tagtcccagc tacttgggag gctgaggcag gagaatggcg tgaacccggg aggtggagct    3540
tgtagtgagc cgagattgtg ccactgcact ccagcctggg cgacagaacg agactccgtc    3600
tcaaaaaaaa aaaaagaaa aagaaaaaa agaaatggtt tcactgcttt taaaaagcta     3660
gaaactactg ctgaataata attgtcattt taggtgtctg tttcttcccc cagaatgccc    3720
ctaaggagca agaactgtac ccacagcacc cagcacaagg atggggggtc tcaggaaagg    3780
tcggccagat agaagggcag atgagaaatg aatgtactgg gagctctctg tgtaatatcc    3840
cctcccccac cctcacccca cccccaatt cctgcaggga agaggccttg agagagttga    3900
gtaagaaata agcaggcaga atgatgcaag gggagctgtc tgtacacatt gcaacagaac    3960
tttctaaaac aagcctgggg ctgctcccaa gggtctcagt cctgcccccat tcctctactg   4020 tcatccagac ctgtcacaca agatagggcc aaaggccatt accaagctct gctaaggcct    4080
```

```
gaccttagag ctgggaggtc tgtgctcttg ggttctggtt tgaaacccgg agccatcttc    4140
aatcaccccc ttccttcctt tcagcccfac atccatgcca tcaaatccta gagactctaa    4200
agcttcagca tctctcaaaa tcaccctcgc ttctcttttg ccttgccacc ccttcagttc    4260
aggctctgtc gtcattatct ctctccttcc tctcatctgc ctccctccct tccatccaat    4320
atcacccagg tccctgtggg ttgtctgtgc cccttcagca aaggccacag cttccatgtg    4380
gcagccctct ccgctcagcc cccattgcac ctgcagtgtc cttctcttag tccttcaggc    4440
cagatcccct gtgaggtgac tagtcctggg ctactgcacc atcccttgag ttttctctat    4500
agcctgctta catctttgca aacagtcttt gtattaaact gtcctcaaat tacccagttt    4560
gggtgggctg tttcccatag ggacactgac taatataagg tagaggtagt taggaagggt    4620
gccatggaga tgacagttaa agatgttctt gcctggacaa tgatctttct aaagcataaa    4680
actcctgcta aaaacctcta tggctcccca ttgccctgag aataaagtcc agactctgta    4740
gcctgccacc caagactata taccatcagg cccctgacca caaagcagca gcagcatgtg    4800
gggaagccac caggaagagg gagagtaggg ggcttggacg tgggaggcaa agacttccaa    4860
gaggagtgca gccatgccac acagctgctc tggctggcaa attcctgtga gtaaggaggc    4920
gggtgagttt ccaggctaga gggccatgcc aggctgcctc tgcttgccag aaccctgccc    4980
gcccactctc caagtgagtt gagcactgaa aggagtttaa ccccaatggg ccctagcctt    5040
gtggcatgag aactggttac atcccaaccc catctggtaa gctattggat tccctgagct    5100
ttcattttgc caactgcaaa atgggactaa cctcccaggg ctgtggaggc gatggatggg    5160
aatttgcttt cgtccagtag ttctgctgtt acaggtgctc cctctcccag ccttgggagg    5220
caggaaaagc gtacaggttt gaggctctgg aagacttggt gtgaatctca gctttactac    5280
ttactccttg tgtgatccag gacaagtcac tttacttccc tgcaccccat gtgcaaagcg    5340 gtggggtga tcaccccttg tgtggtggct gtgaggactg ggcaagctca cacaagccag    5400
ggcctagcac agagcaggga gcttgataca cgtttgtttc tgtctttcta cctgtgcctc    5460
tcttagggca agtgtcctct ctgccttata ggctggccac ttaccctcct catgtgtgca    5520
atggaggagc taagactgct atcactgaag catatctcag aggtgcatgc gtcaaacctc    5580
tcacaagcta caaagctgca cgtgtaatcc ccaatggctg tacaacactg gtgattgaag    5640
tgggtggagg atgagccatc cttgtggatg cctctctgct cacacccctc ctttggtcca    5700
tcccccaaca ggatgaagtc caagcttctt ggtgggacca caaagcccac cctggtcaag    5760
cccttcttgg aggcatgact tgaccggtct ctgattttcc caatatacac atgggttgag    5820
agatgatgaa ggaaaggtaa ccaggtccta gaacacattc tcaagctgtt ctgctcacac    5880
acctgcagga aggtcagggc tggtcattat aggaggctag gaatgtcaag aagcatggga    5940 ggggccagg agaagtcaga gtctggtgta agtccccctt gcccaaactc acacagggga    6000
aaacagtccc aggacacagg aagctgccat gaaacttcct ttccaggcta ctctaagttt    6060
gggtctggtt ttccttccaa atccaatttg gaccaagctg tttaagcagt acccatgggc    6120
atggcggctg gaggccaagg ggaaggagtg ttctagaagt tgggatgcca ggggctgctt    6180
gctctgtgag gtggcacaga agtaagcaat tgtgcctctc agcccttgga ctcacctctg    6240
cgtcctctca cagatgttcc cacacaggaa gggcccaagc tggggaccag attttatggc    6300
cctattcccc aagcacccac ctccaccca acaacccagc ttatcttcct tttttttttt    6360
tttttttgag tcttgctctc tcgcccaggc taccaggctg gagtgcagtg gcacaatctc    6420
ggctcactgc aagctccatc tcctgggttc acgccattct cttgcctcag cctcccgagt    6480
```

```
agctgggact acaggcacct gccaacacgc ctggctaatt tttgtatttt tagcagagag    6540
gaggtttcac cgtgttagcc aggatggtct cgatctactg acctcgtgat ccacccgcct    6600
cggcctcccg aagtgctggg attacaggcg taagccaccg cgctgggccc cagtttatct    6660
ttctaaccca ccaatccaat caaggtgcat ctctgctcac acccctcctt tggtccatcc    6720
ccccacagga tgaagtccaa gcttcctggc aggacccacg aggccgttca gatctgggcc    6780
ctgtcaacct ctccagcctc atttcctacc cctcttctgc ctgtatcttt ctttcagcca    6840
caccagggtg ctcacagggt tcctacctcc aggcctttgt ccatgctgta ccctctgcct    6900
gacacctttc ccctttcccc ctgcctcaca gaatcagact tctcatctta ggtctgcagc    6960
aatatcactt cttcttgacc ttcccaattt accattccct ctacttcctc tatgactcta    7020
ctatactttt tcaggggggca atccaccttg gactaagcgt ctatgccgag ctaggcccac    7080
actgggacat agagtgatga ggttcctgcc cttgggaaac gcctggctcc gtggagaggc    7140
aggcagacag tgacagcaca gggggaaagg ccaaacttgg catagccttc catgttaccc    7200
tgtgccacag gctggctgtc ttgggatcat tggctttagg acaccatctc tcgattgggt    7260
ctcctcaaag ccaaggacta agtccgatta ctctctgtgt cctaaccaag gccgggccca    7320
gagaaggtgc atagcaaaaa tgtgctgaag tagatgaact tgggatctga atgtttcaaa    7380
taggccttgg taaccccaaa tcttgccatt taagacaatg atctcttaca ttacagcaca    7440
gtgataacac tcttttacat gctgtgattt cacttcatcc tcaaatactc aagtgaagtc    7500
agcaaaacag aaactgtcac ctccatttca taatgcagaa aaggaaacct agacaagata    7560
gcgatactga cttgcccagg gtgagtgggt gggccatgag ttccagccca ggcctcctcc    7620
acaggagacc cttctggagc aggcacgagc cacagactga cctgggatct tccaggccag    7680
caggagtctt gcctccaaga gcaccctctc tgaggagagg atgccaggat ttactggcac    7740
cttcagtatc ctcctggctt cactcctctt tgcccaaaaa caaaccacac ctgtttctac    7800
ctcccagcct ttgcacttac cagtccccat gtctccccc atccccaca tgtggcatgc      7860
cactagccta ccctcagttt cctaaaaggc actaagatct ttccagcctc atggcctcac    7920
cacatgctgg gagctctgcc tggaatgctt ttctttctac tcttggccaa ttcgggcctt    7980
ggggcccagt aacacggttg agagatttac tcctgtggcc ttgagagggc tgaacaaatg    8040
gaagcatctc taggttgcac cagaggcatc tattacctgc tgccctgtgc ctgtaacttc    8100
tgtcattctc ctctccccct gtgagaacat gataaagacc acaaaggcag ggaattcctc    8160
tcctcttatg ctgtgacccc acagctatct cgctccagct atgcctaaga aatctgtctt    8220
atcactgaca tgcttgttgt ccccactcgt tccctgagcc tccatccaac aagtcgctcc    8280
accacatgct ggtggatctc gcttcctatg ctcttcccta gatcaggcct tccctccatt    8340
ccctctacca ctgccgtgcc ttgaggctca tcctctctca catggatccc ccgcccctac    8400
agcctcccca ctgccctcct gacctacagc ctctcctgtc catttcccat accatggcta    8460
aggacactta aaacccacct gaccagccat ttccctacta aagctctccc aagacccggc    8520
tccccccaa tatctcaaga gtggcactcc caaacctctc tcagttcaag cacccgcgcc     8580
tctcacttca gcctcatttt ccacagttgc ctgggctcca gccactccag gcccccagc     8640
cctgcccaa acatgctggc ttttctaaca ctttatgcct atctttctgc tttgccctca     8700
caccttccat ctgcaaaatt cctattcatt aatgggcaaa ccattctgga atgctttcta    8760
tgtgccagac actacctagg ctctttttat accttatctc atttacttct caaagtacct    8820
```

```
cacaaaaata ataattatta ttcccatttt acagatatgg aaactgaggc tcaagagagg   8880
cagggcaaga actggactcc tagtctatct gattccaaac ctgctgtgca ccaacctctc   8940
tgggaagtgc accagcgccc ccactccccc agcccagggc agagtcttct ctactctgtg   9000
gttccatagc cccctggttt ctcgcttgtc ccggccgttg tcaccagtga ctgtgtgcgg   9060
ctgtctctgc tgcccccag cgtgagcatc ccaagggcag aacctgggct gatctggctg    9120
ggtccccagc acccagcagg gtataggtgc tctgtgaggt ttcttaataa agagatggaa   9180
agccagaagc agtttgggtg gttgagatac ccagccctaa cctaactaat cctgatacca   9240
gtgaccaaaa gcgggacctt cgcatctttg ctgccaaaag acagcccctc ctaaagagta   9300
aaggcccgac ccctgcacg ccctctgcct gcaccgcacg tgcttggttt tccccgcccg    9360
ggtactggcc gccgggccgt accaatctcc gcggggagc gccgggtc ggactgaggg      9420 agcgagggga ataaccgggc gcgcccttg aagcagggc tcagagctgc tctcctctca     9480
cgcattcccc ggatccgcgc ggagcaggct gctggccagc cccgggcccg cgccaagcag   9540
agcctcaggt gcggttcccc cacaagcaag tggcgcgggc ggcggcttag aacggcccgc   9600
cccgcccgcc gcgtcggcgc ctgccccgtt gtgaggtgat aaagtgttgc gctccgggac   9660
gccagcgccg cggctgccgc ctctgctggg gtctaggctg tttctctcgc gccaccactg   9720
gccgccggcc gcagctccag gtgtcctagc cgcccagcct cgacgccgtc ccgggaccccc  9780 tgtgctctgc gcgaagccct ggccccgggg gccggggcat gggccagggg cgcggggtga  9840
agcggcttcc cgcggggccg tgactgggcg ggcttcagcc atgaagaccc tcatagccgc   9900
ctactccggg gtcctgcgcg gcgagcgtca ggccgaggct gaccggagcc agcgctctca   9960
cggaggacct gcgctgtcgc gcgagggtc tgggagatgg ggtgagtgcc acggcgcagg   10020
ggttatggac ctgcgagaag atttctgga aagggccctg tggcaggctg gtgggtactg   10080
atgagtccac gttcattctc cactgtggca ctcatcaatt tttacgacct ctgttacatc   10140
gctttccacc cgcccccag cttgtttccc tcatccgtga ggtgggagcg gtaccaccca    10200
ccattcttag ttattaggga tattcgagaa ctcctcccca gccccactg cggctggtga    10260 cccctggcac ttccctcccc tctcccttca ccaggtagag cgagctttgg cagtgataga   10320
ctggatgggc aggatggtat gggttttgcc gtctcctgag acagccacca gacggggaac   10380
atgcccgact ggaacaggtg tgtctgccct gtcctctgtc ccacatccat cctctcgccc   10440
aggctctgga gccacatag cagcaactct tgagcctggc atgcttagaa ggcagcggag    10500
aggaccctgc atgtcctcca aggtagaact gaggtcctgc gtgaatcgcg cagagttgaa   10560
atcaaccccc gccccgcacc ccccgcagct tttcccaagc gaggaatagc aactcttcca   10620 accccccacct cccttaccta gagctggaga aactgaagtg ggaggaagca tgcctaagtt   10680
ttccttagct gatgccttga cccctggatt caagtacaaa tccggtagac cctgggaagt   10740
catcacagct gtcctggtct gcgtgtgtgt cttgcatgaa gcccctctcc ctctttctaa   10800
gtctgtattc tgtttgctga gcctctctga catggatttt tctttagtaa ctaacggtcg   10860
cctacaccgc ccacctttgt tacaaaaata aagcttgcta attatggaat ttttgaaaat   10920
atagacaaat gaaaaaaatt tctggtaaat cgactatcca aagataccttt cctattagca   10980 ttttagtata tctcttgatc attttctttta tacacattgc atagatacaa ttgaggacat   11040
gctgtagata tagttatgaa tcttgttttc tccccttaa tgtaacatcg aggtttccct    11100
tctgttaatc agaatcactt acaatgtcct agtggttgca ataacccacc ctgcagctgt   11160
accacacttt aactgtgacc taggcattgg cattgcttct tgtgtgatta tcgctgtggt   11220
```

```
tatctgcccc tcttggtgtg ggtgctgctc gtagcccttg aagaggaacc cagctgctgc   11280
cctgtctcgg gggcgagcag cttgagctgc ccatgtatc cagccagtag cctctgacag   11340 cccttctct cacttgagtc cttttctgtt ccctgtgtcc tttgatgtcc ttagggacat   11400
caatggatga atggacttgc ccttgttcat gctgttaaaa atgttttttgc actgggcagt   11460 gggataggga tgttctctgt ggtagtgctt cctggagacc ccattccgtc ggctctgcca   11520
tccacaggct gggagctgtg tcttccagga ggcagtgacc ctggctgtca tgttttttgac   11580 ttagagtttg ttccttagga gaacttgtac tctagcgaat ggttttaacc aagccactta   11640
atatcatgtc aggaacattt ccccatgttg ttatcagatc ttgaaaactt tttttttttt   11700
aaactgggtg caaggattta catcatggaa tgtaggaagg gctggtatga aatgcaaacc   11760
agtcagttca gctttctggg atctactttg gtgaaagatt gggtggagta ggggagggca   11820
ctgaagcaca ttttgttatc tgggcatctc cattagacct gccttctaga tccttggtcc   11880
ttgaagatac tccccagtgg cctagtttgc ctctgtgggt aaggtcccac tgttgtgagc   11940
tggtgaacag cccgtcagtg acagtattca agtagagacc atggattctg tgaagggaag   12000
tcctgtgacg ggtgagagat tgaaatagat accttggcat ctggtttctt ggccaaaaaa   12060
aaaggccagc tgtgggagta tgggtaggtg ggtgcatgct gggggaagcg ggagtctgtg   12120
ttgatatttc ctaatccttg gagggctgtc ctgtgccaga cgtggagttt gcagagttca   12180
tcaggacagg agggatatat atcctattct ttatccttgc cttttggattg ggggctcttc   12240 gttcagaaga gccctctgac acctgcctgt gtcctcaggg ttcagcacag gacctagcat   12300
gagatgttgg tggtcccagt aaaattttga gctgatttgt tgtgtgcggc tccaaagagt   12360
gaggccagga ataggagtgg gatgatgggt gcaagttttg atgtagcaga ggagtccttt   12420
ctgacagctg ttgaggactg caacaggctg gggtgggtga ggatggagtt ccacatcact   12480
gtggatctgc ttgaaactaa gtggctagat tgttggggga aactgggaac tgagggttga   12540
cagtcaccta acctagtcct aagtcagaat gagaacatta ctctcatgct ccctctcca   12600 attccgtgtg gcttccccccc tcacctacat cacttcccca gctgaataga ggccacttttg   12660 gggctgcgtc accaagggct catctaggct gagaaaggag ggccaagagt aatgttgtat   12720
taacaggctc agtgactcaa tggtcagtgt tgaaatcctg ccccacctcc accctcctgc   12780
cctcaaattc aacagcaagt acttgagttg taaaaattag tgctggatcg ggcccaaccc   12840
tcatgttaca gatgggatca ctggagtctc cagaaagaag ggactttccc agggttatca   12900
aagccaggct agaactcaga tccatctccc agtctgtggc ctgactcctt aagccaagag   12960
aagggttgca aggccgtgaa gggctgagtg cagggctctg tgcattgtag gtgctcagtg   13020
gtttgctgaa tgagtgaagg ttgtctccat ggtgcgggtg gcagctcatc ccttctcaaa   13080 cttttttgagg aagctcccca agcctgcccc t agtggattag agcactaaga tcccccagag   13140
ctttggctgc caggtgaatg ccagttgccc cctacccaca ctcagtcaca cttcagactt   13200
tccaaactct tcctcctggc ctatgaagta agcccaggt gaacagcctc cactgccatc   13260
acgacttcct ctcctagtat gtcacccacc atgctgcaga cgcatggtgg tcttcctgtt   13320
cctgcagcat tactcccaat tcagtcttac ctcagcgcct ttgcatatgc tgcctgtctg   13380
cccaggtctt cgcatggctg gctttacaac agtcaatctc ctctcagagg tcttccctgg   13440 ccacccctatc tagagagcca cttccaatct agagagccac ttccaatcac cacatcttct   13500 tttatttttta tagcctttat cactacctaa attttcatgc gtgcttatct gtttaagcaa   13560
```

```
ttgtctcccc agtaagaata tcagtccctt tgccggccgc gtgccatggc tttcgcctgt   13620
aatcccagca ctttgggagg ccaaagtggg aggatcactt gaggtcagga gttcgagacc   13680
agcctggctg acatggtaaa acccctgtct ctactaaaaa taaaaaaatt tagccaggtg   13740
tggtggtgtg tgcctgtaat cccagctact tgggaggctg aggcaggata gtcgcttgaa   13800
cccaggagga ggaggttaca gtgagccaag gttgtgctac tgcactccag cgtgggtaac   13860
agagcgagac tccatctcaa aacaaaacaa aaagaacaaa cagaaaaaga atatgagtcc   13920
cttggaaaca ggaaccttgt ctgtctttct cagtgctgtg acatctagca cagtgcctgg   13980
cactggtaat aggtacttag taagtatctg ttaaacgaag gaatcattag tgggactgcc   14040
ccattcctct tggaggaagc cctgcttttta gcttcagtgt gattcctcga gccttccttg   14100
ggcctcctct gtccctgtaa ccacctgtgc tagggactgg gtgctggggt tgtagctgtt   14160
ccctgccctg gaggtaccca cagtctggca aggagctggc tccaaggctg agtggcaagt   14220
gggcagagcc agtctcaatg gtcaccctta ctgcttccca gggcttatta gaagcccgag   14280
agctggggtt ccaggcctga catttttctg ggatgtggct gggggcttca cttcctctct   14340
ggggatctca ctccttctat ctggaaaata gggtcagaat tctcagattc tcaaggatgg   14400
agggtttgag ttaacctgag tgtgagtgtt tgtgaacttg tgacattcat gttagtcctt   14460
gtcatttgtc ctgtgttaca cattcagcag gcccccaaca ctgtagagag tggcagaccc   14520
tgctctaggg catccaggaa ggcttcactg aggaagggac ttgggggtgtg gaccccttcat   14580
tttattgatt gagcaccttc tgtgtgtcag ctgcagtccc tgcgtttgag gaagtgagac   14640
caggggggatg tacacaagat gactgtgcag agtgatctga gcaatgacag gaaagactgc   14700
caagaggtga gaccggggag cttgatcacc ctgaggtcag ggaagtcttc ctggaagagg   14760
tgacattcag tccggatctg gaaagatgaa tagacatcag caagacaggc aagaacattc   14820
aggtacagga aatagcataa atagaggcat gagatttgga tgggagaggc agactgactg   14880
cagggcctct gagtgaccaa ctgaggctga ggtcttggtg tactgagagc cagagacaag   14940
agagacagag aggatgctgg atccaggcct gtggtggctc acctgtgtct gcagcaggag   15000
gaagacttga gagctcatgg gaaaggagcc tggtgcagtt agtttattgg cctccagcac   15060
tttgagggcc tcctggtatg gagctgctgg ctgatttgag ggcctcatgg gcagggccca   15120
ggggtaggag tcaggcctgg gctctgtcca gctcctgctt ggccaccgaa ctgctccgca   15180
gcctcagcaa gccactaccc ttccttaccc tcagtctcct catctatgaa atgagcaaaa   15240
gtgtcataag aacctgtgca gattatggtg cagatgcaga caggctacac cctgtgaacc   15300
ttttgggtaa atcaatagaa atgggaaaca caaactcctt ttcttattag agcagaatta   15360
gccattctaa gccctgcctc tgcttcccat gtgaccttgg gtataacact gcctcttagg   15420
gcctcagcct tctcatctgc acagtgagga ggactggttg agatgacccc cttggcttcc   15480
ttacatccct gctggagaaa tgcgattcca ttcttgtccc taactgctgt gggactcttg   15540
aggtcagcca cctcctcatt cttgtcctca gcttctcctt gtgaaaatgg tgcactcatc   15600
cacttggggc caaggtaagt gccccagaag aacctgtctc cccatgcttg cccatatatt   15660
gtgatgggga cgtatttttgg agattccttg gtgacctact cgcaagctag tagtgttgcc   15720
atggcagccc cttccactgc agtagctact ttttgaatgt gcttggtcac agtgggtggg   15780
gtgggggaag tgggcccctg gggtcctcag caatcatgtc cagggtcctg gatgtagatc   15840
catgttcggt atcaggaaca tggcattcta agagtctcac ttccttggcc ttacctcttg   15900
gaactttgtg aaagttctac ttgatgaaaa cggaatacac aaaaacccag gtgtatggag   15960
```

```
tagcccgagg atgggcttat attcccttc  gggagatctt ctgtggataa aaattcattt  16020
gtggattcta gcagagcaca ggtggcccaa gttagcagca ctcagatttc aacaaatcca  16080
ccccagcttc ctaatttagt gctaatgggg aaacctagag aggggaggaa gaggcttagc  16140
gccctgcag  gtctacagat gctcaggatg cctggctccc tgcagcaggc cctgaggact  16200
gacagtgcct gcagggtcct gatggcccac ttcccacctg gcacacctag catagctgtg  16260
tgctggctct ccagtagttt ggcttcccct ttgggccaga tgtcccagtg ggccctgctt  16320
taaggatacc tcatttgcaa aacagaaccg ttaaagcgaa ttgttaatct tttcagaaaa  16380
gaactcactg gcgttttggg accagttcta tagctagcta gctgccctag ggctcttagg  16440
caccagtgga gggagtgagc tctgactggc tgtcttctct gccttcaggg tagaggccag  16500
gactcctaga cctagcatcc cagtccttca tgcctccctg tttctctact tttccaacta  16560
gactcacagt ctctgtgctg cagtctgact aaactgcttg cagttaattc ctcaaacttg  16620
tcttctctct gtttcgggcc tttgcaatgc cttctgggat cctgcccctg taccttcctc  16680
ctggaaggca tccctaagaa caccctcctg tggggttgg  ggcctcccct ggattcctag  16740
tcctgactga tcctttatgt ataattgttc gcagctttgt ctcccagcca tatcttgggt  16800
gggcagccca ggagcagaac tcagcctcta gcagatgccc aagaagcaga ggagaagcag  16860
agtctagaag ctcccctcct ggtgtggagc ctggggtgta aagggtactt agaaagcact  16920
ggtatgaatg ttagtgtttg ggttccaccc ttctctctcc cttcctctgg ggccttccac  16980
cattgccccg acattaacca ccctccagct ggagaagacc tttccctcct gattcccag   17040
aaagctctgc ttgaccctcc atcatggcac aggtcagtca gctgtgggtg gactttttc   17100
tatctttgtc taggccctgt ttattcatca cagtcctctc aagcattcag tcattcagca  17160
aacatcgatc gagcaccttc tctgcgcctg accctgtgct gagcaccagg gcccagatga  17220
atgagacatg gtccctgcaa atgcacacac ataccttttc ccataatgag aaagggctga  17280
gtacaggggt gagatgggac aggcagggat gcggtcaatc caacccaggt ggaggagaag  17340
gaagactttc cagagaaaga gtcaacaggt tggtctctag caggccagtg ctcagtgcct  17400
ggtggatgcc tggtatgcat gtgctaaaag actgaccaaa ctagacttag aagcaataga  17460
actctacctg gaggcactgc agtgaagtcc ctccttcctg gagggaacga gtctctggct  17520
gagcacatgg tgaggcacca agtggagaca gcttcctgtg tgaggcttac gggagcccag  17580
ccctggcctg ggattctaat agcagtgggc atgaccctcc agagatggca gctttgccat  17640
gaccggcctc tcatcatcat gtgtgtggac tcccgctgaa aggtgtctgc ctggaggagc  17700
ctggaagaga gctcacctcc agccttgatg aagtggcatc tctttggcac ttggcctgac  17760
ttcctagacc tccctggggc tggaagagcc tgctaggggt caatatgtac tgaccctcac  17820
tctgctacct ctcctcataa tatacaacct gttactgtgc acctcttaaa aaactgtttg  17880
ctctctctgt ctccgtgcaa cttgtcctca gctctttggg ggtaacttgg gggtgacttt  17940
ctcactcacc tagacccagg gcagacatta ggtccagatg gcccaggtg  tggcatcctt  18000
ggggttgggg atgtgggcag ggtgaccccc acccccaccc ctgcctcaag gagcccaaga  18060
ggctgttcac acctctctta gctggcatct ttctggctct ctcacattga tgccagacat  18120
tctggccctt ttccctaagt tatttagatt ccttatgaca atcctggatt aaagctaagg  18180
aggacactga gtcccaggga cagggagtga tttgcaaggt ctcattgcag gtaagaatca  18240
gagccagggt ttgaatccta agttagcctg tcgcctacgc ctctgttcct aggcagggca  18300
```

```
ggcattattt tacccatcaa acaggagagg acaccgaggc ttacttggta attaatcagc    18360
attcatagag atctttactt tttatgaagc tcttggctat acattatctc atttaattcc    18420
cacaacaatc tggtgaggta ggtattagcc ccactgtata gatgaggaag ctgaagcttg    18480
tataggaagt gactcatcca ggccacttcc tacgagttag aggccaggtt ctcctgactc    18540
tcggcccctg ttttcggcac tgactccagg ttggcatgtc ccctgccaga tgccagtatg    18600
gaggtgaggt gggtggagga cgcggtgtgg gctttcgaga ggcgtgagct gcccacagtc    18660
tctgtctacc agtgcttcgc catgtacgct cagggcctcc tctccatagg ccagggatcc    18720
tcctgcccct ctctctatct cattgcccca aattattttt cttcatagct ctcgtcgctg    18780
cctgatgtta catcatacat taatacgtag gtgttttatc tctccctcag cagaagttaa    18840
gcatcctaac ttaactttag ccagtctgac ttgggcatcc aggcctatag ctgcctctga    18900
ggcaggacat catctgctgt gctcactgct gtttccccag ggctagtatt agcgcttagt    18960
accttgtatg tgctctatgc cttgggtctt agctctgtcc ccacccacct cacccaggaa    19020
gccacctttg actactcatt ccaacttctt tattctcagc ttctatttca ggcagtcact    19080
cacccccctt tctgggttct tgagtatttg ggtctgcctc attagaactc cctgcaaggc    19140
tttgttccag cagtttcccc caaccacagt gcgcactttc ctcctgtttg acccctagat    19200
cttgtcttca gggccctggc gaagcctcat ggcctccttg gagcctcctc tgcgctacca    19260
tcactctgcg acctcttctt gtaacacaga cctgtggcca tgagcctctg gaaaaactct    19320
gcttgctcac tacatatact ccttcccact ctggagatgg gaggagcaat gccagtagcc    19380
accacttaat cacctaacaa atgccacatg tgccttaaac gttttaaaat ttaatgttcc    19440
tggctgggcg tggtggctca tgcctgtaat cgcagcactt tgggaggcct aggcgggcgg    19500
atcacgagat caggagatcg agaccatcct ggctaacatg gtgaaacccc atctctacca    19560
aaaatacaaa taattagccg ggcgttgtgg cgggtgcctg tagtcccagc tactcgggag    19620
gctgaggcag gagaatggag tgaaccctgg aggcggaggt tgcagcgagt cgagatcgca    19680
ccactgcact ccagcctggg cgacagatcg ggactccgtc tcaaaaaaaa aaaaaaaaa    19740 aaaatttaat gttccccaaa atcctgtgag gtgaggatta tcaccctcat cctatagata    19800
agaaaaccaa agctagagtt aggtgacttg cccgaggtca cagagccagg caagggcaga    19860
gctggcccag ggccctcttt ctcagattta gggggttggg gctcagacac tgctgccctc    19920
aggcatgtga gaggaagccc tgaaaacttg ggtttcatca gccccgaggt gtggccttcc    19980
tggtcacttt gatatcagat attgggcaaa gaggtgctca cagacaccct tcaacacccc    20040
agccctgggc tgggccctgg gtctgagaac tgcttgaaag cacatgggtt gcggggtgg    20100 aatccagtct cactagaaca tccacatgag actttgagca tgatatgggc agaggaggga    20160
gctctccttt gccaggatat gttcctgaag tccaggtgtg ggctggcgtg tttggtgggg    20220
ccagcgctca acagcgtagc attgtagaga tgatgaggga ctgggagcct gaataccttc    20280
tttaagtcct ggctcccaca ccctgacctc aagcaagtga ttttgcctct ttgggcttca    20340
cctcacctca gtttccttct ctgtgaaaca ggattgccag ttctcccctt gcctaccttc    20400
ccagagagtg ctgtgggacg gtgaagcccc acataggcgc aggagaaggg gattgctttc    20460
cgggtggtaa aagagctgct ctgggcctct ctggcagctc tactccctct gccttcccca    20520
aaggtaggag caaatgagct gtgtgtaaag caagtgctgc ctgggagcag ccatttgagt    20580
cttctgttgg gaatcttccc ctacagcctg tctcatctgc ccccataaaa cagagacatc    20640
tgtaggtagc agggttgtgt tcccttttata ggtggagaaa cttgtaccta gggagggcaa    20700
```

```
aagaggctca tcccccatct ctggggtcag tcctcagtga tggggctggt tttgcctcct   20760
gccaggcagc ccagtctaac ttgggcatcc aggcctatag ctgcctctga ggctgctctg   20820
gatttgctta tggatttgct cagctatgca gtaaacctct atgagcccct cttaccacag   20880
atgaatcagg taccaagtcc tggcacccat gcgtcactgg cagtgggatg ccaagtaaa    20940
gtgacattgg tgctgtggga gtgtgcagag agagtgcaga tgtggtgagg gggcagatag   21000
gagcagggac ttggctggat gctgaggctc cctggtggcc ccacccagga gtcaggaaca   21060
gtcagactgg gtgtgaaggt ggtggcatgt ggtggcatct gattgcagca tcggcatccc   21120
caccagcttc tgctggactc ctcccagcca cagctggggc agaggaagta ctgacagcca   21180
ggtggcaagg actggcagtg tttggggggt gcccaactga accctcactt cccatctgcc   21240
tgagcaacgg taccagaact actgcaagat ggtaagctct aggtcccaaa taccctgaca   21300
ggagtcctca ggagggtggg tgccagagat cacagacttc accctcctta cccccatttc   21360
atagatgggg aaactgaagc ccagagaggt gaggagactt agcatgggag ttggtggcag   21420
agctgggtct agaaacccaa gtcctgctgc cactctacct gctgtagaag atgcctgctc   21480
ctgacccacc cctctgaagg aaaacagatc attcatttct ccccttcccc ttccagctcc   21540
ccaccactgc cccctgcttt gttgtgggga gcagagagaa ggaacttggg gacatgcaac   21600
atcggagcag atgcaggcct gaaggttggg cctgaattgg gttcagcttt gccagcatct   21660
ggctgagtga ccttgacccg gtatcaccat caaaataggg tgttggtgcc aaactcacag   21720
gagtccaagt gcctgtgcaa gggcatggag ggtctcccaa agctttatgg gcctcttgtg   21780
catcataccct ttcactcagc cctgcatgga gggaactccg ggggcctgaa gagtggccag   21840
agcacctcct tggggctggc ctgacagggc actgggatc cagatatgga tcagacccag    21900
gcctggcctt cgggcagctt ccagtgtgat ggagaatcag cttgtaatca gcagttagaa   21960
caaggccaga ggctgtggga accctgagga ggatgctctt ttgtttctcc attgtgcggg   22020
tctgactta tcttcaaata ggttatttct gtgggtggca agatagcccc tggcaattcc    22080
aggcctgcat agaccttagt gtttatcatc ccagagaagg aaaggccttc tctttccaaa   22140
ggcttcctgg aagactgctg ccttatcacc atctctgggt tttgaaggat gtattgcttt   22200
atctcattat cagggaatca tcaggtaagc aaagcaggga agggcctctg cctagaatat   22260
ttctgaggtg gactgggggc tcccactggc ccggggttca gcatccatgg ccaggccagc   22320
tcccaggcca cggcctccat ggtcagccag gttgggattg cctgagaggg cctgggcctg   22380
agaaagcaga ggtgcagtcc tcccagcttc cctctccagg agcctcccaa ctctaacgcc   22440
cacggaagca cttgccattt ggtatttggg acttagagct caccaccttg cagcagtccc   22500
ggtacagttg cccaggcaga tgggaagtga gggttcactt ggtagactgc atttcccact   22560
tgttggcaga gcgagctgtg ggcggtagtt ggggctggat aaggcagggt gagaaccgaa   22620
ccagcagtgt gggaaaagcc tgagcctgca gacccacctt gctgcgggac ttgggagact   22680
cccgcaggcc ctcaatttcc agtctgtata acggggtgag ggttaacaa gatgcgtgc    22740
gtttcctgcg ctatgacttt acctaatttt aagacaccta ataagcttag cagagagatt   22800
tggattaggc acgatgaaga attttttaggt cttctcagtt gtttcagttg gggatatgtc   22860
atcagtgaaa tttctatact cctcctccaa gctgcatggg ggctggccct ggcgtcaagg   22920
tagggagcta gataagttga ctcccagcat gcctcttccc tacgcacccc tcaaaccact   22980
ggcttcaggg gcctgtctgc aacgggaagc aagtcagcca cgagaaggca tgctttgcct   23040
```

```
tttttttcctg ccaaatagaa ggtggtgttc cccggtgctg tgtctcaccc cagcccctac  23100
ctgagtgttt ggactgaagc atttatagtg gtgtttctca gacttaatca cctggggatc  23160
ttgttaaaat gcagatttttg attcagtaaa tccagtctgg agcccaaagt cctgcatttc  23220
taacccgctc ccaggtgatg ctgatgctgc tgttcccaga ccacgctttg agtaggaaag  23280
tgctagagta cattttgtct tctgtctagc cagggcatcc agcctgcctc agatggaaca  23340
ggaactcacc tgccacttaa ccagcctccg gtggccatgg ctcctgcttc acttcatcca  23400
gcatggctca ggaggcagag ccagctgctg gaagatgact tgtccagccc cagcccttgg  23460
atcaagggtt caagcctgtg cttggacttc acttccctcc cttatatact cacccagtcc  23520
tgtcccactt gtaggtgaag gtgaaaggtt atgagaccct caaggataag catgtgatga  23580
actcatctgg ccaggtccca ctgctgggca ggttgaccag ccctgagca tgaccctccg  23640 actgtgtcct gtgtacagag cctttgcact cagagctgct ctggggaaag gggaggtcct  23700
ctaagcaggg tcaggaatgc tgggtttcag tcctggctct gccgcctact gcctgggtag  23760
ccctgggcta gtcagtgcct gtctctggtc cccagtctcc ctggctgtcc aattaggcta  23820
tactggatga ccccagaggg ctctcaggct ctaagatggg ttgctgggca agtctggagg  23880
tgggaaagtc ctatgaaggt aggattttttg taaaggggggc gaaggagcaa ttatgaggca  23940
gacctctgga atggctctat ggcccagcct ctttatttgc ttttgtgagt tcacatcctg  24000
ccgcctccac cccagttatg ccagtggtgt tattagatgc tactgaacac ccaatttgtg  24060
cactgaggat gtggcagtga accctgcaag cttgcctggg gtcacatagt gagtagaacc  24120
aaagtctgaa cctaggtttg actcttctgc taaactaagc cctttccctc tgatgcatca  24180 caccaggaa aggggccatc ttgaggccta gcatttcctt ccttcctcct aaaagtcaaa  24240
gcagttgtta actttcagct cataagggta gatatctttc taaactctgc tgtggctttg  24300
ttgctttgca gattttgaag aaaagcaaag gcttgagtgt aggcccctaa atccgtcttt  24360
ctccctgctc ccagcttgta ggctcagttg aaaggtcatg agaccctcaa ggacaagatt  24420
gtgactaact catctgtgct ctgggtcttt cacagagcag atggtatgaa ggaatattta  24480
atgggcacac agtaggtgct tggtgaagat gtgttgagca aagggcatgt agtgggggtt  24540
cagcaaagag gggtttgagg tggcccactt cttcagctgc cggaaggaat ggggtatggg  24600
tgaggaacct tcacccatgc tcttccccag tgctgtctcc tgcagtcacc aggcttcctg  24660
tccctactgc ccatcagctg ctggagtcca gggtgtcatc ctaggggcac caagccaatt  24720
aagtgggcac atctcgtcct aacttccagg cttggcactt gattgatagt gaacataatt  24780
acagccctca gtgtccttca ggctgcctga agctcactgg ctactgggcc ctttggggaa  24840
gcaaaggctc ccaccttact cctttctggg ccccacgctt tgggcactga gatgaggctg  24900
aacatttaca tctctctgaa agtggtagtg gtgtggggaa tcagtggtgt tgggggtggg  24960
ggcaagaggg ttcagctcct tggagaaggg gtattagtct gggacataca gaaggcagag  25020
cagggattgg ggatgctcaa agtacacttg gagaaaaaaa accattgcaa attggatgtt  25080
gaacctctgt ccttggcctc acagacagat agcaaaatta aatatttgta ctagattcag  25140
ataagggaca ggagtttgac tggggtggag gggatgggag agaactggca attatgagag  25200
acttcccaag gcctagccct tggactagcc tctttagata cttcatgtgg tctccaaaat  25260
gaccccgagt gcgataccat tcccattgtg tatctataga aaccagggca caggggagca  25320
tgcagacagc ccagagttac aaagccatga ggtggagggc taggatctga acccaggtct  25380
gtctgattct atagctgatg ctcttctcat atctagaagg gtacctgtgg gaggtgaggt  25440
```

```
ttgtactggg acccccatga ctggagagaa gggtgacagt ggactgacat cttccctctg  25500
ctgtaggcac tggatccagc atcctctccg ccctccagga cctcttctct gtcacctggc  25560
tcaataggtc caaggtggaa aagcagctac aggtcatctc agtgctccag tgggtcctgt  25620
ccttccttgt actgggtaag ctgggcctta gagggagggc aggtgggcag gcagtgtcca  25680
cttccccaaa agaggtagag caggagccct gctctacagg ggtgagggaa taagagtaac  25740
tcttacacat gctgccccac agcacctttc cacatctatc ttttgggtcc cagatcaagt  25800
gctctacccc tcagcatgca tgaagattca gcaagattca gtgggaggtg gtgtgatagt  25860
tcccatttac agatgggaaa cctcaagtct tagagaagat aggtaacttg cccaaggtca  25920
cacagatttg aatccctgtc tacaggaccc ccaaagcctg tgccttttcc acaatgccac  25980
cctgcccacc aacagacatt ttccagcagg tatgttactt tgccttaagg tggtttggtg  26040
ccaggtttaa gtcctgaatc tcctgcagac aagctctgtg accttacaca ggttatttga  26100
gctctctgag tgttagtttc ctcatttga gtgtgaggaa agtgcctgct tcacatggct  26160
tttttgagga ttgaagataa gaaatgagag cacctggcac agggcctggt catgatgggc  26220
ccccattaca tgggaatcat cgggaggtgc cctcagaccc cactcccagc ccacacccat  26280
cctcagctga gcacattccc caggtgcttc ccgaggcctg ctccctgcta tctctcagca  26340
cagcccacat cggtgctttg gttgcttttt ctgcaggtct ggctagatac cctcactcct  26400
taggttgcca tccaggccag gggcaggaca acacgaatgt ctgaggggag ggaagaagcc  26460
tcttgttttt ccccagaccc ctgtgctctc agcatagcag gtagcttcct cagcacgtca  26520
aggcagatga acctgctcca gagcatcaca gagtgcattc cagtgcctgt gagccagtcc  26580
ctctgggcaa cccactcttc gggactgtat aggctggtag gggatcatca ggacttacca  26640
tgtcagtgct gagcagctgt ccttcaggca ggtgcatggg gcgctctgag actgagacca  26700
tgtttgcagg gccaagggat agaacttcac aggtgagaaa atgcaaattc acaaaggttc  26760
atcaactacc tgctactgtg aagctcatta aatggcagag ttgggatttt agcagaaact  26820
cagtgcattc cccagggagc ccacattcct ggaagcccag aattagtgaa ctggggctga  26880
aacagccagt cttcaccttt aggcccaaga acgggctttg agtgggggga tccatgaacc  26940
cttaaaatta gatgcaagat tatatatgag tatgtgcaca ttttctggg gagaagggcc  27000 atagctgtcc tcaaagtctt acagggacag gtagcctcaa gaagacaaac actggttgga  27060
agaactgagc aaactaaaca gtctccctca ggactcagac ccctaacatg gcttgcattt  27120
ggccacttac tagaatccta gagtagtgag cacagtgtga ccccttcttg ttaaaaaagg  27180
aagtggaggc ctggcgagga tggagcctta cttggggtca catgagaaga agtactggg  27240 accaggacaa gaacccaggg actccagcct cccagacccc ctgcctagtc tgctacacca  27300
gctctctttg ttccctgttg caccccaaag ctaccactat ccctgtctta atgggtctgg  27360
gcctggctgg tagggagctg agcagcttgt agaacaccag ctcacgcagc atgtgatggg  27420
gactggcccc aggctatagg ttaataattg atcagaccca accacagccc agaaaccggc  27480
ccagcatctt ctcaacaccc tcgcctggcc tcacctcgcc tcgcctcgca taggtgggaa  27540
cctggcctcg ttgacaggc agatctcctg agctactgct aattactgcc ctcagcagcc  27600
ccagccactc cttccctctg cctctcaaac ctgctggcag aagctcacct ggcaagcaaa  27660
gaccgtggtg gccctgttgg tctctccctg gaccagagat ttttcaccac tttgtgccat  27720
ggaaccctct gtcatttga tgaggcctat gcccttctc agtgttttag agtatttaat  27780
```

```
acaaggtgca ttggatttca aaggaaacta ctgataataa aatataaata tctatacatt   27840
aaaaaagctg attagacatg tagtaacagg tgccttttta ttacagtaaa taaaaagatc   27900
tagcagcaca tgtaataatt actatagttc ttaagtagtg atgagaagaa atgattttt    27960 ttaagatatc tgcaactgct acaaagttat atgaaaatac ctttgttatt tatttgtgtc   28020
ataagtactg ctgataattc tgtgatttat tatattggta agtgaaggaa atgccacatt   28080
tccataagag ataagtgaaa atttagatgt catttgtttc cccatccaag tccatggata   28140
ttgtgtgtca ggctgagtaa gttcaaacat catatttaat tttcccaata ccctgtaagg   28200
aaattaaggc ttaggaatgg ggcttggcca gcaagtggca gggccaaggc tccaggtctg   28260
tttggtctca gagtccatgc tcttcaccag gccacactgc tgccttccct gccattgagc   28320
atccacaggc tgccctgcac cacaggcctc gtggcttcag aattttgtat cacaagtgtc   28380
tttgtaggcc accataatgt gcaggaagca ggtgatgtgt gaaagtggtc ctgagccttc   28440
catgtgtggg gcaaagcagg gccttctaag cttctcatga gctcagcaac agtggttttt   28500
actgcagccc acaacctaa gagcatggaa ccagagcctg ttgttcagag acaaggatt    28560 aggctctgag aaaggaaggt catttggtgg atttagttca tccttttgct cttcctgtgt   28620
ttggtttctg gggctggaga gattaatctg acctggtttc tgctcccaag gagctcgggc   28680
tgaagggctg tctgttagtg ggagtccaat gagggaggca gatgatgaaa gggatggtga   28740
gtggtttcag agagggctgt ggacacatag gggaggggag ggagccccca gctgagaaag   28800
gccaggctag aattcagtct ctggataccc catcaggcct cttcttctcc atccaggctg   28860
cctcagcagc agagtaagga caagtgggta gggttacccc ccttcccaga gagaccagcc   28920
ctctaagcag tggggcctgg agctcagccc cctctggtcc tttaccccct caagagagtt   28980
agagatttct ggaagctagg tttccaggat gctcagacca tagcctaaac ctcatcgtcc   29040
ctatctggcc cacctggagc atccacctag aggatgccac tagaggagcc tggatgcctg   29100
tagagtctgg ggggctagag tcttcccttt tcaggcccaa gaaagggaat caggcagact   29160
gctgaacagt aagtatgact ttgtaggcag ccttagaca tagctattca ccaagctacc    29220
gtaagctttt cacagtttgc ttttaacagg ctcttgtagg ctgcacatgc ttccctagaa   29280
acttgtcttc ccttctgcga tgtcacaccc ctaagctggt cctgaaaaat tggacatctc   29340
gtcactctgt attcactgtt cctcccaaca agagagttgt accctgtttt tagctaccct   29400
ggggagaggc tggctcagga gtctagaaca gggctagatt gggggcaac aagggggctac    29460 catttccctc cctttaggct catggagagt ctacatccag ccttatcttc tcccatggga   29520
aaccaaagga ggctcaacat ggtgagaaga gagcatgaca tccagagcca ggcagcctac   29580
agcacctggg accaccaggg aatgggcaca cagcaagggt tggcctccct tcttgggcag   29640
tggaaaaagt cctagaagga gtccatgctt ctcccaccaa acatgagtac ctgctgccct   29700
tgcccttgtg ctgaatgcca aggaccaaag aagatgcctc cccacccagt gtgggaaatt   29760
cacaggcaag agatgatatg tagatagtat gatattgggg aacacttctt gaagagctga   29820
ggtctgagat aggccttaaa ggttgggtaa aaaatgaaaa gagagaagcc ctgctgaggg   29880
cagctagtgg cgagccatga gataaagcag gcatggcaca agctctcctt cctttctgtg   29940
ccaggctaga ttagtctctc ttatgaccta caggcccaga acatggtgac cagtggaagc   30000
cagcccccag gcaagtcttc caagtgtgct gttagggttt ttttttttt acttttgaga   30060 cagagattcc ctctgttgcc caggttgcag tgtagtggcg cgatcatggc tcactgcagc   30120
ttcaaactcc tggcttaagg agtcttccca tctcagcctc ctgagtagct gggactacag   30180
```

```
gcacatgcca ccttgcccag ctaatttttt aaattttttt gtagagatgg agtctcgcta   30240
tgttgcccag gctggtcttg aatttctgag ctcaagcagt ccaccacctc agcttcccaa   30300
agtgctggga ttacgggtgt gagccactgt gcctggctgc tgaagttttt gaagacaggg   30360
aggctgatgg gctctgcgct ttggcctggg acttcctgga ttgccgttat gttggaaggg   30420
agccagccct cctcctgggc aagtgtcccc tctccggtcc ctctagtgat ggtctgggac   30480
tttggtgaat tctaaagcc taatacagag aacggactgt agagtcagac ctgtgtttga    30540
atcctggctc tgccactgtc ctgctgggtg accttgggca agttatctcc cccttgagcc   30600
tcagtgttct tatctctaaa atggggcaaa gtcaccctgc cttacacttg agacagtggc   30660
tcagccccag tcttgagatg cagaggcact gggtaggtgt tccctcccct tatccacagt   30720
gtctgggctg ggtgctggca tgggggcgca cacaaggagg ggacagtaag agcagcttca   30780
caagaagctg aagcctatct cctttggtgc tcctgtccag ataacatgga gcccatgggc   30840
ccctcgatgc caggacagtc catcagagtc tgggagatga ggctcctctt gtcccaggaa   30900
tctgctccta cctgggctga acattcctgt agctatttct caggtttgt gggcccatg     30960 cccatggccc tgggtgtgcc tagcttagtg ccacagtaaa cactcactcc atccaccatg   31020
gcccagaggg gagatgaagc ccagtaggac ctgacctgtg gccatctgcc ccccaggagt   31080
ggcctgcagt gccatcctca tgtacatatt ctgcactgat tgctggctca tcgctgtgct   31140
ctacttcact tggctggtgt ttgactgaa cacacccaag aaaggtaagt gcaaggcctc    31200
ccttgcccca cctctcattc tagggatgct cttccccctg cacaagctga agggcctcat   31260
cctgagtgct gtttctttta acacccactt tgtgaaaagc actggactag tccttttggg   31320
gggaggttaa aagcccctca aagggcactg ttctggtcct gacaagagtt cacactcagt   31380
cgagggtttg cataacatga aggaatgaat gtggaaaggg gcctgatggg aaggggggcat  31440 ggtgcatggg gtgatggtca cctgcttggg tttcacactg gccctgtctt gtctgccttg   31500
cccaaatgta ccccccaccc caccaactct gtattttatt ccctggaagg tggcaggagg   31560
tcacagtggg tccgaaactg ggctgtgtgg cgctactttc gagactactt tcccatccag   31620
gtaaagtgct gtgagtgttg tttggggagg gtgggaatgg atgggaaatc tgaactcagg   31680
ccttaaccca cccacaggga agcaagttta gaccaagttg gtctcttcat ttccttctca   31740
ctgtgtcact ggctgtgctg ggaccccac tgctcttctg agtatccatc ttctttgggc    31800
cagccctgag gtcctgacag ggaaatggtg gctcagtttg gctttcagtc tcagctctgt   31860
ctggcccctg cctggtctgc aagctgggct ggtgaggcac agccatctgg ccctgatgca   31920
tgtgggcaat cctggtgaat tgaggataac tctggcagga tcctgaaggt tttccccaca   31980
ggggaaagac ctgtctggcc agctcactcc acaccccagc tccagcacac cctagctgct   32040
gagtaccctg cagaaggtag gggtgctgaa gagtggaggc agcacgtgaa tgtgaaagag   32100
ttctgtgcag ggtgcagggt ggtgtatatt tgctgttgtg agtcagtgac tgagatcctg   32160
gtgtgttgcc tgggggcagt ggctgggtaa ccctgcatcc ttcactgcat tcggtatttt   32220
gggggtggca gggccagctc cttctgctca tccttagcct aagcccagtc ttcccgggac   32280
cttcctgctc ctcagggtca gcgttccttc tccttttcct gacccatcct ctctaactgc   32340
agaaaatttg aagctgtttt tgttgggaga aagttgcatc ataggaccca accctctaat   32400
tttggaggta aagaaactga gcctcagaga tgggcaggac ttgtccaggc tgcatagtct   32460
agtatgatgg caacattgca accaccatcc aggcttattg aattcagggc ccaggttctt   32520
```

```
ttccactgat ttcctactgc ctgtttctct gggagagatt caatccctgg atttcccccat    32580 tggattgatt ccagcttcct gggtctccct ctcccccgtt gctgctggag atctcagttt    32640
aagttcctgc cctgtcactc catttattaa cctgccacca ttgctccctg tccagtgcag    32700
ggctgtgctg ggcatgggga cacaagtcag ccctgcccct ggggtgtcta ttgcatcctg    32760
atagactttg tcactttctg ccatggggcc atgggcagac tttctcaagc ctgctgagcc    32820
tcatctgcaa aatggagctg tctgtatgat gaaaagtaat cagttctgat tgggtgggag    32880
tgatgataga ctgttctttc tgctttctct ctcacctcag gggccaggct ccagtgttct    32940
ctgttgccac tgtggcctgg tcctctggaa gtctccagga ggccagtagc cccatccact    33000
tagaacagga tgacctgatg attgttggtc agacctggga caggcaggtg tcctttgcta    33060
tctgatctcc acccttccaa aagaaccaaa caaaccctg tgtccttctc acatctctgt    33120
tccaagaagt cagctgggag ttggagcctt agggcacata caacctggcc ctgtgagggc    33180
tccctggggc actaggacaa aagccaaact gggcccgagg caggctgggg tgttgagcct    33240
caacccgggg cttaggctga tcaacccggg gcttaggctg agcctgcctc tctccctctg    33300
ggcctcaatc tcccctttcac ttggccttgg tgatctgaca tcaggtctga cactctatgg    33360
gggtgtgtgt gaccctcctg tcccacccc ttttcctggc ctcttgccag taatcatgta    33420
atgaagatct gccgctgtac ccacccgccc acctactccc ttcctggtgg gactctggtc    33480
tttgctgcca gaacagctca tctggcccag agtgtatccc ttctgttggc acaggtgggg    33540
ttcttgtgtt agcaacagcc accgagacca ccagccacct ggaagaggag cagacagtgc    33600
cccacatcac ctctccccaa agtgtaggca gaatccttgg agaggagact aggaaacact    33660
ctctctaagc ttagaatcac ctgtccatct gcctcatttc actgataggc ttactgaggc    33720
acagagagga gggactatcc caaggtcaca aagcttaagt agtagcagga ctagtgtagg    33780
aaccagggct gtctgctttg gggcccatgg tcttactcct gtgttacttt caccatcacc    33840
atgccgtgct gtgtaaactt aagcaagcct ttgctcttct gtgggtctga atttttcct    33900 ctatgcactg ctgtggtggg acaagcctat ctgagcacct tgcctctcct gggagggagg    33960
gtataaagag tgacttgata ggaatgtgtc ccagactgac attagcgagc aggccgggcc    34020
tgggcatcgt gttgggctgg gactttgcca cgggaaacag gcagcaagag gacacaagag    34080
caggcatgtc aacagaacct tcattggcgg tatccttccc ctccttccag aacggacatt    34140
ctctccagcc ctgggggagg ggagtgtgac atgaaaacag atcagagctg gtcagatgcc    34200
tacattcttc tgggtcctac agcaagggca ttgacttgca ctgtgtccca aggcacctca    34260
ttcaaccaaa tgtcccatca gagccttggg gagggaggaa atgatttaaa gagccacctg    34320
gggcccactg ggtgacacat cttcatccag cagcccaggg aaaagtgcag cgactggcct    34380
gctccagatg tgcaggataa tttgctgtga cctccacagg ggaattgcag ctcccttttc    34440
taggcctcag cttcccccg tcatccaagg aatggcttag acctttcagg gctctgccag    34500
cccatgcagt gctgtgggtt cctggttatc ggcccagtgg gaaggtcggg ggagccatag    34560 gaagggaca aaaagatgct gcacggcgtg atggtcacct gccagggtaa ctatcccagg    34620
cctggccatc agctcaggag caagtttcca agtttcccac ctggtattgg ctgccccagc    34680
tcttccctca atgcctgcct gccttttca tcaaaactag cacaaggaac tttttaattc    34740
cagcttcact gagagctaac ttggtgggca gacctgcttg ttaggcaaaa cattggaaca    34800
gcaatcttaa cagagctcat gtaaacgaga ttttgagatc tgctcgctgc cccgagcccc    34860
actagctatg gattagactg ctgctgtttc ccatttattt ggggagtagc tgagagttgg    34920
```

```
tttggttttt gagcaacttt aatctgtttg ccaagggcaa agcgggagaa agagcatcag    34980
tgccccaagc agtggggatg agagtgaggg agtcttgctc acatttgcac agactggcag    35040
cgtcagagct gggagtggtg ccagccagcc ttttccatcc cctctgtcac ctgaagattt    35100
gcatttcaat tttccaaggc cagccaccag caccctctcc cccagagctg cacacaagtc    35160
cttcagctct gccaggaggc tcccaaatct ggagtcacag aaaacctggg ctcttgacat    35220
tctgctggtg gccagtgact ctgcttccag ctggcaccag tgcagggaag ggcactttg     35280 cagcactcag gtgggagtgt cattgatgtc acctcttttg aggcagggca gccaaaaaga    35340
ccaacgtgtt cattccttgt tatccaggaa ttgtatttct agaagtttgt ttcacaaaag    35400
caatcagata tgtggacaaa gataaggtat ttattgaagc attacttcta agagggaaat    35460
tttggaagct tttaaaatgt ccatcaatca gggtttgagt cagtgctgtt acatgcatga    35520
gagctgtgct gtagaataca aatgcagcca cgagaagata tggaactgag ggattttgat    35580
aaggacagat agctgtatgt ttggtagaaa atgatataaa aatgatatca acccatataa    35640
cctcaatttt gtgggttttg aaaaagagca tgtatatttt tgagtagaaa aaggactcaa    35700
tgcgtcagat ggttttatct ggatggaaat attatggatt ttttaaattt tcttttttgct   35760 ttcctatatt tttaaaattc tctaggagtt tctcttcttt tccctctccc ctcccctccc    35820
ctcccctccc cctcctccgt tcctctcccc tctcctccgt tcctctgccc tctcctccgt    35880
tcctctcccc tctcctctcc tctcccttct ctccttctct cctttccttc tttccttct    35940 tctcactctg tcactcaggc ttgagtgcag tggtgcaatc tcggtttact gcagcctctg    36000
cctcctgggc tcaagccatc tttccacctc agcctcctga gtagctggga ccacaggtgc    36060
gtgccaccat gcccagttaa tttctgtatt tttgtagaga taagcgtttc accatgttgc    36120
ccaggctggt ctcaaactcc tgagctgaag caatcctccc accttggcct cccaaagtgt    36180
tgggataaca ggcatgagcc accatgcctg gccctattat ttttctaatc agaataaaaa    36240
tgatgttttt atgagcagaa taccttact cattgtctct ctcagcctct tccaccccca    36300
tcacattcct tgtaacacag ggtaggtgtc acaggctttg cctctcatga ctcagggttt    36360
agggacactg catcacccac cccttcaagc accagcccca gggcaggagg tgggccctga    36420
ggaagccaat catcgtttag agcatcccag tgtccttagt accacaggtc aggtcctcag    36480
ctgctgcagc cttacaacta acctctaccc caggctggct ggcacagggc tgtcgcttgt    36540
cctgtcttgt cctcctgcc ttagaacctg aactgagccc agctgactgt gggaaagttt     36600
ccatttgggc cagctgcagt gtccctttc caggccaggg gagtaggagg tgggctgcct    36660
gtctcattct gtgagctgtg gaggagccca cagagcacag ggccaagtaa accctacctc    36720
caaggagctc acagtttgga gagactgaca gtgggggcag agcttgcagc caaggccccg    36780
gttgccaaac tcaggaactt ggactttact cacatgaagc cagacacact ctccagtcta    36840
agagtgacaa gggttggatt tgagttttag aataatcact ctggctgttg cgaaaaggat    36900
gggcccagag ggagggaagg caggaggctg gcagagtgca aagaagagct gctgtgtgca    36960
tggctgaaga ctgagaggaa caagggcaaa cattgcccac cccttcccag agacccacag    37020
tgcaaatggt gactgcccaa caccagcact gtggccctgg ggatgagagt ctgaggtaag    37080
gtgtggagat tcattgcagc cctcaggccc atggaggtcc aggggaaatg acacatccaa    37140
tccctcccta ccctccgggt atgccccggt atccctctcc cagccagttt cctctgaccc    37200
aaggtcatcc ttgcagctgg tgaagacaca caacctgctg accaccagga actatatctt    37260
```

```
tggataccac ccccatggta tcatgggcct gggtgccttc tgcaacttca gcacagaggc    37320
cacagaagtg agcaagaagt tcccaggcat acggccttac ctggctacac tggcaggcaa    37380
cttccgaatg cctgtgttga gggagtacct gatgtctgga ggtaagaatc cacccctgt    37440 gctcctgctg ggcactgttg tcaaggcctg agcctctcca tcgggcaggg tgacacaggg    37500
agccaacaca ccattccttg gtgctgggcc tgcattggga gatgcaacct gcttcagaca    37560
tggtgggtca gggctgagga ggagagctgt ccatatggtc ttgagaattc aactcggata    37620
acatcttccc taggaggcct tctttgaccc ccttttctgg gaccccag cccttgtgtt     37680 gccttttgta caacctgatt gttgtccatg gcactgtaat tgtccacctg cctgagacct    37740
cccaccagac tgatgcattg ggatccccaa cacctcgcac cgacttggca gaattagggc    37800
cctgggaatg tttgccaaat gcatgagttc ccaaaacaac cttgtatcat tagctgcatt    37860
ttacagatga ggaaactgag gctcagaaaa atgaatagct tacacagaac cagacaactc    37920 caaagggget gggctaggtc tggggcccag gtccagggtt ctttatgttt tatacctgac    37980
tgtgtgccgg ggatggggag tggatccatg ggcaaccctg actgttgcgt ccttccctcc    38040
cctcaggtat ctgccctgtc agccgggaca ccatagacta tttgctttca aagaatggga    38100
gtggcaatgc tatcatcatc gtggtcgggg gtgcggctga gtctctgagc tccatgcctg    38160
gcaagaatgc agtcaccctg cggaaccgca agggctttgt gaaactggcc ctgcgtcatg    38220
ggtgagtgcc tccctacaca cacacacacc cctccagtgc ccctcagccc agggcagcag    38280
actccttggc ccctgaagac aggacccaga ccccaggaag gcatggaagg gagtcagtca    38340
ttctgttagg gaggggatgt tggagcccag actgcacagt gtgggccaag tttgcccatg    38400
tgtgtctggg tgggcacaga tgcaacctgt ggcctgtggg cccttgcagg tgggccgaga    38460
gtccaggctt atatgcagga ctggaccacc tggggccaga atatatcatt ttgctgggag    38520
accaggaggt caggaaggag ggtggtgtgg aatgtggctg ggggacagca gctgttttct    38580
ctgtcccctg gggaccttac ctcaggcttt ggaagaagag gctgccctgc aggctcagcc    38640
ctgggccagc ccctggggac acattcatat tggacccagt ccctgccttc agggagcacc    38700
aagggtgggg gagggtagag ggatggacag tgacaacaca gtgtgctgag actgtgaaac    38760
aatggtgagt ccagggctga gagaggcctg gtttggtgga gggaccaaga gaacttcctg    38820
gcagaggcag gccctgcagg aagaggtgga aaacaggcat tccagagcag ggcgctcagc    38880
cttccctttg cctggggac ccagagctct gatatgctcc ccagtccta gcagtggggc     38940 agaaggccca tcagaacctg gtagagaggg atcatgtgaa cttgggacac ccaggtaatt    39000
ctggtacacc cagctggggg aggggatgc ttggccagtg tccagggcct ctaggctgac     39060
atagaaactg aagccagtaa gtagggtatg acagaccctg gcctctccct tccagagctg    39120
acctggttcc catctactcc tttggagaga atgaagtgta caagcaggtg atcttcgagg    39180
agggctcctg gggccgatgg gtccagaaga agttccagaa atacattggt ttcgccccat    39240
gcatcttcca tggtcgaggc ctcttctcct ccgacacctg ggggctggtg ccctactcca    39300
agcccatcac cactgttggt aagccccctag cctgcagacc aagggctgtc ctgaacacag    39360
ggtgccatac agctaatcag cagtagagac gggattccaa tgcaggccac ctggctctga    39420
tggccatgcc cttagccatg aggactttga agtgttgggt gctgatattg gtcaggaggg    39480
gtagtagtag gagtcgggga attgagccta tgggatgaac caagctctgt gataagtgag    39540
gaaagaaaat ctgcagtctc tgggtttgca gcacccacta gtctatcagg gaagactatt    39600
gcagcaaaga ctagtggggg aatgtgatga ggatgcgcag gtgctctagg gagtcatagc    39660
```

```
ggacccoagg gaggaggtaa ctcttgcact gctaactgat aggaattatc tagcaaaata    39720
gaggaggaag agaatttta tcagaaacaa tagcctacgt gaagttcaga agcaagattg     39780
tgtagttttt ttgaagaaca gaaagaaaaa cattaatatg actgcagcat agacctgtca   39840
gaagagtgga aaacactggt tgcacttggc cctcgtctgt gttgttttgg gtgtatttgg   39900
gaccatttag aggattctaa agaattacct attgtaggtg tgtgtgtgca tgttaatgga   39960
tcccccagga gcacatgggc ccttggcagt ggacttgagg ggccaaagct cacacagatc   40020
ctttgcgttc ctaggccagg tgtcctgcct tgtacttta ggtagagaca aagcaacagg    40080
gaggcagcag gaacatttcc atgcacaggt gtggctgggg aggggctggg tcctgtgggc   40140
aatgtgaagg aatttgctct tcaccttgag aatggagagc caccagagag tgtttgggag   40200
gggaagttca gatttgcatt taaaaatgat ccttggagct gctggatgga agatgggtta   40260 gaaaatgga agccacgaga ccagcccaga gactgttttg gtagccagtg gcttggacca    40320
agggagtagc agtggagatg aagagatgt gcatgatttg ggaaaattt cagaaatagc     40380 attggcagga cataggaatg gattgggtat ggagatgcag caggataaga aaataaagca   40440
acgcacagat cataaatgct ggtctactcc ctcctctcct gcccttaacc acactttta    40500 tttttttttt ttttattttt gagacagggt ctcattctgt catccaggct ggagtgcagt   40560
ggcgcaatct cggctcactg taacctctgc ctccagtct caagcgatcc tcccacctca    40620
gcctcctgag tagctgggac tacaggcgtg caccaccaca cccagctaat ttttgtatt    40680 ttttttggt agagacgatt ttcaccatgt tacccaggct ggtcttgaac tcatgagctc    40740
aagcaatctg cgggtctttg cctctcacag tgctggaatt acaggcgtga gccaccactc   40800
ctggcctaca ctttttaaag catgtcacat tccttgcaga atccttagaa aacccctatg   40860
aggaagaatc cccatgtgac agatgaggaa actgagggtc agagaggcag gaatggcttg   40920
cccagagcag agcaaaagca aagatgttta cttgatcccc tgactctcat agaccctcct   40980
agcagaatgc agtgggttca accagtcttg atcccatctg cagcttagca cctggtggcc   41040
tcgggtgggt cccttcacat gccctgggc ctcagtcttt tcatctgtaa tagggggacaa   41100 ccagagatgc agcacataaa gcatttggca cagttccttc cacatggcgg gcccacagcc   41160
cagcgtcacc accttcagca tcatggtgga tgcccagggg aagggtgttg actaaccaga   41220
agcctctgcc ctgtccctgc agtgggagag cccatcacca tccccaagct ggagcaccca   41280
acccagcaag acatcgacct gtaccacacc atgtacatgg aggccctggt gaagctcttc   41340
gacaagcaca gaccaagtt cggcctcccg gagactgagg tcctggaggt gaactgagcc    41400
agccttcggg gccaattccc tggaggaacc agctgcaaat cactttttg ctctgtaaat    41460 ttggaagtgt catgggtgtc tgtgggttat ttaaaagaaa ttataacaat tttgctaaac   41520
cattacaatg ttaggtcttt tttaagaagg aaaaagtcag tatttcaagt tctttcactt   41580
ccagcttgcc ctgttctagg tggtggctaa atctgggcct aatctgggtg gctcagctaa   41640
cctctcttct tcccttcctg aagtgacaaa ggaaactcag tcttcttggg gaagaaggat   41700
tgccattagt gacttggacc agttagatga ttcactttt gccccctaggg atgagaggcg   41760 aaagccactt ctcatacaag cccctttatt gccactaccc cacgctcgtc tagtcctgaa   41820
actgcaggac cagtttctct gccaagggga ggagttggag agcacagttg cccgttgtg    41880 tgagggcagt agtaggcatc tggaatgctc cagtttgatc tcccttctgc cacccctacc   41940 tcaccctag tcactcatat cggagcctgg actggcctcc aggatgagga tggggtggc    42000
```

-continued

```
aatgacaccc tgcaggggaa aggactgccc cccatgcacc attgcaggga ggatgccgcc    42060
accatgagct aggtggagta actggttttt cttgggtggc tgatgacatg gatgcagcac    42120
agactcagcc ttggcctgga gcacatgctt actggtggcc tcagtttacc ttccccagat    42180
cctagattct ggatgtgagg aagagatccc tcttcagaag gggcctggcc ttctgagcag    42240
cagattagtt ccaaagcagg tggcccccga acccaagcct cacttttctg tgccttcctg    42300 aggggggttgg gccggggagg aaacccaacc ctctcctgtg tgttctgtta tctcttgatg    42360
agatcattgc accatgtcag acttttgtat atgccttgaa aataaatgaa agtgagaatc    42420
ctctatgagt tattgctggg gctgcatctg catctgctgc tgacacctgg ggaagactgg    42480
gtccccagct ggctgccctc tgagccctct agcccttgc acctttggcc cacatgaccc    42540
tgccatggtg tgtaagttac ctgtcactgt gtaacaaact acttcagagc tcagtggctt    42600
ccaacagcat ctgttgtctc ccagttccaa gtcacgattt gaggcttggc ttggtcctcc    42660
actcagggtt tctcacaggg ctgcagttgt cttggagccg ggctgaggaa ggatccactc    42720
ccaaggccgt tcctgcagtt gttcgcagga ttgacttcct cactggctgt tgacagaggc    42780
cactttcagt tccttgccac atgggccttt ccatggggta gct                       42823
```

<210> SEQ ID NO 19

<400> SEQUENCE: 19

000

<210> SEQ ID NO 20
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 20
ctcctgccac ctttcttggg                                                 20

<210> SEQ ID NO 21
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 21
tggatgggaa agtagtctcg                                                 20

<210> SEQ ID NO 22
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 22
ccagctggat gggaaagtag                                                 20

<210> SEQ ID NO 23
<211> LENGTH: 20
<212> TYPE: DNA
<213> ORGANISM: Artificial Sequence
<220> FEATURE:
<223> OTHER INFORMATION: Antisense Oligonucleotide

```
<400> SEQUENCE: 23
cttcaccagc tggatgggaa                                              20

<210> SEQ ID NO 24
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 24
tgtgtcttca ccagctggat                                              20

<210> SEQ ID NO 25
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 25
ggttgtgtgt cttcaccagc                                              20

<210> SEQ ID NO 26
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 26
cagcaggttg tgtgtcttca                                              20

<210> SEQ ID NO 27
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 27
gtggtcagca ggttgtgtgt                                              20

<210> SEQ ID NO 28
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 28
tcctggtggt cagcaggttg                                              20

<210> SEQ ID NO 29
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 29
atagttcctg gtggtcagca                                              20

<210> SEQ ID NO 30
<211> LENGTH: 20
```

```
<212> TYPE: DNA
<213> ORGANISM: Artificial Sequence
<220> FEATURE:
<223> OTHER INFORMATION: Antisense Oligonucleotide

<400> SEQUENCE: 30
aagatatagt tcctggtggt                                                     20

<210> SEQ ID NO 31
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 31
atccaaagat atagttcctg                                                     20

<210> SEQ ID NO 32
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 32
gtggtatcca aagatatagt                                                     20

<210> SEQ ID NO 33
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 33
aaggcaccca ggcccatgat                                                     20

<210> SEQ ID NO 34
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 34
cctccagaca tcaggtactc                                                     20

<210> SEQ ID NO 35
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 35
gcattgccac tcccattctt                                                     20

<210> SEQ ID NO 36
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 36
```

| tgatagcatt gccactccca | 20 |

<210> SEQ ID NO 37
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 37

| gatgatgata gcattgccac | 20 |

<210> SEQ ID NO 38
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 38

| accacgatga tgatagcatt | 20 |

<210> SEQ ID NO 39
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 39

| ttgccaggca tggagctcag | 20 |

<210> SEQ ID NO 40
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 40

| tggacccatc ggccccagga | 20 |

<210> SEQ ID NO 41
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 41

| tcttctggac ccatcggccc | 20 |

<210> SEQ ID NO 42
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 42

| gaacttcttc tggacccatc | 20 |

<210> SEQ ID NO 43
<211> LENGTH: 20
<212> TYPE: DNA
<213> ORGANISM: Artificial Sequence

```
<220> FEATURE:
<223> OTHER INFORMATION: Antisense Oligonucleotide

<400> SEQUENCE: 43
ttctggaact tcttctggac                                            20

<210> SEQ ID NO 44
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 44
ggcaccagcc cccaggtgtc                                            20

<210> SEQ ID NO 45
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 45
agtagggcac cagcccccag                                            20

<210> SEQ ID NO 46
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 46
cttggagtag ggcaccagcc                                            20

<210> SEQ ID NO 47
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 47
cagggcctcc atgtacatgg                                            20

<210> SEQ ID NO 48
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 48
ttcaccaggg cctccatgta                                            20

<210> SEQ ID NO 49
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 49
agagcttcac cagggcctcc                                            20
```

<210> SEQ ID NO 50
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 50
aacccacaga cacccatgac                                               20

<210> SEQ ID NO 51
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 51
taaataaccc acagacaccc                                               20

<210> SEQ ID NO 52
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 52
tcttttaaat aacccacaga                                               20

<210> SEQ ID NO 53
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 53
acaaaagagc atcctcctca                                               20

<210> SEQ ID NO 54
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 54
actataaatg cttcagtcca                                               20

<210> SEQ ID NO 55
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 55
ttgcacttac ctttcttggg                                               20

<210> SEQ ID NO 56
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 56
agcactttac ctggatggga                                               20

<210> SEQ ID NO 57
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 57
tcagtgaaat gaggcagatg                                               20

<210> SEQ ID NO 58
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 58
ctcaaaagag gtgacatcaa                                               20

<210> SEQ ID NO 59
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 59
ggattcttac ctccagacat                                               20

<210> SEQ ID NO 60
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 60
caggtcagct ctggaaggga                                               20

<210> SEQ ID NO 61
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 61
ttcccctgga cctccatggg                                               20

<210> SEQ ID NO 62
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 62
gtggcgcgag agaaacagcc                                               20

<210> SEQ ID NO 63

-continued

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 63
gccagggctt cgcgcagagc                                                 20

<210> SEQ ID NO 64
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 64
agggtcttca tggctgaagc                                                 20

<210> SEQ ID NO 65
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 65
aggaccccgg agtaggcggc                                                 20

<210> SEQ ID NO 66
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 66
acccactgga gcactgagat                                                 20

<210> SEQ ID NO 67
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 67
gggcagatac ctccagacat                                                 20

<210> SEQ ID NO 68
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 68
cggttccgca gggtgactgc                                                 20

<210> SEQ ID NO 69
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 69
```
aaggctggct cagttcacct                                          20

<210> SEQ ID NO 70
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 70
gggagttggc cccgaaggct                                          20

<210> SEQ ID NO 71
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 71
gctggttcct ccagggagtt                                          20

<210> SEQ ID NO 72
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 72
acttccaaat ttacagagca                                          20

<210> SEQ ID NO 73
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 73
ccacctagaa cagggcaagc                                          20

<210> SEQ ID NO 74
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 74
gggaagaaga gaggttagct                                          20

<210> SEQ ID NO 75
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 75
tcacttcagg aagggaagaa                                          20

<210> SEQ ID NO 76
<211> LENGTH: 20
<212> TYPE: DNA

```
<213> ORGANISM: Artificial Sequence
<220> FEATURE:
<223> OTHER INFORMATION: Antisense Oligonucleotide

<400> SEQUENCE: 76
ccttcttccc caagaagact                                              20

<210> SEQ ID NO 77
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 77
ctaactggtc caagtcacta                                              20

<210> SEQ ID NO 78
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 78
ggcaaaaagt gaatcatcta                                              20

<210> SEQ ID NO 79
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 79
ttcgcctctc atccctaggg                                              20

<210> SEQ ID NO 80
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 80
ggcttgtatg agaagtggct                                              20

<210> SEQ ID NO 81
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 81
tttcaggact agacgagcgt                                              20

<210> SEQ ID NO 82
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 82
ctccgatatg agtgactagg                                              20
```

<210> SEQ ID NO 83
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 83
ctcatcctgg aggccagtcc                                             20

<210> SEQ ID NO 84
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 84
ccatcctcat cctggaggcc                                             20

<210> SEQ ID NO 85
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 85
gtgtcattgc caccccatc                                              20

<210> SEQ ID NO 86
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 86
acctagctca tggtggcggc                                             20

<210> SEQ ID NO 87
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 87
accagttact ccacctagct                                             20

<210> SEQ ID NO 88
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 88
gtcatcagcc acccaagaaa                                             20

<210> SEQ ID NO 89
<211> LENGTH: 20
<212> TYPE: DNA
<213> ORGANISM: Artificial Sequence
<220> FEATURE:

<223> OTHER INFORMATION: Antisense Oligonucleotide

<400> SEQUENCE: 89
gtgctccagg ccaaggctga                                                    20

<210> SEQ ID NO 90
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 90
accagtaagc atgtgctcca                                                    20

<210> SEQ ID NO 91
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 91
gaggccacca gtaagcatgt                                                    20

<210> SEQ ID NO 92
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 92
gtaaactgag gccaccagta                                                    20

<210> SEQ ID NO 93
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 93
cttcctcaca tccagaatct                                                    20

<210> SEQ ID NO 94
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 94
tgctcagaag gccaggcccc                                                    20

<210> SEQ ID NO 95
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 95
acctgctttg gaactaatct                                                    20

```
<210> SEQ ID NO 96
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 96
gaaaagtgag gcttgggttc                                              20

<210> SEQ ID NO 97
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 97
aaaagtctga catggtgcaa                                              20

<210> SEQ ID NO 98
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 98
ccaccctaga tgagcagaaa                                              20

<210> SEQ ID NO 99
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 99
ggtaggtagc cgctgccacc                                              20

<210> SEQ ID NO 100
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 100
agagctgagg taggtagccg                                              20

<210> SEQ ID NO 101
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 101
gcgctgagct ccgggagctg                                              20

<210> SEQ ID NO 102
<211> LENGTH: 20
<212> TYPE: DNA
<213> ORGANISM: Artificial Sequence
<220> FEATURE:
<223> OTHER INFORMATION: Antisense Oligonucleotide
```

```
<400> SEQUENCE: 102
aagccaatgc acgtcacggc                                              20

<210> SEQ ID NO 103
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 103
gagggtcttc atgctgaagc                                              20

<210> SEQ ID NO 104
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 104
gttttcgctg cgggcagctt                                              20

<210> SEQ ID NO 105
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 105
gtttttccac cttagatctg                                              20

<210> SEQ ID NO 106
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 106
tgagatgacc tgcagctgtt                                              20

<210> SEQ ID NO 107
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 107
caggccactc ctagcaccag                                              20

<210> SEQ ID NO 108
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 108
gatgacactg caggccactc                                              20

<210> SEQ ID NO 109
<211> LENGTH: 20
```

```
<212> TYPE: DNA
<213> ORGANISM: Artificial Sequence
<220> FEATURE:
<223> OTHER INFORMATION: Antisense Oligonucleotide

<400> SEQUENCE: 109
ccacacggcc cagtttcgca                                              20

<210> SEQ ID NO 110
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 110
gggcagatgc ctccagacat                                              20

<210> SEQ ID NO 111
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 111
tcggttgaca gggcagatgc                                              20

<210> SEQ ID NO 112
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 112
gggactcagc tgcacctccc                                              20

<210> SEQ ID NO 113
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 113
cagatcagct ccatggcgca                                              20

<210> SEQ ID NO 114
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 114
cacctgcttg tatacctcat                                              20

<210> SEQ ID NO 115
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 115
```
gaagaggcct cggccatgga                                              20

```
<210> SEQ ID NO 116
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 116
```
ggctccccca cgacggtggt                                              20

```
<210> SEQ ID NO 117
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 117
```
ggtcgggtgc tccagcttgg                                              20

```
<210> SEQ ID NO 118
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 118
```
agtctctgga aggccaaatt                                              20

```
<210> SEQ ID NO 119
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 119
```
ggctgggtca gttcacctcc                                              20

```
<210> SEQ ID NO 120
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 120
```
ctcccaggag ctggcacgcg                                              20

```
<210> SEQ ID NO 121
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 121
```
atgcactcaa gaactcggta                                              20

```
<210> SEQ ID NO 122
<211> LENGTH: 20
<212> TYPE: DNA
<213> ORGANISM: Artificial Sequence
```

```
<220> FEATURE:
<223> OTHER INFORMATION: Antisense Oligonucleotide

<400> SEQUENCE: 122
actgactctt cccttcttaa                                               20

<210> SEQ ID NO 123
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 123
acacactaga agtgagctta                                               20

<210> SEQ ID NO 124
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 124
cctccacctt gagcaggaca                                               20

<210> SEQ ID NO 125
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 125
caccaaggcc cataaatatc                                               20

<210> SEQ ID NO 126
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 126
agaaaccacc aaggcccata                                               20

<210> SEQ ID NO 127
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 127
gccagggcca agtgtctgtc                                               20

<210> SEQ ID NO 128
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 128
tggagtcact aaggactgcc                                               20
```

<210> SEQ ID NO 129
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 129
gggacatggc ctctgcctct                                              20

<210> SEQ ID NO 130
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 130
ggtacgagga acccgacctg                                              20

<210> SEQ ID NO 131
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 131
gccagctgtg ccctcagcct                                              20

<210> SEQ ID NO 132
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 132
ccaagccggg cagtccagat                                              20

<210> SEQ ID NO 133
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 133
gggtaggctc agattggaga                                              20

<210> SEQ ID NO 134
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 134
cggcacctgt gggacagccg                                              20

<210> SEQ ID NO 135
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 135
agagtgaaac cagccaacag                                           20

<210> SEQ ID NO 136
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 136
gctcaggagg atatgcgcca                                           20

<210> SEQ ID NO 137
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 137
aagcccttcc tcacaccaga                                           20

<210> SEQ ID NO 138
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 138
ggcacctctg tgaagagaag                                           20

<210> SEQ ID NO 139
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 139
tcctggaccc agtgtgctgc                                           20

<210> SEQ ID NO 140
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 140
cacacacgtg aggcttggtt                                           20

<210> SEQ ID NO 141
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 141
atacaaaagt gtgacatggc                                           20

<210> SEQ ID NO 142

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 142
tccatttatt agtctaggaa                                              20

<210> SEQ ID NO 143
<211> LENGTH: 20
<212> TYPE: DNA
<213> ORGANISM: H. sapiens
<220> FEATURE:

<400> SEQUENCE: 143
cccaagaaag gtggcaggag                                              20

<210> SEQ ID NO 144
<211> LENGTH: 20
<212> TYPE: DNA
<213> ORGANISM: H. sapiens
<220> FEATURE:

<400> SEQUENCE: 144
cgagactact ttcccatcca                                              20

<210> SEQ ID NO 145
<211> LENGTH: 20
<212> TYPE: DNA
<213> ORGANISM: H. sapiens
<220> FEATURE:

<400> SEQUENCE: 145
ttcccatcca gctggtgaag                                              20

<210> SEQ ID NO 146
<211> LENGTH: 20
<212> TYPE: DNA
<213> ORGANISM: H. sapiens
<220> FEATURE:

<400> SEQUENCE: 146
atccagctgg tgaagacaca                                              20

<210> SEQ ID NO 147
<211> LENGTH: 20
<212> TYPE: DNA
<213> ORGANISM: H. sapiens
<220> FEATURE:

<400> SEQUENCE: 147
gctggtgaag acacacaacc                                              20

<210> SEQ ID NO 148
<211> LENGTH: 20
<212> TYPE: DNA
<213> ORGANISM: H. sapiens
<220> FEATURE:

<400> SEQUENCE: 148
tgaagacaca caacctgctg                                              20

<210> SEQ ID NO 149
<211> LENGTH: 20
```

-continued

```
<212> TYPE: DNA
<213> ORGANISM: H. sapiens
<220> FEATURE:

<400> SEQUENCE: 149
acacacaacc tgctgaccac                                             20

<210> SEQ ID NO 150
<211> LENGTH: 20
<212> TYPE: DNA
<213> ORGANISM: H. sapiens
<220> FEATURE:

<400> SEQUENCE: 150
caacctgctg accaccagga                                             20

<210> SEQ ID NO 151
<211> LENGTH: 20
<212> TYPE: DNA
<213> ORGANISM: H. sapiens
<220> FEATURE:

<400> SEQUENCE: 151
tgctgaccac caggaactat                                             20

<210> SEQ ID NO 152
<211> LENGTH: 20
<212> TYPE: DNA
<213> ORGANISM: H. sapiens
<220> FEATURE:

<400> SEQUENCE: 152
accaccagga actatatctt                                             20

<210> SEQ ID NO 153
<211> LENGTH: 20
<212> TYPE: DNA
<213> ORGANISM: H. sapiens
<220> FEATURE:

<400> SEQUENCE: 153
caggaactat atctttggat                                             20

<210> SEQ ID NO 154
<211> LENGTH: 20
<212> TYPE: DNA
<213> ORGANISM: H. sapiens
<220> FEATURE:

<400> SEQUENCE: 154
actatatctt tggataccac                                             20

<210> SEQ ID NO 155
<211> LENGTH: 20
<212> TYPE: DNA
<213> ORGANISM: H. sapiens
<220> FEATURE:

<400> SEQUENCE: 155
atcatgggcc tgggtgcctt                                             20

<210> SEQ ID NO 156
<211> LENGTH: 20
<212> TYPE: DNA
<213> ORGANISM: H. sapiens
```

```
<220> FEATURE:

<400> SEQUENCE: 156
gagtacctga tgtctggagg                                              20

<210> SEQ ID NO 157
<211> LENGTH: 20
<212> TYPE: DNA
<213> ORGANISM: H. sapiens
<220> FEATURE:

<400> SEQUENCE: 157
aagaatggga gtggcaatgc                                              20

<210> SEQ ID NO 158
<211> LENGTH: 20
<212> TYPE: DNA
<213> ORGANISM: H. sapiens
<220> FEATURE:

<400> SEQUENCE: 158
tgggagtggc aatgctatca                                              20

<210> SEQ ID NO 159
<211> LENGTH: 20
<212> TYPE: DNA
<213> ORGANISM: H. sapiens
<220> FEATURE:

<400> SEQUENCE: 159
gtggcaatgc tatcatcatc                                              20

<210> SEQ ID NO 160
<211> LENGTH: 20
<212> TYPE: DNA
<213> ORGANISM: H. sapiens
<220> FEATURE:

<400> SEQUENCE: 160
aatgctatca tcatcgtggt                                              20

<210> SEQ ID NO 161
<211> LENGTH: 20
<212> TYPE: DNA
<213> ORGANISM: H. sapiens
<220> FEATURE:

<400> SEQUENCE: 161
ctgagctcca tgcctggcaa                                              20

<210> SEQ ID NO 162
<211> LENGTH: 20
<212> TYPE: DNA
<213> ORGANISM: H. sapiens
<220> FEATURE:

<400> SEQUENCE: 162
tcctggggcc gatgggtcca                                              20

<210> SEQ ID NO 163
<211> LENGTH: 20
<212> TYPE: DNA
<213> ORGANISM: H. sapiens
<220> FEATURE:
```

```
<400> SEQUENCE: 163
gggccgatgg gtccagaaga                                          20

<210> SEQ ID NO 164
<211> LENGTH: 20
<212> TYPE: DNA
<213> ORGANISM: H. sapiens
<220> FEATURE:

<400> SEQUENCE: 164
gatgggtcca gaagaagttc                                          20

<210> SEQ ID NO 165
<211> LENGTH: 20
<212> TYPE: DNA
<213> ORGANISM: H. sapiens
<220> FEATURE:

<400> SEQUENCE: 165
gtccagaaga agttccagaa                                          20

<210> SEQ ID NO 166
<211> LENGTH: 20
<212> TYPE: DNA
<213> ORGANISM: H. sapiens
<220> FEATURE:

<400> SEQUENCE: 166
gacacctggg ggctggtgcc                                          20

<210> SEQ ID NO 167
<211> LENGTH: 20
<212> TYPE: DNA
<213> ORGANISM: H. sapiens
<220> FEATURE:

<400> SEQUENCE: 167 ctggggggctg gtgccctact                                         20

<210> SEQ ID NO 168
<211> LENGTH: 20
<212> TYPE: DNA
<213> ORGANISM: H. sapiens
<220> FEATURE:

<400> SEQUENCE: 168
ggctggtgcc ctactccaag                                          20

<210> SEQ ID NO 169
<211> LENGTH: 20
<212> TYPE: DNA
<213> ORGANISM: H. sapiens
<220> FEATURE:

<400> SEQUENCE: 169
ccatgtacat ggaggccctg                                          20

<210> SEQ ID NO 170
<211> LENGTH: 20
<212> TYPE: DNA
<213> ORGANISM: H. sapiens
<220> FEATURE:

<400> SEQUENCE: 170
```

| | |
|---|---|
| tacatggagg ccctggtgaa | 20 |

<210> SEQ ID NO 171
<211> LENGTH: 20
<212> TYPE: DNA
<213> ORGANISM: H. sapiens
<220> FEATURE:

<400> SEQUENCE: 171

| | |
|---|---|
| ggaggccctg gtgaagctct | 20 |

<210> SEQ ID NO 172
<211> LENGTH: 20
<212> TYPE: DNA
<213> ORGANISM: H. sapiens
<220> FEATURE:

<400> SEQUENCE: 172

| | |
|---|---|
| gtcatgggtg tctgtgggtt | 20 |

<210> SEQ ID NO 173
<211> LENGTH: 20
<212> TYPE: DNA
<213> ORGANISM: H. sapiens
<220> FEATURE:

<400> SEQUENCE: 173

| | |
|---|---|
| gggtgtctgt gggttattta | 20 |

<210> SEQ ID NO 174
<211> LENGTH: 20
<212> TYPE: DNA
<213> ORGANISM: H. sapiens
<220> FEATURE:

<400> SEQUENCE: 174

| | |
|---|---|
| tctgtgggtt atttaaaaga | 20 |

<210> SEQ ID NO 175
<211> LENGTH: 20
<212> TYPE: DNA
<213> ORGANISM: H. sapiens
<220> FEATURE:

<400> SEQUENCE: 175

| | |
|---|---|
| tgaggaggat gctcttttgt | 20 |

<210> SEQ ID NO 176
<211> LENGTH: 20
<212> TYPE: DNA
<213> ORGANISM: H. sapiens
<220> FEATURE:

<400> SEQUENCE: 176

| | |
|---|---|
| tggactgaag catttatagt | 20 |

<210> SEQ ID NO 177
<211> LENGTH: 20
<212> TYPE: DNA
<213> ORGANISM: H. sapiens
<220> FEATURE:

<400> SEQUENCE: 177

| | |
|---|---|
| tcccatccag gtaaagtgct | 20 |

```
<210> SEQ ID NO 178
<211> LENGTH: 20
<212> TYPE: DNA
<213> ORGANISM: H. sapiens
<220> FEATURE:

<400> SEQUENCE: 178
catctgcctc atttcactga                                               20

<210> SEQ ID NO 179
<211> LENGTH: 20
<212> TYPE: DNA
<213> ORGANISM: H. sapiens
<220> FEATURE:

<400> SEQUENCE: 179
ttgatgtcac ctcttttgag                                               20

<210> SEQ ID NO 180
<211> LENGTH: 20
<212> TYPE: DNA
<213> ORGANISM: H. sapiens
<220> FEATURE:

<400> SEQUENCE: 180
tcccttccag agctgacctg                                               20

<210> SEQ ID NO 181
<211> LENGTH: 20
<212> TYPE: DNA
<213> ORGANISM: H. sapiens
<220> FEATURE:

<400> SEQUENCE: 181
cccatggagg tccagggggaa                                              20

<210> SEQ ID NO 182
<211> LENGTH: 20
<212> TYPE: DNA
<213> ORGANISM: H. sapiens
<220> FEATURE:

<400> SEQUENCE: 182
ggctgtttct ctcgcgccac                                               20

<210> SEQ ID NO 183
<211> LENGTH: 20
<212> TYPE: DNA
<213> ORGANISM: H. sapiens
<220> FEATURE:

<400> SEQUENCE: 183
gctctgcgcg aagccctggc                                               20

<210> SEQ ID NO 184
<211> LENGTH: 20
<212> TYPE: DNA
<213> ORGANISM: H. sapiens
<220> FEATURE:

<400> SEQUENCE: 184
gcttcagcca tgaagaccct                                               20

<210> SEQ ID NO 185
```

```
<211> LENGTH: 20
<212> TYPE: DNA
<213> ORGANISM: H. sapiens
<220> FEATURE:

<400> SEQUENCE: 185
gccgcctact ccggggtcct                                              20

<210> SEQ ID NO 186
<211> LENGTH: 20
<212> TYPE: DNA
<213> ORGANISM: H. sapiens
<220> FEATURE:

<400> SEQUENCE: 186
atctcagtgc tccagtgggt                                              20

<210> SEQ ID NO 187
<211> LENGTH: 20
<212> TYPE: DNA
<213> ORGANISM: H. sapiens
<220> FEATURE:

<400> SEQUENCE: 187
gcagtcaccc tgcggaaccg                                              20

<210> SEQ ID NO 188
<211> LENGTH: 20
<212> TYPE: DNA
<213> ORGANISM: H. sapiens
<220> FEATURE:

<400> SEQUENCE: 188
aggtgaactg agccagcctt                                              20

<210> SEQ ID NO 189
<211> LENGTH: 20
<212> TYPE: DNA
<213> ORGANISM: H. sapiens
<220> FEATURE:

<400> SEQUENCE: 189
agccttcggg gccaactccc                                              20

<210> SEQ ID NO 190
<211> LENGTH: 20
<212> TYPE: DNA
<213> ORGANISM: H. sapiens
<220> FEATURE:

<400> SEQUENCE: 190
aactccctgg aggaaccagc                                              20

<210> SEQ ID NO 191
<211> LENGTH: 20
<212> TYPE: DNA
<213> ORGANISM: H. sapiens
<220> FEATURE:

<400> SEQUENCE: 191
tgctctgtaa atttggaagt                                              20

<210> SEQ ID NO 192
<211> LENGTH: 20
<212> TYPE: DNA
```

<213> ORGANISM: H. sapiens
<220> FEATURE:

<400> SEQUENCE: 192
gcttgccctg ttctaggtgg                                        20

<210> SEQ ID NO 193
<211> LENGTH: 20
<212> TYPE: DNA
<213> ORGANISM: H. sapiens
<220> FEATURE:

<400> SEQUENCE: 193 ttcttcccctt cctgaagtga                                       20

<210> SEQ ID NO 194
<211> LENGTH: 20
<212> TYPE: DNA
<213> ORGANISM: H. sapiens
<220> FEATURE:

<400> SEQUENCE: 194
agtcttcttg gggaagaagg                                        20

<210> SEQ ID NO 195
<211> LENGTH: 20
<212> TYPE: DNA
<213> ORGANISM: H. sapiens
<220> FEATURE:

<400> SEQUENCE: 195
tagtgacttg gaccagttag                                        20

<210> SEQ ID NO 196
<211> LENGTH: 20
<212> TYPE: DNA
<213> ORGANISM: H. sapiens
<220> FEATURE:

<400> SEQUENCE: 196
tagatgattc acttttttgcc                                       20

<210> SEQ ID NO 197
<211> LENGTH: 20
<212> TYPE: DNA
<213> ORGANISM: H. sapiens
<220> FEATURE:

<400> SEQUENCE: 197
agccacttct catacaagcc                                        20

<210> SEQ ID NO 198
<211> LENGTH: 20
<212> TYPE: DNA
<213> ORGANISM: H. sapiens
<220> FEATURE:

<400> SEQUENCE: 198
acgctcgtct agtcctgaaa                                        20

<210> SEQ ID NO 199
<211> LENGTH: 20
<212> TYPE: DNA
<213> ORGANISM: H. sapiens
<220> FEATURE:

```
<400> SEQUENCE: 199
cctagtcact catatcggag                                               20

<210> SEQ ID NO 200
<211> LENGTH: 20
<212> TYPE: DNA
<213> ORGANISM: H. sapiens
<220> FEATURE:

<400> SEQUENCE: 200
ggactggcct ccaggatgag                                               20

<210> SEQ ID NO 201
<211> LENGTH: 20
<212> TYPE: DNA
<213> ORGANISM: H. sapiens
<220> FEATURE:

<400> SEQUENCE: 201
ggcctccagg atgaggatgg                                               20

<210> SEQ ID NO 202
<211> LENGTH: 20
<212> TYPE: DNA
<213> ORGANISM: H. sapiens
<220> FEATURE:

<400> SEQUENCE: 202 gatggggtg gcaatgacac                                                20

<210> SEQ ID NO 203
<211> LENGTH: 20
<212> TYPE: DNA
<213> ORGANISM: H. sapiens
<220> FEATURE:

<400> SEQUENCE: 203
gccgccacca tgagctaggt                                               20

<210> SEQ ID NO 204
<211> LENGTH: 20
<212> TYPE: DNA
<213> ORGANISM: H. sapiens
<220> FEATURE:

<400> SEQUENCE: 204
agctaggtgg agtaactggt                                               20

<210> SEQ ID NO 205
<211> LENGTH: 20
<212> TYPE: DNA
<213> ORGANISM: H. sapiens
<220> FEATURE:

<400> SEQUENCE: 205
tttcttgggt ggctgatgac                                               20

<210> SEQ ID NO 206
<211> LENGTH: 20
<212> TYPE: DNA
<213> ORGANISM: H. sapiens
<220> FEATURE:

<400> SEQUENCE: 206
```

```
tcagccttgg cctggagcac                                               20

<210> SEQ ID NO 207
<211> LENGTH: 20
<212> TYPE: DNA
<213> ORGANISM: H. sapiens
<220> FEATURE:

<400> SEQUENCE: 207
tggagcacat gcttactggt                                               20

<210> SEQ ID NO 208
<211> LENGTH: 20
<212> TYPE: DNA
<213> ORGANISM: H. sapiens
<220> FEATURE:

<400> SEQUENCE: 208
acatgcttac tggtggcctc                                               20

<210> SEQ ID NO 209
<211> LENGTH: 20
<212> TYPE: DNA
<213> ORGANISM: H. sapiens
<220> FEATURE:

<400> SEQUENCE: 209
tactggtggc ctcagtttac                                               20

<210> SEQ ID NO 210
<211> LENGTH: 20
<212> TYPE: DNA
<213> ORGANISM: H. sapiens
<220> FEATURE:

<400> SEQUENCE: 210
ggggcctggc cttctgagca                                               20

<210> SEQ ID NO 211
<211> LENGTH: 20
<212> TYPE: DNA
<213> ORGANISM: H. sapiens
<220> FEATURE:

<400> SEQUENCE: 211
agattagttc caaagcaggt                                               20

<210> SEQ ID NO 212
<211> LENGTH: 20
<212> TYPE: DNA
<213> ORGANISM: H. sapiens
<220> FEATURE:

<400> SEQUENCE: 212
gaacccaagc ctcactttttc                                              20

<210> SEQ ID NO 213
<211> LENGTH: 20
<212> TYPE: DNA
<213> ORGANISM: H. sapiens
<220> FEATURE:

<400> SEQUENCE: 213
ttgcaccatg tcagactttt                                               20
```

```
<210> SEQ ID NO 214
<211> LENGTH: 20
<212> TYPE: DNA
<213> ORGANISM: M. musculus
<220> FEATURE:

<400> SEQUENCE: 214
cagctcccgg agctcagcgc                                               20

<210> SEQ ID NO 215
<211> LENGTH: 20
<212> TYPE: DNA
<213> ORGANISM: M. musculus
<220> FEATURE:

<400> SEQUENCE: 215
tgcgaaactg ggccgtgtgg                                               20

<210> SEQ ID NO 216
<211> LENGTH: 20
<212> TYPE: DNA
<213> ORGANISM: M. musculus
<220> FEATURE:

<400> SEQUENCE: 216
atgaggtata caagcaggtg                                               20

<210> SEQ ID NO 217
<211> LENGTH: 20
<212> TYPE: DNA
<213> ORGANISM: M. musculus
<220> FEATURE:

<400> SEQUENCE: 217
tccatggccg aggcctcttc                                               20

<210> SEQ ID NO 218
<211> LENGTH: 20
<212> TYPE: DNA
<213> ORGANISM: M. musculus
<220> FEATURE:

<400> SEQUENCE: 218
cgcgtgccag ctcctgggag                                               20

<210> SEQ ID NO 219
<211> LENGTH: 20
<212> TYPE: DNA
<213> ORGANISM: M. musculus
<220> FEATURE:

<400> SEQUENCE: 219
taccgagttc ttgagtgcat                                               20

<210> SEQ ID NO 220
<211> LENGTH: 20
<212> TYPE: DNA
<213> ORGANISM: M. musculus
<220> FEATURE:

<400> SEQUENCE: 220
ttaagaaggg aagagtcagt                                               20
```

```
<210> SEQ ID NO 221
<211> LENGTH: 20
<212> TYPE: DNA
<213> ORGANISM: M. musculus
<220> FEATURE:

<400> SEQUENCE: 221
taagctcact tctagtgtgt                                               20

<210> SEQ ID NO 222
<211> LENGTH: 20
<212> TYPE: DNA
<213> ORGANISM: M. musculus
<220> FEATURE:

<400> SEQUENCE: 222
tgtcctgctc aaggtggagg                                               20

<210> SEQ ID NO 223
<211> LENGTH: 20
<212> TYPE: DNA
<213> ORGANISM: M. musculus
<220> FEATURE:

<400> SEQUENCE: 223
gacagacact tggccctggc                                               20

<210> SEQ ID NO 224
<211> LENGTH: 20
<212> TYPE: DNA
<213> ORGANISM: M. musculus
<220> FEATURE:

<400> SEQUENCE: 224
ggcagtcctt agtgactcca                                               20

<210> SEQ ID NO 225
<211> LENGTH: 20
<212> TYPE: DNA
<213> ORGANISM: M. musculus
<220> FEATURE:

<400> SEQUENCE: 225
caggtcgggt tcctcgtacc                                               20

<210> SEQ ID NO 226
<211> LENGTH: 20
<212> TYPE: DNA
<213> ORGANISM: M. musculus
<220> FEATURE:

<400> SEQUENCE: 226
tctccaatct gagcctaccc                                               20

<210> SEQ ID NO 227
<211> LENGTH: 20
<212> TYPE: DNA
<213> ORGANISM: M. musculus
<220> FEATURE:

<400> SEQUENCE: 227
tggcgcatat cctcctgagc                                               20

<210> SEQ ID NO 228
<211> LENGTH: 20
```

```
<212> TYPE: DNA
<213> ORGANISM: M. musculus
<220> FEATURE:

<400> SEQUENCE: 228
ttcctagact aataaatgga                                              20

<210> SEQ ID NO 229
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 229
ccttccctga aggttcctcc                                              20

<210> SEQ ID NO 230
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 230 ctgctagcctc tggatttga                                              20

<210> SEQ ID NO 231
<211> LENGTH: 20
<212> TYPE: RNA
<213> ORGANISM: Artificial Sequence
<220> FEATURE:
<223> OTHER INFORMATION: Oligomeric compound

<400> SEQUENCE: 231
uuugucucug guccuuacuu                                              20

<210> SEQ ID NO 232
<211> LENGTH: 19
<212> TYPE: RNA
<213> ORGANISM: Artificial Sequence
<220> FEATURE:
<223> OTHER INFORMATION: Oligomeric compound

<400> SEQUENCE: 232
uuaucgcuuc ucguugcuu                                               19

<210> SEQ ID NO 233
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 233
tagtgcggac ctacccacga                                              20

<210> SEQ ID NO 234
<211> LENGTH: 19
<212> TYPE: RNA
<213> ORGANISM: Artificial Sequence
<220> FEATURE:
<223> OTHER INFORMATION: Oligomeric compound

<400> SEQUENCE: 234
gaaacagccu agaccccag                                               19
```

```
<210> SEQ ID NO 235
<211> LENGTH: 19
<212> TYPE: RNA
<213> ORGANISM: Artificial Sequence
<220> FEATURE:
<223> OTHER INFORMATION: Oligomeric compound

<400> SEQUENCE: 235
agccagguga cagagaaga                                                  19

<210> SEQ ID NO 236
<211> LENGTH: 19
<212> TYPE: RNA
<213> ORGANISM: Artificial Sequence
<220> FEATURE:
<223> OTHER INFORMATION: Oligomeric compound

<400> SEQUENCE: 236
uuuccaccuu ggaccuauu                                                  19

<210> SEQ ID NO 237
<211> LENGTH: 19
<212> TYPE: RNA
<213> ORGANISM: Artificial Sequence
<220> FEATURE:
<223> OTHER INFORMATION: Oligomeric compound

<400> SEQUENCE: 237
gugcagaaua uguacauga                                                  19

<210> SEQ ID NO 238
<211> LENGTH: 19
<212> TYPE: RNA
<213> ORGANISM: Artificial Sequence
<220> FEATURE:
<223> OTHER INFORMATION: Oligomeric compound

<400> SEQUENCE: 238
guagucucga aaguagcgc                                                  19

<210> SEQ ID NO 239
<211> LENGTH: 19
<212> TYPE: RNA
<213> ORGANISM: Artificial Sequence
<220> FEATURE:
<223> OTHER INFORMATION: Oligomeric compound

<400> SEQUENCE: 239
aacuucuugc ucacuucug                                                  19

<210> SEQ ID NO 240
<211> LENGTH: 19
<212> TYPE: RNA
<213> ORGANISM: Artificial Sequence
<220> FEATURE:
<223> OTHER INFORMATION: Oligomeric compound

<400> SEQUENCE: 240
uaugccuggg aacuucuug                                                  19

<210> SEQ ID NO 241
<211> LENGTH: 19
<212> TYPE: RNA
<213> ORGANISM: Artificial Sequence
<220> FEATURE:
```

```
<223> OTHER INFORMATION: Oligomeric compound

<400> SEQUENCE: 241
aauagucuau ggugucccg                                                    19

<210> SEQ ID NO 242
<211> LENGTH: 19
<212> TYPE: RNA
<213> ORGANISM: Artificial Sequence
<220> FEATURE:
<223> OTHER INFORMATION: Oligomeric compound

<400> SEQUENCE: 242
uuugaaagca aauagucua                                                    19

<210> SEQ ID NO 243
<211> LENGTH: 19
<212> TYPE: RNA
<213> ORGANISM: Artificial Sequence
<220> FEATURE:
<223> OTHER INFORMATION: Oligomeric compound

<400> SEQUENCE: 243
gaugauagca uugccacuc                                                    19

<210> SEQ ID NO 244
<211> LENGTH: 19
<212> TYPE: RNA
<213> ORGANISM: Artificial Sequence
<220> FEATURE:
<223> OTHER INFORMATION: Oligomeric compound

<400> SEQUENCE: 244
acgaugauga uagcauugc                                                    19

<210> SEQ ID NO 245
<211> LENGTH: 19
<212> TYPE: RNA
<213> ORGANISM: Artificial Sequence
<220> FEATURE:
<223> OTHER INFORMATION: Oligomeric compound

<400> SEQUENCE: 245
ccaaaggagu agaugggaa                                                    19

<210> SEQ ID NO 246
<211> LENGTH: 19
<212> TYPE: RNA
<213> ORGANISM: Artificial Sequence
<220> FEATURE:
<223> OTHER INFORMATION: Oligomeric compound

<400> SEQUENCE: 246
cuuguacacu ucauucucu                                                    19

<210> SEQ ID NO 247
<211> LENGTH: 19
<212> TYPE: RNA
<213> ORGANISM: Artificial Sequence
<220> FEATURE:
<223> OTHER INFORMATION: Oligomeric compound

<400> SEQUENCE: 247
agaucaccug cuuguacac                                                    19
```

```
<210> SEQ ID NO 248
<211> LENGTH: 19
<212> TYPE: RNA
<213> ORGANISM: Artificial Sequence
<220> FEATURE:
<223> OTHER INFORMATION: Oligomeric compound

<400> SEQUENCE: 248
accaauguau uucuggaac                                              19

<210> SEQ ID NO 249
<211> LENGTH: 19
<212> TYPE: RNA
<213> ORGANISM: Artificial Sequence
<220> FEATURE:
<223> OTHER INFORMATION: Oligomeric compound

<400> SEQUENCE: 249
gugaugggcu uggaguagg                                              19

<210> SEQ ID NO 250
<211> LENGTH: 19
<212> TYPE: RNA
<213> ORGANISM: Artificial Sequence
<220> FEATURE:
<223> OTHER INFORMATION: Oligomeric compound

<400> SEQUENCE: 250
agagcuucac cagggccuc                                              19

<210> SEQ ID NO 251
<211> LENGTH: 19
<212> TYPE: RNA
<213> ORGANISM: Artificial Sequence
<220> FEATURE:
<223> OTHER INFORMATION: Oligomeric compound

<400> SEQUENCE: 251
ugcuugucga agagcuuca                                              19

<210> SEQ ID NO 252
<211> LENGTH: 19
<212> TYPE: RNA
<213> ORGANISM: Artificial Sequence
<220> FEATURE:
<223> OTHER INFORMATION: Oligomeric compound

<400> SEQUENCE: 252
cuuggucuug ugcuugucg                                              19

<210> SEQ ID NO 253
<211> LENGTH: 19
<212> TYPE: RNA
<213> ORGANISM: Artificial Sequence
<220> FEATURE:
<223> OTHER INFORMATION: Oligomeric compound

<400> SEQUENCE: 253
acccaugaca cuuccaaau                                              19

<210> SEQ ID NO 254
<211> LENGTH: 19
<212> TYPE: RNA
<213> ORGANISM: Artificial Sequence
<220> FEATURE:
<223> OTHER INFORMATION: Oligomeric compound
```

-continued

```
<400> SEQUENCE: 254
uuagcaaaau uguuauaau                                                19

<210> SEQ ID NO 255
<211> LENGTH: 19
<212> TYPE: RNA
<213> ORGANISM: Artificial Sequence
<220> FEATURE:
<223> OTHER INFORMATION: Oligomeric compound

<400> SEQUENCE: 255
uuguaauggu uuagcaaaa                                                19

<210> SEQ ID NO 256
<211> LENGTH: 19
<212> TYPE: RNA
<213> ORGANISM: Artificial Sequence
<220> FEATURE:
<223> OTHER INFORMATION: Oligomeric compound

<400> SEQUENCE: 256
agaccuaaca uuguaaugg                                                19

<210> SEQ ID NO 257
<211> LENGTH: 19
<212> TYPE: RNA
<213> ORGANISM: Artificial Sequence
<220> FEATURE:
<223> OTHER INFORMATION: Oligomeric compound

<400> SEQUENCE: 257
uugaaauacu gacuuuuc                                                 19

<210> SEQ ID NO 258
<211> LENGTH: 19
<212> TYPE: RNA
<213> ORGANISM: Artificial Sequence
<220> FEATURE:
<223> OTHER INFORMATION: Oligomeric compound

<400> SEQUENCE: 258
gugaaagaac uugaaauac                                                19

<210> SEQ ID NO 259
<211> LENGTH: 19
<212> TYPE: RNA
<213> ORGANISM: Artificial Sequence
<220> FEATURE:
<223> OTHER INFORMATION: Oligomeric compound

<400> SEQUENCE: 259
caagcuggaa gugaaagaa                                                19

<210> SEQ ID NO 260
<211> LENGTH: 19
<212> TYPE: RNA
<213> ORGANISM: Artificial Sequence
<220> FEATURE:
<223> OTHER INFORMATION: Oligomeric compound

<400> SEQUENCE: 260 gaguuccuu ugucacuuc                                                 19

<210> SEQ ID NO 261
<211> LENGTH: 19
```

```
<212> TYPE: RNA
<213> ORGANISM: Artificial Sequence
<220> FEATURE:
<223> OTHER INFORMATION: Oligomeric compound

<400> SEQUENCE: 261
uaauggcaau ccuucuucc                                                    19

<210> SEQ ID NO 262
<211> LENGTH: 19
<212> TYPE: RNA
<213> ORGANISM: Artificial Sequence
<220> FEATURE:
<223> OTHER INFORMATION: Oligomeric compound

<400> SEQUENCE: 262
ucaaacugga gcauuccag                                                    19

<210> SEQ ID NO 263
<211> LENGTH: 19
<212> TYPE: RNA
<213> ORGANISM: Artificial Sequence
<220> FEATURE:
<223> OTHER INFORMATION: Oligomeric compound

<400> SEQUENCE: 263
agaagggaga ucaaacugg                                                    19

<210> SEQ ID NO 264
<211> LENGTH: 19
<212> TYPE: RNA
<213> ORGANISM: Artificial Sequence
<220> FEATURE:
<223> OTHER INFORMATION: Oligomeric compound

<400> SEQUENCE: 264
caagaaaaac caguuacuc                                                    19

<210> SEQ ID NO 265
<211> LENGTH: 19
<212> TYPE: RNA
<213> ORGANISM: Artificial Sequence
<220> FEATURE:
<223> OTHER INFORMATION: Oligomeric compound

<400> SEQUENCE: 265
acuaaucugc ugcucagaa                                                    19

<210> SEQ ID NO 266
<211> LENGTH: 19
<212> TYPE: RNA
<213> ORGANISM: Artificial Sequence
<220> FEATURE:
<223> OTHER INFORMATION: Oligomeric compound

<400> SEQUENCE: 266
ggaaggcaca gaaaaguga                                                    19

<210> SEQ ID NO 267
<211> LENGTH: 19
<212> TYPE: RNA
<213> ORGANISM: Artificial Sequence
<220> FEATURE:
<223> OTHER INFORMATION: Oligomeric compound

<400> SEQUENCE: 267
```

```
<210> SEQ ID NO 268
<211> LENGTH: 19
<212> TYPE: RNA
<213> ORGANISM: Artificial Sequence
<220> FEATURE:
<223> OTHER INFORMATION: Oligomeric compound

<400> SEQUENCE: 268
ucucaucaag agauaacag                                                   19

<210> SEQ ID NO 269
<211> LENGTH: 19
<212> TYPE: RNA
<213> ORGANISM: Artificial Sequence
<220> FEATURE:
<223> OTHER INFORMATION: Oligomeric compound

<400> SEQUENCE: 269
ggugcaauga ucucaucaa                                                   19

<210> SEQ ID NO 270
<211> LENGTH: 19
<212> TYPE: RNA
<213> ORGANISM: Artificial Sequence
<220> FEATURE:
<223> OTHER INFORMATION: Oligomeric compound

<400> SEQUENCE: 270
caaggcauau acaaaaguc                                                   19

<210> SEQ ID NO 271
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 271
ttagaatacg tcgcgttatg                                                  20

<210> SEQ ID NO 272
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 272
attcgccaga caacactgac                                                  20

<210> SEQ ID NO 273
<211> LENGTH: 1330
<212> TYPE: DNA
<213> ORGANISM: Mus musculus
<220> FEATURE:
<221> NAME/KEY: CDS
<222> LOCATION: (60)...(1226)

<400> SEQUENCE: 273
ggtcaggggc gcggcgtgag gcggctttct gcacggccgt gacgtgcatt ggcttcagc       59 atg aag acc ctc atc gcc gcc tac tcc ggg gtc ctg cgg ggt gag cgt      107
Met Lys Thr Leu Ile Ala Ala Tyr Ser Gly Val Leu Arg Gly Glu Arg
  1               5                  10                  15
``` continued from previous page (agauaacaga acacacagg — 19) shown at top.

-continued

| | |
|---|---|
| cgg gcg gaa gct gcc cgc agc gaa aac aag aat aaa gga tct gcc ctg<br>Arg Ala Glu Ala Ala Arg Ser Glu Asn Lys Asn Lys Gly Ser Ala Leu<br>        20                 25                30 | 155 |
| tca cgc gag ggg tct ggg cga tgg ggc act ggc tcc agc atc ctc tca<br>Ser Arg Glu Gly Ser Gly Arg Trp Gly Thr Gly Ser Ser Ile Leu Ser<br>     35                   40                  45 | 203 |
| gcc ctc caa gac atc ttc tct gtc acc tgg ctc aac aga tct aag gtg<br>Ala Leu Gln Asp Ile Phe Ser Val Thr Trp Leu Asn Arg Ser Lys Val<br>50                 55                  60 | 251 |
| gaa aaa cag ctg cag gtc atc tca gta cta caa tgg gtc cta tcc ttc<br>Glu Lys Gln Leu Gln Val Ile Ser Val Leu Gln Trp Val Leu Ser Phe<br>65                 70              75            80 | 299 |
| ctg gtg cta gga gtg gcc tgc agt gtc atc ctc atg tac acc ttc tgc<br>Leu Val Leu Gly Val Ala Cys Ser Val Ile Leu Met Tyr Thr Phe Cys<br>                   85                90             95 | 347 |
| aca gac tgc tgg ctg ata gct gtg ctc tac ttc acc tgg ctg gca ttt<br>Thr Asp Cys Trp Leu Ile Ala Val Leu Tyr Phe Thr Trp Leu Ala Phe<br>                  100              105             110 | 395 |
| gac tgg aac acg ccc aag aaa ggt ggc agg aga tcg cag tgg gtg cga<br>Asp Trp Asn Thr Pro Lys Lys Gly Gly Arg Arg Ser Gln Trp Val Arg<br>                115              120             125 | 443 |
| aac tgg gcc gtg tgg cgc tac ttc cga gac tac ttt ccc atc cag ctg<br>Asn Trp Ala Val Trp Arg Tyr Phe Arg Asp Tyr Phe Pro Ile Gln Leu<br>130                135              140 | 491 |
| gtg aag aca cac aac ctg ctg acc acc agg aac tat atc ttt gga tac<br>Val Lys Thr His Asn Leu Leu Thr Thr Arg Asn Tyr Ile Phe Gly Tyr<br>145                150              155             160 | 539 |
| cac ccc cat ggc atc atg ggc ctg ggt gcc ttc tgt aac ttc agc aca<br>His Pro His Gly Ile Met Gly Leu Gly Ala Phe Cys Asn Phe Ser Thr<br>                  165              170             175 | 587 |
| gag gct act gaa gtc agc aag aag ttt cct ggc ata agg ccc tat ttg<br>Glu Ala Thr Glu Val Ser Lys Lys Phe Pro Gly Ile Arg Pro Tyr Leu<br>                  180              185             190 | 635 |
| gct acg ttg gct ggt aac ttc cgg atg cct gtg ctt cgc gag tac ctg<br>Ala Thr Leu Ala Gly Asn Phe Arg Met Pro Val Leu Arg Glu Tyr Leu<br>                  195              200             205 | 683 |
| atg tct gga ggc atc tgc cct gtc aac cga gac acc ata gac tac ttg<br>Met Ser Gly Gly Ile Cys Pro Val Asn Arg Asp Thr Ile Asp Tyr Leu<br>210                215              220 | 731 |
| ctc tcc aag aat ggg agt ggc aat gct atc atc atc gtg gtg gga ggt<br>Leu Ser Lys Asn Gly Ser Gly Asn Ala Ile Ile Ile Val Val Gly Gly<br>225                230              235             240 | 779 |
| gca gct gag tcc ctg agc tcc atg cct ggc aag aac gca gtc acc ctg<br>Ala Ala Glu Ser Leu Ser Ser Met Pro Gly Lys Asn Ala Val Thr Leu<br>                  245              250             255 | 827 |
| aag aac cgc aaa ggc ttt gtg aag ctg gcc ctg cgc cat gga gct gat<br>Lys Asn Arg Lys Gly Phe Val Lys Leu Ala Leu Arg His Gly Ala Asp<br>                  260              265             270 | 875 |
| ctg gtt ccc act tat tcc ttt gga gag aat gag gta tac aag cag gtg<br>Leu Val Pro Thr Tyr Ser Phe Gly Glu Asn Glu Val Tyr Lys Gln Val<br>                 275              280             285 | 923 |
| atc ttt gag gag ggt tcc tgg ggc cga tgg gtc cag aag aag ttc cag<br>Ile Phe Glu Glu Gly Ser Trp Gly Arg Trp Val Gln Lys Lys Phe Gln<br>290                295              300 | 971 |
| aag tat att ggt ttc gcc ccc tgc atc ttc cat ggc gga ggc ctc ttc<br>Lys Tyr Ile Gly Phe Ala Pro Cys Ile Phe His Gly Arg Gly Leu Phe<br>305                310              315             320 | 1019 |
| tcc tct gac acc tgg ggg ctg gtg ccc tac tcc aag ccc atc acc acc<br>Ser Ser Asp Thr Trp Gly Leu Val Pro Tyr Ser Lys Pro Ile Thr Thr<br>                  325              330             335 | 1067 |

```
gtc gtg ggg gag ccc atc act gtc ccc aag ctg gag cac ccg acc cag    1115
Val Val Gly Glu Pro Ile Thr Val Pro Lys Leu Glu His Pro Thr Gln
            340                 345                 350 aaa gac atc gac ctg tac cat gcc atg tac atg gag gcc ctg gtg aag    1163
Lys Asp Ile Asp Leu Tyr His Ala Met Tyr Met Glu Ala Leu Val Lys
            355                 360                 365 ctc ttt gac aat cac aag acc aaa ttt ggc ctt cca gag act gag gtg    1211
Leu Phe Asp Asn His Lys Thr Lys Phe Gly Leu Pro Glu Thr Glu Val
        370                 375                 380 ctg gag gtg aac tga cccagcccgc gcgtgccagc tcctgggagg gacgactgca    1266
Leu Glu Val Asn *
385 gatcctttc taccgagttc tcgagtgcat tttgttctgt aaatttggaa gcgtcatggg    1326
tgtc                                                                1330

<210> SEQ ID NO 274
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 274
atgcactcga gaactcggta                                                 20

<210> SEQ ID NO 275
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 275
cgttattaac ctccgttgaa                                                 20

<210> SEQ ID NO 276
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 276
tcgatctcct tttatgcccg                                                 20

<210> SEQ ID NO 277
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 277
acacctggag ctgcggccgg                                                 20

<210> SEQ ID NO 278
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 278
```
ctaggacacc tggagctgcg                                                  20

<210> SEQ ID NO 279
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 279
ggctatgagg gtcttcatgg                                                  20

<210> SEQ ID NO 280
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 280
taggcggcta tgagggtctt                                                  20

<210> SEQ ID NO 281
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 281
tggatccagt gccccatctc                                                  20

<210> SEQ ID NO 282
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 282
gggcggagag gatgctggat                                                  20

<210> SEQ ID NO 283
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 283
ctggagggcg gagaggatgc                                                  20

<210> SEQ ID NO 284
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 284
gacctattga gccaggtgac                                                  20

<210> SEQ ID NO 285
<211> LENGTH: 20
<212> TYPE: DNA
<213> ORGANISM: Artificial Sequence

```
<220> FEATURE:
<223> OTHER INFORMATION: Antisense oligonucleotide

<400> SEQUENCE: 285
ccttggacct attgagccag                                               20

<210> SEQ ID NO 286
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 286
ttccaccttg gacctattga                                               20

<210> SEQ ID NO 287
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 287
tgcttttcca ccttggacct                                               20

<210> SEQ ID NO 288
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 288
gtagctgctt ttccaccttg                                               20

<210> SEQ ID NO 289
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 289
tggagcactg agatgacctg                                               20

<210> SEQ ID NO 290
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 290
aaggacagga cccactggag                                               20

<210> SEQ ID NO 291
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 291
tacaaggaag gacaggaccc                                               20
```

<210> SEQ ID NO 292
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 292
cccagtacaa ggaaggacag                                           20

<210> SEQ ID NO 293
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 293
atgaggatgg cactgcaggc                                           20

<210> SEQ ID NO 294
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 294
tgtacatgag gatggcactg                                           20

<210> SEQ ID NO 295
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 295
gaatatgtac atgaggatgg                                           20

<210> SEQ ID NO 296
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 296
gtgcagaata tgtacatgag                                           20

<210> SEQ ID NO 297
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 297
acagcgatga gccagcaatc                                           20

<210> SEQ ID NO 298
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 298
tagagcacag cgatgagcca                                               20

<210> SEQ ID NO 299
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 299
tgaagtagag cacagcgatg                                               20

<210> SEQ ID NO 300
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 300
ccaagtgaag tagagcacag                                               20

<210> SEQ ID NO 301
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 301
ccagtcaaac accagccaag                                               20

<210> SEQ ID NO 302
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 302
tgcagaaggc acccaggccc                                               20

<210> SEQ ID NO 303
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 303
gaacttcttg ctcacttctg                                               20

<210> SEQ ID NO 304
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 304
agctcagaga ctcagccgca                                               20

<210> SEQ ID NO 305

```
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 305
catggagctc agagactcag                                              20

<210> SEQ ID NO 306
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 306
tgcattcttg ccaggcatgg                                              20

<210> SEQ ID NO 307
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 307
gcagggtgac tgcattcttg                                              20

<210> SEQ ID NO 308
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 308
ttcacaaagc ccttgcggtt                                              20

<210> SEQ ID NO 309
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 309
cttgtacact tcattctctc                                              20

<210> SEQ ID NO 310
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 310
agatcacctg cttgtacact                                              20

<210> SEQ ID NO 311
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 311
```
catcggcccc aggagccctc          20

<210> SEQ ID NO 312
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 312
ccaatgtatt tctggaactt          20

<210> SEQ ID NO 313
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 313
cgaaaccaat gtatttctgg          20

<210> SEQ ID NO 314
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 314
cccccaggtg tcggaggaga          20

<210> SEQ ID NO 315
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 315
ggtgatgggc ttggagtagg          20

<210> SEQ ID NO 316
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 316
atggtgtggt acaggtcgat          20

<210> SEQ ID NO 317
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 317
tgtacatggt gtggtacagg          20

<210> SEQ ID NO 318
<211> LENGTH: 20
<212> TYPE: DNA

```
<213> ORGANISM: Artificial Sequence
<220> FEATURE:
<223> OTHER INFORMATION: Antisense oligonucleotide

<400> SEQUENCE: 318
tgtcgaagag cttcaccagg                                              20

<210> SEQ ID NO 319
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 319
gtgcttgtcg aagagcttca                                              20

<210> SEQ ID NO 320
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 320
tggtcttgtg cttgtcgaag                                              20

<210> SEQ ID NO 321
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 321
gaacttggtc ttgtgcttgt                                              20

<210> SEQ ID NO 322
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 322
aggccgaact tggtcttgtg                                              20

<210> SEQ ID NO 323
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 323
aacattgtaa tggtttagca                                              20

<210> SEQ ID NO 324
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 324
gacctaacat tgtaatggtt                                              20
```

-continued

```
<210> SEQ ID NO 325
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 325
aaaaagacct aacattgtaa                                              20

<210> SEQ ID NO 326
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 326
ttagccacca cctagaacag                                              20

<210> SEQ ID NO 327
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 327
cagatttagc caccacctag                                              20

<210> SEQ ID NO 328
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 328
aggcccagat ttagccacca                                              20

<210> SEQ ID NO 329
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 329
agattaggcc cagatttagc                                              20

<210> SEQ ID NO 330
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 330
cacccagatt aggcccagat                                              20

<210> SEQ ID NO 331
<211> LENGTH: 20
<212> TYPE: DNA
<213> ORGANISM: Artificial Sequence
<220> FEATURE:
```

```
<223> OTHER INFORMATION: Antisense oligonucleotide

<400> SEQUENCE: 331
tgagccaccc agattaggcc                                               20

<210> SEQ ID NO 332
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 332
ttagctgagc cacccagatt                                               20

<210> SEQ ID NO 333
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 333
aaagtgaatc atctaactgg                                               20

<210> SEQ ID NO 334
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 334
ctgcagtttc aggactagac                                               20

<210> SEQ ID NO 335
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 335
gaaactggtc ctgcagtttc                                               20

<210> SEQ ID NO 336
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 336
gcagagaaac tggtcctgca                                               20

<210> SEQ ID NO 337
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 337
ccttggcaga gaaactggtc                                               20
```

```
<210> SEQ ID NO 338
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 338
attccagatg cctactactg                                               20

<210> SEQ ID NO 339
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 339
ggagcattcc agatgcctac                                               20

<210> SEQ ID NO 340
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 340
ctcatggtgg cggcatcctc                                               20

<210> SEQ ID NO 341
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 341
ccaagaaaaa ccagttactc                                               20

<210> SEQ ID NO 342
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 342
gccacccaag aaaaaccagt                                               20

<210> SEQ ID NO 343
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 343
gcatccatgt catcagccac                                               20

<210> SEQ ID NO 344
<211> LENGTH: 20
<212> TYPE: DNA
<213> ORGANISM: Artificial Sequence
<220> FEATURE:
<223> OTHER INFORMATION: Antisense oligonucleotide
```

-continued

<400> SEQUENCE: 344
aggacacctg gagctgcggc                                          20

<210> SEQ ID NO 345
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 345
ggcggctatg agggtcttca                                          20

<210> SEQ ID NO 346
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 346
gagtaggcgg ctatgagggt                                          20

<210> SEQ ID NO 347
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 347
cgcaggaccc cggagtaggc                                          20

<210> SEQ ID NO 348
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 348
tgctggatcc agtgccccat                                          20

<210> SEQ ID NO 349
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 349
gtcctggagg gcggagagga                                          20

<210> SEQ ID NO 350
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 350
ttggacctat tgagccaggt                                          20

<210> SEQ ID NO 351
<211> LENGTH: 20

```
<212> TYPE: DNA
<213> ORGANISM: Artificial Sequence
<220> FEATURE:
<223> OTHER INFORMATION: Antisense oligonucleotide

<400> SEQUENCE: 351
ccaccttgga cctattgagc                                              20

<210> SEQ ID NO 352
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 352
cttttccacc ttggacctat                                              20

<210> SEQ ID NO 353
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 353
agctgctttt ccaccttgga                                              20

<210> SEQ ID NO 354
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 354
cactggagca ctgagatgac                                              20

<210> SEQ ID NO 355
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 355
aggaaggaca ggacccactg                                              20

<210> SEQ ID NO 356
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 356
cagtacaagg aaggacagga                                              20

<210> SEQ ID NO 357
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 357
```

| | |
|---|---|
| tacatgagga tggcactgca | 20 |

<210> SEQ ID NO 358
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 358

| | |
|---|---|
| atatgtacat gaggatggca | 20 |

<210> SEQ ID NO 359
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 359

| | |
|---|---|
| gcagaatatg tacatgagga | 20 |

<210> SEQ ID NO 360
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 360

| | |
|---|---|
| tcagtgcaga atatgtacat | 20 |

<210> SEQ ID NO 361
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 361

| | |
|---|---|
| agcacagcga tgagccagca | 20 |

<210> SEQ ID NO 362
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 362

| | |
|---|---|
| aagtagagca cagcgatgag | 20 |

<210> SEQ ID NO 363
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 363

| | |
|---|---|
| aagtgaagta gagcacagcg | 20 |

<210> SEQ ID NO 364
<211> LENGTH: 20
<212> TYPE: DNA
<213> ORGANISM: Artificial Sequence

```
<220> FEATURE:
<223> OTHER INFORMATION: Antisense oligonucleotide

<400> SEQUENCE: 364
cagccaagtg aagtagagca                                                    20

<210> SEQ ID NO 365
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 365
gttccagtca aacaccagcc                                                    20

<210> SEQ ID NO 366
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 366
ttgtgtgtct tcaccagctg                                                    20

<210> SEQ ID NO 367
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 367
gcaggttgtg tgtcttcacc                                                    20

<210> SEQ ID NO 368
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 368
ggtcagcagg ttgtgtgtct                                                    20

<210> SEQ ID NO 369
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 369
gatatagttc ctggtggtca                                                    20

<210> SEQ ID NO 370
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 370
tgggaacttc ttgctcactt                                                    20
```

```
<210> SEQ ID NO 371
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 371
atagcattgc cactcccatt                                               20

<210> SEQ ID NO 372
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 372
tgatgatagc attgccactc                                               20

<210> SEQ ID NO 373
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 373
tggagctcag agactcagcc                                               20

<210> SEQ ID NO 374
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 374
aggcatggag ctcagagact                                               20

<210> SEQ ID NO 375
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 375
gactgcattc ttgccaggca                                               20

<210> SEQ ID NO 376
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 376
tccgcagggt gactgcattc                                               20

<210> SEQ ID NO 377
<211> LENGTH: 20
<212> TYPE: DNA
<213> ORGANISM: Artificial Sequence
<220> FEATURE:
<223> OTHER INFORMATION: Antisense oligonucleotide
```

```
<400> SEQUENCE: 377
agtttcacaa agcccttgcg                                               20

<210> SEQ ID NO 378
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 378
ctgcttgtac acttcattct                                               20

<210> SEQ ID NO 379
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 379
cgaagatcac ctgcttgtac                                               20

<210> SEQ ID NO 380
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 380
acccatcggc cccaggagcc                                               20

<210> SEQ ID NO 381
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 381
aaaccaatgt atttctggaa                                               20

<210> SEQ ID NO 382
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 382
gggcgaaacc aatgtatttc                                               20

<210> SEQ ID NO 383
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 383
cagcccccag gtgtcggagg                                               20

<210> SEQ ID NO 384
```

```
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 384
agtggtgatg ggcttggagt                                                   20

<210> SEQ ID NO 385
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 385
tacatggtgt ggtacaggtc                                                   20

<210> SEQ ID NO 386
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 386
ccatgtacat ggtgtggtac                                                   20

<210> SEQ ID NO 387
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 387
gcttgtcgaa gagcttcacc                                                   20

<210> SEQ ID NO 388
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 388
acttggtctt gtgcttgtcg                                                   20

<210> SEQ ID NO 389
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 389
gccgaacttg gtcttgtgct                                                   20

<210> SEQ ID NO 390
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 390
```
gggaggccga acttggtctt                    20

<210> SEQ ID NO 391
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 391
cctaacattg taatggttta                    20

<210> SEQ ID NO 392
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 392
aaagacctaa cattgtaatg                    20

<210> SEQ ID NO 393
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 393
gatttagcca ccacctagaa                    20

<210> SEQ ID NO 394
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 394
gcccagattt agccaccacc                    20

<210> SEQ ID NO 395
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 395
attaggccca gatttagcca                    20

<210> SEQ ID NO 396
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 396
cccagattag gcccagattt                    20

<210> SEQ ID NO 397
<211> LENGTH: 20
<212> TYPE: DNA

```
-continued

<213> ORGANISM: Artificial Sequence
<220> FEATURE:
<223> OTHER INFORMATION: Antisense oligonucleotide

<400> SEQUENCE: 397
agccacccag attaggccca                                                    20

<210> SEQ ID NO 398
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 398
agctgagcca cccagattag                                                    20

<210> SEQ ID NO 399
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 399
aggttagctg agccacccag                                                    20

<210> SEQ ID NO 400
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 400
caaaaagtga atcatctaac                                                    20

<210> SEQ ID NO 401
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 401
gtcctgcagt ttcaggacta                                                    20

<210> SEQ ID NO 402
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 402
agagaaactg gtcctgcagt                                                    20

<210> SEQ ID NO 403
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 403
ttggcagaga aactggtcct                                                    20
```

```
<210> SEQ ID NO 404
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 404
tccccttggc agagaaactg                                              20

<210> SEQ ID NO 405
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 405
agcattccag atgcctacta                                              20

<210> SEQ ID NO 406
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 406
actggagcat tccagatgcc                                              20

<210> SEQ ID NO 407
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 407
tagctcatgg tggcggcatc                                              20

<210> SEQ ID NO 408
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 408
cacccaagaa aaaccagtta                                              20

<210> SEQ ID NO 409
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 409
tcagccaccc aagaaaaacc                                              20

<210> SEQ ID NO 410
<211> LENGTH: 20
<212> TYPE: DNA
<213> ORGANISM: Artificial Sequence
<220> FEATURE:
```

```
<223> OTHER INFORMATION: Antisense oligonucleotide

<400> SEQUENCE: 410
gctgcatcca tgtcatcagc                                                    20

<210> SEQ ID NO 411
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 411
ctatcagtga aatgaggcag                                                    20

<210> SEQ ID NO 412
<211> LENGTH: 1367
<212> TYPE: DNA
<213> ORGANISM: Rattus norvegicus
<220> FEATURE:
<221> NAME/KEY: CDS
<222> LOCATION: (201)...(1367)

<400> SEQUENCE: 412
cgcgcttcgc tagctttctg attgcctagg gtggcagcgg ctacctacct cggatctcga        60
cctgctgcca ccacggcctg agcgctgtcc ctcggctccc ggagctcagc gcgaagccct       120
ggccccggcg gctggggcat ggatcagggg cgctgcgtga ggcggcttcc tgcacggccg       180
tgacgtgcac cggcttcagc atg aag acc ctc atc gct gcc tac tcc ggg gtc      233
                         Met Lys Thr Leu Ile Ala Ala Tyr Ser Gly Val
                          1               5                  10 ctg cgg ggt gag cgt cgg gcc gaa gct gcc cgc agc gag aac aag aat        281
Leu Arg Gly Glu Arg Arg Ala Glu Ala Ala Arg Ser Glu Asn Lys Asn
             15                  20                  25 aaa gga tct gcc ctg tca cgc gag ggg tct ggg cga tgg ggc act ggc        329
Lys Gly Ser Ala Leu Ser Arg Glu Gly Ser Gly Arg Trp Gly Thr Gly
 30                  35                  40 tcc agc atc ctc tcg gcc ctc caa gac atc ttc tct gtc acc tgg ctc        377
Ser Ser Ile Leu Ser Ala Leu Gln Asp Ile Phe Ser Val Thr Trp Leu
         45                  50                  55 aac aga tcc aag gtg gaa aaa cac cta cag gtc atc tca gtc cta cag        425
Asn Arg Ser Lys Val Glu Lys His Leu Gln Val Ile Ser Val Leu Gln
 60                  65                  70                  75 tgg gtc cta tcc ttc ctg gtg cta gga gtg gcc tgc agt gtc atc ctc        473
Trp Val Leu Ser Phe Leu Val Leu Gly Val Ala Cys Ser Val Ile Leu
             80                  85                  90 atg tac acc ttc tgc act gac tgc tgg ctg ata gct gct ctc tac ttc        521
Met Tyr Thr Phe Cys Thr Asp Cys Trp Leu Ile Ala Ala Leu Tyr Phe
         95                 100                 105 acc tgg ctg gca ttt gac tgg aac acg ccc aag aaa ggt ggc agg aga        569
Thr Trp Leu Ala Phe Asp Trp Asn Thr Pro Lys Lys Gly Gly Arg Arg
    110                 115                 120 tca cag tgg gtg cga aac tgg gcc gtg tgg cgc tat ttt cga gac tac        617
Ser Gln Trp Val Arg Asn Trp Ala Val Trp Arg Tyr Phe Arg Asp Tyr
125                 130                 135 ttt ccc atc cag ctg gtg aag aca cac aac ctg ctg acc acc agg aac        665
Phe Pro Ile Gln Leu Val Lys Thr His Asn Leu Leu Thr Thr Arg Asn
140                 145                 150                 155 tat atc ttt gga tac cat ccc cat ggc atc atg ggc ctg ggt gcc ttc        713
Tyr Ile Phe Gly Tyr His Pro His Gly Ile Met Gly Leu Gly Ala Phe
             160                 165                 170
```

| | | |
|---|---|---|
| tgt aac ttc agc acg gag gcc acc gaa gtt agc aag aag ttc cct ggc<br>Cys Asn Phe Ser Thr Glu Ala Thr Glu Val Ser Lys Lys Phe Pro Gly<br>175 180 185 | | 761 |
| ata agg cct tat ttg gcc aca ttg gct ggc aac ttc cgg atg cct gtg<br>Ile Arg Pro Tyr Leu Ala Thr Leu Ala Gly Asn Phe Arg Met Pro Val<br>190 195 200 | | 809 |
| ctt cgg gag tac ctg atg tct gga ggc atc tgc cct gtc aac aga gac<br>Leu Arg Glu Tyr Leu Met Ser Gly Gly Ile Cys Pro Val Asn Arg Asp<br>205 210 215 | | 857 |
| acc ata gac tac ttg ctt tcc aag aat ggg agt ggt aat gcc att gtc<br>Thr Ile Asp Tyr Leu Leu Ser Lys Asn Gly Ser Gly Asn Ala Ile Val<br>220 225 230 235 | | 905 |
| atc gtg gtg gga ggt gca gct gaa tcc ctg agc tcc atg cct ggc aag<br>Ile Val Val Gly Gly Ala Ala Glu Ser Leu Ser Ser Met Pro Gly Lys<br>240 245 250 | | 953 |
| aac gca gtc acc ctg cgg aac cgc aaa ggc ttt gta aag ctg gcc ctg<br>Asn Ala Val Thr Leu Arg Asn Arg Lys Gly Phe Val Lys Leu Ala Leu<br>255 260 265 | | 1001 |
| cgc cat gga gct gat ctg gtt ccc acc tat tcc ttt gga gag aat gag<br>Arg His Gly Ala Asp Leu Val Pro Thr Tyr Ser Phe Gly Glu Asn Glu<br>270 275 280 | | 1049 |
| gta tac aag cag gtg atc ttt gag gag ggc tcc tgg ggc cga tgg gtc<br>Val Tyr Lys Gln Val Ile Phe Glu Glu Gly Ser Trp Gly Arg Trp Val<br>285 290 295 | | 1097 |
| cag aag aag ttc cag aag tat att ggt ttc gcc ccc tgc atc ttc cat<br>Gln Lys Lys Phe Gln Lys Tyr Ile Gly Phe Ala Pro Cys Ile Phe His<br>300 305 310 315 | | 1145 |
| ggc cga ggt ctc ttc tcc tct gac acc tgg ggg ctg gtg ccc tac tcc<br>Gly Arg Gly Leu Phe Ser Ser Asp Thr Trp Gly Leu Val Pro Tyr Ser<br>320 325 330 | | 1193 |
| aag ccc atc acc acc gtt gtg ggg gag ccc atc acc gtc cct aag ctg<br>Lys Pro Ile Thr Thr Val Val Gly Glu Pro Ile Thr Val Pro Lys Leu<br>335 340 345 | | 1241 |
| gag cac ccg acc cag aaa gac atc gac ctg tac cac acc atg tac atg<br>Glu His Pro Thr Gln Lys Asp Ile Asp Leu Tyr His Thr Met Tyr Met<br>350 355 360 | | 1289 |
| gag gcc ctg gtg aag ctc ttt gac aat cac aag acc aaa ttc ggc ctt<br>Glu Ala Leu Val Lys Leu Phe Asp Asn His Lys Thr Lys Phe Gly Leu<br>365 370 375 | | 1337 |
| cca gag act gag gtg ctg gag gtg aac tga<br>Pro Glu Thr Glu Val Leu Glu Val Asn *<br>380 385 | | 1367 |

<210> SEQ ID NO 413
<211> LENGTH: 286
<212> TYPE: DNA
<213> ORGANISM: Rattus norvegicus
<220> FEATURE:
<221> NAME/KEY: CDS
<222> LOCATION: (1)...(286)

<400> SEQUENCE: 413

| | | |
|---|---|---|
| tgc tga cca cca gga act ata tct ttg gat acc atc ccc atg gca tca<br>Cys * Pro Pro Gly Thr Ile Ser Leu Asp Thr Ile Pro Met Ala Ser<br>1 5 10 15 | | 48 |
| tgg acc tgg gtg cct tct gta act tca gca cgg agg cca ccg aag tta<br>Trp Thr Trp Val Pro Ser Val Thr Ser Ala Arg Arg Pro Pro Lys Leu<br>20 25 30 | | 96 |
| gca aga agt tcc ctg gca taa ggc ctt att tgg cca cat tgg ctg gca<br>Ala Arg Ser Ser Leu Ala * Gly Leu Ile Trp Pro His Trp Leu Ala<br>35 40 45 | | 144 |

```
act tcc gga tgc ctg tgc ttc ggg agt acc tga tgt ctg gag gca tct      192
Thr Ser Gly Cys Leu Cys Phe Gly Ser Thr  *  Cys Leu Glu Ala Ser
             50                  55                  60 gcc ctg tca aca gag aca cca tag act act tgc ttt cca aga atg gga      240
Ala Leu Ser Thr Glu Thr Pro  *  Thr Thr Cys Phe Pro Arg Met Gly
         65                  70                  75 gtg gta atg cca ttg tca tcg tgg tgg ggt cgc gcg ccc gcg gcc g        286
Val Val Met Pro Leu Ser Ser Trp Trp Gly Arg Ala Pro Ala Ala
             80                  85                  90
```

<210> SEQ ID NO 414
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 414
cagaaagcta gcgaagcgcg                                                 20

<210> SEQ ID NO 415
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 415
cgctgccacc ctaggcaatc                                                 20

<210> SEQ ID NO 416
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 416
cgagatccga ggtaggtagc                                                 20

<210> SEQ ID NO 417
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 417
aggccgtggt ggcagcaggt                                                 20

<210> SEQ ID NO 418
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 418
ggagccgagg gacagcgctc                                                 20

<210> SEQ ID NO 419
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 419
gggcttcgcg ctgagctccg					20

<210> SEQ ID NO 420
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 420
tccatgcccc agccgccggg					20

<210> SEQ ID NO 421
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 421
cacgcagcgc ccctgatcca					20

<210> SEQ ID NO 422
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 422
ggccgtgcag gaagccgcct					20

<210> SEQ ID NO 423
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 423
ctgaagccgg tgcacgtcac					20

<210> SEQ ID NO 424
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 424
gcgatgaggg tcttcatgct					20

<210> SEQ ID NO 425
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 425
aggaccccgg agtaggcagc					20

<210> SEQ ID NO 426

```
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 426
ccgcaggacc ccggagtagg                                               20

<210> SEQ ID NO 427
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 427
gcttcggccc gacgctcacc                                               20

<210> SEQ ID NO 428
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 428
tcttgttctc gctgcgggca                                               20

<210> SEQ ID NO 429
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 429
tgacagggca gatcctttat                                               20

<210> SEQ ID NO 430
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 430
catcgcccag acccctcgcg                                               20

<210> SEQ ID NO 431
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 431
ggatgctgga gccagtgccc                                               20

<210> SEQ ID NO 432
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 432
```
gatgtcttgg agggccgaga 20

<210> SEQ ID NO 433
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 433
ttgagccagg tgacagagaa 20

<210> SEQ ID NO 434
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 434
gtttttccac cttggatctg 20

<210> SEQ ID NO 435
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 435
gactgagatg acctgtaggt 20

<210> SEQ ID NO 436
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 436
aaggatagga cccactgtag 20

<210> SEQ ID NO 437
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 437
ggccactcct agcaccagga 20

<210> SEQ ID NO 438
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 438
gtacatgagg atgacactgc 20

<210> SEQ ID NO 439
<211> LENGTH: 20
<212> TYPE: DNA

```
<213> ORGANISM: Artificial Sequence
<220> FEATURE:
<223> OTHER INFORMATION: Antisense oligonucleotide

<400> SEQUENCE: 439
cagcagtcag tgcagaaggt                                              20

<210> SEQ ID NO 440
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 440
agtagagagc agctatcagc                                              20

<210> SEQ ID NO 441
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 441
gtcaaatgcc agccaggtga                                              20

<210> SEQ ID NO 442
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 442
cctttcttgg gcgtgttcca                                              20

<210> SEQ ID NO 443
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 443
cccactgtga tctcctgcca                                              20

<210> SEQ ID NO 444
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 444
agtagtctcg aaaatagcgc                                              20

<210> SEQ ID NO 445
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 445
tcttcaccag ctggatggga                                              20
```

```
<210> SEQ ID NO 446
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 446
ggtggtcagc aggttgtgtg                                           20

<210> SEQ ID NO 447
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 447
tatccaaaga tatagttcct                                           20

<210> SEQ ID NO 448
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 448
caggcccatg atgccatggg                                           20

<210> SEQ ID NO 449
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 449
gttacagaag gcacccaggc                                           20

<210> SEQ ID NO 450
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 450
tcggtggcct ccgtgctgaa                                           20

<210> SEQ ID NO 451
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 451
cagggaactt cttgctaact                                           20

<210> SEQ ID NO 452
<211> LENGTH: 20
<212> TYPE: DNA
<213> ORGANISM: Artificial Sequence
<220> FEATURE:
```

<223> OTHER INFORMATION: Antisense oligonucleotide

<400> SEQUENCE: 452
tggccaaata aggccttatg                                                 20

<210> SEQ ID NO 453
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 453
cggaagttgc cagccaatgt                                                 20

<210> SEQ ID NO 454
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 454
actcccgaag cacaggcatc                                                 20

<210> SEQ ID NO 455
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 455
gatgcctcca gacatcaggt                                                 20

<210> SEQ ID NO 456
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 456
gtgtctctgt tgacagggca                                                 20

<210> SEQ ID NO 457
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 457
aagtagtcta tggtgtctct                                                 20

<210> SEQ ID NO 458
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 458
agcaagtagt ctatggtgtc                                                 20

```
<210> SEQ ID NO 459
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 459
cttggaaagc aagtagtcta                                              20

<210> SEQ ID NO 460
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 460
accactccca ttcttggaaa                                              20

<210> SEQ ID NO 461
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 461
gcattaccac tcccattctt                                              20

<210> SEQ ID NO 462
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 462
caatggcatt accactccca                                              20

<210> SEQ ID NO 463
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 463
gatgacaatg gcattaccac                                              20

<210> SEQ ID NO 464
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 464
cctcccacca cgatgacaat                                              20

<210> SEQ ID NO 465
<211> LENGTH: 20
<212> TYPE: DNA
<213> ORGANISM: Artificial Sequence
<220> FEATURE:
<223> OTHER INFORMATION: Antisense oligonucleotide
```

```
<400> SEQUENCE: 465
agctcaggga ttcagctgca                                          20

<210> SEQ ID NO 466
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 466
tgcgttcttg ccaggcatgg                                          20

<210> SEQ ID NO 467
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 467
ttgcggttcc gcagggtgac                                          20

<210> SEQ ID NO 468
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 468
agggccagct ttacaaagcc                                          20

<210> SEQ ID NO 469
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 469
ccaaaggaat aggtgggaac                                          20

<210> SEQ ID NO 470
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 470
gcttgtatac ctcattctct                                          20

<210> SEQ ID NO 471
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 471
ccctcctcaa agatcacctg                                          20

<210> SEQ ID NO 472
<211> LENGTH: 20
```

```
<212> TYPE: DNA
<213> ORGANISM: Artificial Sequence
<220> FEATURE:
<223> OTHER INFORMATION: Antisense oligonucleotide

<400> SEQUENCE: 472
tatacttctg gaacttcttc                                               20

<210> SEQ ID NO 473
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 473
gggcgaaacc aatatacttc                                               20

<210> SEQ ID NO 474
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 474
aagagacctc ggccatggaa                                               20

<210> SEQ ID NO 475
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 475
gcccccaggt gtcagaggag                                               20

<210> SEQ ID NO 476
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 476
gggcttggag tagggcacca                                               20

<210> SEQ ID NO 477
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 477
tcccccacaa cggtggtgat                                               20

<210> SEQ ID NO 478
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 478
```

-continued agcttaggga cggtgatggg                                       20

<210> SEQ ID NO 479
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 479
ctttctgggt cgggtgctcc                                       20

<210> SEQ ID NO 480
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 480
ggtgtggtac aggtcgatgt                                       20

<210> SEQ ID NO 481
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 481
ccagggcctc catgtacatg                                       20

<210> SEQ ID NO 482
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 482
gtgattgtca aagagcttca                                       20

<210> SEQ ID NO 483
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 483
ggaaggccga atttggtctt                                       20

<210> SEQ ID NO 484
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 484
cctccagcac ctcagtctct                                       20

<210> SEQ ID NO 485
<211> LENGTH: 20
<212> TYPE: DNA
<213> ORGANISM: Artificial Sequence

```
<220> FEATURE:
<223> OTHER INFORMATION: Antisense oligonucleotide

<400> SEQUENCE: 485
atgcactcaa gaactcggta                                              20

<210> SEQ ID NO 486
<211> LENGTH: 20
<212> TYPE: DNA
<213> ORGANISM: Artificial Sequence
<220> FEATURE:
<223> OTHER INFORMATION: PCR Primer

<400> SEQUENCE: 486
ggaaccgcaa aggctttgta                                              20

<210> SEQ ID NO 487
<211> LENGTH: 22
<212> TYPE: DNA
<213> ORGANISM: Artificial Sequence
<220> FEATURE:
<223> OTHER INFORMATION: PCR Primer

<400> SEQUENCE: 487
aataggtggg aaccagatca gc                                           22

<210> SEQ ID NO 488
<211> LENGTH: 19
<212> TYPE: DNA
<213> ORGANISM: Artificial Sequence
<220> FEATURE:
<223> OTHER INFORMATION: PCR Probe

<400> SEQUENCE: 488
agctggccct gcgccatgg                                               19

<210> SEQ ID NO 489
<211> LENGTH: 19
<212> TYPE: DNA
<213> ORGANISM: Artificial Sequence
<220> FEATURE:
<223> OTHER INFORMATION: antisense Oligonucleotide

<400> SEQUENCE: 489
cgagaggcgg acgggaccg                                               19

<210> SEQ ID NO 490
<211> LENGTH: 21
<212> TYPE: DNA
<213> ORGANISM: Artificial Sequence
<220> FEATURE:
<223> OTHER INFORMATION: antisense Oligonucleotide

<400> SEQUENCE: 490
cgagaggcgg acgggaccgt t                                            21

<210> SEQ ID NO 491
<211> LENGTH: 21
<212> TYPE: DNA
<213> ORGANISM: Artificial Sequence
<220> FEATURE:
<223> OTHER INFORMATION: complement Oligonucleotide

<400> SEQUENCE: 491
ttgctctccg cctgccctgg c                                            21
```

```
<210> SEQ ID NO 492
<211> LENGTH: 19
<212> TYPE: DNA
<213> ORGANISM: Artificial Sequence
<220> FEATURE:
<223> OTHER INFORMATION: complement Oligonucleotide

<400> SEQUENCE: 492
gctctccgcc tgccctggc                                              19
```

MODULATION OF DIACYLGLYCEROL ACYLTRANSFERASE 2 EXPRESSION

CROSS-REFERENCE TO RELATED APPLICATIONS

This application is a continuation of PCT Application No. PCT/US2004/024384, filed Aug. 18, 2004, which is a continuation-in-part of U.S. application Ser. No. 10/643,801, filed Aug. 18, 2003, the entire contents of each are herein incorporated by reference.

FIELD OF THE INVENTION

The present invention provides compositions and methods for modulating the expression of diacylglycerol acyltransferase 2. In particular, this invention relates to antisense compounds, particularly oligonucleotide compounds, which, in preferred embodiments, hybridize with nucleic acid molecules encoding diacylglycerol acyltransferase 2. Such compounds are shown herein to modulate the expression of diacylglycerol acyltransferase 2.

BACKGROUND OF THE INVENTION

Triglycerides are one of the major energy storage molecules in eukaryotes. The absorption of triglycerides (also called triacylglycerols) from food is a very efficient process which occurs by a series of steps wherein the dietary triacylglycerols are hydrolyzed in the intestinal lumen and then resynthesized within enterocytes. The resynthesis of triacylglycerols can occur via the monoacylglycerol pathway which commences with monoacylglycerol acyltransferase (MGAT) catalyzing the synthesis of diacylglycerol from monoacylglycerol and fatty acyl-CoA. An alternative synthesis of diacylglycerols is provided by the glycerol-phosphate pathway which describes the coupling of two molecules of fatty acyl-CoA to glycerol-3-phosphate. In either case, diacylglycerol is then acylated with another molecule of fatty acyl-CoA in a reaction catalyzed by one of two diacylglycerol acyltransferase enzymes to form the triglyceride (Farese et al., *Curr. Opin. Lipidol.*, 2000, 11, 229-234).

The reaction catalyzed by diacylglycerol acyltransferase is the final and only committed step in triglyceride synthesis. As such, diacylglycerol acyltransferase is involved in intestinal fat absorption, lipoprotein assembly, regulating plasma triglyceride concentrations, and fat storage in adipocytes. The first diacylglycerol acyltransferase, diacylglycerol transferase 1, was identified in 1960 and the human and mouse genes encoding this protein were isolated in 1998 (Cases et al., *Proc. Natl. Acad. Sci. U.S.A.*, 1998, 95, 13018-13023; Oelkers et al., *J. Biol. Chem.*, 1998, 273, 26765-26771). Mice lacking diacylglycerol acyltransferase 1 are viable and can still synthesize triglycerides through other biological routes, suggesting the existence of multiple mechanisms for triglyceride synthesis (Smith et al., *Nat. Genet.*, 2000, 25, 87-90).

A second diacylglycerol transferase, diacylglycerol transferase 2 (also known as DGAT2, diacylglycerol O-transferase 2, acyl-CoA:diacylglycerol acyltransferase 2), was subsequently identified in the fungus Mortierella, humans and mice (Cases et al., *J. Biol. Chem.*, 2001, 276, 38870-38876; Lardizabal et al., *J. Biol. Chem.*, 2001, 276, 38862-38869). Enzymatic assays indicate that this recently identified protein does possess diacylglycerol transferase activity that utilizes a broad range of long chain fatty acyl-CoA substrates (Cases et al., *J. Biol. Chem.*, 2001, 276, 38870-38876).

Diacylglycerol transferase 2 is a member of a family of genes whose sequences are unrelated to diacylglycerol transferase 1. In addition to differing in sequence compared to diacylglycerol transferase 1, in vitro assays illustrate that diacylglycerol transferase 2 has higher activity at lower concentrations of magnesium chloride and oleoyl-CoA (Cases et al., *J. Biol. Chem.*, 2001, 276, 38870-38876). The predicted protein sequence of diacylglycerol transferase 2 contains at least one putative transmembrane domain, three potential N-linked glycosylation sites, six potential protein kinase C phosphorylation consensus sites, as well as sequences in common with a putative glycerol phosphorylation site found in acyltransferase enzymes (Cases et al., *J. Biol. Chem.*, 2001, 276, 38870-38876). The International Radiation Hybrid Mapping Consortium has mapped human diacylglycerol transferase 2 to chromosome 11q13.3.

In human tissues, the highest levels of diacylglycerol transferase 2 are detected in liver and white adipose tissues, with lower levels found in mammary gland, testis and peripheral blood leukocytes (Cases et al., *J. Biol. Chem.*, 2001, 276, 38870-38876). Two mRNA species of 2.4 and 1.8 kilobases are detected in human tissues, whereas the major diacylglycerol transferase 2 mRNA species in mouse tissues is 2.4 kilobases. In addition to liver and white adipose tissues, diacylglycerol transferase 2 is expressed in all segments of the small intestine in mice, with higher expression in the proximal intestine and lower expression in the distal intestine (Cases et al., *J. Biol. Chem.*, 2001, 276, 38870-38876).

Diacylglycerol transferase activity exhibits distinct patterns during postnatal development of the rat liver. As there is no correlation between the mRNA expression and activity patterns, post-translational modifications may participate in the regulation of diacylglycerol transferase 2 activity during rat development (Waterman et al., *J. Lipid Res.*, 2002, 43, 1555-1562).

Diacylglycerol transferase 2 mRNA is preferentially upregulated by insulin treatment, as shown by in vitro assays measuring the diacylglycerol activity from the membrane fraction of cultured mouse adipocytes (Meegalla et al., *Biochem. Biophys. Res. Commun.*, 2002, 298, 317-323). In fasting mice, diacylglycerol transferase 2 expression is greatly reduced, and dramatically increases upon refeeding. The expression patterns of two enzymes that participate in fatty acid synthesis, acetyl-CoA carboxylase and fatty acid synthase, respond to fasting and refeeding in a similar fashion. These results, combined with the observation that diacylglycerol transferase 2 is abundantly expressed in liver, suggest that diacylglycerol transferase 2 is tightly linked to the endogenous fatty acid synthesis pathway (Meegalla et al., *Biochem. Biophys. Res. Commun.*, 2002, 298, 317-323).

Studies of mice harboring a disruption in the diacylglycerol acyltransferase 1 gene provide evidence that diacylglycerol acyltransferase 2 contributes to triglyceride synthesis. Levels of diacylglycerol transferase 2 mRNA expression are similar in intestinal segments from both wild type and diacylglycerol transferase 1-deficient mice (Buhman et al., *J. Biol. Chem.*, 2002, 277, 25474-25479). Using magnesium chloride to distinguish between diacylglycerol transferase 1 and 2 activity, Buhman, et al. observed that, in diacylglycerol transferase 1-deficient mice, diacylglycerol transferase activity is reduced to 50% in the proximal intestine and to 10-15% in the distal intestine (Buhman et al., *J. Biol. Chem.*, 2002, 277, 25474-25479).

Additionally, diacylglycerol transferase 2 mRNA levels are not up-regulated the liver or adipose tissues of diacylglycerol transferase 1-deficient mice, even after weeks of high-fat diet (Cases et al., *J. Biol. Chem.*, 2001, 276, 38870-38876;

Chen et al., *J. Clin. Invest.*, 2002, 109, 1049-1055). However, in ob/ob mice, which have a mutation in the leptin gene that results in obesity, diacylglycerol transferase 2 is more highly expressed than in wild type mice, suggesting that diacylglycerol transferase 2 may be partly responsible for the highly accumulated fat mass seen in these mice. Furthermore, the combined mutations of leptin and diacylglycerol transferase 1 leads to a three-fold elevation in diacylglycerol transferase 2 expression in white adipose tissue, compared to the levels in the same tissue from diacylglycerol transferase 1-deficient mice (Chen et al., *J. Clin. Invest.*, 2002, 109, 1049-1055). Diacylglycerol transferase 2 mRNA is also upregulated in the skin of these mice (Chen et al., *J. Clin. Invest.*, 2002, 109, 175-181). These data suggest leptin normally downregulates diacylglycerol transferase 2 expression, and that the upregulation of diacylglycerol transferase 2 in white adipose tissue in these mice may provide an alternate pathway for the triglyceride synthesis that still occurs in leptin deficient/diacylglycerol transferase 1-deficient mice (Chen et al., *J. Clin. Invest.*, 2002, 109, 1049-1055).

Diacylglycerol acyltransferase 1 knockout mice exhibit interesting phenotypes in that they are lean, resistant to diet-induce obesity, have decreased levels of tissue triglycerides and increased sensitivity to insulin and leptin (Chen et al., *J. Clin. Invest.*, 2002, 109, 1049-1055; Smith et al., *Nat. Genet.*, 2000, 25, 87-90). As diacylglycerol transferase 2 also participates in triglyceride synthesis, interfering with diacylglycerol transferase 2 may similarly lead to reduced body fat content.

The U.S. pre-grant publication Nos. 20030124126 and 20020119138 claim and disclose a nucleic acid molecule encoding human diacylglycerol transferase 2 alpha, as well as compositions, including antisense oligonucleotides, for modulating the activity of said diacylglycerol transferase 2 alpha (Cases et al., 2003).

The U.S. pre-grant publication No. 20030104414 refers to nucleic acid sequences which are members of a group of genes referred to as "protein cluster V" as well as the method for identification of an agent capable of modulating nucleic acid molecules in the protein cluster V group. This application also refers to the use of RNA interference or double-stranded RNA to disrupt the function of protein cluster V gene family members (Attersand, 2003).

The U.S. pre-grant publication No. 20030100480 refers to modifying diacylglycerol transferase activity, including that of diacylglycerol transferase 2, by a variety of methods, including antisense, RNA interference and diacylglycerol transferase 2 antisense plasmid constructs (Smith et al., 2003).

The U.S. pre-grant publication No. 20030028923 refers to a method for modifying the triacylglycerol composition in a plant cell, comprising transforming a plant cell with a nucleic acid construct encoding an enzyme active in the formation of triacylglycerol from diacylglycerol and fatty acyl substrates, including nucleic acid constructs in the antisense orientation. Also referred to is a method for ameliorating a disease or condition associated with altered diacylglycerol acyltransferase activity by administering to a subject a therapeutically effective amount of a diacylglycerol acyltransferase agonist. This application indicates that such antagonists can include antisense molecules (Lardizabal et al., 2003).

The PCT publication WO 00/78961 refers to isolated nucleic acid molecules selected from a group including a nucleic acid sequence encoding diacylglycerol acyltransferase 2. This publication also comments that sense or antisense oligonucleotides binding to target nucleic acid sequences can interfere with transcription or translation of the disclosed and claimed nucleic acid molecules (Baker et al., 2000).

The PCT publication WO 01/77389 refers to polynucleotides selected from a group of sequences including a nucleotide sequence encoding a human diacylglycerol acyltransferase. A method for screening for the altered expression of said polynucleotides and a method for screening a library of molecules that specifically bind to said polynucleotide sequences are discussed (Shiffman et al., 2001).

The PCT publication WO 01/68848 refers to a nucleic acid molecules encoding secreted and transmembrane polypeptides, including a human diacylglycerol acyltransferase 2 nucleic acid molecule, and oligonucleotide probes derived from any of these sequences (Baker et al., 2001).

European Patent Application No. EP 1 308 459 refers to a group of polynucleotide sequences, including a nucleic acid molecule encoding human diacylglycerol acyltransferase 2, and antisense polynucleotides against this group of polynucleotide sequences (Isogai et al., 2003).

The PCT publication WO 02/08260 refers to an isolated, purified polynucleotide sequence with identity to a human diacylglycerol transferase 2 nucleotide sequence. This application also refers to a substantially purified oligonucleotide that includes a region of nucleotide sequence that hybridizes to at least 8 consecutive nucleotides of sense or antisense sequence of a nucleotide sequence selected from a group consisting of sequences with identity to human diacylglycerol acyltransferase 2 (Botstein et al., 2002).

Currently, there are no known therapeutic agents that effectively inhibit the synthesis of diacylglycerol acyltransferase 2. Consequently, there remains a long felt need for additional agents capable of effectively inhibiting diacylglycerol acyltransferase 2 function.

The present invention provides compositions and methods for modulating diacylglycerol acyltransferase 2 expression.

SUMMARY OF THE INVENTION

The present invention is directed to compounds, especially nucleic acid and nucleic acid-like oligomers, which are targeted to a nucleic acid encoding diacylglycerol acyltransferase 2, and which modulate the expression of diacylglycerol acyltransferase 2. Pharmaceutical and other compositions comprising the compounds of the invention are also provided. Further provided are methods of screening for modulators of diacylglycerol acyltransferase 2 and methods of modulating the expression of diacylglycerol acyltransferase 2 in cells, tissues or animals comprising contacting said cells, tissues or animals with one or more of the compounds or compositions of the invention.

Antisense technology is an effective means for reducing the expression of specific gene products and may therefore prove to be uniquely useful in a number of therapeutic, diagnostic, and research applications for the modulation of diacylglycerol acyltransferase 2 expression.

Methods of treating an animal, particularly a human, suspected of having or being prone to a disease or condition associated with expression of diacylglycerol acyltransferase 2 are also set forth herein. Such methods comprise administering a therapeutically or prophylactically effective amount of one or more of the compounds or compositions of the invention to the person in need of treatment.

In one aspect, the invention provides the use of a compound or composition of the invention in the manufacture of a medicament for the treatment of any and all conditions disclosed herein.

DETAILED DESCRIPTION OF THE INVENTION

A. Overview of the Invention

The present invention employs antisense compounds, preferably oligonucleotides and similar species for use in modulating the function or effect of nucleic acid molecules encoding diacylglycerol acyltransferase 2. This is accomplished by providing oligonucleotides that specifically hybridize with one or more nucleic acid molecules encoding diacylglycerol acyltransferase 2. As used herein, the terms "target nucleic acid" and "nucleic acid molecule encoding diacylglycerol acyltransferase 2" have been used for convenience to encompass DNA encoding diacylglycerol acyltransferase 2, RNA (including pre-mRNA and mRNA or portions thereof) transcribed from such DNA, and also cDNA derived from such RNA. The hybridization of a compound of this invention with its target nucleic acid is generally referred to as "antisense". Consequently, the preferred mechanism believed to be included in the practice of some preferred embodiments of the invention is referred to herein as "antisense inhibition." Such antisense inhibition is typically based upon hydrogen bonding-based hybridization of oligonucleotide strands or segments such that at least one strand or segment is cleaved, degraded, or otherwise rendered inoperable. In this regard, it is presently preferred to target specific nucleic acid molecules and their functions for such antisense inhibition.

The functions of DNA to be interfered with can include replication and transcription. Replication and transcription, for example, can be from an endogenous cellular template, a vector, a plasmid construct or otherwise. The functions of RNA to be interfered with can include functions such as translocation of the RNA to a site of protein translation, translocation of the RNA to sites within the cell which are distant from the site of RNA synthesis, translation of protein from the RNA, splicing of the RNA to yield one or more RNA species, and catalytic activity or complex formation involving the RNA which may be engaged in or facilitated by the RNA. One preferred result of such interference with target nucleic acid function is modulation of the expression of diacylglycerol acyltransferase 2. In the context of the present invention, "modulation" and "modulation of expression" mean either an increase (stimulation) or a decrease (inhibition) in the amount or levels of a nucleic acid molecule encoding the gene, e.g., DNA or RNA. Inhibition is often the preferred form of modulation of expression and mRNA is often a preferred target nucleic acid.

In the context of this invention, "hybridization" means the pairing of complementary strands of oligomeric compounds. In the present invention, the preferred mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases which pair through the formation of hydrogen bonds. Hybridization can occur under varying circumstances.

An antisense compound is specifically hybridizable when binding of the compound to the target nucleic acid interferes with the normal function of the target nucleic acid to cause a loss of activity, and there is a sufficient degree of complementarity to avoid non-specific binding of the antisense compound to non-target nucleic acid sequences under conditions in which specific binding is desired, e.g., under physiological conditions in the case of in vivo assays or therapeutic treatment, and under conditions in which assays are performed in the case of in vitro assays.

In the present invention the phrase "stringent hybridization conditions" or "stringent conditions" refers to conditions under which a compound of the invention will hybridize to its target sequence, but to a minimal number of other sequences. Stringent conditions are sequence-dependent and will be different in different circumstances and in the context of this invention, "stringent conditions" under which oligomeric compounds hybridize to a target sequence are determined by the nature and composition of the oligomeric compounds and the assays in which they are being investigated.

"Complementary," as used herein, refers to the capacity hydrogen bonding between the oligonucleotide and the target nucleic acid is considered to be a complementary position. The oligonucleotide and the further DNA, RNA, or oligonucleotide molecule are complementary to each other when a sufficient number of complementary positions in each molecule are occupied by nucleobases which can hydrogen bond with each other. Thus, "specifically hybridizable" and "complementary" are terms which are used to indicate a sufficient degree of precise pairing or complementarity over a sufficient number of nucleobases such that stable and specific binding occurs between the oligonucleotide and a target nucleic acid.

It is understood in the art that the sequence of an antisense compound may be, but need not be, 100% complementary to that of its target nucleic acid to be specifically hybridizable. Moreover, an oligonucleotide may hybridize over one or more segments such that intervening or adjacent segments are not involved in the hybridization event (e.g., a loop structure or hairpin structure). It is preferred that the antisense compounds of the present invention comprise at least 70%, or at least 75%, or at least 80%, or at least 85% sequence complementarity to a target region within the target nucleic acid. Moreover, they may comprise at least 90% sequence complementarity, at least 95% or at least 99% sequence complementarity to the target region within the target nucleic acid sequence to which they are targeted. For example, an antisense compound in which 18 of 20 nucleobases of the antisense compound are complementary to a target region, and would therefore specifically hybridize, would represent 90 percent complementarity. In this example, the remaining non-complementary nucleobases may be clustered or interspersed with complementary nucleobases, and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., *J. Mol. Biol.,* 1990, 215, 403410; Zhang and Madden, *Genome Res.,* 1997, 7, 649-656).

Percent homology, sequence identity, or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489). In some preferred embodiments, homology, sequence identity, or complementarity, between the oligomeric compound and target is between about 50% to about 60%. In some embodiments, homology, sequence identity or complementarity, is between about 60% to about 70%. In some embodiments, homology, sequence identity or complementarity, is between about 70% and about 80%. In further embodiments, homology, sequence identity or complementarity, is between about 80% and about 90%. In some embodiments, homology, sequence identity or complementarity, is about 90%, about 92%, about 94%, about 95%, about 96%, about 97%, about 98%, about 99% or about 100%.

B. Compounds of the Invention

According to the present invention, antisense compounds include antisense oligomeric compounds, antisense oligonucleotides, siRNAs, external guide sequence (EGS) oligonucleotides, alternate splicers, and other oligomeric compounds which hybridize to at least a portion of the target nucleic acid. As such, these compounds may be introduced in the form of single-stranded, double-stranded, circular or hairpin oligomeric compounds and may contain structural elements such as internal or terminal bulges or loops. Once introduced to a system, the compounds of the invention may elicit the action of one or more enzymes or structural proteins to effect modification of the target nucleic acid.

One non-limiting example of such an enzyme is RNase H, a cellular endonuclease which cleaves the RNA strand of an RNA:DNA duplex. It is known in the art that single-stranded antisense compounds that are "DNA-like" elicit RNase H. Activation of RNase H, therefore, results in cleavage of the RNA target, thereby greatly enhancing the efficiency of oligonucleotide-mediated inhibition of gene expression. Similar roles have been postulated for other ribonucleases such as those in the RNase III and ribonuclease L family of enzymes.

While the one form of antisense compound is a single-stranded antisense oligonucleotide, in many species the introduction of double-stranded structures, such as double-stranded RNA (dsRNA) molecules, has been shown to induce potent and specific antisense-mediated reduction of the function of a gene or its associated gene products. This phenomenon occurs in both plants and animals and is believed to have an evolutionary connection to viral defense and transposon silencing.

The first evidence that dsRNA could lead to gene silencing in animals came in 1995 from work in the nematode, *Caenorhabditis elegans* (Guo and Kempheus, *Cell,* 1995, 81, 611-620). The primary interference effects of dsRNA are posttranscriptional (Montgomery et al., *Proc. Natl. Acad. Sci. USA,* 1998, 95, 15502-15507). The posttranscriptional antisense mechanism defined in *Caenorhabditis elegans* resulting from exposure to double-stranded RNA (dsRNA) has since been designated RNA interference (RNAi). This term has been generalized to mean antisense-mediated gene silencing involving the introduction of dsRNA leading to the sequence-specific reduction of endogenous targeted mRNA levels (Fire et al., *Nature,* 1998, 391, 806-811). Recently, the single-stranded RNA oligomers of antisense polarity of the dsRNAs have been reported to be the potent inducers of RNAi (Tijsterman et al., *Science,* 2002, 295, 694-697).

The antisense compounds of the present invention also include modified compounds in which a different base is present at one or more of the nucleotide positions in the compound. For example, if the first nucleotide is an adenosine, modified compounds may be produced which contain thymidine, guanosine or cytidine at this position. This may be done at any of the positions of the antisense compound. These compounds are then tested using the methods described herein to determine their ability to inhibit expression of diacylglycerol acyltransferase 2 mRNA.

In the context of this invention, the term "oligomeric compound" refers to a polymer or oligomer comprising a plurality of monomeric units. In the context of this invention, the term "oligonucleotide" refers to an oligomer or polymer of ribonucleic acid (RNA) or deoxyribonucleic acid (DNA) or mimetics, chimeras, analogs and homologs thereof. This term includes oligonucleotides composed of naturally occurring nucleobases, sugars and covalent internucleoside (backbone) linkages as well as oligonucleotides having non-naturally occurring portions which function similarly. Such modified or substituted oligonucleotides are often preferred over native forms because of desirable properties such as, for example, enhanced cellular uptake, enhanced affinity for a target nucleic acid and increased stability in the presence of nucleases.

While oligonucleotides are a preferred form of the antisense compounds of this invention, the present invention comprehends other families of antisense compounds as well, including but not limited to oligonucleotide analogs and mimetics such as those described herein.

The antisense compounds in accordance with this invention preferably comprise from about 8 to about 80 nucleobases (i.e. from about 8 to about 80 linked nucleosides). One of ordinary skill in the art will appreciate that the invention embodies compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleobases in length.

In one embodiment, the antisense compounds of the invention are 12 to 50 nucleobases in length. One having ordinary skill in the art will appreciate that this embodies compounds of 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleobases in length.

In one embodiment, the antisense compounds of the invention are 13 to 40 nucleobases in length. One having ordinary skill in the art will appreciate that this embodies compounds of 13, 14, 15, 16, 17, 18, 19, 20, 21, 22, 23, 24, 25, 26, 27, 28, 29, 30, 31, 32, 33, 34, 35, 36, 37, 38, 39 or 40 nucleobases in length.

In another embodiment, the antisense compounds of the invention are 15 to 30 nucleobases in length. One having ordinary skill in the art will appreciate that this embodies compounds of 15, 16, 17, 18, 19, 20, 21, 22, 23, 24, 25, 26, 27, 28, 29, or 30 nucleobases in length.

In further embodiments, the antisense compounds are oligonucleotides from about 12 to about 50 nucleobases, or from about 13 to 40 nucleobases, or from about 15 to about 30 nucleobases.

In another embodiment, the antisense compounds comprise at least 8 contiguous nucleobases of an antisense compound disclosed herein.

Antisense compounds 8-80 nucleobases in length comprising a stretch of at least eight (8) consecutive nucleobases selected from within the illustrative antisense compounds are considered to be suitable antisense compounds as well.

Further antisense compounds include oligonucleotide sequences that comprise at least the 8 consecutive nucleobases from the 5'-terminus of one of the illustrative preferred antisense compounds (the remaining nucleobases being a consecutive stretch of the same oligonucleotide beginning immediately upstream of the 5'-terminus of the antisense compound that is specifically hybridizable to the target nucleic acid and continuing until the oligonucleotide contains about 8 to about 80 nucleobases). Similarly, antisense compounds are represented by oligonucleotide sequences that comprise at least the 8 consecutive nucleobases from the 3'-terminus of one of the illustrative preferred antisense compounds (the remaining nucleobases being a consecutive stretch of the same oligonucleotide beginning immediately downstream of the 3'-terminus of the antisense compound that is specifically hybridizable to the target nucleic acid and continuing until the oligonucleotide contains about 8 to about 80 nucleobases). It is also understood that antisense compounds may be represented by oligonucleotide sequences that comprise at least 8 consecutive nucleobases from an internal portion of the sequence of an illustrative preferred antisense compound, and may extend in either or both directions until the oligonucleotide contains about 8 to about 80 nucleobases.

In one embodiment, the antisense compound includes SEQ ID NOS: 20, 21, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 56, 57, 58, 60, 61, 62, 63, 64, 65, 66, 68, 69, 70, 71, 72, 73, 75, 76, 77, 78, 80, 81, 82, 83, 84, 85, 86, 87, 88, 89, 90, 91, 92, 94, 95, 96, 97, 101, 109, 114, 115, 120, 121, 122, 123, 124, 127, 128, 130, 133, 136 or 142. In still other embodiments, the antisense compounds are one or more of SEQ ID NOS: 277 through 411.

In another embodiment, the antisense compound includes SEQ ID NOS: 21, 24, 25, 26, 28, 29, 35, 36, 47, 49, 57, 62, 65, 66, 71, 73, 77, 81, 82, 90, 92 or 94.

One having skill in the art armed with the preferred antisense compounds illustrated herein will be able, without undue experimentation, to identify further preferred antisense compounds.

C. Targets of the Invention

"Targeting" an antisense compound to a particular nucleic acid molecule, in the context of this invention, can be a multistep process. The process usually begins with the identification of a target nucleic acid whose function is to be modulated. This target nucleic acid may be, for example, a cellular gene (or mRNA transcribed from the gene) whose expression is associated with a particular disorder or disease state, or a nucleic acid molecule from an infectious agent. In the present invention, the target nucleic acid encodes diacylglycerol acyltransferase 2.

The targeting process usually also includes determination of at least one target region, segment, or site within the target nucleic acid for the antisense interaction to occur such that the desired effect, e.g., modulation of expression, will result. Within the context of the present invention, the term "region" is defined as a portion of the target nucleic acid having at least one identifiable structure, function, or characteristic. Within regions of target nucleic acids are segments. "Segments" are defined as smaller or sub-portions of regions within a target nucleic acid. "Sites," as used in the present invention, are defined as positions within a target nucleic acid.

Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes having a translation initiation codon with the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA transcribed from a gene encoding diacylglycerol acyltransferase 2, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5-TAG and 5'-TGA, respectively).

The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. Consequently, the "start codon region" (or "translation initiation codon region") and the "stop codon region" (or "translation termination codon region") are all regions which may be targeted effectively with the antisense compounds of the present invention.

The open reading frame (ORF) or "coding region," which is known in the art to refer to the region between the translation initiation codon and the translation termination codon, is also a region which may be targeted effectively. Within the context of the present invention, a preferred region is the intragenic region encompassing the translation initiation or termination codon of the open reading frame (ORF) of a gene.

Other target regions include the 5' untranslated region (5'UTR), known in the art to refer to the portion of an mRNA in the 5' direction from the translation initiation codon, and thus including nucleotides between the 5' cap site and the translation initiation codon of an mRNA (or corresponding nucleotides on the gene), and the 3' untranslated region (3'UTR), known in the art to refer to the portion of an mRNA in the 3' direction from the translation termination codon, and thus including nucleotides between the translation termination codon and 3' end of an mRNA (or corresponding nucleotides on the gene). The 5' cap-site of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap site. It is also preferred to target the 5' cap region.

Accordingly, the present invention provides antisense compounds that target a portion of nucleotides 1-2439 as set forth in SEQ ID NO: 4. In another embodiment, the antisense compounds target at least an 8-nucleobase portion of nucleotides 1-230, comprising the 5'UTR as set forth in SEQ ID NO: 4. In another embodiment, the antisense compounds target at least an 8-nucleobase portion of nucleotides 1395-2439, comprising the 3'UTR as set forth in SEQ ID NO: 4. In another embodiment, the antisense compounds target at least an 8-nucleobase portion of nucleotides 231-1394, comprising the coding region as set forth in SEQ ID NO: 4. In still other embodiments, the antisense compounds target at least an 8-nucleobase portion of a "preferred target segment" (as defined herein) as set forth in Table 3 or additional Tables in the Examples below.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence, resulting in exon-exon junctions at the sites where exons are joined. Targeting exon-exon junctions can be useful in situations where the overproduction of a normal splice product is implicated in disease, or where the overproduction of an aberrant splice product is implicated in disease. Targeting splice sites, i.e., intron-exon junctions or exon-intron junctions, may also be particularly useful in situations where aberrant splicing is implicated in disease, or where an overproduction of a particular splice product is implicated in disease. Aberrant fusion junctions due to rearrangements or deletions are also preferred target sites. mRNA transcripts produced via the process of splicing of two (or more) mRNAs from different gene sources, known as "fusion transcripts", are also suitable target sites. It is also known that introns can be effectively targeted using antisense compounds targeted to, for example, DNA or pre-mRNA.

It is also known in the art that alternative RNA transcripts can be produced from the same genomic region of DNA. These alternative transcripts are generally known as "variants". More specifically, "pre-mRNA variants" are transcripts produced from the same genomic DNA that differ from other transcripts produced from the same genomic DNA in either their start or stop position and contain both intronic and exonic sequence.

Upon excision of one or more exon or intron regions, or portions thereof during splicing, pre-mRNA variants produce smaller "mRNA variants". Consequently, mRNA variants are processed pre-mRNA variants, and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

It is also known in the art that variants can be produced through the use of alternative signals to start or stop transcription and that pre-mRNAs and mRNAs can possess more that one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites. Within the context of the invention, the types of variants described herein are also preferred target nucleic acids.

The locations on the target nucleic acid to which the preferred antisense compounds hybridize are hereinbelow referred to as "preferred target segments." As used herein the term "preferred target segment" is defined as at least an 8-nucleobase portion of a target region to which an active antisense compound is targeted. While not wishing to be bound by theory, it is presently believed that these target segments represent portions of the target nucleic acid which are accessible for hybridization.

While the specific sequences of certain preferred target segments are set forth herein, one of skill in the art will recognize that these serve to illustrate and describe particular embodiments within the scope of the present invention. Additional preferred target segments may be identified by one having ordinary skill.

Target segments 8-80 nucleobases in length comprising a stretch of at least eight (8) consecutive nucleobases selected from within the illustrative preferred target segments are considered to be suitable for targeting as well.

Target segments can include DNA or RNA sequences that comprise at least the 8 consecutive nucleobases from the 5'-terminus of one of the illustrative preferred target segments (the remaining nucleobases being a consecutive stretch of the same DNA or RNA beginning immediately upstream of the 5'-terminus of the target segment and continuing until the DNA or RNA contains about 8 to about 80 nucleobases). Similarly preferred target segments are represented by DNA or RNA sequences that comprise at least the 8 consecutive nucleobases from the 3'-terminus of one of the illustrative preferred target segments (the remaining nucleobases being a consecutive stretch of the same DNA or RNA beginning immediately downstream of the 3'-terminus of the target segment and continuing until the DNA or RNA contains about 8 to about 80 nucleobases). It is also understood that preferred antisense target segments may be represented by DNA or RNA sequences that comprise at least 8 consecutive nucleobases from an internal portion of the sequence of an illustrative preferred target segment, and may extend in either or both directions until the oligonucleotide contains about 8 to about 80 nucleobases. One having skill in the art armed with the preferred target segments illustrated herein will be able, without undue experimentation, to identify further preferred target segments.

Once one or more target regions, segments or sites have been identified, antisense compounds are chosen which are sufficiently complementary to the target, i.e., hybridize sufficiently well and with sufficient specificity, to give the desired effect.

The oligomeric antisense compounds can also be targeted to regions of a target nucleobase sequence, such as those disclosed herein (e.g., in Example 13) All regions of a nucleobase sequence to which an oligomeric antisense compound can be targeted, wherein the regions are greater than or equal to 8 and less than or equal to 80 nucleobases, are described as follows:

Let $R(n, n+m-1)$ be a region from a target nucleobase sequence, where "n" is the 5'-most nucleobase position of the region, where "n+m-1" is the 3'-most nucleobase position of the region and where "m" is the length of the region. A set "$S(m)$", of regions of length "m" is defined as the regions where n ranges from 1 to $L-m+1$, where L is the length of the target nucleobase sequence and $L>m$. A set, "A", of all regions can be constructed as a union of the sets of regions for each length from where m is greater than or equal to 8 and is less than or equal to 80.

This set of regions can be represented using the following mathematical notation:

$$A = \bigcup_m S(m) \text{ where } m \in N \mid 8 \leq m \leq 80 \text{ and}$$

$$S(m) = \{R_{n,n+m-1} \mid n \in \{1, 2, 3, \ldots, L-m+1\}\}$$

where the mathematical operator $\mid$ indicates "such that", where the mathematical operator $\in$ indicates "a member of a set" (e.g. $y \in Z$ indicates that element y is a member of set Z), where x is a variable, where N indicates all natural numbers, defined as positive integers, and where the mathematical operator $\bigcup$ indicates "the union of sets".

For example, the set of regions for m equal to 8, 20 and 80 can be constructed in the following manner. The set of regions, each 8 nucleobases in length, $S(m=8)$, in a target nucleobase sequence 100 nucleobases in length (L=100), beginning at position 1 (n=1) of the target nucleobase sequence, can be created using the following expression:

$$S(8)=\{R_{1,8}|n\epsilon\{1,2,3,\ldots,93\}\}$$

and describes the set of regions comprising nucleobases 1-8, 2-9, 3-10, 4-11, 5-12, 6-13, 7-14, 8-15, 9-16, 10-17, 11-18, 12-19, 13-20, 14-21, 15-22, 16-23, 17-24, 18-25, 19-26, 20-27, 21-28, 22-29, 23-30, 24-31, 25-32, 26-33, 27-34, 28-35, 29-36, 30-37, 31-38, 32-39, 33-40, 34-41, 35-42, 36-43, 37-44, 38-45, 39-46, 40-47, 41-48, 42-49, 43-50, 44-51, 45-52, 46-53, 47-54, 48-55, 49-56, 50-57, 51-58, 52-59, 53-60, 54-61, 55-62, 56-63, 57-64, 58-65, 59-66, 60-67, 61-68, 62-69, 63-70, 64-71, 65-72, 66-73, 67-74, 68-75, 69-76, 70-77, 71-78, 72-79, 73-80, 74-81, 75-82, 76-83, 77-84, 78-85, 79-86, 80-87, 81-88, 82-89, 83-90, 84-91, 85-92, 86-93, 87-94, 88-95, 89-96, 90-97, 91-98, 92-99, 93-100.

An additional set for regions 20 nucleobases in length, in a target sequence 100 nucleobases in length, beginning at position 1 of the target nucleobase sequence, can be described using the following expression:

$$S(20)=\{R_{1,20}|n\epsilon\{1,2,3,\ldots,81\}\}$$

and describes the set of regions comprising nucleobases 1-20, 2-21, 3-22, 4-23, 5-24, 6-25, 7-26, 8-27, 9-28, 10-29, 11-30, 12-31, 13-32, 14-33, 15-34, 16-35, 17-36, 18-37, 19-38, 20-39, 21-40, 22-41, 23-42, 24-43, 25-44, 26-45, 27-46, 28-47, 29-48, 30-49, 31-50, 32-51, 33-52, 34-53, 35-54, 36-55, 37-56, 38-57, 39-58, 40-59, 41-60, 42-61, 43-62, 44-63, 45-64, 46-65, 47-66, 48-67, 49-68, 50-69, 51-70, 52-71, 53-72, 54-73, 55-74, 56-75, 57-76, 58-77, 59-78, 60-79, 61-80, 62-81, 63-82, 64-83, 65-84, 66-85, 67-86, 68-87, 69-88, 70-89, 71-90, 72-91, 73-92, 74-93, 75-94, 76-95, 77-96, 78-97, 79-98, 80-99, 81-100.

An additional set for regions 80 nucleobases in length, in a target sequence 100 nucleobases in length, beginning at position 1 of the target nucleobase sequence, can be described using the following expression:

$$S(80)=\{R_{1,80}|n\epsilon\{1,2,3,\ldots,21\}\}$$

and describes the set of regions comprising nucleobases 1-80, 2-81, 3-82, 4-83, 5-84, 6-85, 7-86, 8-87, 9-88, 10-89, 11-90, 12-91, 13-92, 14-93, 15-94, 16-95, 17-96, 18-97, 19-98, 20-99, 21-100.

Thus, in this example, A would include regions 1-8, 2-9, 3-10 . . . 93-100, 1-20, 2-21, 3-22 . . . 81-100, 1-80, 2-81, 3-82 . . . 21-100.

The union of these aforementioned example sets and other sets for lengths from 10 to 19 and 21 to 79 can be described using the mathematical expression:

$$A = \bigcup_m S(m)$$

where U represents the union of the sets obtained by combining all members of all sets.

The mathematical expressions described herein define all possible target regions in a target nucleobase sequence of any length L, where the region is of length m, and where m is greater than or equal to 8 and less than or equal to 80 nucleobases, and where m is less than L, and where n is less than L−m+1.

D. Screening and Target Validation

In a further embodiment, the "preferred target segments" identified herein may be employed in a screen for additional compounds that modulate the expression of diacylglycerol acyltransferase 2. "Modulators" are those compounds that decrease or increase the expression of a nucleic acid molecule encoding diacylglycerol acyltransferase 2 and which comprise at least an 8-nucleobase portion which is complementary to a preferred target segment. The screening method comprises the steps of contacting a preferred target segment of a nucleic acid molecule encoding diacylglycerol acyltransferase 2 with one or more candidate modulators, and selecting for one or more candidate modulators which decrease or increase the expression of a nucleic acid molecule encoding diacylglycerol acyltransferase 2. Once it is shown that the candidate modulator or modulators are capable of modulating (e.g. either decreasing or increasing) the expression of a nucleic acid molecule encoding diacylglycerol acyltransferase 2, the modulator may then be employed in further investigative studies of the function of diacylglycerol acyltransferase 2, or for use as a research, diagnostic, or therapeutic agent in accordance with the present invention.

The preferred target segments of the present invention may be also be combined with their respective complementary antisense compounds of the present invention to form stabilized double-stranded (duplexed) oligonucleotides.

Such double stranded oligonucleotide moieties have been shown in the art to modulate target expression and regulate translation as well as RNA processing via an antisense mechanism. Moreover, the double-stranded moieties may be subject to chemical modifications (Fire et al., *Nature*, 1998, 391, 806-811; Timmons and Fire, *Nature* 1998, 395, 854; Timmons et al., *Gene*, 2001, 263, 103-112; Tabara et al., *Science*, 1998, 282, 430-431; Montgomery et al., *Proc. Natl. Acad. Sci. USA*, 1998, 95, 15502-15507; Tuschl et al., *Genes Dev.*, 1999, 13, 3191-3197; Elbashir et al., *Nature*, 2001, 411, 494-498; Elbashir et al., *Genes Dev.* 2001, 15, 188-200). For example, such double-stranded moieties have been shown to inhibit the target by the classical hybridization of the antisense strand of the duplex to the target, thereby triggering enzymatic degradation of the target (Tijsterman et al., *Science*, 2002, 295, 694-697).

The compounds of the present invention can also be applied in the areas of drug discovery and target validation. The present invention comprehends the use of the compounds and preferred target segments identified herein in drug discovery efforts to elucidate relationships that exist between diacylglycerol acyltransferase 2 and a disease state, phenotype, or condition. These methods include detecting or modulating diacylglycerol acyltransferase 2 comprising contacting a sample, tissue, cell, or organism with the compounds of the present invention, measuring the nucleic acid or protein level of diacylglycerol acyltransferase 2 and/or a related phenotypic or chemical endpoint at some time after treatment, and optionally comparing the measured value to a non-treated sample or sample treated with a further compound of the invention. These methods can also be performed in parallel or in combination with other experiments to determine the function of unknown genes for the process of target validation or to determine the validity of a particular gene product as a target for treatment or prevention of a particular disease, condition, or phenotype.

E. Kits, Research Reagents, Diagnostics, and Therapeutics

The antisense compounds of the present invention are utilized for diagnostics, therapeutics, prophylaxis and as research reagents and kits. Furthermore, antisense oligonucleotides, which are able to inhibit gene expression with exquisite specificity, are often used by those of ordinary skill to elucidate the function of particular genes or to distinguish between functions of various members of a biological pathway.

For use in kits and diagnostics, the compounds of the present invention, either alone or in combination with other compounds or therapeutics, are used as tools in differential and/or combinatorial analyses to elucidate expression patterns of a portion or the entire complement of genes expressed within cells and tissues.

As one nonlimiting example, expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

Examples of methods of gene expression analysis known in the art include DNA arrays or microarrays (Brazma and Vilo, *FEBS Lett.*, 2000, 480, 17-24; Celis, et al., *FEBS Lett.*, 2000, 480, 2-16), SAGE (serial analysis of gene expression) (Madden, et al., *Drug Discov. Today*, 2000, 5, 415-425), READS (restriction enzyme amplification of digested cDNAs) (Prashar and Weissman, *Methods Enzymol.*, 1999, 303, 258-72), TOGA (total gene expression analysis) (Sutcliffe, et al., *Proc. Natl. Acad. Sci. U.S.A.*, 2000, 97, 1976-81), protein arrays and proteomics (Celis, et al., *FEBS Lett.*, 2000, 480, 2-16; Jungblut, et al., *Electrophoresis*, 1999, 20, 2100-10), expressed sequence tag (EST) sequencing (Celis, et al., *FEBS Lett.*, 2000, 480, 2-16; Larsson, et al., *J. Biotechnol.*, 2000, 80, 143-57), subtractive RNA fingerprinting (SuRF) (Fuchs, et al., *Anal. Biochem.*, 2000, 286, 91-98; Larson, et al., *Cytometry*, 2000, 41, 203-208), subtractive cloning, differential display (DD) (Jurecic and Belmont, *Curr. Opin. Microbiol.*, 2000, 3, 316-21), comparative genomic hybridization (Carulli, et al., *J. Cell Biochem. Suppl.*, 1998, 31, 286-96), FISH (fluorescent in situ hybridization) techniques (Going and Gusterson, *Eur. J. Cancer*, 1999, 35, 1895-904) and mass spectrometry methods (To, *Comb. Chem. High Throughput Screen*, 2000, 3, 235-41).

The antisense compounds of the invention are useful for research and diagnostics, because these compounds hybridize to nucleic acids encoding diacylglycerol acyltransferase 2. The primers and probes disclosed herein are useful in methods requiring the specific detection of nucleic acid molecules encoding diacylglycerol acyltransferase 2 and in the amplification of said nucleic acid molecules for detection or for use in further studies of diacylglycerol acyltransferase 2. Hybridization of the primers and probes with a nucleic acid encoding diacylglycerol acyltransferase 2 can be detected by means known in the art. Such means may include conjugation of an enzyme to the primer or probe or any other suitable detection means. Kits using such detection means for detecting the level of diacylglycerol acyltransferase 2 in a sample may also be prepared.

The invention further provides for the use of a compound or composition of the invention in the manufacture of a medicament for the treatment of any and all conditions disclosed herein.

The specificity and sensitivity of antisense are also harnessed by those of skill in the art for therapeutic uses. Antisense compounds have been employed as therapeutic moieties in the treatment of disease states in animals, including humans. Antisense oligonucleotide drugs, including ribozymes, have been safely and effectively administered to humans and numerous clinical trials are underway. It is thus established that antisense compounds can be useful therapeutic modalities that can be configured to be useful in treatment regimes for the treatment of cells, tissues and animals, especially humans.

For therapeutics, an animal, preferably a human, suspected of having a disease or disorder which can be treated by modulating the expression of diacylglycerol acyltransferase 2 is treated by administering antisense compounds in accordance with this invention. For example, in one non-limiting embodiment, the methods comprise the step of administering to the animal in need of treatment, a therapeutically effective amount of a diacylglycerol acyltransferase 2 inhibitor. The diacylglycerol acyltransferase 2 inhibitors of the present invention effectively inhibit the activity of the diacylglycerol acyltransferase 2 protein or inhibit the expression of the diacylglycerol acyltransferase 2 protein. In one embodiment, the activity or expression of diacylglycerol acyltransferase 2 in an animal is inhibited by about 10%. Preferably, the activity or expression of diacylglycerol acyltransferase 2 in an animal is inhibited by about 30%. More preferably, the activity or expression of diacylglycerol acyltransferase 2 in an animal is inhibited by 50% or more. Thus, the antisense compounds modulate expression of diacylglycerol acyltransferase 2 mRNA by at least 10%, by at least 20%, by at least 25%, by at least 30%, by at least 40%, by at least 50%, by at least 60%, by at least 70%, by at least 75%, by at least 80%, by at least 85%, by at least 90%, by at least 95%, by at least 98%, by at least 99%, or by 100%.

For example, the reduction of the expression of diacylglycerol acyltransferase 2 may be measured in serum, adipose tissue, liver or any other body fluid, tissue or organ of the animal. Preferably, the cells contained within said fluids, tissues or organs being analyzed contain a nucleic acid molecule encoding diacylglycerol acyltransferase 2 protein and/or the diacylglycerol acyltransferase 2 protein itself.

The antisense compounds of the invention can be utilized in pharmaceutical compositions by adding an effective amount of a compound to a suitable pharmaceutically acceptable diluent or carrier. The compounds and methods of the invention may also be useful prophylactically.

The antisense compounds of the present invention are also useful for identifying diseased states associated with diacylglycerol acyltransferase 2 expression. The methods include identifying the presence of a nucleic acid encoding diacylglycerol acyltransferase 2 in a sample using at least one of the primers comprising SEQ ID NOs: 6 or 7, or the probe comprising SEQ ID NO: 8.

The antisense compounds are further useful for treating or preventing a variety of conditions. Typically, the compounds of the present invention are utilized to ameliorate or lessen the severity of a condition in an animal. The conditions can include cardiovascular disorder, obesity such as diet induced obesity, diabetes, cholesterolemia, and liver steatosis, among others. There are several physical indicia of obesity and include increased fat, among others. The treatment or prevention of a condition using the compounds of the invention can include contacting an animal with an effective amount of a compound of the invention. Preferably, expression of diacylglycerol acyltransferase 2 is inhibited and the measurement of one or more physical indicia of the condition indicates a lessening of the severity of the condition. Typically, the animal is obese.

The antisense compounds are additionally utilized for lowering certain components of blood from an animal. Typically, the compounds of the invention are useful for lowering serum free fatty acids, serum triglycerides, lowering HDL cholesterol, lowering total serum cholesterol, plasma or serum insulin, or hepatic triglycerides in an animal. Typically, the animal is contacted with an effective amount of a compound of the invention. Preferably, the plasma insulin levels are lowered at about two or four weeks after contacting the animal with a compound of the invention.

The compounds of the invention are also useful in inhibiting the expression of diacylglycerol acyltransferase 2 in a cell or tissue of an animal. The method includes contacting the cell or tissue with a compound of the invention. Preferably, expression of diacylglycerol acyltransferase 2 is inhibited in the present method. Typically, the tissue of the animal is white adipose tissue or brown adipose tissue.

The compounds of the invention are further useful in methods for modulating fatty acid synthesis, lipogenesis, or gluconeogenesis, among others, in an animal. Typically, the animal is contacted with a compound of the invention. The modulation of lipogenesis can be determined by a change in the mRNA level of a nucleic acid encoding a lipogenic gene. The lipogenic gene is selected from among glycerol kinase, ATP-citrate lyase, acetyl-CoA carboxylase 1, acetyl-CoA carboxylase 2, fatty acid synthase, carnitine palmitoyltransferase I, stearoyl-CoA desaturase, HMG-CoA reductase, lipoprotein lipase and sterol regulatory binding element protein 1.

The compounds of the invention are additionally useful for reducing the liver weight of an animal. For this use, the animal is contacted with a compound of the invention. Typically, the animal is obese or diabetic.

F. Modifications

As is known in the art, a nucleoside is a base-sugar combination. The base portion of the nucleoside is normally a heterocyclic base sometimes referred to as a "nucleobase" or simply a "base". The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound, however, linear compounds are generally preferred. In addition, linear compounds may have internal nucleobase complementarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Modified Internucleoside Linkages (Backbones)

Antisense compounds useful in this invention include oligonucleotides containing modified backbones or non-natural internucleoside linkages. As used herein, and "oligonucleotide mimetic" or "mimetic" refers to any compound of the invention which is modified from the naturally occurring RNA or DNA nucleic acids. As defined herein, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be a basic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, each of which is herein incorporated by reference.

Modified Sugar and Internucleoside Linkages-Mimetics

In other preferred antisense compounds, e.g., oligonucleotide mimetics, both the sugar and the internucleoside linkage (i.e. the backbone) of the nucleotide units are replaced with novel groups. The nucleobase units are maintained for hybridization with an appropriate target nucleic acid. One such oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., *Science*, 1991, 254, 1497-1500.

In certain embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also included are oligonucleotides having morpholino backbone structures of the above-referenced U.S. Pat. No. 5,034,506.

Modified Sugars

Oligonucleotide mimetics may also contain one or more substituted sugar moieties. As such these may comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[($CH_2$)$_n$O]$_m$$CH_3$, O($CH_2$)$_n$O$CH_3$, O($CH_2$)$_n$$NH_2$, O($CH_2$)$_n$$CH_3$, O($CH_2$)$_n$$ONH_2$, and O($CH_2$)$_n$ON[($CH_2$)$_n$$CH_3$]$_2$, where n and m are from 1 to about 10. Other oligonucleotide mimetics may comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. One modification includes 2'-methoxyethoxy (2'-O—$CH_2CH_2OCH_3$, also known as 2'-O-(2-methoxyethyl) or 2'-O-methoxyethyl or 2'-MOE) (Martin et al., *Helv. Chim. Acta*, 1995, 78, 486-504) i.e., an alkoxyalkoxy group. A further modification includes 2'-dimethylaminooxyethoxy, i.e., a O($CH_2$)$_2$ON($CH_3$)$_2$ group, also known as 2'-DMAOE, as described in examples hereinbelow, and 2'-dimethylaminoethoxyethoxy (also known in the art as 2'-O-dimethyl-amino-ethoxy-ethyl or 2'-DMAEOE), i.e., 2'-O—$CH_2$—O—$CH_2$—N($CH_3$)$_2$, also described in examples hereinbelow.

Other modifications include 2'-methoxy (2'-O—$CH_3$), 2'-amino (2'-$NH_2$) 2'-aminopropoxy (2'-O$CH_2CH_2CH_2NH_2$), 2'-allyl (2'-$CH_2$—CH=$CH_2$), 2'-O-allyl (2'-O—$CH_2$—CH=$CH_2$) and 2'-fluoro (2'-F). The 2'-modification may be in the arabino (up) position or ribo (down) position. One 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotide mimetics involving the sugar, such as cyclobutyl moieties in place of the pentofuranosyl sugar are also within the scope of the present invention. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, each of which is herein incorporated by reference in its entirety.

A further modification of the sugar includes Locked Nucleic Acids (LNAs) in which the 2'-hydroxyl group is linked to the 3' or 4' carbon atom of the sugar ring, thereby forming a bicyclic sugar moiety. The linkage is preferably a methylene (—$CH_2$—)$_n$ group bridging the 2' oxygen atom and the 4' carbon atom wherein n is 1 or 2. However, the present invention comprehends ethylene linkages as well. LNAs and preparation thereof are described in International Patent Publication Nos. WO 98/39352 and WO 99/14226.

Natural and Modified Nucleobases

Oligonucleotide mimetics also include nucleobase (often referred to in the art as heterocyclic base or simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine (1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858-859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Anti-* sense Research and Applications, pages 289-302, Crooke, S. T. and Lebleu, B., ed., CRC Press, 1993. Certain of these nucleobases are particularly useful for increasing the binding affinity of the compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,830,653; 5,763,588; 6,005,096; 5,681,941; and 5,570,692, each of which is herein incorporated by reference.

Conjugates

Another modification of the antisense compounds of the invention involves chemically linking to the antisense compound one or more moieties or conjugates which enhance the activity, cellular distribution or cellular uptake of the oligonucleotide. These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterol, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application No. PCT/US92/09196, filed Oct. 23, 1992, and U.S. Pat. No. 6,287,860, the entire disclosures of which are incorporated herein by reference. Conjugate moieties include but are not limited to lipid moieties such as a cholesterol moiety, cholic acid, a thioether, e.g., hexyl-S-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety.

Antisense compounds of the invention may also be conjugated to drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. Pat. No. 6,656,730 which is incorporated herein by reference in its entirety.

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

Oligomeric compounds used in the compositions of the present invention can also be modified to have one or more stabilizing groups that are generally attached to one or both termini of oligomeric compounds to enhance properties such as for example nuclease stability. Included in stabilizing groups are cap structures. By "cap structure or terminal cap moiety" is meant chemical modifications, which have been incorporated at either terminus of oligonucleotides (see for example Wincott et al. and International Patent Publication No. WO 97/26270, incorporated by reference herein). These terminal modifications protect the oligomeric compounds having terminal nucleic acid molecules from exonuclease degradation, and can help in delivery and/or localization within a cell. The cap can be present at the 5'-terminus (5'-cap) or at the 3'-terminus (3'-cap) or at both termini. In non-limiting examples, the 5'-cap includes inverted abasic residue (moiety), 4',5'-methylene nucleotide; 1-(beta-D-erythrofuranosyl) nucleotide, 4'-thio nucleotide, carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl ribonucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety (for more details see Wincott et al., International Patent Publication No. WO 97/26270, incorporated by reference herein).

Particularly preferred 3'-cap structures of the present invention include, for example 4',5'-methylene nucleotide; 1-(beta-D-erythrofuranosyl) nucleotide; 4'-thio nucleotide, carbocyclic nucleotide; 5'-amino-alkyl phosphate; 1,3-di-amino-2-propyl phosphate, 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moieties (for more details see Beaucage and Tyer, 1993, Tetrahedron 49, 1925; incorporated by reference herein).

Further 3' and 5'-stabilizing groups that can be used to cap one or both ends of an oligomeric compound to impart nuclease stability include those disclosed in International Patent Publication No. WO 03/004602, published Jan. 16, 2003.

Chimeric Compounds

It is not necessary for all positions in a given compound or oligonucleotide mimetic to be uniformly modified, and in fact one or more of the aforementioned modifications may be incorporated in a single compound or even at a single nucleoside within an oligonucleotide.

The present invention also includes antisense compounds or mimetics which are chimeric compounds. "Chimeric" antisense compounds or "chimeras," in the context of this invention, are antisense compounds, particularly oligonucleotides, which contain at least two chemically distinct regions, each made up of at least one monomer unit, i.e., a nucleotide in the case of an oligonucleotide compound. Chimeric antisense oligonucleotides are thus a form of antisense compound. These oligonucleotides typically contain at least one chemically distinct region wherein the oligonucleotide is modified so as to confer upon the oligonucleotide increased resistance to nuclease degradation, increased cellular uptake, increased stability and/or increased binding affinity for the target nucleic acid. An additional chemically distinct region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Modifications that activate, recruit or trigger RNase H and result in cleavage of the RNA target thereby greatly enhance the efficiency of oligonucleotide-mediated inhibition of gene expression. The cleavage of RNA:RNA hybrids can, in like fashion, be accomplished through the actions of endoribonucleases such as RnaseL, which cleaves both cellular and viral RNA. Cleavage of the RNA target can be routinely detected by gel electrophoresis and, if necessary, associated nucleic acid hybridization techniques known in the art.

Preferred chimeric oligonucleotides are those disclosed in the Examples herein. Particularly preferred chimeric oligonucleotides are those referred to as SEQ ID NOS: 65, 26, 29, and 35, as well as those chimeric oligonucleotides set forth in Tables 2, 3, 14, and 15 and specified in the Examples below. Preferred siRNAs are those referred to as SEQ ID Nos: 238, 242, 243, 251, and 252, as well as those set forth in Table 11 and specified in the Examples below. Chimeric antisense compounds of the invention may be formed as composite structures of two or more oligonucleotides, modified oligonucleotides, oligonucleosides and/or oligonucleotide mimetics as described above. Chimeric antisense compounds can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the chimeric antisense compound. Compounds of the first type are also known in the art as "gapmers" or gapped oligonucleotides. Compounds of the second type are also known in the art as "hemimers" or "wingmers". Such compounds have also been referred to in the art as hybrids. In a gapmer that is 20 nucleotides in length, a gap or wing can be 1, 2, 3, 4, 5, 6, 7, 8, 9, 10, 11, 12, 13, 14, 15, 16, 17 or 18 nucleotides in length. In one embodiment, a 20-nucleotide gapmer is comprised of a gap 8 nucleotides in length, flanked on both the 5' and 3' sides by wings 6 nucleotides in length. In another embodiment, a 20-nucleotide gapmer is comprised of a gap 10 nucleotides in length, flanked on both the 5' and 3' sides by wings 5 nucleotides in length. In another embodiment, a 20-nucleotide gapmer is comprised of a gap 12 nucleotides in length flanked on both the 5' and 3' sides by wings 4 nucleotides in length. In a further embodiment, a 20-nucleotide gapmer is comprised of a gap 14 nucleotides in length flanked on both the 5' and 3' sides by wings 3 nucleotides in length. In another embodiment, a 20-nucleotide gapmer is comprised of a gap 16 nucleotides in length flanked on both the 5' and 3' sides by wings 2 nucleotides in length. In a further embodiment, a 20-nucleotide gapmer is comprised of a gap 18 nucleotides in length flanked on both the 5' and 3' ends by wings 1 nucleotide in length. Alternatively, the wings are of different lengths, for example, a 20-nucleotide gapmer may be comprised of a gap 10 nucleotides in length, flanked by a 6-nucleotide wing on one side (5' or 3') and a 4-nucleotide wing on the other side (5' or 3').

In a hemimer, an "open end" chimeric antisense compound having two chemically distinct regions, a first chemically distinct region, or the gap segment, in a compound 20 nucleotides in length can be located at either the 5' or 3' terminus of the oligomeric compound, can be 1, 2, 3, 4, 5, 6, 7, 8, 9, 10, 11, 12, 13, 14, 15, 16, 17, 18 or 19 nucleotides in length. A second chemically distinct region in a compound 20 nucleotides in length can be located at the 3' terminus of the compound and can be 1, 2, 3, 4, 5, 6, 7, 8, 9, 10, 11, 12, 13, 14, 15, 16, 17, 18 or 19 nucleotides in length. For example, a 20-nucleotide hemimer can have a first chemically distinct region, or a gap segment, of 10 nucleotides at the 5' end and a second segment of 10 nucleotides at the 3' end.

Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference in its entirety.

G. Formulations

The compounds of the invention may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The antisense compounds of the invention encompass any pharmaceutically acceptable salts, esters, or salts of such esters, or any other compound which, upon administration to an animal, including a human, is capable of providing (directly or indirectly) the biologically active metabolite or residue thereof Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in International Patent Publication No. WO 93/24510 to Gosselin et al., published Dec. 9, 1993 or in International Patent Publication No. WO 94/26764 and U.S. Pat. No. 5,770,713 to Imbach et al.

The term "pharmaceutically acceptable salts" refers to physiologically and pharmaceutically acceptable salts of the compounds of the invention: i.e., salts that retain the desired biological activity of the parent compound and do not impart undesired toxicological effects thereto. For oligonucleotides, preferred examples of pharmaceutically acceptable salts and their uses are further described in U.S. Pat. No. 6,287,860, which is incorporated herein in its entirety.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al., "Pharmaceutical Salts," J. of Pharma Sci., 1977, 66, 1-19). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Preferred topical formulations include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA). Oligonucleotides of the invention may be encapsulated within liposomes or may form complexes thereto, in particular to cationic liposomes. Alternatively, oligonucleotides may be complexed to lipids, in particular to cationic lipids. Preferred fatty acids and esters include but are not limited arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-10}$ alkyl ester (e.g. isopropylmyristate IPM), monoglyceride, diglyceride or pharmaceutically acceptable salt thereof. Topical formulations are described in detail in U.S. Pat. No. 6,747,014, which is incorporated herein by reference in its entirety.

In some embodiments, an oligonucleotide may be administered to a subject via an oral route of administration. The subjects of the present invention comprise animals. An animal subject may be a mammal, such as a mouse, a rat, a dog, a guinea pig, a human, a non-human primate, a cat or a pig. Non-human primates include monkeys and chimpanzees. A suitable animal subject may be an experimental animal, such as a mouse, a rat, a dog, a non-human primate, a cat or a pig.

In some embodiments, the subject may be a human. In certain embodiments, the subject may be a human patient as discussed in more detail herein. In certain embodiments, it may be necessary to modulate the expression of one or more genes of the human patient. In some particular embodiments, it may be necessary to inhibit expression of one or more genes of the human patient. In particular embodiments, it may be necessary to modulate, i.e. inhibit or enhance, diacylglycerol acyltransferase 2 in order to obtain therapeutic outcomes discussed herein.

In some embodiments, non-parenteral (e.g. oral) oligonucleotide formulations according to the present invention result in enhanced bioavailability of the oligonucleotide. In this context, the term "bioavailability" refers to a measurement of that portion of an administered drug which reaches the circulatory system (e.g. blood, especially blood plasma) when a particular mode of administration is used to deliver the drug. Enhanced bioavailability refers to a particular mode of administration's ability to deliver oligonucleotide to the peripheral blood plasma of a subject relative to another mode of administration. For example, when a non-parenteral mode of administration (e.g. an oral mode) is used to introduce the drug into a subject, the bioavailability for that mode of administration may be compared to a different mode of administration, e.g. an IV mode of administration. In some embodiments, the area under a compound's blood plasma concentration curve ($AUC_O$) after non-parenteral administration may be divided by the area under the drug's plasma concentration curve after intravenous (i.v.) administration ($AUC_{iv}$) to provide a dimensionless quotient (relative bioavailability, RB) that represents fraction of compound absorbed via the non-parenteral route as compared to the IV route. A composition's bioavailability is said to be enhanced in comparison to another composition's bioavailability when the first composition's relative bioavailability ($RB_1$) is greater than the second composition's relative bioavailability ($RB_2$).

In general, bioavailability correlates with therapeutic efficacy when a compound's therapeutic efficacy is related to the blood concentration achieved, even if the drug's ultimate site of action is intracellular (van Berge-Henegouwen et al., *Gastroenterol.*, 1977, 73, 300). Bioavailability studies have been used to determine the degree of intestinal absorption of a drug by measuring the change in peripheral blood levels of the drug after an oral dose (DiSanto, Chapter 76 *In: Remington's Pharmaceutical Sciences,* 18th Ed., Gennaro, ed., Mack Publishing Co., Easton, Pa., 1990, pages 1451-1458).

In general, the bioavailability of an oral composition (comprising an oligonucleotide) is said to be "enhanced" when its relative bioavailability is greater than the bioavailability of a composition substantially consisting of pure oligonucleotide, i.e. oligonucleotide in the absence of a penetration enhancer.

Organ bioavailability refers to the concentration of compound in an organ. Organ bioavailability may be measured in test subjects by a number of means, such as by whole-body radiography. Organ bioavailability may be modified, e.g. enhanced, by one or more modifications to the oligonucleotide, by use of one or more carrier compounds or excipients, etc. as discussed in more detail herein. In general, an increase in bioavailability will result in an increase in organ bioavailability.

Oral oligonucleotide compositions according to the present invention may comprise one or more "mucosal penetration enhancers," also known as "absorption enhancers" or simply as "penetration enhancers." Accordingly, some embodiments of the invention comprise at least one oligonucleotide in combination with at least one penetration enhancer. In general, a penetration enhancer is a substance that facilitates the transport of a drug across mucous membrane(s) associated with the desired mode of administration, e.g. intestinal epithelial membranes. Accordingly it is desirable to select one or more penetration enhancers that facilitate the uptake of an oligonucleotide, without interfering with the activity of the oligonucleotide, and in such a manner the oligonucleotide can be introduced into the body of an animal without unacceptable degrees of side-effects such as toxicity, irritation or allergic response.

Embodiments of the present invention provide compositions comprising one or more pharmaceutically acceptable penetration enhancers, and methods of using such compositions, which result in the improved bioavailability of oligonucleotides administered via non-parenteral modes of administration. Heretofore, certain penetration enhancers have been used to improve the bioavailability of certain drugs. See Muranishi, *Crit. Rev. Ther. Drug Carrier Systems,* 1990, 7, 1 and Lee et al., *Crit. Rev. Ther. Drug Carrier Systems,* 1991, 8, 91. It has been found that the uptake and delivery of oligonucleotides can be greatly improved even when administered by non-parenteral means through the use of a number of different classes of penetration enhancers.

In some embodiments, compositions for non-parenteral administration include one or more modifications to naturally-occurring oligonucleotides (i.e. full-phosphodiester deoxyribosyl or full-phosphodiester ribosyl oligonucleotides). Such modifications may increase binding affinity, nuclease stability, cell or tissue permeability, tissue distribution, or other biological or pharmacokinetic property. Modifications may be made to the base, the linker, or the sugar, in general, as discussed in more detail herein with regards to oligonucleotide chemistry. In some embodiments of the invention, compositions for administration to a subject, and in particular oral compositions for administration to an animal (human or non-human) subject, will comprise modified oligonucleotides having one or more modifications for enhancing affinity, stability, tissue distribution, or other biological property.

Suitable modified linkers include phosphorothioate linkers. In some embodiments according to the invention, the oligonucleotide has at least one phosphorothioate linker. Phosphorothioate linkers provide nuclease stability as well as plasma protein binding characteristics to the oligonucleotide. Nuclease stability is useful for increasing the in vivo lifetime of oligonucleotides, while plasma protein binding decreases the rate of first pass clearance of oligonucleotide via renal excretion. In some embodiments according to the present invention, the oligonucleotide has at least two phosphorothioate linkers. In some embodiments, wherein the oligonucleotide has exactly n nucleosides, the oligonucleotide has from one to n−1 phosphorothioate linkages. In some embodiments, wherein the oligonucleotide has exactly n nucleosides, the oligonucleotide has n−1 phosphorothioate linkages. In other embodiments wherein the oligonucleotide has exactly n nucleoside, and n is even, the oligonucleotide has from 1 to n/2 phosphorothioate linkages, or, when n is odd, from 1 to (n−1)/2 phosphorothioate linkages. In some embodiments, the oligonucleotide has alternating phosphodiester (PO) and phosphorothioate (PS) linkages. In other embodiments, the oligonucleotide has at least one stretch of two or more consecutive PO linkages and at least one stretch of two or more PS linkages. In other embodiments, the oligonucleotide has at least two stretches of PO linkages interrupted by at least one PS linkage.

In some embodiments, at least one of the nucleosides is modified on the ribosyl sugar unit by a modification that imparts nuclease stability, binding affinity or some other beneficial biological property to the sugar. In some cases, the sugar modification includes a 2'-modification, e.g. the 2'-OH of the ribosyl sugar is replaced or substituted. Suitable replacements for 2'-OH include 2'-F and 2'-arabino-F. Suitable substitutions for OH include 2'-O-alkyl, e.g. 2-O-methyl, and 2'-O-substituted alkyl, e.g. 2'-O-methoxyethyl, 2'-NH$_2$, 2'-O-aminopropyl, etc. In some embodiments, the oligonucleotide contains at least one 2'-modification. In some embodiments, the oligonucleotide contains at least two 2'-modifications. In some embodiments, the oligonucleotide has at least one 2'-modification at each of the termini (i.e. the 3'- and 5'-terminal nucleosides each have the same or different 2'-modifications). In some embodiments, the oligonucleotide has at least two sequential 2'-modifications at each end of the oligonucleotide. In some embodiments, oligonucleotides further comprise at least one deoxynucleoside. In particular embodiments, oligonucleotides comprise a stretch of deoxynucleosides such that the stretch is capable of activating RNase (e.g. RNase H) cleavage of an RNA to which the oligonucleotide is capable of hybridizing. In some embodiments, a stretch of deoxynucleosides capable of activating RNase-mediated cleavage of RNA comprises about 6 to about 16, e.g. about 8 to about 16 consecutive deoxynucleosides. In further embodiments, oligonucleotides are capable of eliciting cleaveage by dsRNAse enzymes which act on RNA:RNA hybrids.

Oligonucleotide compositions of the present invention may be formulated in various dosage forms such as, but not limited to, tablets, capsules, liquid syrups, soft gels, suppositories, and enemas. The term "alimentary delivery" encompasses e.g. oral, rectal, endoscopic and sublingual/buccal administration. A common requirement for these modes of administration is absorption over some portion or all of the alimentary tract and a need for efficient mucosal penetration of the oligonucleotides or mimetics thereof so administered.

Delivery of a drug via the oral mucosa, as in the case of buccal and sublingual administration, has several desirable features, including, in many instances, a more rapid rise in plasma concentration of the drug (Harvey, Chapter 35 In: Remington's Pharmaceutical Sciences, 18th Ed., Gennaro, ed., Mack Publishing Co., Easton, Pa., 1990, page 711).

Endoscopy may be used for drug delivery directly to an interior portion of the alimentary tract. For example, endoscopic retrograde cystopancreatography (ERCP) takes advantage of extended gastroscopy and permits selective access to the biliary tract and the pancreatic duct (Hirahata et al., Gan To Kagaku Ryoho, 1992, 19(10 Suppl), 1591). Pharmaceutical compositions, including liposomal formulations, can be delivered directly into portions of the alimentary canal, such as, e.g., the duodenum (Somogyi et al., Pharm. Res., 1995, 12, 149) or the gastric submucosa (Akamo et al., Japanese J. Cancer Res., 1994, 85, 652) via endoscopic means. Gastric lavage devices (Inoue et al., Artif. Organs, 1997, 21, 28) and percutaneous endoscopic feeding devices (Pennington et al., Ailment Pharmacol. Ther., 1995, 9, 471) can also be used for direct alimentary delivery of pharmaceutical compositions.

In some embodiments, oligonucleotide formulations may be administered through the anus into the rectum or lower intestine. Rectal suppositories, retention enemas or rectal catheters can be used for this purpose and may be preferred when patient compliance might otherwise be difficult to achieve (e.g., in pediatric and geriatric applications, or when the patient is vomiting or unconscious). Rectal administration can result in more prompt and higher blood levels than the oral route. (Harvey, Chapter 35 In: Remington's Pharmaceutical Sciences, 18th Ed., Gennaro, ed., Mack Publishing Co., Easton, Pa., 1990, page 711). Because about 50% of the drug that is absorbed from the rectum will likely bypass the liver, administration by this route significantly reduces the potential for first-pass metabolism (Benet et al., Chapter 1 In: Goodman & Gilman's The Pharmacological Basis of Therapeutics, 9th Ed., Hardman et al., eds., McGraw-Hill, New York, N.Y., 1996).

Some embodiments employ various penetration enhancers in order to effect transport of oligonucleotides and other nucleic acids across mucosal and epithelial membranes. Penetration enhancers may be classified as belonging to one of five broad categories—surfactants, fatty acids, bile salts, chelating agents, and non-chelating non-surfactants (Lee et al., Critical Reviews in Therapeutic Drug Carrier Systems, 1991, p. 92). Accordingly, some embodiments comprise oral oligonucleotide compositions comprising at least one member of the group consisting of surfactants, fatty acids, bile salts, chelating agents, and non-chelating surfactants. Further embodiments comprise oral oligonucleotide compositions comprising at least one fatty acid, e.g. capric or lauric acid, or combinations or salts thereof. Other embodiments comprise methods of enhancing the oral bioavailability of an oligonucleotide, the method comprising co-administering the oligonucleotide and at least one penetration enhancer.

Other excipients that may be added to oral oligonucleotide compositions include surfactants (or "surface-active agents"). These are chemical entities which, when dissolved in an aqueous solution, reduce the surface tension of the solution or the interfacial tension between the aqueous solution and another liquid, with the result that absorption of oligonucleotides through the alimentary mucosa and other epithelial membranes is enhanced. In addition to bile salts and fatty acids, surfactants include, for example, sodium lauryl sulfate, polyoxyethylene-9-lauryl ether and polyoxyethylene-20-cetyl ether (Lee et al., Critical Reviews in Therapeutic Drug Carrier Systems, 1991, page 92); and perfluorohemical emulsions, such as FC-43 (Takahashi et al., J. Pharm. Pharmacol., 1988, 40, 252).

Fatty acids and their derivatives which act as penetration enhancers and may be used in compositions of the present invention include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glyceryl 1-monocaprate, 1-dodecylazacycloheptan-2-one, acylcarnitines, acylcholines and mono- and di-glycerides thereof and/or physiologically acceptable salts thereof (i.e., oleate, laurate, caprate, myristate, palmitate, stearate, linoleate, etc.) (Lee et al., Critical Reviews in Therapeutic Drug Carrier Systems, 1991, page 92; Muranishi, Critical Reviews in Therapeutic Drug Carrier Systems, 1990, 7, 1; El-Hariri et al., J. Pharm. Pharmacol., 1992, 44, 651).

A variety of bile salts also function as penetration enhancers to facilitate the uptake and bioavailability of drugs. The physiological roles of bile include the facilitation of dispersion and absorption of lipids and fat-soluble vitamins (Brunton, Chapter 38 In: Goodman & Gilman's The Pharmacological Basis of Therapeutics, 9th Ed., Hardman et al., eds., McGraw-Hill, New York, N.Y., 1996, pages 934-935). Various natural bile salts, and their synthetic derivatives, act as penetration enhancers. Thus, the term "bile salt" includes any of the naturally occurring components of bile as well as any of their synthetic derivatives. The bile salts of the invention include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (CDCA, sodium chenodeoxycholate), ursodeoxycholic acid (UDCA), sodium tauro-24,25-dihydrofusidate (STDHF), sodium glycodihydrofusidate and polyoxyethylene-9-lauryl ether (POE) (Lee et al., *Critical Reviews in Therapeutic Drug Carrier Systems,* 1991, page 92; Swinyard, Chapter 39 *In: Remington's Pharmaceutical Sciences,* 18th Ed., Gennaro, ed., Mack Publishing Co., Easton, Pa., 1990, pages 782-783; Muranishi, *Critical Reviews in Therapeutic Drug Carrier Systems,* 1990, 7, 1; Yamamoto et al., *J. Pharm. Exp. Ther.,* 1992, 263, 25; Yamashita et al., *J. Pharm. Sci.,* 1990, 79, 579).

In some embodiments, penetration enhancers of the present invention are mixtures of penetration enhancing compounds. One such penetration mixture is UDCA (and/or CDCA) with capric and/or lauric acids or salts thereof e.g. sodium. Such mixtures are useful for enhancing the delivery of biologically active substances across mucosal membranes, in particular intestinal mucosa. Other penetration enhancer mixtures comprise about 5-95% of bile acid or salt(s) UDCA and/or CDCA with 5-95% capric and/or lauric acid. Particular penetration enhancers are mixtures of the sodium salts of UDCA, capric acid and lauric acid in a ratio of about 1:2:2 respectively. Another such penetration enhancer is a mixture of capric and lauric acid (or salts thereof) in a 0.01:1 to 1:0.01 ratio (mole basis). In particular embodiments capric acid and lauric acid are present in molar ratios of e.g. about 0.1:1 to about 1:0.1, in particular about 0.5:1 to about 1:0.5.

Other excipients include chelating agents, i.e. compounds that remove metallic ions from solution by forming complexes therewith, with the result that absorption of oligonucleotides through the alimentary and other mucosa is enhanced. With regards to their use as penetration enhancers in compositions containing DNA-like oligonucleotides of the present invention, chelating agents have the added advantage of also serving as DNase inhibitors, as most characterized DNA nucleases require a divalent metal ion for catalysis and are thus inhibited by chelating agents (Jarrett, *J. Chromatogr.,* 1993, 618, 315). Chelating agents of the invention include, but are not limited to, disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(Lee et al., *Critical Reviews in Therapeutic Drug Carrier Systems,* 1991, page 92; Muranishi, *Critical Reviews in Therapeutic Drug Carrier Systems,* 1990, 7, 1; Buur et al., *J. Control Rel.,* 1990, 14, 43).

As used herein, non-chelating non-surfactant penetration enhancers may be defined as compounds that demonstrate insignificant activity as chelating agents or as surfactants but that nonetheless enhance absorption of oligonucleotides through the alimentary and other mucosal membranes (Muranishi, *Critical Reviews in Therapeutic Drug Carrier Systems,* 1990, 7, 1). This class of penetration enhancers includes, but is not limited to, unsaturated cyclic ureas, 1-alkyl- and 1-alkenylazacyclo-alkanone derivatives (Lee et al., *Critical Reviews in Therapeutic Drug Carrier Systems,* 1991, page 92); and non-steroidal anti-inflammatory agents such as diclofenac sodium, indomethacin and phenylbutazone (Yamashita et al., *J. Pharm. Pharmacol.,* 1987, 39, 621).

In some embodiments, oligonucleotide compositions for oral delivery comprise at least two discrete phases, which phases may comprise particles, capsules, gel-capsules, microspheres, etc. Each phase may contain one or more oligonucleotides, penetration enhancers, surfactants, bioadhesives, effervescent agents, or other adjuvant, excipient or diluent. In some embodiments, one phase comprises at least one oligonucleotide and at least one penetration enhancer. In some embodiments, a first phase comprises at least one oligonucleotide and at least one penetration enhancer, while a second phase comprises at least one penetration enhancer. In some embodiments, a first phase comprises at least one oligonucleotide and at least one penetration enhancer, while a second phase comprises at least one penetration enhancer and substantially no oligonucleotide. In some embodiments, at least one phase is compounded with at least one degradation retardant, such as a coating or a matrix, which delays release of the contents of that phase. In some embodiments, a first phase comprises at least one oligonucleotide and at least one penetration enhancer, while a second phase comprises at least one penetration enhancer and a release-retardant. In particular embodiments, an oral oligonucleotide composition comprises a first phase comprising particles containing an oligonucleotide and a penetration enhancer, and a second phase comprising particles coated with a release-retarding agent and containing penetration enhancer.

Agents that enhance uptake of oligonucleotides at the cellular level may also be added to the pharmaceutical, therapeutic and other compositions of the present invention. For example, cationic lipids, such as LIPOFECTIN™ reagent (Junichi et al, U.S. Pat. No. 5,705,188), cationic glycerol derivatives, and polycationic molecules, such as polylysine (Lollo et al., International Patent Publication No. WO 97/30731), can be used.

A "pharmaceutical carrier" or "excipient" may be a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a an oligonucleotide and the other components of a given pharmaceutical composition. Typical pharmaceutical carriers include, but are not limited to, binding agents (e.g., pregelatinised maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, EXPLOTAB™); and wetting agents (e.g., sodium lauryl sulphate, etc.).

Oral oligonucleotide compositions may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the composition of present invention, such as dyes, flavoring agents, preservatives, antioxidants, opacifiers, thickening agents and stabilizers. However, such materials, when added, should not unduly interfere with the biological activities of the components of the compositions of the present invention.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

Pharmaceutical compositions of the present invention include, but are not limited to, foams, solutions, emulsions, and liposome-containing formulations. These compositions may be generated from a variety of components that include, but are not limited to, preformed liquids, self-emulsifying solids and self-emulsifying semisolids. The pharmaceutical compositions and formulations of the present invention may comprise one or more penetration enhancers, carriers, excipients or other active or inactive ingredients.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the compositions of the present invention.

The compounds of the present invention may be prepared and formulated as emulsions. Emulsions are typically heterogeneous systems of one liquid dispersed in another in the form of droplets usually exceeding 0.1 µm in diameter (Idson, in *Pharmaceutical Dosage Forms*, Lieberman, Rieger and Banker (Eds.), 1988, Marcel Dekker, Inc., New York, N.Y., volume 1, p. 199; Rosoff, in *Pharmaceutical Dosage Forms*, Lieberman; Rieger and Banker (Eds.), 1988, Marcel Dekker, Inc., New York, N.Y., Volume 1, p. 245; Block in *Pharmaceutical Dosage Forms*, Lieberman, Rieger and Banker (Eds.), 1988, Marcel Dekker, Inc., New York, N.Y., volume 2, p. 335; Higuchi et al., in *Remington's Pharmaceutical Sciences*, Mack Publishing Co., Easton, Pa., 1985, p. 301). Emulsions are often biphasic systems comprising of two immiscible liquid phases intimately mixed and dispersed with each other. In general, emulsions may be either water-in-oil (w/o) or of the oil-in-water (o/w) variety. When an aqueous phase is finely divided into and dispersed as minute droplets into a bulk oily phase the resulting composition is called a water-in-oil (w/o) emulsion. Alternatively, when an oily phase is finely divided into and dispersed as minute droplets into a bulk aqueous phase the resulting composition is called an oil-in-water (o/w) emulsion. Emulsions may contain additional components in addition to the dispersed phases and the active drug which may be present as a solution in either the aqueous phase, oily phase or itself as a separate phase. Pharmaceutical excipients such as emulsifiers, stabilizers, dyes, and anti-oxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous provides an o/w/o emulsion.

Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (Idson, in *Pharmaceutical Dosage Forms*, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (Rieger, in *Pharmaceutical Dosage Forms*, Lieberman, Rieger and Banker (Eds.), 1988, Marcel Dekker, Inc., New York, N.Y., volume 1, p. 285; Idson, in *Pharmaceutical Dosage Forms*, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: nonionic, anionic, cationic and amphoteric (Rieger, in *Pharmaceutical Dosage Forms*, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in *Pharmaceutical Dosage Forms*, Lieberman, Rieger and Banker (Eds.), 1988, Marcel Dekker, Inc., New York, N.Y., volume 1, p. 335; Idson, in *Pharmaceutical Dosage Forms*, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used may be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (Idson, in *Pharmaceutical Dosage Forms*, Lieberman, Rieger and Banker (Eds.), 1988, Marcel Dekker, Inc., New York, N.Y., volume 1, p. 199). Emulsion formulations for oral delivery have been very widely used because of reasons of ease of formulation, efficacy from an absorption and bioavailability standpoint. (Rosoff, in *Pharmaceutical Dosage Forms*, Lieberman, Rieger and Banker (Eds.), 1988, Marcel Dekker, Inc., New York, N.Y., volume 1, p. 245; Idson, in *Pharmaceutical Dosage Forms*, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

In one embodiment of the present invention, the compositions of oligonucleotides are formulated as microemulsions. A microemulsion may be defined as a system of water, oil and amphiphile which is a single optically isotropic and thermodynamically stable liquid solution (Rosoff, in *Pharmaceutical Dosage Forms*, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: *Controlled Release of Drugs: Polymers and Aggregate Systems*, Rosoff, M., Ed., 1989, VCH Publishers, New York, pages 185-215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in *Remington's Pharmaceutical Sciences*, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (Rosoff, in *Pharmaceutical Dosage Forms*, Lieberman, Rieger and Banker (Eds.), 1988, Marcel Dekker, Inc., New York, N.Y., volume 1, p. 245; Block, in *Pharmaceutical Dosage Forms*, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain (C8-C12) mono, di, and tri-glycerides, polyoxyethylated glyceryl fatty acid esters, fatty alcohols, polyglycolized glycerides, saturated polyglycolized C8-C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (Constantinides et al., *Pharmaceutical Research*, 1994, 11, 1385-1390; Ritschel, *Meth. Find Exp. Clin. Pharmacol.*, 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., *Pharmaceutical Research*, 1994, 11, 1385; Ho et al., *J. Pharm. Sci.*, 1996, 85, 138-143). Often microemulsions may form spontaneously when their components are brought together at ambient temperature. This may be particularly advantageous when formulating thermolabile drugs, peptides or oligonucleotides. Microemulsions have also been effective in the transdermal delivery of active components in both cosmetic and pharmaceutical applications. It is expected that the microemulsion compositions and formulations of the present invention will facilitate the increased systemic absorption of oligonucleotides from the gastrointestinal tract, as well as improve the local cellular uptake of oligonucleotides within the gastrointestinal tract, vagina, buccal cavity and other areas of administration.

Microemulsions of the present invention may also contain additional components and additives such as sorbitan monostearate (Grill 3), Labrasol, and penetration enhancers to improve the properties of the formulation and to enhance the absorption of the oligonucleotides and nucleic acids of the present invention. Penetration enhancers used in the microemulsions of the present invention may be classified as belonging to one of five broad categories described herein.

There are many organized surfactant structures besides microemulsions that have been studied and used in the formulation of drugs. These include monolayers, micelles, bilayers and vesicles. Vesicles, such as liposomes, have attracted great interest because of their specificity and the duration of action they offer from the standpoint of drug delivery.

Formulations of the present invention include liposomal formulations. As used in the present invention, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered.

In order to cross intact mammalian skin, lipid vesicles must pass through a series of fine pores, each with a diameter less than 50 nm, under the influence of a suitable transdermal gradient. Therefore, it is desirable to use a liposome which is highly deformable and able to pass through such fine pores.

Further advantages of liposomes include: liposomes obtained from natural phospholipids are biocompatible and biodegradable; liposomes can incorporate a wide range of water and lipid soluble drugs; and liposomes can protect encapsulated drugs in their internal compartments from metabolism and degradation (Rosoff, in *Pharmaceutical Dosage Forms*, Lieberman, Rieger and Banker (Eds.), 1988, Marcel Dekker, Inc., New York, N.Y., volume 1, p. 245). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes. As the merging of the liposome and cell progresses, the liposomal contents are emptied into the cell where the active agent may act.

Liposomal formulations have been the focus of extensive investigation as the mode of delivery for many drugs. There is growing evidence that for topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis.

Liposomes fall into two broad classes, cationic and non-cationic, both of which are useful for the delivery of DNA, RNA or any nucleic acid-based construct into cells. Cationic liposomes are positively charged liposomes which interact with negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., *Biochem. Biophys. Res. Commun.*, 1987, 147, 980-985).

Liposomes which are pH-sensitive or negatively-charged, also known as non-cationic liposomes, entrap DNA rather than complex with it. Since both the DNA and the lipid are similarly charged, repulsion rather than complex formation occurs. Nevertheless, some DNA is entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., *Journal of Controlled Release*, 1992, 19, 269-274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g. as a solution or as an emulsion) were ineffective (Weiner et al., *Journal of Drug Targeting*, 1992, 2, 405-410). Further, an additional study tested the efficacy of interferon administered as part of a liposomal formulation to the administration of interferon using an aqueous system, and concluded that the liposomal formulation was superior to aqueous administration (du Plessis et al., *Antiviral Research*, 1992, 18, 259-265).

Non-ionic liposomal systems have also been examined to determine their utility in the delivery of drugs to the skin, in particular systems comprising non-ionic surfactant and cholesterol. Non-ionic liposomal formulations comprising the Novasome™ I (glyceryl dilaurate/cholesterol/polyoxyethylene-10-stearyl ether) and Novasome™ II (glyceryl distearate/cholesterol/polyoxyethylene-10-stearyl ether) reagents were used to deliver cyclosporin-A into the dermis of mouse skin. Results indicated that such non-ionic liposomal systems were effective in facilitating the deposition of cyclosporin-A into different layers of the skin (Hu et al. *S.T.P. Pharma. Sci.*, 1994, 4, 6, 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., *FEBS Letters*, 1987, 223, 42; Wu et al., *Cancer Research*, 1993, 53, 3765). Liposomes and their uses are further described in U.S. Pat. No. 6,287,860, which is incorporated herein in its entirety.

Various liposomes comprising one or more glycolipids are known in the art. Papahadjopoulos et al. (*Ann. N.Y. Acad. Sci.*, 1987, 507, 64) reported the ability of monosialoganglioside $G_{M1}$, galactocerebroside sulfate and phosphatidylinositol to improve blood half-lives of liposomes. These findings were expounded upon by Gabizon et al. (*Proc. Natl. Acad. Sci. U.S.A.*, 1988, 85, 6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al.).

Many liposomes comprising lipids derivatized with one or more hydrophilic polymers, and methods of preparation thereof, are known in the art. Sunamoto et al. (*Bull. Chem. Soc. Jpn.*, 1980, 53, 2778) described liposomes comprising a nonionic detergent, $2C_{12}15G$, that contains a PEG moiety. Illum et al. (*FEBS Lett.*, 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (*FEBS Lett.*, 1990, 268, 235) described experiments demonstrating that liposomes comprising phosphatidylethanolamine (PE) derivatized with PEG or PEG stearate have significant increases in blood circulation half-lives. Blume et al. (*Biochimica et Biophysica Acta*, 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 B1 and WO 90/04384 to Fisher. Liposome compositions containing 1-20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO-91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al.). U.S. Pat. No. 5,540,935 (Miyazaki et al.) and U.S. Pat. No. 5,556,948 (Tagawa et al.) describe PEG-containing liposomes that can be further derivatized with functional moieties on their surfaces.

International Patent Publication No. WO 96/40062 to Thierry et al. refers to methods for encapsulating high molecular weight nucleic acids in liposomes. U.S. Pat. No. 5,264,221 to Tagawa et al. refers to protein-bonded liposomes and asserts that the contents of such liposomes may include an antisense RNA. U.S. Pat. No. 5,665,710 to Rahman et al. refers to certain methods of encapsulating oligodeoxynucleotides in liposomes. International Patent Publication No. WO 97/04787 to Love et al. refers to liposomes comprising antisense oligonucleotides targeted to the raf gene.

Transfersomes are yet another type of liposome, and are highly deformable lipid aggregates which are attractive candidates for drug delivery vehicles. Transfersomes may be described as lipid droplets which are so highly deformable that they are easily able to penetrate through pores which are smaller than the droplet. Transfersomes are adaptable to the environment in which they are used, e.g. they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in *Pharmaceutical Dosage Forms*, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in *Pharmaceutical Dosage Forms*, Marcel Dekker, Inc., New York, N.Y., 1988, p. 285).

In one embodiment, the present invention employs various penetration enhancers to effect the efficient delivery of nucleic acids, particularly oligonucleotides, to the skin of animals. Most drugs are present in solution in both ionized and nonionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs.

Other agents may be utilized to enhance the penetration of the administered nucleic acids, including glycols such as ethylene glycol and propylene glycol, pyrrols such as 2-pyrrol, azones, and terpenes such as limonene and menthone.

The pharmaceutical formulations and compositions of the present invention may also include surfactants. The use of surfactants in drug products, formulations and in emulsions is well known in the art. Surfactants and their uses are further described in U.S. Pat. No. 6,287,860, which is incorporated herein in its entirety.

One of skill in the art will recognize that formulations are routinely designed according to their intended use, i.e., route of administration.

Preferred formulations for topical administration include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA). For topical or other administration, oligonucleotides of the invention may be encapsulated within liposomes or may form complexes thereto, in particular to cationic liposomes. Alternatively, oligonucleotides may be complexed to lipids, in particular to cationic lipids. Preferred fatty acids and esters, pharmaceutically acceptable salts thereof, and their uses are further described in U.S. Pat. No. 6,287,860, which is incorporated herein in its entirety Topical formulations are described in detail in U.S. Pat. No. 6,747,014, which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligonucleotides of the invention are administered in conjunction with one or more penetration enhancers surfactants and chelators. Preferred surfactants include fatty acids and/or esters or salts thereof, bile acids and/or salts thereof. Preferred bile acids/salts and fatty acids and their uses are further described in U.S. Pat. No. 6,287,860, which is incorporated herein in its entirety. Also preferred are combinations of penetration enhancers, for example, fatty acids/salts in combination with bile acids/salts. A particularly preferred combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally, in granular form including sprayed dried particles, or complexed to form micro or nanoparticles. Oligonucleotide complexing agents and their uses are further described in U.S. Pat. No. 6,287,860, which is incorporated herein in its entirety. Oral formulations for oligonucleotides and their preparation are described in detail in U.S. Pat. No. 6,747,014; U.S. patent Publication No. 2003/0027780 (Feb. 6, 2003) and its parent applications; and U.S. patent application Ser. No. 09/082,624 (filed May 21, 1998), each of which is incorporated herein by reference in its entirety.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Oligonucleotides may be formulated for delivery in vivo in an acceptable dosage form, e.g. as parenteral or non-parenteral formulations. Parenteral formulations include intravenous (IV), subcutaneous (SC), intraperitoneal (IP), intravitreal and intramuscular (IM) formulations, as well as formulations for delivery via pulmonary inhalation, intranasal administration, topical administration, etc. Non-parenteral formulations include formulations for delivery via the alimentary canal, e.g. oral administration, rectal administration, intrajejunal instillation, etc. Rectal administration includes administration as an enema or a suppository. Oral administration includes administration as a capsule, a gel capsule, a pill, an elixir, etc.

The compounds of the present invention may also be administered by pulsatile delivery. "Pulsatile delivery" refers to a pharmaceutical formulation that delivers a first pulse of drug (e.g. an antisense compound) combined with a penetration enhancer and a second pulse of penetration enhancer to promote absorption of drug which is not absorbed upon release with the first pulse of penetration enhancer.

One embodiment of the present invention is a delayed release oral formulation for enhanced intestinal drug absorption, comprising:

(a) a first population of carrier particles comprising said drug and a penetration enhancer, wherein said drug and said penetration enhancer are released at a first location in the intestine; and (b) a second population of carrier particles comprising a penetration enhancer and a delayed release coating or matrix, wherein the penetration enhancer is released at a second location in the intestine downstream from the first location, whereby absorption of the drug is enhanced when the drug reaches the second location.

Alternatively, the penetration enhancer in (a) and (b) is different. This enhancement is obtained by encapsulating at least two populations of carrier particles. The first population of carrier particles comprises a biologically active substance and a penetration enhancer, and the second (and optionally additional) population of carrier particles comprises a penetration enhancer and a delayed release coating or matrix.

A "first pass effect" that applies to orally administered drugs is degradation due to the action of gastric acid and various digestive enzymes. One means of ameliorating first pass clearance effects is to increase the dose of administered drug, thereby compensating for proportion of drug lost to first pass clearance. This may be readily achieved with i.v. administration by, for example, simply providing more of the drug to an animal. However, other factors influence the bioavailability of drugs administered via non-parenteral means. For example, a drug may be enzymatically or chemically degraded in the alimentary canal or blood stream and/or may be impermeable or semipermeable to various mucosal membranes.

These pharmaceutical compositions are capable of enhancing absorption of biologically active substances when administered via the rectal, vaginal, nasal or pulmonary routes.

Release of the biologically active substance can be achieved in any part of the gastrointestinal tract.

Liquid pharmaceutical compositions of oligonucleotide can be prepared by combining the oligonucleotide with a suitable vehicle, for example sterile pyrogen free water, or saline solution. Other therapeutic compounds may optionally be included.

The present invention also contemplates the use of solid particulate compositions. Such compositions preferably comprise particles of oligonucleotide that are of respirable size. Such particles can be prepared by, for example, grinding dry oligonucleotide by conventional means, fore example with a mortar and pestle, and then passing the resulting powder composition through a 400 mesh screen to segregate large particles and agglomerates. A solid particulate composition comprised of an active oligonucleotide can optionally contain a dispersant which serves to facilitate the formation of an aerosol, for example lactose.

In accordance with the present invention, oligonucleotide compositions can be aerosolized. Aerosolization of liquid particles can be produced by any suitable means, such as with a nebulizer. See, for example, U.S. Pat. No. 4,501,729. Nebulizers are commercially available devices which transform solutions or suspensions into a therapeutic aerosol mist either by means of acceleration of a compressed gas, typically air or oxygen, through a narrow venturi orifice or by means of ultrasonic agitation. Suitable nebulizers include those sold by Blairex® under the name PARI LC PLUS, PARI DURA-NEB 2000, PARI-BABY Size, PARI PRONEB Compressor with LC PLUS, PARI WALKHALER Compressor/Nebulizer System, PARI LC PLUS Reusable Nebulizer, and PARI LC Jet+®Nebulizer.

Formulations for use in nebulizers may consist of an oligonucleotide in a liquid, such as sterile, pyragen free water, or saline solution, wherein the oligonucleotide comprises up to about 40% w/w of the formulation. Preferably, the oligonucleotide comprises less than 20% w/w. If desired, further additives such as preservatives (for example, methyl hydroxybenzoate) antioxidants, and flavoring agents can be added to the composition.

Solid particles comprising an oligonucleotide can also be aerosolized using any solid particulate medicament aerosol generator known in the art. Such aerosol generators produce respirable particles, as described above, and further produce reproducible metered dose per unit volume of aerosol. Suitable solid particulate aerosol generators include insufflators and metered dose inhalers. Metered dose inhalers are used in the art and are useful in the present invention. Preferably, liquid or solid aerosols are produced at a rate of from about 10 to 150 liters per minute, more preferably from about 30 to 150 liters per minute, and most preferably about 60 liters per minute.

Enhanced bioavailability of biologically active substances is also achieved via the oral administration of the compositions and methods of the present invention.

The compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions may contain substances which increase the viscosity of the suspension including, for example, sodium carboxymethylcellulose, sorbitol and/or dextran. The suspension may also contain stabilizers.

Certain embodiments of the invention provide pharmaceutical compositions containing one or more oligomeric compounds and one or more other chemotherapeutic agents which function by a non-antisense mechanism. Examples of such chemotherapeutic agents include but are not limited to cancer chemotherapeutic drugs such as daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. Combinations of antisense compounds and other non-antisense drugs are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. Alternatively, compositions of the invention may contain two or more antisense compounds targeted to different regions of the same nucleic acid target. Numerous examples of antisense compounds are known in the art. Two or more combined compounds may be used together or sequentially.

H. Dosing

The formulation of therapeutic compositions and their subsequent administration (dosing) is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 µg to 100 g per kg of body weight, from 0.1 µg to 10 g per kg of body weight, from 1.0 µg to 1 g per kg of body weight, from 10.0 µg to 100 mg per kg of body weight, from 100 µg to 10 mg per kg of body weight, or from 1 mg to 5 mg per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 100 g per kg of body weight, once or more daily, to once every 20 years.

The effects of treatments with therapeutic compositions can be assessed following collection of tissues or fluids from a patient or subject receiving said treatments. It is known in the art that a biopsy sample can be procured from certain tissues without resulting in detrimental effects to a patient or subject. In certain embodiments, a tissue and its constituent cells comprise, but are not limited to, blood (e.g., hematopoietic cells, such as human hematopoietic progenitor cells, human hematopoietic stem cells, CD34+ cells CD4+ cells), lymphocytes and other blood lineage cells, bone marrow, breast, cervix, colon, esophagus, lymph node, muscle, peripheral blood, oral mucosa and skin. In other embodiments, a fluid and its constituent cells comprise, but are not limited to, blood, urine, semen, synovial fluid, lymphatic fluid and cerebro-spinal fluid. Tissues or fluids procured from patients can be evaluated for expression levels of the target mRNA or protein. Additionally, the mRNA or protein expression levels of other genes known or suspected to be associated with the specific disease state, condition or phenotype can be assessed. mRNA levels can be measured or evaluated by real-time PCR, Northern blot, in situ hybridization or DNA array analysis. Protein levels can be measured or evaluated by ELISA, immunoblotting, quantitative protein assays, protein activity assays (for example, caspase activity assays) immunohistochemistry or immunocytochemistry. Furthermore, the effects of treatment can be assessed by measuring biomarkers associated with the disease or condition in the aforementioned tissues and fluids, collected from a patient or subject receiving treatment, by routine clinical methods known in the art. These biomarkers include but are not limited to: glucose, cholesterol, lipoproteins, triglycerides, free fatty acids and other markers of glucose and lipid metabolism; lipoprotein(a) or Lp(a) or apolipoprotein B; liver transaminases, bilirubin, albumin, blood urea nitrogen, creatine and other markers of kidney and liver function; interleukins, tumor necrosis factors, intracellular adhesion molecules, C-reactive protein and other markers of inflammation; testosterone, estrogen and other hormones; tumor markers; vitamins, minerals and electrolytes.

While the present invention has been described with specificity in accordance with certain of its preferred embodiments, the following examples serve only to illustrate the invention and are not intended to limit the same. Each of the references, GENBANK® accession numbers, and the like recited in the present application is incorporated herein by reference in its entirety.

EXAMPLES

Example 1

Synthesis of Nucleoside Phosphoramidites

The following compounds, including amidites and their intermediates were prepared as described in U.S. Pat. No. 6,426,220 and International Patent Publication No. WO 02/36743; 5'-O-Dimethoxytrityl-thymidine intermediate for 5-methyl dC amidite, 5'-O-Dimethoxytrityl-2'-deoxy-5-methylcytidine intermediate for 5-methyl-dC amidite, 5'-O-Dimethoxytrityl-2'-deoxy-N$^4$-benzoyl-5-methylcytidine penultimate intermediate for 5-methyl dC amidite, [5'-O-(4,4'-Dimethoxytriphenylmethyl)-2'-deoxy-N4-benzoyl-5-methylcytidin-3'-O-yl]-2-cyanoethyl-N,N-diisopropylphosphoramidite (5-methyl dC amidite), 2'-Fluorodeoxyadenosine, 2'-Fluorodeoxyguanosine, 2'-Fluorouridine, 2'-Fluorodeoxycytidine, 2'-O-(2-Methoxyethyl) modified amidites, 2'-O-(2-methoxyethyl)-5-methyluridine intermediate, 5'-O-DMT-2'-O-(2-methoxyethyl)-5-methyluridine penultimate intermediate, [5'-O-(4,4'-Dimethoxytriphenylmethyl)-2'-O-(2-methoxyethyl)-5-methyluridin-3'-O-yl]-2-cyanoethyl-N,N-diisopropylphosphoramidite (MOE T amidite), 5'-O-Dimethoxytrityl-2'-O-(2-methoxyethyl)-5-methylcytidine intermediate, 5'-O-dimethoxytrityl-2'-O-(2-methoxyethyl)-N$^4$-benzoyl-5-methyl-cytidine penultimate intermediate, [5'-O-(4,4'-Dimethoxytriphenylmethyl)-2'-O-(2-methoxyethyl)-N$^4$-benzoyl-5-methylcytidin-3'-O-yl]-2-cyanoethyl-N,N-diisopropylphosphoramidite (MOE 5-Me-C amidite), [5'-O-(4,4'-Dimethoxytriphenylmethyl)-2'-O-(2-methoxyethyl)-N6-benzoyladenosin-3'-O-yl]-2-cyanoethyl-N,N-diisopropylphosphoramidite (MOE A amidite), [5'-O-(4,4'-Dimethoxytriphenylmethyl)-2'-O-(2-methoxyethyl)-N$^4$-isobutyrylguanosin-3'-O-yl]-2-cyanoethyl-N,N-disopropylphosphoramidite (MOE G amidite), 2'-O-(Aminooxyethyl) nucleoside amidites and 2'-O-(dimethylaminooxyethyl) nucleoside amidites, 2'-(Dimethylaminooxyethoxy) nucleoside amidites, 5'-O-tert-Butyldiphenylsilyl-O$^2$-2'-anhydro-5-methyluridine, 5'-O-tert-Butyldiphenylsilyl-2'-O-(2-hydroxyethyl)-5-methyluridine, 2'-O-([2-phthalimidoxy)ethyl]-5'-t-butyldiphenylsilyl-5-methyluridine, 5'-O-tert-butyldiphenylsilyl-2'-O-[(2-formadoximinooxy)ethyl]-5-methyluridine, 5'-O-tert-Butyldiphenylsilyl-2'-O—[N,N dimethylaminooxyethyl]-5-methyluridine, 2'-O-(dimethylaminooxyethyl)-5-methyluridine, 5'-O-DMT-2'-O-(dimethylaminooxyethyl)-5-methyluridine, 5'-O-DMT-2'-O-(2-N,N-dimethylaminooxyethyl)-5-methyluridine-3'-[(2-cyanoethyl)-N,N-diisopropylphosphoramidite], 2'-(Aminooxyethoxy) nucleoside amidites, N2-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite],
2'-dimethylaminoethoxyethoxy (2'-DMAEOE) nucleoside amidites, 2'-O-[2(2-N,N-dimethylaminoethoxy)ethyl]-5-methyl uridine, 5'-O-dimethoxytrityl-2'-O-[2(2-N,N-dimethyl-aminoethoxy)-ethyl)]-5-methyl uridine and 5'-O-Dimethoxytrityl-2'-O-[2(2-N,N-dimethylaminoethoxy)-ethyl)]-5-methyl uridine-3'-O-(cyanoethyl-N,N-diisopropyl) phosphoramidite.

Example 2

Oligonucleotide and Oligonucleoside Synthesis

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

Oligonucleotides: Unsubstituted and substituted phosphodiester (P=O) oligonucleotides are synthesized on an automated DNA synthesizer (Applied Biosystems model 394) using standard phosphoramidite chemistry with oxidation by iodine.

Phosphorothioates (P=S) are synthesized similar to phosphodiester oligonucleotides with the following exceptions: thiation was effected by utilizing a 10% w/v solution of 3,H-1,2-benzodithiole-3-one 1,1-dioxide in acetonitrile for the oxidation of the phosphite linkages. The thiation reaction step time was increased to 180 sec and preceded by the normal capping step. After cleavage from the CPG column and deblocking in concentrated ammonium hydroxide at 55° C. (12-16 hr), the oligonucleotides were recovered by precipitating with >3 volumes of ethanol from a 1 M $NH_4OAc$ solution. Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. No. 5,610,289 or 5,625,050, herein incorporated by reference.

Phosphoramidite oligonucleotides are prepared as described in U.S. Pat. No. 5,256,775 or 5,366,878, herein incorporated by reference.

Alkylphosphonothioate oligonucleotides are prepared as described in International Patent Application Nos. PCT/US94/00902 and PCT/US93/06976 (published as International Patent Publication Nos. WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

Oligonucleosides: Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P=O or P=S linkages are prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 3

RNA Synthesis

In general, RNA synthesis chemistry is based on the selective incorporation of various protecting groups at strategic intermediary reactions. Although one of ordinary skill in the art will understand the use of protecting groups in organic synthesis, a useful class of protecting groups includes silyl ethers. In particular bulky silyl ethers are used to protect the 5'-hydroxyl in combination with an acid-labile orthoester protecting group on the 2'-hydroxyl. This set of protecting groups is then used with standard solid-phase synthesis technology. It is important to lastly remove the acid labile orthoester protecting group after all other synthetic steps. Moreover, the early use of the silyl protecting groups during synthesis ensures facile removal when desired, without undesired deprotection of 2' hydroxyl.

Following this procedure for the sequential protection of the 5'-hydroxyl in combination with protection of the 2'-hydroxyl by protecting groups that are differentially removed and are differentially chemically labile, RNA oligonucleotides were synthesized.

RNA oligonucleotides are synthesized in a stepwise fashion. Each nucleotide is added sequentially (3'- to 5'-direction) to a solid support-bound oligonucleotide. The first nucleoside at the 3'-end of the chain is covalently attached to a solid support. The nucleotide precursor, a ribonucleoside phosphoramidite, and activator are added, coupling the second base onto the 5'-end of the first nucleoside. The support is washed and any unreacted 5'-hydroxyl groups are capped with acetic anhydride to yield 5'-acetyl moieties. The linkage is then oxidized to the more stable and ultimately desired P(V) linkage. At the end of the nucleotide addition cycle, the 5'-silyl group is cleaved with fluoride. The cycle is repeated for each subsequent nucleotide.

Following synthesis, the methyl protecting groups on the phosphates are cleaved in 30 minutes utilizing 1 M disodium-2-carbamoyl-2-cyanoethylene-1,1-dithiolate trihydrate ($S_2Na_2$) in DMF. The deprotection solution is washed from the solid support-bound oligonucleotide using water. The support is then treated with 40% methylamine in water for 10 minutes at 55° C. This releases the RNA oligonucleotides into solution, deprotects the exocyclic amines, and modifies the 2'-groups. The oligonucleotides can be analyzed by anion exchange HPLC at this stage.

The 2'-orthoester groups are the last protecting groups to be removed. The ethylene glycol monoacetate orthoester protecting group developed by Pharmacon Research, Inc. (Lafayette, Colo.), is one example of a useful orthoester protecting group which, has the following important properties. It is stable to the conditions of nucleoside phosphoramidite synthesis and oligonucleotide synthesis. However, after oligonucleotide synthesis the oligonucleotide is treated with methylamine which not only cleaves the oligonucleotide from the solid support but also removes the acetyl groups from the orthoesters. The resulting 2-ethyl-hydroxyl substituents on the orthoester are less electron withdrawing than the acetylated precursor. As a result, the modified orthoester becomes more labile to acid-catalyzed hydrolysis. Specifically, the rate of cleavage is approximately 10 times faster after the acetyl groups are removed. Therefore, this orthoester possesses sufficient stability in order to be compatible with oligonucleotide synthesis and yet, when subsequently modified, permits deprotection to be carried out under relatively mild aqueous conditions compatible with the final RNA oligonucleotide product.

Additionally, methods of RNA synthesis are well known in the art (Scaringe, S. A. Ph.D. Thesis, University of Colorado, 1996; Scaringe, S. A., et al., *J. Am. Chem. Soc.*, 1998, 120, 11820-11821; Matteucci, M. D. and Caruthers, M. H. *J. Am. Chem. Soc.*, 1981, 103, 3185-3191; Beaucage, S. L. and Caruthers, M. H. *Tetrahedron Lett.*, 1981, 22, 1859-1862; Dahl, B. J., et al., *Acta Chem. Scand*, 1990, 44, 639-641; Reddy, M. P., et al., *Tetrahedron. Lett.*, 1994, 25, 4311-4314; Wincott, F. et al., *Nucleic Acids Res.*, 1995, 23, 2677-2684; Griffin, B. E., et al., *Tetrahedron*, 1967, 23, 2301-2313; Griffin, B. E., et al., *Tetrahedron*, 1967, 23, 2315-2331).

RNA antisense compounds (RNA oligonucleotides) of the present invention can be synthesized by the methods herein or purchased from Dharmacon Research, Inc (Lafayette, Colo.). Once synthesized, complementary RNA antisense compounds can then be annealed by methods known in the art to form double stranded (duplexed) antisense compounds. For example, duplexes can be formed by combining 30 µl of each of the complementary strands of RNA oligonucleotides (50 µM RNA oligonucleotide solution) and 15 µl of 5× annealing buffer (100 mM potassium acetate, 30 mM HEPES-KOH pH 7.4, 2 mM magnesium acetate) followed by heating for 1 minute at 90° C., then 1 hour at 37° C. The resulting duplexed antisense compounds can be used in kits, assays, screens, or other methods to investigate the role of a target nucleic acid, or for diagnostic or therapeutic purposes.

Example 4

Synthesis of Chimeric Compounds

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers".

[2'-O—Me]-[2'-deoxy]-[2'-O—Me] Chimeric Phosphorothioate Oligonucleotides

Chimeric oligonucleotides having 2'-O-alkyl phosphorothioate and 2'-deoxy phosphorothioate oligonucleotide segments are synthesized using an Applied Biosystems automated DNA synthesizer Model 394, as above. Oligonucleotides are synthesized using the automated synthesizer and 2'-deoxy-5'-dimethoxytrityl-3'-O-phosphoramidite for the DNA portion and 5'-dimethoxytrityl-2'-O-methyl-3'-O-phosphoramidite for 5' and 3' wings. The standard synthesis cycle is modified by incorporating coupling steps with increased reaction times for the 5'-dimethoxytrityl-2'-O-methyl-3'-O-phosphoramidite. The fully protected oligonucleotide is cleaved from the support and deprotected in concentrated ammonia (NH$_4$OH) for 12-16 hr at 55° C. The deprotected oligo is then recovered by an appropriate method (precipitation, column chromatography, volume reduced in vacuo and analyzed spectrophotometrically for yield and for purity by capillary electrophoresis and by mass spectrometry).

[2'-O-(2-Methoxyethyl)]-[2'-deoxy]-[2'-O-(Methoxyethyl)] Chimeric Phosphorothioate Oligonucleotides

[2'-O-(2-methoxyethyl)]-[2'-deoxy]-[-2'-O-(methoxyethyl)] chimeric phosphorothioate oligonucleotides were prepared as per the procedure above for the 2'-O-methyl chimeric oligonucleotide, with the substitution of 2'-O-(methoxyethyl) amidites for the 2'-O-methyl amidites.

[2'-O-(2-Methoxyethyl)Phosphodiester]-[2'-deoxy Phosphorothioate]-[2'-O-(2-Methoxyethyl)Phosphodiester] Chimeric Oligonucleotides

[2'-O-(2-methoxyethyl phosphodiester]-[2'-deoxy phosphorothioate]-[2'-O-(methoxyethyl)phosphodiester] chimeric oligonucleotides are prepared as per the above procedure for the 2'-O-methyl chimeric oligonucleotide with the substitution of 2'-O-(methoxyethyl) amidites for the 2'-O-methyl amidites, oxidation with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

Example 5

Design and Screening of Duplexed Antisense Compounds Targeting Diacylglycerol Acyltransferase 2

In accordance with the present invention, a series of nucleic acid duplexes, also known as double-strand RNAs (dsRNAs) or small interfering RNAs (siRNAs), comprising the antisense compounds of the present invention and their complements can be designed to target diacylglycerol acyltransferase 2. The nucleobase sequence of the antisense strand of the duplex comprises at least an 8-nucleobase portion of an oligonucleotide in Table 1. The ends of the strands may be modified by the addition of one or more natural or modified nucleobases to form an overhang. The sense strand of the dsRNA is then designed and synthesized as the complement of the antisense strand and may also contain modifications or additions to either terminus. For example, in one embodiment, both strands of the dsRNA duplex would be complementary over the central nucleobases, each having overhangs at one or both termini. The antisense and sense strands of the duplex comprise from about 17 to 25 nucleotides, or from about 19 to 23 nucleotides. Alternatively, the antisense and sense strands comprise 20, 21 or 22 nucleotides.

For example, a duplex comprising an antisense strand having the sequence CGAGAGGCGGACGGGACCG (SEQ ID NO: 489) and having a two-nucleobase overhang of deoxythymidine (dT) has the following structure (Antisense SEQ ID NO: 490 and Complement SEQ ID NO: 491):

```
cgagaggcggacgggaccgTT    Antisense Strand
||||||||||||||||||
TTgctctccgcctgccctggc    Complement
```

Overhangs can range from 1 to 6 nucleobases and these nucleobases may or may not be complementary to the target nucleic acid. One of skill in the art will understand that the overhang may be 1, 2, 3, 4, 5 or 6 nucleobases in length. In another embodiment, the duplexes may have an overhang on only one terminus.

In another embodiment, a duplex comprising an antisense strand having the same sequence CGAGAGGCGGACGG-GACCG (SEQ ID NO: 489) may be prepared with blunt ends (no single stranded overhang) as shown (Antisense SEQ ID NO: 489 and Complement SEQ ID NO: 492):

```
cgagaggcggacgggaccg      Antisense Strand
|||||||||||||||||||
gctctccgcctgccctggc      Complement
```

The RNA duplex can be unimolecular or bimolecular; i.e., the two strands can be part of a single molecule or may be separate molecules.

RNA strands of the duplex can be synthesized by methods disclosed herein or purchased from Dharmacon Research Inc., (Lafayette, Colo.). Once synthesized, the complementary strands are annealed. The single strands are aliquoted and diluted to a concentration of 50 μM. Once diluted, 30 μL of each strand is combined with 15 μL of a 5× solution of annealing buffer. The final concentration of said buffer is 100 mM potassium acetate, 30 mM HEPES-KOH pH 7.4, and 2 mM magnesium acetate. The final volume is 75 μL. This solution is incubated for 1 minute at 90° C. and then centrifuged for 15 seconds. The tube is allowed to sit for 1 hour at 37° C. at which time the dsRNA duplexes are used in experimentation. The final concentration of the dsRNA duplex is 20 μM. This solution can be stored frozen (−20° C.) and freeze-thawed up to 5 times.

Once prepared, the duplexed antisense compounds are evaluated for their ability to modulate diacylglycerol acyltransferase 2 expression.

When cells reached 80% confluency, they are treated with duplexed antisense compounds of the invention. For cells grown in 96-well plates, wells are washed once with 200 μL OPTI-MEM-1 reduced-serum medium (Gibco BRL) and then treated with 130 μL of OPTI-MEM-1 containing 12 μg/mL LIPOFECTIN™ reagent (Gibco BRL) and the desired duplex antisense compound at a final concentration of 200 nM. After 5 hours of treatment, the medium is replaced with fresh medium. Cells are harvested 16 hours after treatment, at which time RNA is isolated and target reduction measured by RT-PCR.

Example 6

Oligonucleotide Isolation

After cleavage from the controlled pore glass solid support and deblocking in concentrated ammonium hydroxide at 55° C. for 12-16 hours, the oligonucleotides or oligonucleosides are recovered by precipitation out of 1 M NH$_4$OAc with >3 volumes of ethanol. Synthesized oligonucleotides were analyzed by electrospray mass spectroscopy (molecular weight determination) and by capillary gel electrophoresis and judged to be at least 70% full-length material. The relative amounts of phosphorothioate and phosphodiester linkages obtained in the synthesis was determined by the ratio of correct molecular weight relative to the −16 amu product (+/−32+/−48). For some studies oligonucleotides were purified by HPLC, as described by Chiang et al., *J. Biol. Chem.* 1991, 266, 18162-18171. Results obtained with HPLC-purified material were similar to those obtained with non-HPLC purified material.

Example 7

Oligonucleotide Synthesis

96 Well Plate Format

Oligonucleotides were synthesized via solid phase P(III) phosphoramidite chemistry on an automated synthesizer capable of assembling 96 sequences simultaneously in a 96-well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyl-diiso-propyl phosphoramidites were purchased from commercial vendors (e.g. PE-Applied Biosystems, Foster City, Calif., or Pharmacia, Piscataway, N.J.). Non-standard nucleosides are synthesized as per standard or patented methods. They are utilized as base protected beta-cyanoethyldiisopropyl phosphoramidites.

Oligonucleotides were cleaved from support and deprotected with concentrated NH$_4$OH at elevated temperature (55-60° C.) for 12-16 hours and the released product then dried in vacuo. The dried product was then re-suspended in sterile water to afford a master plate from which all analytical and test plate samples are then diluted utilizing robotic pipettors.

Example 8

Oligonucleotide Analysis

96-Well Plate Format

The concentration of oligonucleotide in each well was assessed by dilution of samples and UV absorption spectroscopy. The full-length integrity of the individual products was evaluated by capillary electrophoresis (CE) in either the 96-well format (Beckman P/ACE™ MDQ apparatus) or, for individually prepared samples, on a commercial CE apparatus (e.g., Beckman P/ACE™ 5000, ABI 270 apparatus). Base and backbone composition was confirmed by mass analysis of the compounds utilizing electrospray-mass spectroscopy. All assay test plates were diluted from the master plate using single and multi-channel robotic pipettors. Plates were judged to be acceptable if at least 85% of the compounds on the plate were at least 85% full length.

Example 9

Cell Culture and Oligonucleotide Treatment

The effect of antisense compounds on target nucleic acid expression can be tested in any of a variety of cell types provided that the target nucleic acid is present at measurable levels. This can be routinely determined using, for example, PCR or Northern blot analysis. The following cell types are provided for illustrative purposes, but other cell types can be routinely used, provided that the target is expressed in the cell type chosen. This can be readily determined by methods routine in the art, for example Northern blot analysis, ribonuclease protection assays, or real-time PCR.

T-24 Cells:

The human transitional cell bladder carcinoma cell line T-24 was obtained from the American Type Culture Collection (ATCC) (Manassas, Va.). T-24 cells were routinely cultured in complete McCoy's 5A basal media (Invitrogen Corporation, Carlsbad, Calif.) supplemented with 10% fetal bovine serum (Invitrogen Corporation, Carlsbad, Calif.), penicillin 100 units per mL, and streptomycin 100 micrograms per mL (Invitrogen Corporation, Carlsbad, Calif.). Cells were routinely passaged by trypsinization and dilution when they reached 90% confluence. Cells were seeded into 96-well plates (Falcon-Primaria #353872) at a density of 7000 cells/well for use in RT-PCR analysis.

For Northern blotting or other analysis, cells may be seeded onto 100 mm or other standard tissue culture plates and treated similarly, using appropriate volumes of medium and oligonucleotide.

A549 Cells:

The human lung carcinoma cell line A549 was obtained from the American Type Culture Collection (ATCC) (Manassas, Va.). A549 cells were routinely cultured in DMEM basal media (Invitrogen Corporation, Carlsbad, Calif.) supplemented with 10% fetal bovine serum (Invitrogen Corporation, Carlsbad, Calif.), penicillin 100 units per mL, and streptomycin 100 micrograms per mL (Invitrogen Corporation, Carlsbad, Calif.). Cells were routinely passaged by trypsinization and dilution when they reached 90% confluence.

NHDF Cells:

Human neonatal dermal fibroblast (NHDF) were obtained from the Clonetics Corporation (Walkersville, Md.). NHDFs were routinely maintained in Fibroblast Growth Medium (Clonetics Corporation, Walkersville, Md.) supplemented as recommended by the supplier. Cells were maintained for up to 10 passages as recommended by the supplier.

HEK Cells:

Human embryonic keratinocytes (HEK) were obtained from the Clonetics Corporation (Walkersville, Md.). HEKs were routinely maintained in Keratinocyte Growth Medium (Clonetics Corporation, Walkersville, Md.) formulated as recommended by the supplier. Cells were routinely maintained for up to 10 passages as recommended by the supplier.

3T3-L1 Cells:

The mouse embryonic adipocyte-like cell line 3T3-L1 was obtained from the American Type Culture Collection (Manassas, Va.). 3T3-L1 cells were routinely cultured in DMEM, high glucose (Invitrogen Corporation, Carlsbad, Calif.) supplemented with 10% fetal bovine serum (Invitrogen Corporation, Carlsbad, Calif.). Cells were routinely passaged by trypsinization and dilution when they reached 80% confluence. Cells were seeded into 96-well plates (Falcon-Primaria #3872) at a density of 4000 cells/well for use in RT-PCR analysis.

For Northern blotting or other analyses, cells may be seeded onto 100 mm or other standard tissue culture plates and treated similarly, using appropriate volumes of medium and oligonucleotide.

Primary Mouse Hepatocytes:

Primary mouse hepatocytes were prepared from CD-1 mice purchased from Charles River Labs. Primary mouse hepatocytes were routinely cultured in Hepatocyte Attachment Media supplemented with 10% fetal bovine serum, 1% penicillin/streptomycin, 1% antibiotic-antimitotic (Invitrogen Life Technologies, Carlsbad, Calif.) and 10 nM bovine insulin (Sigma-Aldrich, St. Louis, Mo.). Cells were seeded into 96-well plates (Falcon-Primaria #3872) coated with 0.1 mg/ml collagen at a density of approximately 10,000 cells/well for use in oligomeric compound transfection experiments.

Treatment with Antisense Compounds:

When cells reached 65-75% confluency, they were treated with oligonucleotide. For cells grown in 96-well plates, wells were washed once with 100 µL OPTI-MEM™-1 reduced-serum medium (Invitrogen Corporation, Carlsbad, Calif.) and then treated with 130 µL of the OPTI-MEM™-1 medium containing 2.5 or 3 µg/mL LIPOFECTIN™ reagent (Invitrogen Corporation, Carlsbad, Calif.) per 100 nM of oligonucleotide. Cells are treated and data are obtained in triplicate. After 4-7 hours of treatment at 37° C., the medium was replaced with fresh medium. Cells were harvested 16-24 hours after oligonucleotide treatment.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide is selected from either ISIS 13920 (TCCGTCATCGCTCCT-CAGGG, SEQ ID NO: 1) which is targeted to human H-ras, or ISIS 18078, (GTGCGCGCGAGCCCGAAATC, SEQ ID NO: 2) which is targeted to human Jun-N-terminal kinase-2 (JNK2). Both controls are 2'-O-methoxyethyl gapmers (2'-O-methoxyethyls shown in bold) with a phosphorothioate backbone. For mouse or rat cells the positive control oligonucleotide is ISIS 15770, ATGCATTCTGCCCCCAAGGA, SEQ ID NO: 3, a 2'-O-methoxyethyl gapmer (2'-O-methoxyethyls shown in bold) with a phosphorothioate backbone which is targeted to both mouse and rat c-raf. The concentration of positive control oligonucleotide that results in 80% inhibition of c-H-ras (for ISIS 13920), JNK2 (for ISIS 18078) or c-raf (for ISIS 15770) mRNA is then utilized as the screening concentration for new oligonucleotides in subsequent experiments for that cell line. If 80% inhibition is not achieved, the lowest concentration of positive control oligonucleotide that results in 60% inhibition of c-H-ras, JNK2 or c-raf mRNA is then utilized as the oligonucleotide screening concentration in subsequent experiments for that cell line. If 60% inhibition is not achieved, that particular cell line is deemed as unsuitable for oligonucleotide transfection experiments. The concentrations of antisense oligonucleotides used herein are from 50 nM to 300 nM.

Example 10

Analysis of Oligonucleotide Inhibition of Diacylglycerol Acyltransferase 2 Expression Antisense modulation of diacylglycerol acyltransferase 2 expression can be assayed in a variety of ways known in the art. For example, diacylglycerol acyltransferase 2 mRNA levels can be quantitated by, e.g., Northern blot analysis, competitive polymerase chain reaction (PCR), or real-time PCR. Quantitative real-time PCR is presently preferred. RNA analysis can be performed on total cellular RNA or poly(A)+ mRNA. The preferred method of RNA analysis of the present invention is the use of total cellular RNA as described in other examples herein. Methods of RNA isolation are well known in the art. Northern blot analysis is also routine in the art.

Real-time quantitative (PCR) can be conveniently accomplished using the commercially available ABI PRISM™ 7600, 7700, or 7900 Sequence Detection System, available from PE-Applied Biosystems, Foster City, Calif. and used according to manufacturer's instructions.

Protein levels of diacylglycerol acyltransferase 2 can be quantitated in a variety of ways well known in the art, such as immunoprecipitation, Western blot analysis (immunoblotting), enzyme-linked immunosorbent assay (ELISA) or fluorescence-activated cell sorting (FACS). Antibodies directed to diacylglycerol acyltransferase 2 can be identified and obtained from a variety of sources, such as the MSRS catalog of antibodies (Aerie Corporation, Birmingham, Mich.), or can be prepared via conventional monoclonal or polyclonal antibody generation methods well known in the art.

Example 11

Design of Phenotypic Assays for the Use of Diacylglycerol Acyltransferase 2 Inhibitors Once diacylglycerol acyltransferase 2 inhibitors have been identified by the methods disclosed herein, the compounds are further investigated in one or more phenotypic assays, each having measurable endpoints predictive of efficacy in the treatment of a particular disease state or condition.

Phenotypic assays, kits and reagents for their use are well known to those skilled in the art and are herein used to investigate the role and/or association of diacylglycerol acyltransferase 2 in health and disease. Representative phenotypic assays, which can be purchased from any one of several commercial vendors, include those for determining cell viability, cytotoxicity, proliferation or cell survival (Molecular Probes, Eugene, Oreg.; PerkinElmer, Boston, Mass.), protein-based assays including enzymatic assays (Panvera, LLC, Madison, Wis.; BD Biosciences, Franklin Lakes, N.J.; Oncogene Research Products, San Diego, Calif.), cell regulation, signal transduction, inflammation, oxidative processes and apoptosis (Assay Designs Inc., Ann Arbor, Mich.), triglyceride accumulation (Sigma-Aldrich, St. Louis, Mo.), angiogenesis assays, tube formation assays, cytokine and hormone assays and metabolic assays (Chemicon International Inc., Temecula, Calif.; Amersham Biosciences, Piscataway, N.J.).

In one non-limiting example, cells determined to be appropriate for a particular phenotypic assay (i.e., MCF-7 cells selected for breast cancer studies; adipocytes for obesity studies) are treated with diacylglycerol acyltransferase 2 inhibitors identified from the in vitro studies as well as control compounds at optimal concentrations which are determined by the methods described above. At the end of the treatment period, treated and untreated cells are analyzed by one or more methods specific for the assay to determine phenotypic outcomes and endpoints.

Phenotypic endpoints include changes in cell morphology over time or treatment dose as well as changes in levels of cellular components such as proteins, lipids, nucleic acids, hormones, saccharides or metals. Measurements of cellular status which include pH, stage of the cell cycle, intake or excretion of biological indicators by the cell, are also endpoints of interest.

Analysis of the expression of one or more genes in the cell after treatment is also used as an indicator of the efficacy or potency of the diacylglycerol acyltransferase 2 inhibitors. Hallmark genes, or those genes suspected to be associated with a specific disease state, condition, or phenotype, are measured in both treated and untreated cells.

Example 12

RNA Isolation

Poly(A)+ mRNA Isolation

Poly(A)+ mRNA was isolated according to Miura et al., (*Clin. Chem.*, 1996, 42, 1758-1764). Other methods for poly (A)+ mRNA isolation are routine in the art. Briefly, for cells grown on 96-well plates, growth medium was removed from the cells and each well was washed with 200 µL cold PBS. 60 µL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 µL of lysate was transferred to Oligo d(T) coated 96-well plates (AGCT Inc., Irvine Calif.). Plates were incubated for 60 minutes at room temperature, washed 3 times with 200 µL of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 µL of elution buffer (5 mM Tris-HCl pH 7.6), preheated to 70° C., was added to each well, the plate was incubated on a 90° C. hot plate for 5 minutes, and the eluate was then transferred to a fresh 96-well plate.

Cells grown on 100 mm or other standard plates may be treated similarly, using appropriate volumes of all solutions.

Total RNA Isolation

Total RNA was isolated using an RNEASY™ 96 kit and buffers purchased from Qiagen, Inc. (Valencia, Calif.) following the manufacturer's recommended procedures. Briefly, for cells grown on 96-well plates, growth medium was removed from the cells and each well was washed with 200 µL cold PBS. 150 µL Buffer RLT was added to each well and the plate vigorously agitated for 20 seconds. 150 µL of 70% ethanol was then added to each well and the contents mixed by pipetting three times up and down. The samples were then transferred to the RNEASY™ 96 well plate attached to a QIAVAC™ manifold fitted with a waste collection tray and attached to a vacuum source. Vacuum was applied for 1 minute. 500 µL of Buffer RW1 was added to each well of the RNEASY™ 96 plate and incubated for 15 minutes and the vacuum was again applied for 1 minute. An additional 500 µL of Buffer RW1 was added to each well of the RNEASY™ 96 plate and the vacuum was applied for 2 minutes. 1 mL of Buffer RPE was then added to each well of the RNEASY™ 96 plate and the vacuum applied for a period of 90 seconds. The Buffer RPE wash was then repeated and the vacuum was applied for an additional 3 minutes. The plate was then removed from the QIAVAC™ manifold and blotted dry on paper towels. The plate was then re-attached to the QIAVAC™ manifold fitted with a collection tube rack containing 1.2 mL collection tubes. RNA was then eluted by pipetting 140 µL of RNase free water into each well, incubating 1 minute, and then applying the vacuum for 3 minutes.

The repetitive pipetting and elution steps may be automated using a QIAGEN® Bio-Robot™ 9604 instrument (Qiagen, Inc., Valencia Calif.). Essentially, after lysing of the cells on the culture plate, the plate is transferred to the robot deck where the pipetting, DNase treatment and elution steps are carried out.

Example 13

Real-Time Quantitative PCR Analysis of Diacylglycerol Acyltransferase 2 mRNA Levels Quantitation of diacylglycerol acyltransferase 2 mRNA levels was accomplished by real-time quantitative PCR using the ABI PRISM™ 7600, 7700, or 7900 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., FAM or JOE, obtained from either PE-Applied Biosystems, Foster City, Calif., Operon Technologies Inc., Alameda, Calif. or Integrated DNA Technologies Inc., Coralville, Iowa) is attached to the 5' end of the probe and a quencher dye (e.g., TAMRA, obtained from either PE-Applied Biosystems, Foster City, Calif., Operon Technologies Inc., Alameda, Calif. or Integrated DNA Technologies Inc., Coralville, Iowa) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

Gene target quantities are obtained by real-time PCR. Prior to the real-time PCR, isolated RNA is subjected to a reverse transcriptase (RT) reaction, for the purpose of generating complementary DNA (cDNA). The real-time PCR is then performed on the resulting cDNA. Reverse transcriptase and PCR reagents were obtained from Invitrogen Corporation, (Carlsbad, Calif.). RT, real-time PCR reactions were carried out by adding 20 μL PCR cocktail (2.5×PCR buffer minus MgCl$_2$, 6.6 mM MgCl$_2$, 375 μM each of dATP, dCTP, dCTP and dGTP, 375 nM each of forward primer and reverse primer, 125 nM of probe, 4 Units RNase inhibitor, 1.25 Units PLATINUM® Taq polymerase, 5 Units MuLV reverse transcriptase, and 2.5×ROX dye) to 96-well plates containing 30 μL total RNA solution (20-200 ng). The RT reaction was carried out by incubation for 30 minutes at 48° C. Following a 10 minute incubation at 95° C. to activate the PLATINUM® Taq polymerase, 40 cycles of a two-step PCR protocol were carried out: 95° C. for 15 seconds (denaturation) followed by 60° C. for 1.5 minutes (annealing/extension). The method of obtaining gene target quantities by RT, real-time PCR is often referred to as simply real-time PCR.

Gene target quantities obtained by real-time PCR are normalized using either the expression level of GAPDH, a gene whose expression is constant, or by quantifying total RNA using the RIBOGREEN™ reagent (Molecular Probes, Inc. Eugene, Oreg.). GAPDH expression is quantified by real time real-time PCR, by being run simultaneously with the target, multiplexing, or separately. Total RNA is quantified using RIBOGREEN™ RNA quantification reagent (Molecular Probes, Inc. Eugene, Oreg.). Methods of RNA quantification by the RIBOGREEN™ reagent are taught in Jones, L. J., et al, (Analytical Biochemistry, 1998, 265, 368-374).

In this assay, 170 μL of RiboGreen™ working reagent (the RIBOGREEN™ reagent diluted 1:350 in 10 mM Tris-HCl, 1 mM EDTA, pH 7.5) was pipetted into a 96-well plate containing 30 μL purified, cellular RNA. The plate was read in a CytoFluor 4000 apparatus (PE Applied Biosystems) with excitation at 485 nm and emission at 530 nm.

Probes and primers to human diacylglycerol acyltransferase 2 were designed to hybridize to a human diacylglycerol acyltransferase 2 sequence, using published sequence information (GENBANK® accession number NM_032564.2, incorporated herein as SEQ ID NO: 4). For human diacylglycerol acyltransferase 2 the PCR primers were:

forward primer: CATACGGCCTTACCTGGCTACA (SEQ ID NO: 5)

reverse primer: CAGACATCAGGTACTCCCTCAACA (SEQ ID NO: 6) and the PCR probe was: FAM-TGGCAG-GCAACTTCCGAATGCC-TAMRA (SEQ ID NO: 7) where FAM is the fluorescent dye and TAMRA is the quencher dye. For human GAPDH the PCR primers were:

forward primer: GAAGGTGAAGGTCGGAGTC(SEQ ID NO:8)

reverse primer: GAAGATGGTGATGGGATTTC (SEQ ID NO:9) and the PCR probe was: 5' JOE-CAAGCTTCCCGT-TCTCAGCC-TAMRA 3' (SEQ ID NO: 10) where JOE is the fluorescent reporter dye and TAMRA is the quencher dye.

Probes and primers to mouse diacylglycerol acyltransferase 2 were designed to hybridize to a mouse diacylglycerol acyltransferase 2 sequence, using published sequence information (GENBANK® accession number AK002443.1, incorporated herein as SEQ ID NO:11). For mouse diacylglycerol acyltransferase 2 the PCR primers were:

forward primer: ACTCTGGAGGTTGGCACCAT (SEQ ID NO: 12)

reverse primer: GGGTGTGGCTCAGGAGGAT (SEQ ID NO: 13) and the PCR probe was: FAM-CAGCGT-TGCTCTGGCGCA-TAMRA (SEQ ID NO: 14) where FAM is the fluorescent reporter dye and TAMRA is the quencher dye. For mouse GAPDH the PCR primers were:

forward primer: GGCAAATTCAACGGCACAGT (SEQ ID NO:15)

reverse primer: GGGTCTCGCTCCTGGAAGAT (SEQ ID NO:16) and the PCR probe was: 5' JOE-AAGGC-CGAGAATGGGAAGCTTGTCATC-TAMRA 3' (SEQ ID NO: 17) where JOE is the fluorescent reporter dye and TAMRA is the quencher dye.

Example 14

Northern Blot Analysis of Diacylglycerol Acyltransferase 2 mRNA Levels

Eighteen hours after antisense treatment, cell monolayers were washed twice with cold PBS and lysed in 1 mL RNA-ZOL™ reagent (TEL-TEST "B" Inc., Friendswood, Tex.). Total RNA was prepared following manufacturer's recommended protocols. Twenty micrograms of total RNA was fractionated by electrophoresis through 1.2% agarose gels containing 1.1% formaldehyde using a MOPS buffer system (AMRESCO, Inc. Solon, Ohio). RNA was transferred from the gel to HYBOND™-N+ nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STRATALINKER™ UV Crosslinker 2400 instrument (Stratagene, Inc, La Jolla, Calif.) and then probed using QUICKHYB™ hybridization solution (Stratagene, La Jolla, Calif.) using manufacturer's recommendations for stringent conditions.

To detect human diacylglycerol acyltransferase 2, a human diacylglycerol acyltransferase 2 specific probe was prepared by PCR using the forward primer CATACGGCCTTACCTG-GCTACA (SEQ ID NO: 5) and the reverse primer CAGA-CATCAGGTACTCCCTCAACA (SEQ ID NO: 6). To normalize for variations in loading and transfer efficiency membranes were stripped and probed for human glyceraldehyde-3-phosphate dehydrogenase (GAPDH) RNA (Clontech, Palo Alto, Calif.).

To detect mouse diacylglycerol acyltransferase 2, a mouse diacylglycerol acyltransferase 2 specific probe was prepared by PCR using the forward primer ACTCTGGAGGTTG-GCACCAT (SEQ ID NO: 12) and the reverse primer GGGT-GTGGCTCAGGAGGAT (SEQ ID NO: 13). To normalize for variations in loading and transfer efficiency membranes were stripped and probed for mouse glyceraldehyde-3-phosphate dehydrogenase (GAPDH) RNA (Clontech, Palo Alto, Calif.).

Hybridized membranes were visualized and quantitated using PHOSPHORIMAGER™ and IMAGEQUANT™ Software V3.3 (Molecular Dynamics, Sunnyvale, Calif.). Data was normalized to GAPDH levels in untreated controls.

Example 15

Antisense Inhibition of Human Diacylglycerol Acyltransferase 2 Expression by Chimeric Phosphorothioate Oligonucleotides Having 2'-MOE Wings and a Deoxy Gap In accordance with the present invention, a series of antisense compounds was designed to target different regions of the human diacylglycerol acyltransferase 2 RNA, using published sequences (GENBANK® accession number NM_032564.2, incorporated herein as SEQ ID NO: 4, nucleotides 5669186 to 5712008 of the nucleotide sequence with the GenBank accession number NT_033927.5, incorporated herein as SEQ ID NO: 18). The compounds are shown in Table 1. "Target site" indicates the first (5'-most) nucleotide number on the particular target sequence to which the compound binds. All compounds in Table 1 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-O-methoxyethyl (2'-MOE) nucleotides. The internucleoside (backbone) linkages are phosphorothioate (P=S) throughout the oligonucleotide. All cytidine residues are 5-methylcytidines. The compounds were analyzed for their effect on human diacylglycerol acyltransferase 2 mRNA levels by quantitative real-time PCR as described in other examples herein. Data are averages from three experiments in which A549 cells were treated with 125 nM of the antisense oligonucleotides of the present invention. If present, "N.D." indicates "no data". ISIS 18078 (SEQ ID NO: 2) was used in this assay as a negative control.

TABLE 1

Inhibition of human diacylglycerol acyltransferase 2 mRNA levels by chimeric phosphorothioate oligonucleotides having 2'-MOE wings and a deoxy gap

| ISIS # | REGION | TARGET SEQ ID NO | TARGET SITE | SEQUENCE (5' TO 3') | % INHIB | SEQ ID NO |
|---|---|---|---|---|---|---|
| 217310 | Coding | 4 | 579 | ctcctgccacctttcttggg | 79 | 20 |
| 217312 | Coding | 4 | 639 | tggatgggaaagtagtctcg | 82 | 21 |
| 217313 | Coding | 4 | 644 | ccagctggatgggaaagtag | 34 | 22 |
| 217314 | Coding | 4 | 649 | cttcaccagctggatgggaa | 40 | 23 |
| 217315 | Coding | 4 | 654 | tgtgtcttcaccagctggat | 86 | 24 |
| 217316 | Coding | 4 | 659 | ggttgtgtgtcttcaccagc | 88 | 25 |

TABLE 1-continued

Inhibition of human diacylglycerol acyltransferase 2 mRNA levels by chimeric phosphorothioate oligonucleotides having 2'-MOE wings and a deoxy gap

| ISIS # | REGION | TARGET SEQ ID NO | TARGET SITE | SEQUENCE (5' TO 3') | % INHIB | SEQ ID NO |
|---|---|---|---|---|---|---|
| 217317 | Coding | 4 | 664 | cagcaggttgtgtgtcttca | 93 | 26 |
| 217318 | Coding | 4 | 669 | gtggtcagcaggttgtgtgt | 74 | 27 |
| 217319 | Coding | 4 | 674 | tcctggtggtcagcaggttg | 84 | 28 |
| 217320 | Coding | 4 | 679 | atagttcctggtggtcagca | 90 | 29 |
| 217321 | Coding | 4 | 684 | aagatatagttcctggtggt | 77 | 30 |
| 217322 | Coding | 4 | 689 | atccaaagatatagttcctg | 73 | 31 |
| 217323 | Coding | 4 | 694 | gtggtatccaaagatatagt | 70 | 32 |
| 217324 | Coding | 4 | 723 | aaggcacccaggcccatgat | 74 | 33 |
| 217325 | Coding | 4 | 846 | cctccagacatcaggtactc | 73 | 34 |
| 217328 | Coding | 4 | 909 | gcattgccactcccattctt | 89 | 35 |
| 217329 | Coding | 4 | 914 | tgatagcattgccactccca | 88 | 36 |
| 217330 | Coding | 4 | 919 | gatgatgatagcattgccac | 77 | 37 |
| 217331 | Coding | 4 | 924 | accacgatgatgatagcatt | 77 | 38 |
| 217333 | Coding | 4 | 963 | ttgccaggcatggagctcag | 79 | 39 |
| 217336 | Coding | 4 | 1110 | tggacccatcggccccagga | 72 | 40 |
| 217337 | Coding | 4 | 1115 | tcttctggacccatcggccc | 76 | 41 |
| 217338 | Coding | 4 | 1120 | gaacttcttctggacccatc | 43 | 42 |
| 217339 | Coding | 4 | 1125 | ttctggaacttcttctggac | 62 | 43 |
| 217341 | Coding | 4 | 1197 | ggcaccagcccccaggtgtc | 68 | 44 |
| 217342 | Coding | 4 | 1202 | agtagggcaccagcccccag | 54 | 45 |
| 217343 | Coding | 4 | 1207 | cttggagtagggcaccagcc | 69 | 46 |
| 217346 | Coding | 4 | 1309 | cagggcctccatgtacatgg | 81 | 47 |
| 217347 | Coding | 4 | 1314 | ttcaccagggcctccatgta | 54 | 48 |
| 217348 | Coding | 4 | 1319 | agagcttcaccagggcctcc | 83 | 49 |
| 217353 | 3'UTR | 4 | 1469 | aacccacagacacccatgac | 65 | 50 |
| 217354 | 3'UTR | 4 | 1474 | taaataacccacagacaccc | 40 | 51 |
| 217355 | 3'UTR | 4 | 1479 | tcttttaaataacccacaga | 47 | 52 |
| 334165 | intron | 18 | 21985 | acaaagagcatcctcctca | 64 | 53 |
| 334166 | intron | 18 | 23110 | actataaatgcttcagtcca | 78 | 54 |
| 334167 | exon:intron | 18 | 31175 | ttgcacttacctttcttggg | 8 | 55 |
| 334168 | exon:intron | 18 | 31611 | agcactttacctggatggga | 63 | 56 |
| 334169 | intron | 18 | 33686 | tcagtgaaatgaggcagatg | 84 | 57 |
| 334170 | intron | 18 | 35303 | ctcaaaagaggtgacatcaa | 72 | 58 |
| 334171 | exon:intron | 18 | 37412 | ggattcttacctccagacat | 22 | 59 |
| 334172 | intron:exon | 18 | 39106 | caggtcagctctggaaggga | 47 | 60 |

TABLE 1-continued

Inhibition of human diacylglycerol acyltransferase 2 mRNA levels by chimeric phosphorothioate oligonucleotides having 2'-MOE wings and a deoxy gap

| ISIS # | REGION | TARGET SEQ ID NO | TARGET SITE | SEQUENCE (5' TO 3') | % INHIB | SEQ ID NO |
|---|---|---|---|---|---|---|
| 334173 | intron | 18 | 37108 | ttccctggacctccatggg | 76 | 61 |
| 334174 | 5'UTR | 4 | 46 | gtggcgcgagagaaacagcc | 82 | 62 |
| 334175 | 5'UTR | 4 | 134 | gccagggcttcgcgcagagc | 75 | 63 |
| 334176 | Start Codon | 4 | 222 | agggtcttcatggctgaagc | 53 | 64 |
| 334177 | Coding | 4 | 246 | aggaccccggagtaggcggc | 95 | 65 |
| 334178 | Coding | 4 | 441 | acccactggagcactgagat | 83 | 66 |
| 334179 | Coding | 4 | 855 | gggcagatacctccagacat | 28 | 67 |
| 334180 | Coding | 4 | 987 | cggttccgcagggtgactgc | 72 | 68 |
| 334181 | Stop Codon | 4 | 1387 | aaggctggctcagttcacct | 78 | 69 |
| 334182 | 3'UTR | 4 | 1401 | gggagttggccccgaaggct | 64 | 70 |
| 334183 | 3'UTR | 4 | 1414 | gctggttcctccagggagtt | 81 | 71 |
| 334184 | 3'UTR | 4 | 1449 | acttccaaatttacagagca | 72 | 72 |
| 334185 | 3'UTR | 4 | 1584 | ccacctagaacagggcaagc | 80 | 73 |
| 334186 | 3'UTR | 4 | 1635 | gggaagaagagaggttagct | 35 | 74 |
| 334187 | 3'UTR | 4 | 1647 | tcacttcaggaagggaagaa | 63 | 75 |
| 334188 | 3'UTR | 4 | 1679 | ccttcttccccaagaagact | 51 | 76 |
| 334189 | 3'UTR | 4 | 1707 | ctaactggtccaagtcacta | 82 | 77 |
| 334190 | 3'UTR | 4 | 1724 | ggcaaaaagtgaatcatcta | 76 | 78 |
| 334191 | 3'UTR | 4 | 1743 | ttcgcctctcatccctaggg | 13 | 79 |
| 334192 | 3'UTR | 4 | 1763 | ggcttgtatgagaagtggct | 77 | 80 |
| 334193 | 3'UTR | 4 | 1802 | tttcaggactagacgagcgt | 82 | 81 |
| 334194 | 3'UTR | 4 | 1946 | ctccgatatgagtgactagg | 85 | 82 |
| 334195 | 3'UTR | 4 | 1969 | ctcatcctggaggccagtcc | 72 | 83 |
| 334196 | 3'UTR | 4 | 1974 | ccatcctcatcctggaggcc | 50 | 84 |
| 334197 | 3'UTR | 4 | 1989 | gtgtcattgccaccccatc | 49 | 85 |
| 334198 | 3'UTR | 4 | 2055 | acctagctcatggtggcggc | 67 | 86 |
| 334199 | 3'UTR | 4 | 2067 | accagttactccacctagct | 73 | 87 |
| 334200 | 3'UTR | 4 | 2088 | gtcatcagccacccaagaaa | 73 | 88 |
| 334201 | 3'UTR | 4 | 2125 | gtgctccaggccaaggctga | 75 | 89 |
| 334202 | 3'UTR | 4 | 2137 | accagtaagcatgtgctcca | 84 | 90 |
| 334203 | 3'UTR | 4 | 2143 | gaggccaccagtaagcatgt | 65 | 91 |
| 334204 | 3'UTR | 4 | 2150 | gtaaactgaggccaccagta | 82 | 92 |
| 334205 | 3'UTR | 4 | 2184 | cttcctcacatccagaatct | 22 | 93 |
| 334206 | 3'UTR | 4 | 2220 | tgctcagaaggccaggcccc | 89 | 94 |
| 334207 | 3'UTR | 4 | 2242 | acctgctttggaactaatct | 76 | 95 |

TABLE 1-continued

Inhibition of human diacylglycerol acyltransferase 2 mRNA levels by chimeric phosphorothioate oligonucleotides having 2'-MOE wings and a deoxy gap

| ISIS # | REGION | TARGET SEQ ID NO | TARGET SITE | SEQUENCE (5' TO 3') | % INHIB | SEQ ID NO |
|---|---|---|---|---|---|---|
| 334208 | 3'UTR | 4 | 2269 | gaaaagtgaggcttgggttc | 44 | 96 |
| 334209 | 3'UTR | 4 | 2367 | aaaagtctgacatggtgcaa | 75 | 97 |

As shown in Table 1, SEQ ID Nos: 20, 21, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 56, 57, 58, 60, 61, 62, 63, 64, 65, 66, 67, 68, 69, 70, 71, 72, 73, 75, 76, 77, 78, 80, 81, 82, 83, 84, 85, 86, 87, 88, 89, 90, 91, 92, 94, 95, 96 and 97 demonstrated at least 40% inhibition of human diacylglycerol acyltransferase 2 expression in this assay and are therefore preferred. More preferred are SEQ ID Nos: 65, 26, 29 and 35. The target regions to which these preferred sequences are complementary are herein referred to as "preferred target segments" and are therefore preferred for targeting by compounds of the present invention. These preferred target segments are shown in Table 3. These sequences are shown to contain thymine (T) but one of skill in the art will appreciate that thymine (T) is generally replaced by uracil (U) in RNA sequences. The sequences represent the reverse complement of the preferred antisense compounds shown in Table 1. "Target site" indicates the first (5'-most) nucleotide number on the particular target nucleic acid to which the oligonucleotide binds. Also shown in Table 3 is the species in which each of the preferred target segments was found.

Example 16

Antisense Inhibition of Mouse Diacylglycerol Acyltransferase 2 Expression by Chimeric Phosphorothiate Oligonucleotides Having 2'-MOE Wings and a Deoxy Gap In accordance with the present invention, a series of antisense compounds was designed to target difference regions of the mouse diacylglycerol acyltransferase 2 RNA, using published sequences (GENBANK® accession number AK002443.1, incorporated herein as SEQ ID NO: 11). The compounds are shown in Table 2. "Target site" indicates the first (5'-most) nucleotide number on the particular target nucleic acid to which the compound binds. All compounds in Table 2 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-O-methoxyethyl (2'-MOE)nucleotides. The internucleoside (backbone) linkages are phosphorothioate (P=S) throughout the oligonucleotide. All cytidine residues are 5-methylcytidines. The compounds were analyzed for their effect on mouse diacylglycerol acyltransferase 2 mRNA levels by quantitative real-time PCR as described in other examples herein. Data are averages from three experiments in which 3T3-L1 cells were treated with 150 nM of the antisense oligonucleotides of the present invention. If present, "N.D." indicates "no data". ISIS 18078 (SEQ ID NO: 2) was used as a negative control in this assay.

TABLE 2

Inhibition of mouse diacyiglycerol acyltransferase 2 mRNA levels by chimeric phosphorotbioate oligonucleotides having 2'-MOE wings and a deoxy gap

| ISIS # | REGION | TARGET SEQ ID NO | TARGET SITE | SEQUENCE (5' TO 3') | % INHIB | SEQ ID NO |
|---|---|---|---|---|---|---|
| 217310 | Coding | 11 | 555 | ctcctgccacctttcttggg | 1 | 20 |
| 217312 | Coding | 11 | 615 | tggatgggaaagtagtctcg | 59 | 21 |
| 217313 | Coding | 11 | 620 | ccagctggatgggaaagtag | 20 | 22 |
| 217314 | Coding | 11 | 625 | cttcaccagctggatgggaa | 0 | 23 |
| 217315 | Coding | 11 | 630 | tgtgtcttcaccagctggat | 26 | 24 |
| 217316 | Coding | 11 | 635 | ggttgtgtgtcttcaccagc | 46 | 25 |
| 217317 | Coding | 11 | 640 | cagcaggttgtgtgtcttca | 36 | 26 |

TABLE 2-continued

Inhibition of mouse diacyiglycerol acyltransferase 2 mRNA levels by chimeric phosphorotbioate oligonucleotides having 2'-MOE wings and a deoxy gap

| ISIS # | REGION | TARGET SEQ ID NO | TARGET SITE | SEQUENCE (5' TO 3') | % INHIB | SEQ ID NO |
|---|---|---|---|---|---|---|
| 217318 | Coding | 11 | 645 | gtggtcagcaggttgtgtgt | 25 | 27 |
| 217319 | Coding | 11 | 650 | tcctggtggtcagcaggttg | 30 | 28 |
| 217320 | Coding | 11 | 655 | atagttcctggtggtcagca | 31 | 29 |
| 217321 | Coding | 11 | 660 | aagatatagttcctggtggt | 0 | 30 |
| 217322 | Coding | 11 | 665 | atccaaagatatagttcctg | 0 | 31 |
| 217323 | Coding | 11 | 670 | gtggtatccaaagatatagt | 31 | 32 |
| 217324 | Coding | 11 | 699 | aaggcacccaggcccatgat | 0 | 33 |
| 217325 | Coding | 11 | 822 | cctccagacatcaggtactc | 2 | 34 |
| 217328 | Coding | 11 | 885 | gcattgccactcccattctt | 37 | 35 |
| 217329 | Coding | 11 | 890 | tgatagcattgccactccca | 30 | 36 |
| 217330 | Coding | 11 | 895 | gatgatgatagcattgccac | 0 | 37 |
| 217331 | Coding | 11 | 900 | accacgatgatgatagcatt | 35 | 38 |
| 217333 | Coding | 11 | 939 | ttgccaggcatggagctcag | 57 | 39 |
| 217336 | Coding | 11 | 1086 | tggacccatcggccccagga | 0 | 40 |
| 217337 | Coding | 11 | 1091 | tcttctggacccatcggccc | 16 | 41 |
| 217338 | Coding | 11 | 1096 | gaacttcttctggacccatc | 34 | 42 |
| 217339 | Coding | 11 | 1101 | ttctggaacttcttctggac | 20 | 43 |
| 217341 | Coding | 11 | 1173 | ggcaccagcccccaggtgtc | 14 | 44 |
| 217342 | Coding | 11 | 1178 | agtagggcaccagcccccag | 0 | 45 |
| 217343 | Coding | 11 | 1183 | cttggagtagggcaccagcc | 18 | 46 |
| 217346 | Coding | 11 | 1285 | cagggcctccatgtacatgg | 36 | 47 |
| 217347 | Coding | 11 | 1290 | ttcaccagggcctccatgta | 0 | 48 |
| 217348 | Coding | 11 | 1295 | agagcttcaccagggcctcc | 12 | 49 |
| 217353 | 3'UTR | 11 | 1466 | aacccacagacacccatgac | 1 | 50 |
| 217354 | 3'UTR | 11 | 1471 | taaataacccacagacaccc | 11 | 51 |
| 217355 | 3'UTR | 11 | 1476 | tcttttaaataacccacaga | 19 | 52 |
| 217299 | 5'UTR | 11 | 21 | ccaccctagatgagcagaaa | 0 | 98 |
| 217300 | 5'UTR | 11 | 36 | ggtaggtagccgctgccacc | 26 | 99 |
| 217301 | 5'UTR | 11 | 44 | agagctgaggtaggtagccg | 24 | 100 |
| 217302 | 5'UTR | 11 | 99 | gcgctgagctccgggagctg | 50 | 101 |
| 217303 | 5'UTR | 11 | 183 | aagccaatgcacgtcacggc | 18 | 102 |
| 217304 | Start Codon | 11 | 199 | gagggtcttcatgctgaagc | 19 | 103 |
| 217305 | Coding | 11 | 262 | gttttcgctgcgggcagctt | 10 | 104 |
| 217306 | Coding | 11 | 386 | gttttccaccttagatctg | 0 | 105 |
| 217307 | Coding | 11 | 403 | tgagatgacctgcagctgtt | 0 | 106 |

TABLE 2-continued

Inhibition of mouse diacylglycerol acyltransferase 2 mRNA levels by chimeric phosphorothioate oligonucleotides having 2'-MOE wings and a deoxy gap

| ISIS # | REGION | TARGET SEQ ID NO | TARGET SITE | SEQUENCE (5' TO 3') | % INHIB | SEQ ID NO |
|---|---|---|---|---|---|---|
| 217308 | Coding | 11 | 447 | caggccactcctagcaccag | 0 | 107 |
| 217309 | Coding | 11 | 457 | gatgacactgcaggccactc | 29 | 108 |
| 217311 | Coding | 11 | 586 | ccacacggcccagtttcgca | 64 | 109 |
| 217326 | Coding | 11 | 831 | gggcagatgcctccagacat | 15 | 110 |
| 217327 | Coding | 11 | 841 | tcggttgacagggcagatgc | 31 | 111 |
| 217332 | Coding | 11 | 920 | gggactcagctgcacctccc | 18 | 112 |
| 217334 | Coding | 11 | 1006 | cagatcagctccatggcgca | 30 | 113 |
| 217335 | Coding | 11 | 1051 | cacctgcttgtatacctcat | 41 | 114 |
| 217340 | Coding | 11 | 1147 | gaagaggcctcggccatgga | 39 | 115 |
| 217344 | Coding | 11 | 1209 | ggctccccacgacggtggt | 0 | 116 |
| 217345 | Coding | 11 | 1240 | ggtcgggtgctccagcttgg | 28 | 117 |
| 217349 | Coding | 11 | 1333 | agtctctggaaggccaaatt | 3 | 118 |
| 217350 | Stop Codon | 11 | 1361 | ggctgggtcagttcacctcc | 0 | 119 |
| 217351 | 3'UTR | 11 | 1383 | ctcccaggagctggcacgcg | 47 | 120 |
| 217352 | 3'UTR | 11 | 1424 | atgcactcaagaactcggta | 60 | 121 |
| 217356 | 3'UTR | 11 | 1536 | actgactcttcccttcttaa | 39 | 122 |
| 217357 | 3'UTR | 11 | 1560 | acacactagaagtgagctta | 57 | 123 |
| 217358 | 3'UTR | 11 | 1577 | cctccaccttgagcaggaca | 45 | 124 |
| 217359 | 3'UTR | 11 | 1599 | caccaaggcccataaatatc | 6 | 125 |
| 217360 | 3'UTR | 11 | 1605 | agaaaccaccaaggcccata | 0 | 126 |
| 217361 | 3'UTR | 11 | 1653 | gccagggcaagtgtctgtc | 46 | 127 |
| 217362 | 3'UTR | 11 | 1685 | tggagtcactaaggactgcc | 45 | 128 |
| 217363 | 3'UTR | 11 | 1715 | gggacatggcctctgcctct | 0 | 129 |
| 217364 | 3'UTR | 11 | 1746 | ggtacgaggaacccgacctg | 43 | 130 |
| 217365 | 3'UTR | 11 | 1772 | gccagctgtgccctcagcct | 0 | 131 |
| 217366 | 3'UTR | 11 | 1815 | ccaagccgggcagtccagat | 18 | 132 |
| 217367 | 3'UTR | 11 | 1861 | gggtaggctcagattggaga | 35 | 133 |
| 217368 | 3'UTR | 11 | 1908 | cggcacctgtgggacagccg | 32 | 134 |
| 217369 | 3'UTR | 11 | 1946 | agagtgaaaccagccaacag | 23 | 135 |
| 217370 | 3'UTR | 11 | 2002 | gctcaggaggatatgcgcca | 90 | 136 |
| 217371 | 3'UTR | 11 | 2033 | aagcccttcctcacaccaga | 9 | 137 |
| 217372 | 3'UTR | 11 | 2055 | ggcacctctgtgaagagaag | 24 | 138 |
| 217373 | 3'UTR | 11 | 2086 | tcctggacccagtgtgctgc | 32 | 139 |
| 217374 | 3'UTR | 11 | 2124 | cacacacgtgaggcttggtt | 31 | 140 |

TABLE 2-continued

Inhibition of mouse diacyiglycerol acyltransferase 2 mRNA levels by chimeric phosphorotbioate oligonucleotides having 2'-MOE wings and a deoxy gap

| ISIS # | REGION | TAR-GET SEQ ID NO | TAR-GET SITE | SEQUENCE (5' TO 3') | % INHIB | SEQ ID NO |
|---|---|---|---|---|---|---|
| 217375 | 3'UTR | 11 | 2209 | atacaaaagtgtgacatggc | 30 | 141 |
| 217376 | 3'UTR | 11 | 2230 | tccatttattagtctaggaa | 76 | 142 |

As shown in Table 2, SEQ ID Nos: 21, 25, 26, 38, 39, 47, 101, 109, 114, 115, 120, 121, 122, 123, 124, 127, 128, 130, 133, 136 and 142 demonstrated at least 35% inhibition of mouse diacylglycerol acyltransferase 2 expression in this experiment and are therefore preferred. More preferred are SEQ ID Nos: 142, 109 and 121. The target regions to which these preferred sequences are complementary are herein referred to as "preferred target segments" and are therefore preferred for targeting by compounds of the present invention. These preferred target segments are shown in Table 3.

These sequences are shown to contain thymine (T) but one of skill in the art will appreciate that thymine (T) is generally replaced by uracil (U) in RNA sequences. The sequences represent the reverse complement of the preferred antisense compounds shown in Tables 1 and 2. "Target site" indicates the first (5'-most) nucleotide number on the particular target nucleic acid to which the oligonucleotide binds. Also shown in Table 3 is the species in which each of the preferred target segments was found.

TABLE 3

Sequence and position of preferred target segments identified in diacylglycerol acyltransferase 2.

| SITE ID | TARGET SEQ ID NO | TARGET SITE | SEQUENCE (5' TO 3') | REV COMP OF SEQ ID | ACTIVE IN | SEQ ID NO |
|---|---|---|---|---|---|---|
| 134026 | 4 | 579 | cccaagaaaggtggcaggag | 20 | H. sapiens | 143 |
| 134028 | 4 | 639 | cgagactactttcccatcca | 21 | H. sapiens | 144 |
| 134030 | 4 | 649 | ttcccatccagctggtgaag | 23 | H. sapiens | 145 |
| 134031 | 4 | 654 | atccagctggtgaagacaca | 24 | H. sapiens | 146 |
| 134032 | 4 | 659 | gctggtgaagacacacaacc | 25 | H. sapiens | 147 |
| 134033 | 4 | 664 | tgaagacacacaacctgctg | 26 | H. sapiens | 148 |
| 134034 | 4 | 669 | acacacaacctgctgaccac | 27 | H. sapiens | 149 |
| 134035 | 4 | 674 | caacctgctgaccaccagga | 28 | H. sapiens | 150 |
| 134036 | 4 | 679 | tgctgaccaccaggaactat | 29 | H. sapiens | 151 |
| 134037 | 4 | 684 | accaccaggaactatatctt | 30 | H. sapiens | 152 |
| 134038 | 4 | 689 | caggaactatatctttggat | 31 | H. sapiens | 153 |
| 134039 | 4 | 694 | actatctttggataccac | 32 | H. sapiens | 154 |
| 134040 | 4 | 723 | atcatgggcctgggtgcctt | 33 | H. sapiens | 155 |
| 134041 | 4 | 846 | gagtacctgatgtctggagg | 34 | H. sapiens | 156 |
| 134044 | 4 | 909 | aagaatgggagtggcaatgc | 35 | H. sapiens | 157 |
| 134045 | 4 | 914 | tgggagtggcaatgctatca | 36 | H. sapiens | 158 |
| 134046 | 4 | 919 | gtggcaatgctatcatcatc | 37 | H. sapiens | 159 |
| 134047 | 4 | 924 | aatgctatcatcatcgtggt | 38 | H. sapiens | 160 |
| 134049 | 4 | 963 | ctgagctccatgcctggcaa | 39 | H. sapiens | 161 |

TABLE 3-continued

Sequence and position of preferred target segments
identified in diacylglycerol acyltransferase 2.

| SITE ID | TARGET SEQ ID NO | TARGET SITE | SEQUENCE (5' TO 3') | REV COMP OF SEQ ID | ACTIVE IN | SEQ ID NO |
|---|---|---|---|---|---|---|
| 134052 | 4 | 1110 | tcctggggccgatgggtcca | 40 | H. sapiens | 162 |
| 134053 | 4 | 1115 | gggccgatgggtccagaaga | 41 | H. sapiens | 163 |
| 134054 | 4 | 1120 | gatgggtccagaagaagttc | 42 | H. sapiens | 164 |
| 134055 | 4 | 1125 | gtccagaagaagttccagaa | 43 | H. sapiens | 165 |
| 134057 | 4 | 1197 | gacacctgggggctggtgcc | 44 | H. sapiens | 166 |
| 134058 | 4 | 1202 | ctgggggctggtgccctact | 45 | H. sapiens | 167 |
| 134059 | 4 | 1207 | ggctggtgccctactccaag | 46 | H. sapiens | 168 |
| 134062 | 4 | 1309 | ccatgtacatggaggccctg | 47 | H. sapiens | 169 |
| 134063 | 4 | 1314 | tacatggaggccctggtgaa | 48 | H. sapiens | 170 |
| 134064 | 4 | 1319 | ggaggccctggtgaagctct | 49 | H. sapiens | 171 |
| 134069 | 4 | 1469 | gtcatgggtgtctgtgggtt | 50 | H. sapiens | 172 |
| 134070 | 4 | 1474 | gggtgtctgtgggttattta | 51 | H. sapiens | 173 |
| 134071 | 4 | 1479 | tctgtgggttatttaaaaga | 52 | H. sapiens | 174 |
| 250517 | 18 | 21985 | tgaggaggatgctcttttgt | 53 | H. sapiens | 175 |
| 250518 | 18 | 23110 | tggactgaagcatttatagt | 54 | H. sapiens | 176 |
| 250520 | 18 | 31611 | tcccatccaggtaaagtgct | 56 | H. sapiens | 177 |
| 250521 | 18 | 33686 | catctgcctcatttcactga | 57 | H. sapiens | 178 |
| 250522 | 18 | 35303 | ttgatgtcacctcttttgag | 58 | H. sapiens | 179 |
| 250524 | 18 | 39106 | tcccttccagagctgacctg | 60 | H. sapiens | 180 |
| 250525 | 18 | 37108 | cccatggaggtccaggggaa | 61 | H. sapiens | 181 |
| 250526 | 4 | 46 | ggctgtttctctcgcgccac | 62 | H. sapiens | 182 |
| 250527 | 4 | 134 | gctctgcgcgaagccctggc | 63 | H. sapiens | 183 |
| 250528 | 4 | 222 | gcttcagccatgaagaccct | 64 | H. sapiens | 184 |
| 250529 | 4 | 246 | gccgcctactccggggtcct | 65 | H. sapiens | 185 |
| 250530 | 4 | 441 | atctcagtgctccagtgggt | 66 | H. sapiens | 186 |
| 250532 | 4 | 987 | gcagtcaccctgcggaaccg | 68 | H. sapiens | 187 |
| 250533 | 4 | 1387 | aggtgaactgagccagcctt | 69 | H. sapiens | 188 |
| 250534 | 4 | 1401 | agccttcggggccaactccc | 70 | H. sapiens | 189 |
| 250535 | 4 | 1414 | aactccctggaggaaccagc | 71 | H. sapiens | 190 |
| 250536 | 4 | 1449 | tgctctgtaaatttggaagt | 72 | H. sapiens | 191 |
| 250537 | 4 | 1584 | gcttgccctgttctaggtgg | 73 | H. sapiens | 192 |
| 250539 | 4 | 1647 | ttcttcccttcctgaagtga | 75 | H. sapiens | 193 |
| 250540 | 4 | 1679 | agtcttcttggggaagaagg | 76 | H. sapiens | 194 |
| 250541 | 4 | 1707 | tagtgacttggaccagttag | 77 | H. sapiens | 195 |
| 250542 | 4 | 1724 | tagatgattcacttttgcc | 78 | H. sapiens | 196 |

TABLE 3-continued

Sequence and position of preferred target segments identified in diacylglycerol acyltransferase 2.

| SITE ID | TARGET SEQ ID NO | TARGET SITE | SEQUENCE (5' TO 3') | REV COMP OF SEQ ID | ACTIVE IN | SEQ ID NO |
|---|---|---|---|---|---|---|
| 250544 | 4 | 1763 | agccacttctcatacaagcc | 80 | H. sapiens | 197 |
| 250545 | 4 | 1802 | acgctcgtctagtcctgaaa | 81 | H. sapiens | 198 |
| 250546 | 4 | 1946 | cctagtcactcatatcggag | 82 | H. sapiens | 199 |
| 250547 | 4 | 1969 | ggactggcctccaggatgag | 83 | H. sapiens | 200 |
| 250548 | 4 | 1974 | ggcctccaggatgaggatgg | 84 | H. sapiens | 201 |
| 250549 | 4 | 1989 | gatggggtggcaatgacac | 85 | H. sapiens | 202 |
| 250550 | 4 | 2055 | gccgccaccatgagctaggt | 86 | H. sapiens | 203 |
| 250551 | 4 | 2067 | agctaggtggagtaactggt | 87 | H. sapiens | 204 |
| 250552 | 4 | 2088 | tttcttgggtggctgatgac | 88 | H. sapiens | 205 |
| 250553 | 4 | 2125 | tcagccttggcctggagcac | 89 | H. sapiens | 206 |
| 250554 | 4 | 2137 | tggagcacatgcttactggt | 90 | H. sapiens | 207 |
| 250555 | 4 | 2143 | acatgcttactggtggcctc | 91 | H. sapiens | 208 |
| 250556 | 4 | 2150 | tactggtggcctcagtttac | 92 | H. sapiens | 209 |
| 250558 | 4 | 2220 | ggggcctggccttctgagca | 94 | H. sapiens | 210 |
| 250559 | 4 | 2242 | agattagttccaaagcaggt | 95 | H. sapiens | 211 |
| 250560 | 4 | 2269 | gaacccaagcctcactttc | 96 | H. sapiens | 212 |
| 250561 | 4 | 2367 | ttgcaccatgtcagactttt | 97 | H. sapiens | 213 |
| 134018 | 11 | 99 | cagctcccggagctcagcgc | 101 | M musculus | 214 |
| 134027 | 11 | 586 | tgcgaaactgggccgtgtgg | 109 | M musculus | 215 |
| 134051 | 11 | 1051 | atgaggtatacaagcaggtg | 114 | M musculus | 216 |
| 134056 | 11 | 1147 | tccatggccgaggcctcttc | 115 | M musculus | 217 |
| 134067 | 11 | 1383 | cgcgtgccagctcctgggag | 120 | Mmusculus | 218 |
| 134068 | 11 | 1424 | taccgagttcttgagtgcat | 121 | M musculus | 219 |
| 134072 | 11 | 1536 | ttaagaagggaagagtcagt | 122 | M musculus | 220 |
| 134073 | 11 | 1560 | taagctcacttctagtgtgt | 123 | M musculus | 221 |
| 134074 | 11 | 1577 | tgtcctgctcaaggtggagg | 124 | M musculus | 222 |
| 134077 | 11 | 1653 | gacagacacttggccctggc | 127 | M musculus | 223 |
| 134078 | 11 | 1685 | ggcagtccttagtgactcca | 128 | M musculus | 224 |
| 134080 | 11 | 1746 | caggtcgggttcctcgtacc | 130 | M musculus | 225 |
| 134083 | 11 | 1861 | tctccaatctgagcctaccc | 133 | M musculus | 226 |
| 134086 | 11 | 2002 | tggcgcatatcctcctgagc | 136 | M musculus | 227 |
| 134092 | 11 | 2230 | ttcctagactaataaatgga | 142 | M musculus | 228 |

As these "preferred target segments" have been found by experimentation to be open to, and accessible for, hybridization with the antisense compounds of the present invention, one of skill in the art will recognize or be able to ascertain, using no more than routine experimentation, further embodiments of the invention that encompass other compounds that specifically hybridize to these preferred target segments and consequently inhibit the expression of diacylglycerol acyltransferase 2.

According to the present invention, antisense compounds include antisense oligomeric compounds, antisense oligonucleotides, siRNAs, external guide sequence (EGS) oligonucleotides, alternate splicers, and other short oligomeric compounds which hybridize to at least a portion of the target nucleic acid.

Example 17

Western Blot Analysis of Diacylglycerol Acyltransferase 2 Protein Levels

Western blot analysis (immunoblot analysis) is carried out using standard methods. Cells are harvested 16-20 h after oligonucleotide treatment, washed once with PBS, suspended in Laemmli buffer (100 ul/well), boiled for 5 minutes and loaded on a 16% SDS-PAGE gel. Gels are run for 1.5 hours at 150 V, and transferred to membrane for western blotting. Appropriate primary antibody directed to diacylglycerol acyltransferase 2 is used, with a radiolabeled or fluorescently labeled secondary antibody directed against the primary antibody species. Bands are visualized using a PHOSPHORIMAGER™ instrument (Molecular Dynamics, Sunnyvale Calif.).

Example 18

Effects of Antisense Inhibition on Diacylglycerol Acyltransferase 2 Levels

In Vivo Studies in a Diet-Induced Model of Obesity

The C57BL/6 mouse strain is reported to be susceptible to hyperlipidemia-induced atherosclerotic plaque formation. Accordingly, these mice were fed a high-fat diet and used in the following studies to evaluate the effects of diacylglycerol acyltransferase 2 antisense oligonucleotides on mRNA expression in a model of diet-induced obesity.

Male C57BL/6 mice at 6 weeks of age were purchased from Jackson Laboratories (Ben Harbor, Me.). Mice were fed-regular rodent chow (#8604, Harlan-Teklad, Madison, Wis.) for 5 days and were subsequently placed on a high-fat diet containing 60% calories from fat (Research Diet D12492, Research Diets Inc., New Brunswick, N.J.). After 8 weeks on the high-fat diet, mice were divided into one of three treatment groups of eight animals each, based on body weight. One group received subcutaneous injections of ISIS 217376 (SEQ ID No: 142) at a dose of 25 mg/kg twice per week for 7 weeks. The second group received subcutaneous injections of control oligonucleotide ISIS 141923 (CCTTC-CCTGAAGGTTCCTCC, SEQ ID NO: 229) at a dose of 25 mg/kg twice per week for 7 weeks. Oligonucleotides were dissolved in 0.9% saline for injection. The third group received subcutaneous injections of saline twice weekly for 7 weeks. This saline-injected group served as the control group to which the oligonucleotide-treated groups were compared.

A group of 8 C57Bl/6 mice, fed regular rodent chow and treated with saline, was used as a normal, lean group.

ISIS 141923, which is not complementary to any known gene, is a chimeric oligonucleotide ("gapmer") 20 nucleotides in length, composed of a central "gap" region consisting of ten 2'-deoxynucleotides, which is flanked on both sides (5' and 3' directions) by five-nucleotide "wings". The wings are composed of 2'-O-methoxyethyl (2'-MOE) nucleotides. The internucleoside (backbone) linkages are phosphorothioate (P=S) throughout the oligonucleotide. All cytidine residues are 5-methylcytidines.

After the 7 week treatment period, the mice were sacrificed and diacylglycerol acyltransferase 2 (DGAT2) mRNA levels were evaluated in liver, brown adipose tissue (BAT) and white adipose tissue (WAT). In addition, diacylglycerol acyltransferase 1 (DGAT1) mRNA levels were measured in these tissues. mRNA expression levels were quantitated by real-time PCR as described in other examples herein. The results are presented in Table 4 and are expressed as percent inhibition relative to saline-treated mice receiving a high fat diet. A "+" preceding the number indicates that gene expression was increased, rather than inhibited.

TABLE 4

Antisense inhibition of diacylglycerol acyltransferase 2 expression in liver, brown adipose and white adipose tissues from diet-induced obese mice

| | % Inhibition of diacylglycerol acyltransferase mRNAs | | | | | |
|---|---|---|---|---|---|---|
| | Liver | | WAT | | BAT | |
| ISIS # | DGAT 2 | DGAT 1 | DGAT 2 | DGAT 1 | DGAT 2 | DGAT 1 |
| 141923 | 2 | 7 | +26 | +23 | 25 | 33 |
| 217376 | 80 | 47 | 87 | 0 | 78 | 21 |

The data demonstrate that diacylglycerol acyltransferase 2 antisense oligonucleotide treatment can effectively inhibit target mRNA expression in liver, brown adipose and white adipose tissue. Diacylglycerol acyltransferase 1 expression levels were lowered in liver and brown adipose tissue.

Body weight and food intake were monitored throughout the study. Metabolic rate was measured using indirect calorimetry in a metabolic chamber (Oxymax System, Columbus Instruments, Columbus, Ohio). Adipose tissue weight was also measured at the end of the study. Body weight, adipose tissue weight, food intake and metabolic rate were not changed in diet-induced obese mice treated with ISIS 217376.

In a similar study, animals received twice weekly, subcutaneous injections of saline, 25 mg/kg ISIS 217376 or 25 mg/kg ISIS 141923, for a period of 5 weeks. In these mice, diacylglycerol acyltransferase 2 mRNA was reduced by approximately 90% in liver and white adipose fat tissues.

Example 19

Effects of Antisense Inhibition of Diacylglycerol Acyltransferase 2 on Markers of Lipid and Glucose Metabolism In accordance with the present invention, ISIS 217376 (SEQ ID NO: 142) was tested for its ability to affect lipid and glucose metabolism in the diet-induced obese mice that received antisense oligonucleotide treatment, as described in Example 18. These mice were further evaluated at the end of the 7 week treatment period for levels of serum free fatty acids, which were measured using a NEFA C assay kit (part #994-75409, Wako Chemicals, GmbH, Germany). Also measured at the end of the 7 week treatment period were triglycerides (TRIG), cholesterol, including total cholesterol (CHOL) and high (HDL) and low (LDL) density lipoprotein cholesterol, all of which were measured using the Hitachi 717® analyzer instrument (Roche Diagnostics, Indianapolis, Ind.). The data, expressed as percent reduction relative to the saline control, are presented in Table 5.

TABLE 5

Effects of antisense inhibition of diacylglycerol acyltransferase 2 on serum cholesterol and lipids in diet-induced obese mice

| | Percent Reduction in | | | | |
|---|---|---|---|---|---|
| | Serum Lipids | | Cholesterol | | |
| ISIS # | Free Fatty Acids | TRIG | Total CHOL | HDL CHOL | LDL CHOL |
| 141923 | 17 | 13 | 13 | 11 | 30 |
| 217376 | 33 | 41 | 31 | 28 | 24 |

The results demonstrate that antisense inhibition of diacylglycerol acyltransferase 2 expression, which was presented in Example 18, leads to significant reductions in of 335, 41% and 31% in serum free fatty acids, serum triglycerides and total cholesterol, respectively. Furthermore, HDL cholesterol was reduced. No significant change was observed in LDL cholesterol levels.

Plasma glucose concentrations (n=8 mice) were measured at 0 (beginning of study), 3 and 7 (end of study) weeks of treatment by routine clinical analysis using a YS12700 Select™ Biochemistry Analyzer (YSI Inc., Yellow Spring, Ohio). Plasma insulin levels (n=6 to 8 mice) were measured in the fed state at 0, 3 and 7 weeks and following a 4-hour fast at 4 weeks, using an insulin ELISA kit (#10-1137-10, ALPCO Diagnostics, Windham, N.H.) according to the manufacturer's instructions. After 4 weeks of treatment, an insulin tolerance test (n=8 mice) was performed after a 3-hour fast. After 5 weeks of treatment, a glucose tolerance test (n=8 mice) was performed after an overnight fast. For the tolerance tests, a baseline tail blood glucose measurement was obtained, after which 1.0 g/kg glucose or 0.5 units/kg insulin was administered intraperitoneally. Tail blood glucose levels were measured at 15, 30, 60, 90 and 120 minutes following the challenge with glucose or insulin, using a Glucometer® instrument (Abbott Laboratories, Bedford, Mass.).

Treatment with an antisense oligonucleotide targeted to diacylglycerol acyltransferase 2 reduced plasma insulin levels by 50% in the fasted state at 4 weeks and by 69% in the fed state at the 7 weeks. Plasma glucose levels were unchanged by treatment with ISIS 217376 in diet-induced obese mice. Neither insulin sensitivity nor glucose tolerance was improved by treatment with ISIS 217376.

Example 20

Effects of Antisense Inhibition of Diacylglycerol Acyltransferase 2 on Hepatic Triglycerides and Steatosis in Diet-Induced Obese Mice In accordance with the present invention, ISIS 217376 (SEQ ID NO: 142) was tested for its ability to affect triglyceride and glycogen content in the livers of diet-induced obese mice. The diet-induced obese mice that received antisense oligonucleotide treatment, as described in Example 18, were further evaluated at the end of the 7 week treatment period for hepatic triglycerides and glycogen content. Hepatic triglyceride content, which is evaluated by biochemical analysis of liver triglyceride concentration and histological examination of liver tissue, was used to assess hepatic steatosis, or accumulation of lipids in the liver. To measure liver tissue triglyceride concentration, triglycerides were extracted from liver tissue in HPLC-grade acetone, using a weight:volume ratio of 1:20. Triglycerides were measured using an Infinity Triglycerides Reagent Kit (Sigma-Aldrich, St. Louis, Mo.). Liver and muscle glycogen concentrations were measured as described by Desai, et al. (*Diabetes,* 2001, 50, 2287-2295). To measure glycogen concentrations, liver and muscle tissue were homogenized in 0.03 N HCl (to a final concentration of 0.5 mg/mL). 100 μL of homogenate was mixed with 400 μL of 1.25 N HCl and heated for 1 hour at 100° C. Following centrifugation of the samples at 14,000 rpm, 10 μL of the supernatant was mixed with 1 mL of glucose oxidase reagent (Sigma-Aldrich, St. Louis, Mo.). After a 10 minute incubation at 37° C., the absorbance was read at 505 nm. A standard curve was generated using glycogen type II from rabbit liver and used to determine the glycogen concentrations. The data for hepatic lipid and glycogen content (n=8 mice) are shown in Table 6 and are expressed as percent reduction relative to saline-treated, high-fat diet mice.

TABLE 6

Effects of antisense inhibition of diacylglycerol acyltransferase 2 on hepatic lipid and glycogen content

| | Percent reduction in | |
|---|---|---|
| ISIS # | Hepatic Triglycerides | Hepatic Glycogen |
| 141923 | 30 | 5 |
| 217376 | 56 | 3 |

The results in Table 6 demonstrate that 7 weeks of treatment with antisense oligonucleotide targeted to diacylglycerol acyltransferase 2 yields a marked reduction of 56% in hepatic triglyceride content compared to saline- and control oligonucleotide-treated mice, indicating an improvement in hepatic steatosis. Hepatic glycogen content at 7 weeks, shown in Table 6, was unchanged by ISIS 217376 treatment.

In the 5-week study, hepatic triglyceride content was lowered by 62% at the end of the treatment period. Muscle glycogen content after 5 weeks of treatment was unchanged by ISIS 217376 treatment.

The reduction in hepatic triglycerides was also evaluated by histological examination of liver tissue (n=4 mice). Liver tissue was fixed in 10% neutral buffered formalin and embedded in paraffin wax. Multiple adjacent 4-um sections were cut and mounted on glass slides. After dehydration, the sections were stained with hematoxylin and eosin, which stain nuclei and cytoplasm, respectively. This histological analysis revealed a marked improvement in hepatic steatosis following 7 weeks of treatment with ISIS 217376, as compared to saline-treated or ISIS 141923-treated mice. Thus, an improvement in hepatic steatosis was demonstrated by both histological and biochemical methods.

Example 21

Effects of Antisense Inhibition of Diacylglycerol Acyltransferase 2 on Hepatic Lipogenic and Gluconeogenic Genes In accordance with the present invention, ISIS 217376 (SEQ ID NO: 142) was tested for its ability to affect the expression of genes involved in fatty acid synthesis and glucose metabolism. The diet-induced obese mice that received antisense oligonucleotide treatment, as described in Example 18, were further evaluated at the end of the 7 week treatment period for expression levels of genes that participate in lipid metabolism, gluconeogenesis and glucose metabolism. mRNA levels in liver and white adipose tissue were quantitated by real-time PCR as described in other examples herein, using primer-probe sets that were generated using the GenBank® accession numbers provided in Table 7. The results are presented as percent change relative to saline-treated, high-fat diet control mice and are shown in Table 7 (n=6 to 8 mice).

TABLE 7

Lipid and glucose metabolism gene expression following antisense inhibition of diacylglycerol acyltransferase 2

| | | Percent Change | |
|---|---|---|---|
| Gene Name | GenBank ® Accession # | ISIS 141923 | ISIS 217376 |
| Liver tissue | | | |
| carnitine palmitoyltransferase I | NM_013495.1 | −17 | −49 |
| acetyl-CoA carboxylase 1 | NM_000664.1 | −18 | −66 |
| acetyl-CoA carboxylase 2 | NM_001093.1 | −5 | −90 |
| fatty acid synthase | U29344.1 | −48 | −50 |
| glucose-6-phosphatase, catalytic | U00445.1 | −27 | −9 |
| phosphoenolpyruvate carboxykinase 1 | NM_011044.1 | +14 | +23 |
| pyruvate kinase | NM_013631.1 | −47 | −73 |
| glucose transporter type 2 | NM_031197.1 | −6 | +8 |
| pyruvate dehydrogenase alpha subunit | NM_008810.1 | −22 | −25 |
| glycogen phosphorylase | AF288783 | −2 | −19 |
| HMGCoA reductase | M62766.1 | −19 | −45 |
| ATP-citrate lyase | AF332052 | −13 | 47 |
| Stearoyl-CoA desaturase 1 | NM_009127 | −17 | −4 |
| Glycerol kinase | NM_008194 | −13 | −37 |
| Lipoprotein lipase | BC003305.1 | +28 | +15 |
| sterol regulatory element-binding protein-1 | AB017337.1 | −22 | −43 |
| Ppar gamma | AB011365.1 | −20 | −35 |
| White adipose tissue | | | |
| glucose transporter 4 | AB008453.1 | +85 | +8 |
| glucose transporter type 2 | NM_031197.1 | −7 | +3 |
| hormone sensitive lipase | U08188.1 | +75 | +42 |
| lipoprotein lipase | NM_000237.1 | +13 | −25 |

These data demonstrate that treatment with ISIS 217376, in addition to reducing the expression of diacylglycerol acyltransferase 2 mRNA in diet-induced obese mice, caused concordant reductions in the expression of additional genes that participate in lipid metabolism. For example, in liver, decreases were observed in the expression of genes involved in triglyceride synthesis (e.g., glycerol kinase), de novo fatty acid synthesis (e.g., ATP-citrate lyase, acetyl-CoA carboxylase 1, acetyl-CoA carboxylase 2 and fatty acid synthase) fatty acid oxidation (e.g., carnitine palmitoyltransferase I), fatty acid desaturation (e.g., stearoyl-CoA desaturase 1) and cholesterol synthesis (e.g., HMG-CoA reductase). Furthermore, the expression of glycogen phosphorylase, which participates in glycogen metabolism, was reduced following ISIS 217376 treatment of diet-induced obese mice. Lipoprotein lipase, which participates in fatty acid storage in adipose tissue, exhibited reduced expression as well. The expression of sterol regulatory binding element protein 1, which functions as a hepatic transcription factor in the context of lipid metabolism, was lowered in diet-induced mice treated with ISIS 217376, as compared to control groups. The expression levels of genes related to gluconeogenesis (e.g., glucose-6-phosphatase and phosphoenolpyruvate carboxykinase 1), glucose uptake in both liver and fat (e.g., glucose transporter type 2 and glucose transporter type 4) and lipid homeostasis in fat (e.g., hormone sensitive lipase and lipoprotein lipase) were not significantly lowered.

These data demonstrate that antisense inhibition of diacylglycerol acyltransferase 2 results in the down-regulation of genes in the lipogenic pathway.

Example 22

Effects of Antisense Inhibition of Diacylglycerol Acyltransferase 2 in the ob/ob Mouse Model of Obesity Leptin is a hormone produced by fat that regulates appetite. Deficiencies in this hormone in both humans and non-human animals leads to obesity. ob/ob mice have a mutation in the leptin gene which results in obesity and hyperglycemia. As such, these mice are a useful model for the investigation of obesity and treatments designed to reduce obesity.

In accordance with the present invention, the effects of antisense inhibition of diacylglycerol acyltransferase 2 were investigated in the ob/ob mouse model of obesity. Male ob/ob (C57Bl/6J-Lep$^{ob}$/Lep$^{ob}$) mice at 6-7 weeks of age were purchased from Jackson Laboratories (Bar Harbor, Me.). During a 1 week acclimation period and throughout the study, mice were fed a diet with a fat content of 10-15% (Labdiets #5015, Purina, St. Louis, Mo.). After the 1 week acclimation period, mice were placed into treatment groups based on body weight, as well as tail blood glucose, which was measured using a Glucometer® instrument (Abbott Laboratories, Bedford, Mass.) as described herein. For a period of 4 weeks, mice received subcutaneous, twice-weekly injections of ISIS 217376 (SEQ ID NO: 142) or ISIS 116847 (CTGCTAGC-CTCTGGATTGA, SEQ ID NO: 230) at a dose of 25 mg/kg. ISIS 116847 does not target the diacylglycerol acyltransferase 2 gene and was used as a control. A group of saline-injected mice served as the control group to which the oligonucleotide-treated animals were compared. Each group contained 10 animals.

ISIS 116847 is a chimeric oligonucleotide ("gapmer") 20 nucleotides in length, composed of a central "gap" region consisting of ten 2'-deoxynucleotides, which is flanked on both sides (5' and 3' directions) by five-nucleotide "wings". The wings are composed of 2'-O-methoxyethyl (2'-MOE) nucleotides. The internucleoside (backbone) linkages are phosphorothioate (P=S) throughout the oligonucleotide. All cytidine residues are 5-methylcytidines. A group of saline-injected mice served as an untreated control. Each treatment group consisted of 8 mice.

At the end of the four week treatment period, the mice were sacrificed and target expression, as well as diacylglycerol acyltransferase 1 expression, was measured in liver and fat tissue. mRNA expression was quantitated by real-time PCR as described in other examples herein. These organs were also weighed. The data are expressed as percent inhibition relative to saline control and are presented in Table 8. A "+" preceding the number indicates that gene expression was increased, rather than inhibited.

TABLE 8

Antisense inhibition of diacylglycerol acyltransferase 2 mRNA expression in liver and fat tissues from ob/ob mice

| | % Inhibition of diacylglycerol acyltransferase mRNAs | | | |
|---|---|---|---|---|
| | Liver | | Fat tissue | |
| ISIS # | DGAT 2 | DGAT 1 | DGAT 2 | DGAT 1 |
| 116847 | 17 | 11 | 14 | 16 |
| 217376 | 83 | 7 | 90 | +14 |

The results shown in Table 8 illustrate that treatment of ob/ob mice with ISIS 217376 effectively inhibited, by 83% and 90%, the expression of target mRNA in both liver and fat tissues, respectively. Liver weight was reduced by 21% in ob/ob mice treated with the antisense oligonucleotide of the present invention, but fat tissue weight was not significantly changed. No significant reduction in diacylglycerol acyltransferase 1 mRNA expression was observed.

Throughout the study period, body weight and food intake were monitored, however, no changes were observed in ISIS 217376-treated mice relative to saline-treated mice. Similarly, no change was observed in adipose tissue weight. Metabolic rate, measured as described herein, was also unchanged following treatment with ISIS 217376.

The expression of genes involved in lipogenesis, for example, fatty acid synthase, acetyl-CoA carboxylase 1 and acetyl-CoA carboxylase 2, were decreased following treatment with ISIS 217386.

Example 23

Effects of Antisense Inhibition of Diacylglycerol Acyltransferase 2 in ob/ob Mice on Serum and Liver Lipid Content In accordance with the present invention, ISIS 217376 (SEQ ID NO: 142) was tested for its effect on serum lipids and free fatty acids, as well as tissue triglyceride levels, in ob/ob mice.

The ob/ob mice that received antisense oligonucleotide treatment, as described in Example 22, were further evaluated at the end of the 4 week treatment period for serum free fatty acids, serum cholesterol (CHOL), and serum, liver tissue and fat tissue triglycerides (TRIG), all of which were measured as described herein. Hepatic steatosis, or accumulation of lipids in the liver, was assessed biochemically and histologically, as described herein. The data describing serum and tissue lipid levels, shown in Table 9, are expressed as percent reduction relative to saline-treated control ob/ob mice. As in Example 22, the results are the average of measurements from 8 mice.

TABLE 9

Serum and tissue lipid content following antisense inhibition of diacylglycerol acyltransferase 2

| | % Reduction of serum and tissue lipid content | | | | |
|---|---|---|---|---|---|
| | Serum Lipids | | | Tissue TRIG | |
| ISIS # | TRIG | CHOL | Free Fatty Acids | Liver | Fat |
| 116847 | 22 | 10 | 8 | 12 | 14 |
| 217376 | 0 | 0 | 22 | 21 | 13 |

The data illustrate that antisense inhibition of diacylglycerol acyltransferase 2 in ob/ob mice causes a reduction of 21% in triglyceride levels in liver tissue and a reduction of 22% in serum free fatty acids. The decrease in liver tissue triglyceride content indicates an improvement in hepatic steatosis. Furthermore, histological evaluation of liver tissue indicated a marked improvement in hepatic steatosis. No significant change in serum triglyceride, fat tissue triglyceride or cholesterol was observed.

Example 24

Plasma Insulin and Glucose Levels Following Antisense Inhibition of Diacylglycerolacyltransferase 2 in ob/ob Mice In accordance with the present invention, the ob/ob mice treated as described in Example 22 were further evaluated for insulin and glucose levels. Plasma glucose was measured at the start of the antisense oligonucleotide treatment and after 2 weeks and 4 weeks of treatment. Plasma insulin was measured as described herein following 2 weeks and 4 weeks of treatment. After 3 weeks of treatment, glucose and insulin tolerance tests were also performed (as described herein) in mice fasting for 16 and 4 hours, respectively. Relative to saline-treated control ob/ob mice, plasma insulin in ob/ob mice receiving ISIS 217376 was reduced by 43% at both 2 weeks and 4 weeks of antisense oligonucleotide treatment. No significant change was observed in plasma glucose levels, and no improvements in glucose tolerance or insulin sensitivity were observed.

Example 25

Effects of Antisense Inhibition of Diacylglycerol Acyltransferase 2 in the db/db Mouse Model of Obesity A deficiency in the leptin hormone receptor mice also results in obesity and hyperglycemia. These mice are referred to as db/db mice and, like the ob/ob mice, are used as a mouse model of obesity.

In accordance with the present invention, antisense inhibition of diacylglycerol acyltransferase 2 with ISIS 217276 (SEQ ID NO: 142) was investigated for its effects in db/db mice. Six-week old male db/db (C57Bl/6J-Lepr$^{db}$/Lepr$^{db}$) mice were fed a 15-20% fat diet (Labdiets #5008, Purina, St. Louis, Mo.) for a 7-day acclimation period and throughout the study. Following the acclimation period, the mice were placed into treatment groups based on body weight, as well as tail blood glucose, which was measured using a Glucometer® instrument (Abbott Laboratories, Bedford, Mass.) as described herein. Mice received subcutaneous injections of ISIS 217376 (SEQ ID NO: 142) or the control oligonucleotide ISIS 116847 (CTGCTAGCCTCTGGATTTGA, SEQ ID NO: 230) at a dose of 25 mg/kg twice per week for 5 weeks. A group of saline-injected mice served as untreated controls. Each treatment group contained 10 mice.

After the 5 week treatment period, mice were sacrificed and diacylglycerol acyltransferase 2 mRNA levels (n=4 mice) were evaluated in liver, brown adipose tissue (BAT) and white adipose tissue (WAT). Diacylglycerol acyltransferase 1 mRNA levels were also measured in these tissues. mRNA expression levels were quantitated by real-time PCR as described in other examples herein. In addition, liver triglycerides (n=6 mice) and plasma glucose (n=8 mice) were measured as described herein. The results are presented in Table 10 and are expressed as percent inhibition (for mRNA expression) or reduction (for glucose and triglycerides) relative to saline treated mice. An increase in gene expression or liver triglycerides is indicated by a "+" preceding the number. Liver tissue samples were processed for histological examination, as described herein, for the evaluation of hepatic steatosis, or accumulation of lipids in the liver. Liver sections were stained with oil red O stain, which is commonly used to visualize lipid deposits, and counterstained with hematoxylin and eosin, to visualize nuclei and cytoplasm, respectively.

TABLE 10

Effects of antisense inhibition of diacylglycerol acyltransferase 2 in db/db mice

| Biological Marker Measured | | Treatment | |
|---|---|---|---|
| | | ISIS 116847 | ISIS 217376 |
| | Week | | |
| % Reduction in plasma glucose | 0 | 0 | 0 |
| | 2 | 34 | 5 |
| | 4 | 55 | 14 |
| % Reduction in liver triglycerides | 4 | +41 | 41 |
| | mRNA expression in tissue | | |
| % Inhibition of diacyglycerol acyltransferase 2 | Liver | +17 | 95 |
| | WAT | 0 | 80 |
| | BAT | 19 | 87 |
| % Inhibition of diacyglycerol acyltransferase 1 | Liver | +9 | +5 |
| | WAT | +11 | 5 |
| | BAT | 13 | 28 |

These data illustrate that target mRNA expression was effectively inhibited by 95%, 80% and 87% in liver, white adipose and brown adipose tissues, respectively, of db/db mice treated with ISIS 217376. Furthermore, inhibition of diacylglycerol acyltransferase 2 expression in db/db mice resulted in a 41% reduction in hepatic triglyceride content as measured biochemically and marked reductions in lipid accumulation as measured histologically, demonstrating an improvement in hepatic steatosis. No significant change in plasma glucose was observed.

The expression of genes involved in lipogenesis, for example, fatty acid synthase, acetyl-CoA carboxylase 1 and acetyl-CoA carboxylase 2 were decreased following treatment with ISIS 217386.

Together with the data described herein, these data illustrate that the antisense inhibition of diacylglycerol acyltransferase 2 in mouse models of diet-induced obesity, leptin deficiency and defects in leptin signaling reduced hepatic steatosis and hepatic lipogenesis, as well as hyperlipidimia.

Example 26

Design and Screening of siRNAs Targeting Human Diacylglycerol Acyltransferase 2

In a further embodiment, a series of nucleic acid duplexes (siRNAs) was designed to target human diacylglycerol acyltransferase 2 mRNA (SEQ ID NO: 4) and is shown in Table 11. All compounds in Table 11 are oligoribonucleotides 19 nucleotides in length with phosphodiester internucleoside linkages (backbones) throughout the compound. The compounds were prepared as described herein with blunt ends. Table 11 shows the antisense strand of the siRNA, and the sense strand is synthesized as the complement of the antisense strand. These sequences are shown to contain uracil (U) but one of skill in the art will appreciate that uracil (U) is generally replaced by thymine (T) in DNA sequences. "Target site" indicates the first (5'-most) nucleotide number on the particular target sequence to which the compound binds.

The compounds in Table 11 were tested for their effects on human diacylglycerol acyltransferase 2 mRNA levels in A549 cells. siRNA controls that do not target human diacylglycerol acyltransferase 2 included the duplex of ISIS 335449 (TTTGTCTCTGGTCCTTACTT; incorporated herein as SEQ ID NO: 231) and its complement, and the duplex of ISIS 359661 (TTATCGCTTCTCGTTGCTT; incorporated herein as SEQ ID NO: 232) and its complement. ISIS 335449 is an oligoribonucleotide 20 nucleotides in length with phosphodiester internucleoside linkages (backbones) throughout the compound. ISIS 359661 is an oligoribonucleotide 19 nucleotides in length with phosphodiester internucleoside linkages (backbones) throughout the compound. Both ISIS 335449 and ISIS 359661 and their complements were prepared with blunt ends. Control RNase H oligonucleotides were the gapmers ISIS 141923 (SEQ ID NO: 229) and ISIS 129700 (TAGTGCGGACCTACCCACGA; incorporated herein as SEQ ID NO: 233), neither of which targets human diacylglycerol acyltransferase 2. ISIS 129700 is a chimeric oligonucleotide ("gapmer") 20 nucleotides in length, composed of a central "gap" region consisting of 9 2'-deoxynucleotides, which is flanked on the 5' and 3' ends by a five-nucleotide "wing" and a six-nucleotide "wing", respectively. The wings are composed of 2'-O-methoxyethyl (2'-MOE) nucleotides. The internucleoside (backbone) linkages are phosphorothioate (P=S) throughout the oligonucleotide. All cytidines are 5-methylcytidines.

A549 cells were treated with 150 nM of siRNA compounds mixed with 15 μg/mL LIPOFECTIN™ reagent (Invitrogen Corporation, Carlsbad, Calif.) or with 150 nM of single-strand oligonucleotides mixed with 15 μg/mL LIPOFECTIN™ reagent for a period of 4 hours, followed by 20 hours of culture in normal growth medium.

Human diacylglycerol acyltransferase 2 mRNA expression was measured by quantitative real-time PCR as described herein. Results were normalized to untreated control cells, which were not treated with dsRNA compounds or RNase H oligonucleotides. Data are the average of 2 experiments and are presented in Table 11. Where present, "N.D." indicates "not determined".

TABLE 11

Inhibition of human diacylglycerol acyltransferase 2 mRNA by dsRNAs in A549 cells

| ISIS | REGION | TARGET SEQ ID NO | TARGET SITE | SEQUENCE | % INHIB | SEQ ID NO |
|---|---|---|---|---|---|---|
| 361884 | 5'UTR | 4 | 36 | GAAACAGCCUAGACCCCAG | 0 | 234 |
| 361885 | Coding | 4 | 388 | AGCCAGGUGACAGAGAAGA | 23 | 235 |
| 361886 | Coding | 4 | 408 | UUUCCACCUUGGACCUAUU | 24 | 236 |
| 361887 | Coding | 4 | 502 | GUGCAGAAUAUGUACAUGA | 22 | 237 |
| 361888 | Coding | 4 | 629 | GUAGUCUCGAAAGUAGCGC | 82 | 238 |
| 361889 | Coding | 4 | 766 | AACUUCUUGCUCACUUCUG | 55 | 239 |
| 361890 | Coding | 4 | 776 | UAUGCCUGGGAACUUCUUG | 50 | 240 |
| 361891 | Coding | 4 | 882 | AAUAGUCUAUGGUGUCCCG | 66 | 241 |
| 361892 | Coding | 4 | 892 | UUUGAAAGCAAAUAGUCUA | 89 | 242 |
| 361893 | Coding | 4 | 917 | GAUGAUAGCAUUGCCACUC | 87 | 243 |
| 361894 | Coding | 4 | 922 | ACGAUGAUGAUAGCAUUGC | 44 | 244 |
| 361895 | Coding | 4 | 1051 | CCAAAGGAGUAGAUGGGAA | 31 | 245 |
| 361896 | Coding | 4 | 1070 | CUUGUACACUUCAUUCUCU | 20 | 246 |
| 361897 | Coding | 4 | 1080 | AGAUCACCUGCUUGUACAC | 52 | 247 |
| 361898 | Coding | 4 | 1136 | ACCAAUGUAUUUCUGGAAC | 55 | 248 |
| 361899 | Coding | 4 | 1216 | GUGAUGGGCUUGGAGUAGG | 2 | 249 |
| 361900 | Coding | 4 | 1320 | AGAGCUUCACCAGGGCCUC | 36 | 250 |
| 361901 | Coding | 4 | 1330 | UGCUUGUCGAAGAGCUUCA | 77 | 251 |
| 361902 | Coding | 4 | 1340 | CUUGGUCUUGUGCUUGUCG | 73 | 252 |
| 361903 | 3'UTR | 4 | 1459 | ACCCAUGACACUUCCAAAU | 50 | 253 |
| 361904 | 3'UTR | 4 | 1500 | UUAGCAAAAUUGUUAUAAU | 6 | 254 |
| 361905 | 3'UTR | 4 | 1510 | UUGUAAUGGUUUAGCAAAA | 42 | 255 |
| 361906 | 3'UTR | 4 | 1520 | AGACCUAACAUUGUAAUGG | N.D. | 256 |
| 361907 | 3'UTR | 4 | 1550 | UUGAAAUACUGACUUUUUC | 55 | 257 |
| 361908 | 3'UTR | 4 | 1560 | GUGAAAGAACUUGAAAUAC | 42 | 258 |
| 361909 | 3'UTR | 4 | 1570 | CAAGCUGGAAGUGAAAGAA | 47 | 259 |
| 361910 | 3'UTR | 4 | 1660 | GAGUUUCCUUUGUCACUUC | 25 | 260 |
| 361911 | 3'UTR | 4 | 1690 | UAAUGGCAAUCCUUCUUCC | 36 | 261 |
| 361912 | 3'UTR | 4 | 1900 | UCAAACUGGAGCAUUCCAG | 55 | 262 |
| 361913 | 3'UTR | 4 | 1910 | AGAAGGGAGAUCAAACUGG | 22 | 263 |
| 361914 | 3'UTR | 4 | 2076 | CAAGAAAAACCAGUUACUC | 4 | 264 |
| 361915 | 3'UTR | 4 | 2231 | ACUAAUCUGCUGCUCAGAA | 52 | 265 |
| 361916 | 3'UTR | 4 | 2280 | GGAAGGCACAGAAAAGUGA | 41 | 266 |
| 361917 | 3'UTR | 4 | 2335 | AGAUAACAGAACACACAGG | 24 | 267 |
| 361918 | 3'UTR | 4 | 2345 | UCUCAUCAAGAGAUAACAG | 33 | 268 |
| 361919 | 3'UTR | 4 | 2355 | GGUGCAAUGAUCUCAUCAA | 29 | 269 |
| 361920 | 3'UTR | 4 | 2380 | CAAGGCAUAUACAAAAGUC | 41 | 270 |

These data demonstrated that siRNAs targeted to diacylglycerol acyltransferase 2, for example, duplexes of ISIS 361888, ISIS 361892, ISIS 361893, ISIS 361901 and ISIS 361902, and their respective complements, inhibited expression of the target mRNA.

Example 27

Inhibition of Mouse Diacylglycerol Acyltransferase 2 mRNA Expression in Mouse Primary Hepatocytes

Dose Response Studies

In a further embodiment, four oligonucleotides targeted to mouse diacylglycerol acyltransferase 2 were selected for additional dose-response studies. These compounds were ISIS 217312 (SEQ ID NO: 21), ISIS 217311 (SEQ ID NO: 109), ISIS 217352 (SEQ ID NO: 121), and ISIS 217376 (SEQ ID NO: 142). ISIS 129690 (TTAGAATACGTCGCGTTATG, incorporated herein as SEQ ID NO: 271), and ISIS 129696 (ATTCGCCAGACAACACTGAC, incorporated herein as SEQ ID NO: 272) which are not targeted to diacylglycerol acyltransferase 2, served as controls. ISIS 129690 and ISIS 129696 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-O-methoxyethyl (2'-MOE) nucleotides. The internucleoside (backbone) linkages are phosphorothioate (P=S) throughout the oligonucleotide. All cytidine residues are 5-methylcytidines.

Primary mouse hepatocytes were prepared from CD-1 mice purchased from Charles River Labs (Wilmington, Mass.). Primary mouse hepatocytes were routinely cultured in William's Medium E, supplemented with 10% fetal bovine serum, 1% penicillin/streptomycin, 2 mM L-glutamine, and 0.01 M HEPES (medium and supplements from Invitrogen Corporation, Carlsbad, Calif.). Cells were seeded into 96-well plates (Falcon-Primaria #3872, BD Biosciences) coated with 0.1 mg/ml collagen at a density of approximately 10,000 cells/well for use in oligonucleotide transfection experiments. Cells were transfected using OPTI-MEM™ medium containing 2.5 µl per 100 nM of oligonucleotide.

Diacylglycerol acyltransferase 2 mRNA expression was quantitated by real-time PCR as described herein. Results of these studies are shown in Table 12. Data are averages from three experiments and are expressed as percent inhibition of untreated control. Also shown is the IC50 for each oligonucleotide, which represents the concentration required for 50% inhibition of target expression. Where present, "N.D." indicates not determined.

TABLE 12

Inhibition of mouse diacylglycerol acyltransferase 2 mRNA expression in mouse primary hepatocytes: dose response

| | SEQ ID | % Inhibition Dose of oligonucleotide (nM) | | | | IC50 |
|---|---|---|---|---|---|---|
| ISIS # | NO | 6.25 | 25 | 100 | 400 | (nM) |
| 217311 | 102 | 0 | 1 | 38 | 40 | 406 |
| 217312 | 21 | 0 | 10 | 32 | 45 | 407 |
| 217352 | 121 | 0 | 27 | 65 | 71 | 215 |
| 217376 | 142 | 0 | 15 | 68 | 91 | 173 |
| 129690 | 271 | 9 | 0 | 0 | 0 | N.D. |
| 129696 | 272 | 0 | 0 | 0 | 0 | N.D. |

As demonstrated in Table 12, ISIS 217311, ISIS 217312, ISIS 217352 and ISIS 217376 inhibited diacylglycerol acyltransferase 2 mRNA expression in a dose-dependent manner.

Example 28

Inhibition of Mouse Diacylglycerol Acyltransferase 2 in Primary Mouse Hepatocytes Additional Dose Response Studies In a further embodiment, an additional antisense compound was designed to target mouse diacylglycerol acyltransferase 2 RNA, using published sequence data (GenBank accession number AF384160.1, incorporated herein as SEQ ID NO: 273). The compound was designated ISIS 287498 (ATGCACTCGAGAACTCGGTA, incorporated herein as SEQ ID NO: 274), and the target site is nucleotide 1277 of the 3' UTR region of SEQ ID NO: 4.

ISIS 287498 and ISIS 217352 (SEQ ID NO: 121) were analyzed for their effects on mouse diacylglycerol acyltransferase 2 mRNA. Control oligonucleotides were ISIS 129686 (CGTTATTAACCTCCGTTGAA, incorporated herein as SEQ ID NO: 275) and 129690 (SEQ ID NO: 271). ISIS 129686 and ISIS 129690 are not targeted to diacylglycerol acyltransferase 2. ISIS 129686 and ISIS 287498 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-O-methoxyethyl (2'-MOE) nucleotides. The internucleoside (backbone) linkages are phosphorothioate (P=S) throughout the oligonucleotide. All cytidine residues are 5-methylcytidines.

Primary mouse hepatocytes, isolated and cultured as described in Example 27, were treated with 50, 100, 200, and 400 nM of ISIS 287498, ISIS 217352, ISIS 129686 and ISIS 129690. Diacylglycerol acyltransferase 2 mRNA levels were quantitated by real-time PCR as described herein. Results of these studies are shown in Table 13. Data are averages from three experiments and are expressed as percent inhibition normalized to expression in untreated control cells.

TABLE 13

Inhibition of mouse diacylglycerol acyltransferase 2 mRNA expression in primary mouse hepatocytes: dose response

| | SEQ ID | % Inhibition Dose of oligonucleotide (nM) | | | |
|---|---|---|---|---|---|
| ISIS # | NO | 50 | 100 | 200 | 400 |
| 217352 | 121 | 56 | 73 | 84 | 87 |
| 287498 | 274 | 61 | 79 | 90 | 89 |
| 129686 | 275 | 4 | 0 | 0 | 0 |
| 129690 | 271 | 0 | 0 | 0 | 0 |

As demonstrated in Table 13, ISIS 217352 and ISIS 287498 inhibited diacylglycerol acyltransferase 2 mRNA expression in a dose-dependent manner.

Example 29

Chimeric Phosphorothioate Oligonucleotides Having 2'-MOE Wings and a Deoxy Gap Targeting Human Diacylglycerol Acyltransferase 2

In a further embodiment, an additional series of antisense compounds was designed to target different regions of the human diacylglycerol acyltransferase 2 RNA, using published sequence data (SEQ ID NO: 4 and SEQ ID NO: 18). The compounds are shown in Tables 14 and 15. "Target site" indicates the first (5'-most) nucleotide number on the particular target sequence to which the compound binds. All compounds in Tables 14 and 15 are chimeric oligonucleotides ("gapmers") 20 nucleotides in length. The compounds in Table 14 are composed of a central "gap" region consisting of ten 2'-deoxynucleotides, which is flanked on both sides (5' and 3' directions) by five-nucleotide "wings". The wings are composed of 2'-O-methoxyethyl (2'-MOE) nucleotides. The compounds in Table 15 are composed of a central "gap" region consisting of sixteen 2'-deoxynucleotides, which is flanked on both sides (5' and 3' directions) by two-nucleotide "wings". The wings are composed of 2'-O-methoxyethyl (2'-MOE) nucleotides. In all compounds the internucleoside (backbone) linkages are phosphorothioate (P=S) throughout the oligonucleotides. All cytidine residues are 5-methylcytidines.

TABLE 14

Chimeric phosphorothioate oligonucleotides having 5-nucleotide 2'-MOE wings and a 10-nucleotide deoxy gap targeted to human diacylglycerol acyltransferase 2 mRNA

| ISIS | REGION | TARGET SEQ ID NO | TARGET SITE | SEQUENCE (5' to 3') | SEQ ID NO |
|---|---|---|---|---|---|
| 366703 | 5'UTR | 4 | 75 | ACACCTGGAGCTGCGGCCGG | 277 |
| 366704 | 5'UTR | 4 | 80 | CTAGGACACCTGGAGCTGCG | 278 |
| 366705 | Start Codon | 4 | 229 | GGCTATGAGGGTCTTCATGG | 279 |
| 366706 | Coding | 4 | 234 | TAGGCGGCTATGAGGGTCTT | 280 |
| 366707 | Coding | 4 | 344 | TGGATCCAGTGCCCCATCTC | 281 |
| 366708 | Coding | 4 | 359 | GGGCGGAGAGGATGCTGGAT | 282 |
| 366709 | Coding | 4 | 364 | CTGGAGGGCGGAGAGGATGC | 283 |

TABLE 14-continued

Chimeric phosphorothioate oligonucleotides having 5-nucleotide 2'-MOE wings and a 10-nucleotide deoxy gap targeted to human diacylglycerol acyltransferase 2 mRNA

| ISIS | REGION | TARGET SEQ ID NO | TARGET SITE | SEQUENCE (5' to 3') | SEQ ID NO |
|---|---|---|---|---|---|
| 366710 | Coding | 4 | 396 | GACCTATTGAGCCAGGTGAC | 284 |
| 366711 | Coding | 4 | 401 | CCTTGGACCTATTGAGCCAG | 285 |
| 366712 | Coding | 4 | 406 | TTCCACCTTGGACCTATTGA | 286 |
| 366713 | Coding | 4 | 411 | TGCTTTTCCACCTTGGACCT | 287 |
| 366714 | Coding | 4 | 416 | GTAGCTGCTTTTCCACCTTG | 288 |
| 366715 | Coding | 4 | 435 | TGGAGCACTGAGATGACCTG | 289 |
| 366716 | Coding | 4 | 450 | AAGGACAGGACCCACTGGAG | 290 |
| 366717 | Coding | 4 | 457 | TACAAGGAAGGACAGGACCC | 291 |
| 366718 | Coding | 4 | 462 | CCCAGTACAAGGAAGGACAG | 292 |
| 366719 | Coding | 4 | 486 | ATGAGGATGGCACTGCAGGC | 293 |
| 366720 | Coding | 4 | 491 | TGTACATGAGGATGGCACTG | 294 |
| 366721 | Coding | 4 | 496 | GAATATGTACATGAGGATGG | 295 |
| 366722 | Coding | 4 | 501 | GTGCAGAATATGTACATGAG | 296 |
| 366723 | Coding | 4 | 522 | ACAGCGATGAGCCAGCAATC | 297 |
| 366724 | Coding | 4 | 528 | TAGAGCACAGCGATGAGCCA | 298 |
| 366725 | Coding | 4 | 533 | TGAAGTAGAGCACAGCGATG | 299 |
| 366726 | Coding | 4 | 538 | CCAGTGAAGTAGAGCACAG | 300 |
| 366727 | Coding | 4 | 553 | CCAGTCAAACACCAGCCAAG | 301 |
| 366728 | Coding | 4 | 728 | TGCAGAAGGCACCCAGGCCC | 302 |
| 366729 | Coding | 4 | 766 | GAACTTCTTGCTCACTTCTG | 303 |
| 366730 | Coding | 4 | 950 | AGCTCAGAGACTCAGCCGCA | 304 |
| 366731 | Coding | 4 | 955 | CATGGAGCTCAGAGACTCAG | 305 |
| 366732 | Coding | 4 | 970 | TGCATTCTTGCCAGGCATGG | 306 |
| 366733 | Coding | 4 | 980 | GCAGGGTGACTGCATTCTTG | 307 |
| 366734 | Coding | 4 | 1002 | TTCACAAAGCCCTTGCGGTT | 308 |
| 366735 | Coding | 4 | 1069 | CTTGTACACTTCATTCTCTC | 309 |
| 366736 | Coding | 4 | 1079 | AGATCACCTGCTTGTACACT | 310 |
| 366737 | Coding | 4 | 1104 | CATCGGCCCCAGGAGCCCTC | 311 |
| 366738 | Coding | 4 | 1134 | CCAATGTATTTCTGGAACTT | 312 |
| 366739 | Coding | 4 | 1139 | CGAAACCAATGTATTTCTGG | 313 |
| 366740 | Coding | 4 | 1189 | CCCCCAGGTGTCGGAGGAGA | 314 |
| 366741 | Coding | 4 | 1216 | GGTGATGGGCTTGGAGTAGG | 315 |
| 366742 | Coding | 4 | 1293 | ATGGTGTGGTACAGGTCGAT | 316 |
| 366743 | Coding | 4 | 1298 | TGTACATGGTGTGGTACAGG | 317 |
| 366744 | Coding | 4 | 1325 | TGTCGAAGAGCTTCACCAGG | 318 |
| 366745 | Coding | 4 | 1330 | GTGCTTGTCGAAGAGCTTCA | 319 |
| 366746 | Coding | 4 | 1337 | TGGTCTTGTGCTTGTCGAAG | 320 |
| 366747 | Coding | 4 | 1342 | GAACTTGGTCTTGTGCTTGT | 321 |
| 366748 | Coding | 4 | 1347 | AGGCCGAACTTGGTCTTGTG | 322 |
| 366749 | 3'UTR | 4 | 1513 | AACATTGTAATGGTTTAGCA | 323 |
| 366750 | 3'UTR | 4 | 1518 | GACCTAACATTGTAATGGTT | 324 |
| 366751 | 3'UTR | 4 | 1523 | AAAAGACCTAACATTGTAA | 325 |
| 366752 | 3'UTR | 4 | 1591 | TTAGCCACCACCTAGAACAG | 326 |
| 366753 | 3'UTR | 4 | 1596 | CAGATTTAGCCACCACCTAG | 327 |
| 366754 | 3'UTR | 4 | 1601 | AGGCCCAGATTTAGCCACCA | 328 |
| 366755 | 3'UTR | 4 | 1606 | AGATTAGGCCCAGATTTAGC | 329 |
| 366756 | 3'UTR | 4 | 1611 | CACCCAGATTAGGCCCAGAT | 330 |
| 366757 | 3'UTR | 4 | 1616 | TGAGCCACCCAGATTAGGCC | 331 |
| 366758 | 3'UTR | 4 | 1621 | TTAGCTGAGCCACCCAGATT | 332 |
| 366759 | 3'UTR | 4 | 1719 | AAAGTGAATCATCTAACTGG | 333 |
| 366760 | 3'UTR | 4 | 1808 | CTGCAGTTTCAGGACTAGAC | 334 |
| 366761 | 3'UTR | 4 | 1818 | GAAACTGGTCCTGCAGTTTC | 335 |
| 366762 | 3'UTR | 4 | 1823 | GCAGAGAAACTGGTCCTGCA | 336 |
| 366763 | 3'UTR | 4 | 1828 | CCTTGGCAGAGAAACTGGTC | 337 |
| 366764 | 3'UTR | 4 | 1887 | ATTCCAGATGCCTACTACTG | 338 |
| 366765 | 3'UTR | 4 | 1892 | GGAGCATTCCAGATGCCTAC | 339 |
| 366766 | 3'UTR | 4 | 2049 | CTCATGGTGGCGGCATCCTC | 340 |
| 366767 | 3'UTR | 4 | 2076 | CCAAGAAAACCAGTTACTC | 341 |
| 366768 | 3'UTR | 4 | 2081 | GCCACCCAAGAAAACCAGT | 342 |
| 366769 | 3'UTR | 4 | 2096 | GCATCCATGTCATCAGCCAC | 343 |

TABLE 15

Chimeric phosphorothioate oligonucleotides having 2-nucleotide 2'-MOE wings and a 16-nucleotide deoxy gap targeted to human diacylglycerol acyltransferase 2 mRNA

| ISIS | REGION | TARGET SEQ ID NO | TARGET SITE | SEQUENCE (5' to 3') | SEQ ID NO |
|---|---|---|---|---|---|
| 370718 | 5'UTR | 4 | 78 | AGGACACCTGGAGCTGCGGC | 344 |
| 370719 | Start Codon | 4 | 232 | GGCGGCTATGAGGGTCTTCA | 345 |
| 370720 | Coding | 4 | 237 | GAGTAGGCGGCTATGAGGGT | 346 |

TABLE 15-continued

Chimeric phosphorothioate oligonucleotides having 2-nucleotide 2'-MOE wings and a 16-nucleotide deoxy gap targeted to human diacylglycerol acyltransferase 2 mRNA

| ISIS | REGION | TARGET SEQ ID NO | TARGET SITE | SEQUENCE (5' to 3') | |
|---|---|---|---|---|---|
| 370721 | Coding | 4 | 249 | CGCAGGACCCCGGAGTAGGC | 347 |
| 370722 | Coding | 4 | 347 | TGCTGGATCCAGTGCCCCAT | 348 |
| 370723 | Coding | 4 | 367 | GTCCTGGAGGGCGGAGAGGA | 349 |
| 370724 | Coding | 4 | 399 | TTGGACCTATTGAGCCAGGT | 350 |
| 370725 | Coding | 4 | 404 | CCACCTTGGACCTATTGAGC | 351 |
| 370726 | Coding | 4 | 409 | CTTTTCCACCTTGGACCTAT | 352 |
| 370727 | Coding | 4 | 414 | AGCTGCTTTTCCACCTTGGA | 353 |
| 370728 | Coding | 4 | 438 | CACTGGAGCACTGAGATGAC | 354 |
| 370729 | Coding | 4 | 453 | AGGAAGGACAGGACCCACTG | 355 |
| 370730 | Coding | 4 | 460 | CAGTACAAGGAAGGACAGGA | 356 |
| 370731 | Coding | 4 | 489 | TACATGAGGATGGCACTGCA | 357 |
| 370732 | Coding | 4 | 494 | ATATGTACATGAGGATGGCA | 358 |
| 370733 | Coding | 4 | 499 | GCAGAATATGTACATGAGGA | 359 |
| 370734 | Coding | 4 | 504 | TCAGTGCAGAATATGTACAT | 360 |
| 370735 | Coding | 4 | 525 | AGCACAGCGATGAGCCAGCA | 361 |
| 370736 | Coding | 4 | 531 | AAGTAGAGCACAGCGATGAG | 362 |
| 370737 | Coding | 4 | 536 | AAGTGAAGTAGAGCACAGCG | 363 |
| 370738 | Coding | 4 | 541 | CAGCCAAGTGAAGTAGAGCA | 364 |
| 370739 | Coding | 4 | 556 | GTTCCAGTCAAACACCAGCC | 365 |
| 370740 | Coding | 4 | 657 | TTGTGTGTCTTCACCAGCTG | 366 |
| 370741 | Coding | 4 | 662 | GCAGGTTGTGTGTCTTCACC | 367 |
| 370742 | Coding | 4 | 667 | GGTCAGCAGGTTGTGTGTCT | 368 |
| 370743 | Coding | 4 | 682 | GATATAGTTCCTGGTGGTCA | 369 |
| 370744 | Coding | 4 | 769 | TGGGAACTTCTTGCTCACTT | 370 |
| 370745 | Coding | 4 | 912 | ATAGCATTGCCACTCCCATT | 371 |
| 370746 | Coding | 4 | 917 | TGATGATAGCATTGCCACTC | 372 |
| 370747 | Coding | 4 | 953 | TGGAGCTCAGAGACTCAGCC | 373 |
| 370748 | Coding | 4 | 958 | AGGCATGGAGCTCAGAGACT | 374 |
| 370749 | Coding | 4 | 973 | GACTGCATTCTTGCCAGGCA | 375 |
| 370750 | Coding | 4 | 983 | TCCGCAGGGTGACTGCATTC | 376 |
| 370751 | Coding | 4 | 1005 | AGTTTCACAAAGCCCTTGCG | 377 |
| 370752 | Coding | 4 | 1072 | CTGCTTGTACACTTCATTCT | 378 |
| 370753 | Coding | 4 | 1082 | CGAAGATCACCTGCTTGTAC | 379 |
| 370754 | Coding | 4 | 1107 | ACCCATCGGCCCCAGGAGCC | 380 |
| 370755 | Coding | 4 | 1137 | AAACCAATGTATTTCTGAA | 381 |
| 370756 | Coding | 4 | 1142 | GGGCGAAACCAATGTATTTC | 382 |
| 370757 | Coding | 4 | 1192 | CAGCCCCCAGGTGTCGGAGG | 383 |
| 370758 | Coding | 4 | 1219 | AGTGGTGATGGGCTTGGAGT | 384 |
| 370759 | Coding | 4 | 1296 | TACATGGTGTGGTACAGGTC | 385 |
| 370760 | Coding | 4 | 1301 | CCATGTACATGGTGTGGTAC | 386 |
| 370761 | Coding | 4 | 1328 | GCTTGTCGAAGAGCTTCACC | 387 |
| 370762 | Coding | 4 | 1340 | ACTTGGTCTTGTGCTTGTCG | 388 |
| 370763 | Coding | 4 | 1345 | GCCGAACTTGGTCTTGTGCT | 389 |
| 370764 | Coding | 4 | 1350 | GGGAGGCCGAACTTGGTCTT | 390 |
| 370765 | 3'UTR | 4 | 1516 | CCTAACATTGTAATGGTTTA | 391 |
| 370766 | 3'UTR | 4 | 1521 | AAAGACCTAACATTGTAATG | 392 |
| 370767 | 3'UTR | 4 | 1594 | GATTTAGCCACCACCTAGAA | 393 |
| 370768 | 3'UTR | 4 | 1599 | GCCCAGATTTAGCCACCACC | 394 |
| 370769 | 3'UTR | 4 | 1604 | ATTAGGCCCAGATTTAGCCA | 395 |
| 370770 | 3'UTR | 4 | 1609 | CCCAGATTAGGCCCAGATTT | 396 |
| 370771 | 3'UTR | 4 | 1614 | AGCCACCCAGATTAGGCCCA | 397 |
| 370772 | 3'UTR | 4 | 1619 | AGCTGAGCCACCCAGATTAG | 398 |
| 370773 | 3'UTR | 4 | 1624 | AGGTTAGCTGAGCCACCCAG | 399 |
| 370774 | 3'UTR | 4 | 1722 | CAAAAAGTGAATCATCTAAC | 400 |
| 370775 | 3'UTR | 4 | 1811 | GTCCTGCAGTTTCAGGAC | 401 |
| 370776 | 3'UTR | 4 | 1821 | AGAGAAACTGGTCCTGCAGT | 402 |
| 370777 | 3'UTR | 4 | 1826 | TTGGCAGAGAAACTGGTCCT | 403 |
| 370778 | 3'UTR | 4 | 1831 | TCCCCTTGGCAGAGAAACTG | 404 |
| 370779 | 3'UTR | 4 | 1890 | AGCATTCCAGATGCCTACTA | 405 |
| 370780 | 3'UTR | 4 | 1895 | ACTGGAGCATTCCAGATGCC | 406 |
| 370781 | 3'UTR | 4 | 2052 | TAGCTCATGGTGGCGGCATC | 407 |
| 370782 | 3'UTR | 4 | 2079 | CACCCAAGAAAACCAGTTA | 408 |
| 370783 | 3'UTR | 4 | 2084 | TCAGCCACCCAAGAAAAACC | 409 |
| 370784 | 3'UTR | 4 | 2099 | GCTGCATCCATGTCATCAGC | 410 |
| 370785 | Intron | 184 | 33689 | CTATCAGTGAAATGAGGCAG | 411 |

Example 30

Chimeric Phosphorothioate Oligonucleotides Having 2'-MOE Wings and a Deoxy Gap and Targeting Rat Diacylglycerol Acyltransferase 2

In a further embodiment, a series of antisense compounds was designed to target different regions of the rat diacylglycerol acyltransferase 2 RNA, using published sequence data (GenBank accession number XM_341887.1, incorporated herein as SEQ ID NO: 412, GenBank accession number AA956461.1, the complement of which is incorporated herein as SEQ ID NO: 413). The compounds are shown in Table 16. "Target site" indicates the first (5'-most) nucleotide number on the particular target sequence to which the compound binds. All compounds in Table 16 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-O-methoxyethyl (2'-MOE) nucleotides. The internucleoside (backbone) linkages are phosphorothioate (P=S) throughout the oligonucleotides. All cytidine residues are 5-methylcytidines.

TABLE 16

Chimeric phosphorothioate oligonucleotides having 2'-MOE wings and a deoxy gap and targeting rat diacylglycerol acyltransferase 2 mRNA

| ISIS | REGION | TARGET SEQ ID NO | TARGET SITE | SEQUENCE (5' to 3') | SEQ ID NO |
|---|---|---|---|---|---|
| 369163 | 5'UTR | 412 | 1 | CAGAAAGCTAGCGAAGCGCG | 414 |
| 369164 | 5'UTR | 412 | 20 | CGCTGCCACCCTAGGCAATC | 415 |
| 369166 | 5'UTR | 412 | 40 | CGAGATCCGAGGTAGGTAGC | 416 |
| 369168 | 5'UTR | 412 | 60 | AGGCCGTGGTGGCAGCAGGT | 417 |
| 369170 | 5'UTR | 412 | 80 | GGAGCCGAGGGACAGCGCTC | 418 |
| 369172 | 5'UTR | 412 | 100 | GGGCTTCGCGCTGAGCTCCG | 419 |
| 369174 | 5'UTR | 412 | 124 | TCCATGCCCCAGCCGCCGGG | 420 |
| 369176 | 5'UTR | 412 | 140 | CACGCAGCGCCCCTGATCCA | 421 |
| 369178 | 5'UTR | 412 | 160 | GGCCGTGCAGGAAGCCGCCT | 422 |
| 369179 | 5'UTR | 412 | 180 | CTGAAGCCGGTGCACGTCAC | 423 |
| 369181 | 5'UTR | 412 | 198 | GCGATGAGGGTCTTCATGCT | 424 |
| 369183 | Coding | 412 | 216 | AGGACCCCGGAGTAGGCAGC | 425 |
| 369185 | Coding | 412 | 220 | CCGCAGGACCCCGGAGTAGG | 426 |
| 369187 | Coding | 412 | 240 | GCTTCGGCCCGACGCTCACC | 427 |
| 369189 | Coding | 412 | 260 | TCTTGTTCTCGCTGCGGGCA | 428 |
| 369191 | Coding | 412 | 280 | TGACAGGGCAGATCCTTTAT | 429 |
| 369192 | Coding | 412 | 300 | CATCGCCCAGACCCCTCGCG | 430 |
| 369194 | Coding | 412 | 320 | GGATGCTGGAGCCAGTGCCC | 431 |
| 369196 | Coding | 412 | 340 | GATGTCTTGGAGGGCCGAGA | 432 |
| 369198 | Codin | 412 | 360 | TTGAGCCAGGTGACAGAGAA | 433 |
| 369200 | Coding | 412 | 380 | GTTTTTCCACCTTGGATCTG | 434 |
| 369201 | Coding | 412 | 400 | GACTGAGATGACCTGTAGGT | 435 |
| 369204 | Coding | 412 | 420 | AAGGATAGGACCCACTGTAG | 436 |
| 369206 | Coding | 412 | 439 | GGCCACTCCTAGCACCAGGA | 437 |
| 369207 | Coding | 412 | 460 | GTACATGAGGATGACACTGC | 438 |

TABLE 16-continued

Chimeric phosphorothioate oligonucleotides having 2'-MOE wings and a deoxy gap and targeting rat diacylglycerol acyltransferase 2 mRNA

| ISIS | REGION | TARGET SEQ ID NO | TARGET SITE | SEQUENCE (5' to 3') | SEQ ID NO |
|---|---|---|---|---|---|
| 369209 | Coding | 412 | 480 | CAGCAGTCAGTGCAGAAGGT | 439 |
| 369211 | Coding | 412 | 500 | AGTAGAGAGCAGCTATCAGC | 440 |
| 369213 | Coding | 412 | 520 | GTCAAATGCCAGCCAGGTGA | 441 |
| 369215 | Coding | 412 | 540 | CCTTTCTTGGGCGTGTTCCA | 442 |
| 369217 | Coding | 412 | 560 | CCCACTGTGATCTCCTGCCA | 443 |
| 369218 | Coding | 412 | 599 | AGTAGTCTCGAAAATAGCGC | 444 |
| 369219 | Coding | 412 | 620 | TCTTCACCAGCTGGATGGGA | 445 |
| 369220 | Coding | 412 | 640 | GGTGGTCAGCAGGTTGTGTG | 446 |
| 369221 | Coding | 412 | 660 | TATCCAAAGATATAGTTCCT | 447 |
| 369222 | Coding | 412 | 685 | CAGGCCCATGATGCCATGGG | 448 |
| 369223 | Coding | 412 | 700 | GTTACAGAAGGCACCCAGGC | 449 |
| 369224 | Coding | 412 | 720 | TCGGTGGCCTCCGTGCTGAA | 450 |
| 369225 | Coding | 412 | 740 | CAGGGAACTTCTTGCTAACT | 451 |
| 369226 | Coding | 412 | 761 | TGGCCAAATAAGGCCTTATG | 452 |
| 369227 | Coding | 412 | 780 | CGGAAGTTGCCAGCCAATGT | 453 |
| 369228 | Coding | 412 | 800 | ACTCCCGAAGCACAGGCATC | 454 |
| 369229 | Coding | 412 | 820 | GATGCCTCCAGACATCAGGT | 455 |
| 369230 | Coding | 412 | 840 | GTGTCTCTGTTGACAGGGCA | 456 |
| 369231 | Coding | 412 | 852 | AAGTAGTCTATGGTGTCTCT | 457 |
| 369232 | Coding | 412 | 855 | AGCAAGTAGTCTATGGTGTC | 458 |
| 369233 | Coding | 412 | 862 | CTTGGAAAGCAAGTAGTCTA | 459 |
| 369234 | Coding | 412 | 874 | ACCACTCCCATTCTTGGAAA | 460 |
| 369235 | Coding | 413 | 231 | GCATTACCACTCCCATTCTT | 461 |
| 369236 | Coding | 412 | 884 | CAATGGCATTACCACTCCCA | 462 |
| 369237 | Coding | 412 | 889 | GATGACAATGGCATTACCAC | 463 |
| 369238 | Coding | 412 | 900 | CCTCCCACCACGATGACAAT | 464 |
| 369239 | Coding | 412 | 920 | AGCTCAGGGATTCAGCTGCA | 465 |
| 369240 | Coding | 412 | 940 | TGCGTTCTTGCCAGGCATGG | 466 |
| 369241 | Coding | 412 | 960 | TTGCGGTTCCGCAGGGTGAC | 467 |
| 369242 | Coding | 412 | 981 | AGGGCCAGCTTTACAAAGCC | 468 |
| 369243 | Coding | 412 | 1020 | CCAAAGGAATAGGTGGGAAC | 469 |
| 369244 | Coding | 412 | 1040 | GCTTGTATACCTCATTCTCT | 470 |
| 369245 | Coding | 412 | 1059 | CCCTCCTCAAAGATCACCTG | 471 |
| 369246 | Coding | 412 | 1100 | TATACTTCTGGAACTTCTTC | 472 |
| 369247 | Coding | 412 | 1112 | GGGCGAAACCAATATACTTC | 473 |

TABLE 16-continued

Chimeric phosphorothioate oligonucleotides having 2'-MOE wings and a deoxy gap and targeting rat diacylglycerol acyltransferase 2 mRNA

| ISIS | REGION | TARGET SEQ ID NO | TARGET SITE | SEQUENCE (5' to 3') | SEQ ID NO |
|---|---|---|---|---|---|
| 369248 | Coding | 412 | 1140 | AAGAGACCTCGGCCATGGAA | 474 |
| 369249 | Coding | 412 | 1160 | GCCCCCAGGTGTCAGAGGAG | 475 |
| 369250 | Coding | 412 | 1180 | GGGCTTGGAGTAGGGCACCA | 476 |
| 369251 | Coding | 412 | 1200 | TCCCCCACAACGGTGGTGAT | 477 |
| 369252 | Coding | 412 | 1221 | AGCTTAGGGACGGTGATGGG | 478 |
| 369253 | Coding | 412 | 1241 | CTTTCTGGGTCGGGTGCTCC | 479 |
| 369254 | Coding | 412 | 1261 | GGTGTGGTACAGGTCGATGT | 480 |
| 369255 | Coding | 412 | 1280 | CCAGGGCCTCCATGTACATG | 481 |
| 369256 | Coding | 412 | 1300 | GTGATTGTCAAAGAGCTTCA | 482 |
| 369257 | Coding | 412 | 1320 | GGAAGGCCGAATTTGGTCTT | 483 |
| 369258 | Coding | 412 | 1340 | CCTCCAGCACCTCAGTCTCT | 484 |

Example 31

Design of an Antisense Chimeric Phosphorothioate Oligonucleotides Having 2'-MOE Wings and a Deoxy Gap and Targeting Mouse Diacylglycerol Acyltransferase 2 Expression In a further embodiment, an antisense compound ISIS 337205 (ATGCACTCAAGAACTCGGTA, incorporated herein as SEQ ID NO: 485) was designed to target the 3' UTR region of the mouse diacylglycerol acyltransferase 2 RNA, using published sequence data (SEQ ID NO: 11). ISIS 337205 is a chimeric oligonucleotide ("gapmer") 20 nucleotides in length, composed of a central "gap" region consisting of 14 2'-deoxynucleotides, which is flanked on both sides (5' and 3' directions) by 3-nucleotide "wings". The wings are composed of 2'-O-methoxyethyl (2'-MOE) nucleotides. The internucleoside (backbone) linkages are phosphorothioate (P=S) throughout the oligonucleotide. All cytidine residues are 5-methylcytidines.

Example 32

Effects of Antisense Inhibition of Diacylglycerol Acyltransferase 2 on Triglyceride Synthesis in Primary Rodent Hepatocytes Diacylglycerol acyltransferase 2, which is abundantly expressed in the liver and white adipose tissues, participates in triglyceride synthesis and its activity is also tightly linked to the endogenous fatty acid synthesis pathway. Thus, it was of interest to determine whether antisense inhibition of diacylglycerol acyltransferase 2 would affect triglyceride synthesis in hepatocytes. In a further embodiment, rat and mouse hepatocytes were isolated and treated with ISIS 217357 (SEQ ID NO: 123) and ISIS 217376 (SEQ ID NO: 142), respectively. ISIS 217357 is a cross species oligonucleotide which exhibits 100% complementarity to rat diacylglycerol acyltransferase 2.

Primary hepatocytes were isolated from C57BL/6J mice or Sprague Dawley rats (Charles River Laboratories, Wilmington, Mass.). The animals were anesthetized according to routine procedures. The livers were perfused via the portal vein, first with $Ca^{2+}/Mg^{2+}$-free Hanks' balanced salt solution (Invitrogen Corporation, Carlsbad, Calif.) containing 10 mM Hepes and 0.5 mM EGTA (pH 7.4) for approximately 3 minutes and subsequently with digestion buffer (William Medium E, 10 mM Hepes, 2 mM glutamine acid, 0.63 mg/ml collagenase B from Roche, and 0.01 mg/ml gentamycin) for approximately 5 minutes. Perfused livers were removed from the mice or rats and dissociated in ice-cold wash buffer (above digestion buffer with no collagenase but with addition of 10% fetal bovine serum) by agitation. Parenchymal cells were separated from non-parenchymal cells by spinning the harvested cells at 500 rpm for 4 min in a CR412™ centrifuge (Jouan Inc, Winchester, Va.). Cells were then washed twice with cold PBS. The parenchymal hepatocytes with >85% viability, as assessed by staining with trypan blue, were seeded onto 60-mm culture plates coated with collagen type I (BD Biosciences) at 1,000,000 cells per plate in culture medium (William Medium E with 10% fetal bovine serum and 10 nm insulin) and cultured overnight at 37° C. and 5% $CO_2$.

For transfection with antisense oligonucleotides, the culture medium was aspirated and the hepatocytes were washed once with PBS, and subsequently incubated for 4-6 hr with 1 ml transfection mixture, which contained 150 nM of antisense oligonucleotide and 4.5 µg/mL LIPOFECTIN™ reagent (Invitrogen Corporation, Carlsbad, Calif.) in Williams' Medium E. The mixture was then aspirated and replaced with the culture medium for approximately 24 hours.

Triglyceride synthesis in transfected hepatocytes was determined by measuring the incorporation of tritiated glycerol ([$^3$H]glycerol) into triglycerides. Approximately 24 hours following transfection, the culture medium was replaced with 1 ml of high glucose DMEM medium containing 10% fetal bovine serum, 0.5% bovine serum albumin (medium and supplements from Invitrogen Corporation, Carlsbad, Calif.) and 10 uCi of [$^3$H]glycerol with or without 0.5 mM oleate. As oleate is a free fatty acid, and free fatty acids are incorporated into triglycerides during triglyceride synthesis, oleate was added to the culture medium of some cells to provide an additional supply of fatty acids and to stimulate triglyceride synthesis. Insulin, present in the culture medium, is also known to stimulate triglyceride synthesis.

After continued culture overnight, the cells were harvested. One small fraction of the harvested cells was used for RNA extraction and gene expression analysis; the remaining fraction was used for lipid extraction with hexane:isopropanol (3:2 in volume) mixture. The extracted lipids were separated by thin layer chromatography by methods routine in the art. The amount of incorporated [$^3$H]glycerol into triglyceride was determined by liquid scintillation counting. Data are normalized to untreated control cells and are presented as disintegrations per minute (DPM) per mg in the cultured cell sample. Tables 17a and 17b show the effects of antisense inhibition of diacylgyercol acyltransferase 2 in rat primary hepatocytes and in mouse primary hepatocytes, respectively.

Real-time PCR quantitation was performed to measure diacylglycerol acyltransferase 2 mRNA levels. Mouse primers and probe used were SEQ ID NOs: 12, 13 and 14. For rat diacylglycerol acyltransferase 2, probes and primers were designed to hybridize to a rat diacylglycerol acyltransferase 2 sequence, using published sequence information (SEQ ID NO: XM_341887.1, SEQ ID NO: 412). For rat diacylglycerol acyltransferase 2 the PCR primers were:

forward primer: GGAACCGCAAAGGCTTTGTA (SEQ ID NO: 486)

reverse primer: AATAGGTGGGAACCAGATCAGC (SEQ ID NO: 487) and the PCR probe was:

FAM-AGCTGGCCCTGCGCCATGG-TAMRA (SEQ ID NO: 488) where FAM is the fluorescent reporter dye and TAMRA is the quencher dye.

Target expression was normalized to that in cells treated with the control oligonucleotide ISIS 141923.

TABLE 17a

Triglyceride synthesis in primary rat hepatocytes

|  | ISIS # | SEQ ID NO | Target mRNA expression (% of ISIS 141923) | Mean incorporation of [$^3$H]glycerol into triglycerides DPM × 10$^3$/mg protein |
|---|---|---|---|---|
| Without oleate | 141923 | 229 | 100 | 40 |
|  | 217357 | 123 | 27 | 8 |
| With oleate | 141923 | 229 | 100 | 581 |
|  | 217357 | 123 | 23 | 193 |

TABLE 17b

Triglyceride synthesis in primary mouse hepatocytes

|  | ISIS # | SEQ ID NO | Target mRNA expression (% of ISIS 141923) | Mean incorporation of [$^3$H]glycerol into triglycerides DPM × 10$^3$/mg protein |
|---|---|---|---|---|
| Without oleate | 141923 | 229 | 100 | 28 |
|  | 217376 | 142 | 25 | 11 |
| With oleate | 141923 | 229 | 100 | 506 |
|  | 217376 | 142 | 2 | 94 |

These data reveal that the inhibition of diacylglycerol acyltransferase 2 in rat hepatocytes dramatically reduced triglyceride synthesis by 5-fold and 3-fold in the absence and presence of oleate, respectively. In primary mouse hepatoctyes, triglyceride synthesis was reduced 2.5-fold and 5.4-fold in the absence and presence of oleate, respectively, following inhibition of target mRNA expression. These reductions occurred regardless of the supply of free fatty acid or the concentration of insulin in the medium.

The expression levels of lipogenic genes in response to inhibition of diacylglycerol acyltransferase 2 were also measured. Real-time PCR was performed as described herein, using primer-probe sets designed using published sequence information available from GenBank® database and indicated in Tables 18 and 19. Gene expression levels in primary rat hepatocytes and primary mouse hepatocytes were normalized to levels in ISIS 141923-treated cells and are shown in Tables 18 and 19, respectively.

TABLE 18

Lipogenic gene expression in primary rat hepatocytes following treatment with ISIS 217357

|  | Target | GenBank Accession # | mRNA expression (% of ISIS 141923) |
|---|---|---|---|
| Without oleate | Diacylglycerol acyltransferase 1 | AF078752.1 | 150 |
|  | Stearoyl CoA-desaturase 1 | NM_009127 | 38 |
|  | Acetyl-CoA carboxylase 1 | BF151634.1 | 83 |
|  | Acetyl-CoA carboxylase 2 | AF290178.2 | 44 |
|  | Apolipoprotein C-III | L04150.1 | 111 |
| With oleate | Diacylglycerol acyltransferase 1 | AF078752.1 | 96 |
|  | Stearoyl CoA-desaturase 1 | NM_009127 | 56 |
|  | Acetyl-Coa carboxylase 1 | BF151634.1 | 53 |
|  | Acetyl-CoA carboxylase 2 | AF290178.2 | 32 |
|  | Apolipoprotein C-III | L04150.1 | 94 |

As shown in Table 18, reductions in the expression of stearoyl-CoA desaturase 1, acetyl-CoA carboxylase 1 and acetyl-CoA carboxylase 2 were observed, both in the presence and absence of oleate. Reductions in these genes were also observed in vivo following antisense inhibition of diacylglycerol acyltransferase 2, as described herein.

TABLE 19

Lipogenic gene expression in primary mouse hepatocytes following treatment with ISIS 217376

|  | Target | GenBank Accession # | mRNA expression (% of ISIS 141923) |
|---|---|---|---|
| Without oleate | Diacylglycerol acyltransferase 1 | AF078752.1 | 95 |
|  | Stearoyl CoA-desaturase 1 | NM_009127 | 77 |
|  | Acetyl-CoA carboxylase 2 | AF290178.2 | 116 |
| With oleate | Diacylglycerol acyltransferase 1 | AF078752.1 | 88 |

As shown in Table 19, in the absence of oleate, a reduction in stearoyl-CoA desaturase 1 was observed in primary mouse hepatocytes treated with ISIS 217376. Reduction in the expression of this gene was also observed following treatment of mice with ISIS 217376.

Example 33

Antisense Inhibition of Diacylglycerol Acyltransferase 2 in Lean Rats

In a further embodiment, the effects of antisense inhibition of diacylglycerol acyltransferase 2 were investigated in normal rats fed a lean diet. Male Sprague-Dawley rats, at 6 weeks of age, were purchased from Charles River Laboratories (Wilmington, Mass.). Rats were maintained on a diet of normal rodent chow (lean diet) and were placed into one of three treatment groups based on body weight. One treatment group received subcutaneous injections of saline, twice weekly. Two treatment groups received twice weekly, subcutaneous injections of 50 mg/kg oligonucleotide; one group received ISIS 217354 (SEQ ID NO: 51) and the other group received ISIS 217357 (SEQ ID NO: 123). ISIS 217354 and ISIS 217357 are cross species oligonucleotides which exhibit 100% complementarity to human, rat and mouse diacylglycerol acyltransferase 2.

Rats received a total of 5 doses and were sacrificed 2 days following the 5 and final dose of oligonucleotide or saline.

At the end of the study, liver tissue and white adipose tissue (WAT) were collected for quantitative real-time PCR of diacylglycerol acyltransferase 2 mRNA levels. Real-time PCR was performed as described herein. The data are shown in Table 20, normalized to mRNA expression levels in saline-treated mice.

TABLE 20

Antisense inhibition of diacylglycerol acyltransferase 2 mRNA expression in liver and white adipose tissues from lean rats

| ISIS # | % Inhibition of diacylglycerol acyltransferase 2 mRNA | |
|---|---|---|
| | Liver | WAT |
| 217354 | 27 | 14 |
| 217357 | 44 | 27 |

These data reveal that ISIS 217354 and ISIS 217357 inhibited the expression of diacylglycerol acyltransferase 2 mRNA expression in liver and white adipose tissue from lean rats.

Plasma cholesterol and triglycerides were measured by chemical analysis as described herein at that start (t=0 weeks) and end (t=2 weeks) of treatment. Triglyceride and cholesterol levels are shown as mg/dL in Table 21a.

TABLE 21a

Plasma triglyceride and cholesterol levels in lean rats following antisense inhibition of diacylglycerol acyltransferase 2

| | Week 0 | | Week 2 | |
|---|---|---|---|---|
| ISIS # | Cholesterol (mg/dL) | Triglycerides (mg/dL) | Cholesterol (mg/dL) | Triglycerides (mg/dL) |
| Saline | 99 | 46 | 91 | 95 |
| 217354 | 90 | 52 | 51 | 36 |
| 217357 | 88 | 68 | 72 | 61 |

As shown in Table 21a, whereas cholesterol and triglycerides in all treatment groups were similar at the start of treatment, 2 weeks of treatment with ISIS 217354 or ISIS 217357 resulted in 56% and 79% reductions in plasma cholesterol, respectively and in 38% and 64% reductions in triglycerides, respectively, relative to levels observed in saline-treated mice.

Plasma glucose and insulin were measured as described herein using a YSI2700 Select™ Biochemistry Analyzer and an ELISA kit, respectively, at the start (t=0 weeks) and end (t=2 weeks) of treatment. In Table 21b, glucose and insulin levels are displayed as mg/dL and ng/mL, respectively.

TABLE 21b

Plasma glucose and insulin levels in lean rats following antisense inhibition of diacylglycerol acyltransferase 2

| | Week 0 | | Week 2 | |
|---|---|---|---|---|
| ISIS # | Glucose (mg/dL) | Insulin (ng/ml) | Glucose (mg/dL) | Insulin (ng/ml) |
| Saline | 156 | .46 | 134 | 1.3 |
| 217354 | 139 | .41 | 113 | .63 |
| 217357 | 144 | .47 | 132 | .78 |

These data illustrate that while insulin levels in all treatment groups were similar at t=0 weeks, 2 weeks of treatment with ISIS 217354 or ISIS 217357 decreased insulin levels by 52% and 40%, respectively, relative to those in saline-treated mice. Glucose levels, after 2 weeks of treatment, were unchanged in oligonucleotide-treated mice relative to saline-treated mice.

The serum transaminases ALT and AST were measured at the start and end of treatment, by routine analysis using an Olympus Clinical Lab Automation System (Olympus America Inc., Melville, N.Y.). Increases in ALT or AST are indicative of treatment-induced toxicity. ALT and AST levels are presented in Table 22 in units per liter (U/L).

TABLE 22

| | Plasma ALT and AST levels | | | |
|---|---|---|---|---|
| | Week 0 | | Week 2 | |
| ISIS # | ALT (U/L) | AST (U/L) | ALT (U/L) | AST (U/L) |
| Saline | 56 | 104 | 57 | 92 |
| 217354 | 55 | 96 | 55 | 60 |
| 217357 | 61 | 94 | 56 | 64 |

The data in Table 22 demonstrate no toxicities resulting from treatment with ISIS 217354 and ISIS 217357.

Body weight was monitored throughout the study. As shown in Table 23, increases in body weights were observed in all treatment groups and thus were not due to treatment with oligonucleotides. No changes were observed food intake, which was also monitored throughout the treatment period.

TABLE 23

Body weights in lean rats treated with antisense oligonucleotides targeting diacylglycerol acyltransferase 2

| ISIS # | Week 0 Body weight (g) | Week 1 Body weight (g) | Week 2 Body weight (g) |
|---|---|---|---|
| Saline | 192 | 249 | 306 |
| 217354 | 194 | 246 | 290 |
| 217357 | 193 | 250 | 296 |

These data reveal that antisense oligonucleotides targeted to rat diacylglycerol acyltransferase 2 effectively inhibited target expression in lean rats, without causing toxicity. Furthermore, insulin, cholesterol and triglyceride levels were reduced after 2 weeks of treatment.

Example 34

Antisense Inhibition of Diacylglycerol Acyltransferase-2 in a Rat Model of Genetic Obesity The Zucker fatty (fa/fa) rat is an example of a genetic obesity with an autosomal recessive pattern of inheritance. The obesity in fa/fa animals is correlated with excessive eating, decreased energy expenditure, compromised thermoregulatory heat production, hyperinsulinemia (overproduction of insulin), and hypercorticosteronemia (overproduction of corticosteroids). The fa mutation has been identified as an amino acid substitution in the extracellular domain of the receptor for leptin. As a consequence, the fa/fa animal has elevated plasma leptin levels and is resistant to exogenous leptin administration.

In a further embodiment, the effects of antisense inhibition of diacylglycerol acyltransferase 2 are evaluated in the Zucker fa/fa rat model of obesity. Male Zucker fa/fa rats, 6 weeks of age, are purchased from Charles River Laboratories (Wilmington, Mass.). Rats are maintained on a normal rodent diet. Animals are placed into treatments groups of 6 animals each. The control group receives twice weekly, subcutaneous injections of sterile phosphate-buffered saline. The oligonucleotide-treated groups receive twice weekly, subcutaneous injections of an antisense oligonucleotide targeted to rat diacylglycerol acyltransferase 2. By way of example, rats are treated with 25, 37.5 or 50 mg/kg of ISIS 217357 (SEQ ID NO: 123). Rats receive a total of 16 to 20 doses over an 8 week period. The rats are sacrificed at the end of the treatment period.

Body weight and food intake are measured at the start of the treatment period and weekly thereafter. Body composition is measured approximately 3 days prior to the start of the treatment period and during weeks 2, 4 and 5 of treatment.

Serum is collected 2 days prior to the first dose, and every two weeks thereafter. The serum samples, analyzed as described herein, are subjected to measurements of: the liver transaminases ALT and AST, using an Olympus Clinical Lab Automation System (Olympus America Inc., Melville, N.Y.); triglycerides and cholesterol, using the Hitachi 717® analyzer instrument (Roche Diagnostics, Indianapolis, Ind.); free fatty acids, using a NEFA C assay kit (part #994-75409 from Wako Chemicals, GmbH, Germany); and glucose, using a YSI2700 Select™ Biochemistry Analyzer (YSI Inc., Yellow Spring, Ohio). Insulin levels are measured using a rat-specific ELISA kit (ALPCO Diagnostics, Windham, N.H.).

To assess the effects of oligonucleotide treatment on glucose tolerance, an oral glucose tolerance test is administered during week 5 and is performed as described herein.

At the end of the study, liver tissue and epididymal fat tissue are collected for RNA isolation and quantitative real-time PCR. Diacylglycerol acyltransferase mRNA levels in these tissues are measured as described herein.

Liver tissue and epididymal fat tissue are also collected for routine histological analysis. The tissues are first fixed in neutral-buffered formalin and are subsequently dehydrated, embedded in paraffin wax, sectioned and stained. Hematoxylin and eosin are used to stain nuclei and cytoplasm, respectively, and oil red O is used to visualize lipids.

Liver, spleen, epididymal fat and brown adipose fat tissues are weighed at the end of the study.

The expression levels of genes involved in lipogenic and gluconeogenic pathways in liver and fat tissue are measured using quantitative real-time PCR. For example, the genes measured are involved in triglyceride synthesis (e.g., glycerol kinase), de novo fatty acid synthesis (e.g., ATP-citrate lyase, acetyl-CoA carboxylase 1, acetyl-CoA carboxylase 2 and fatty acid synthase) fatty acid oxidation (e.g., carnitine palmitoyltransferase I), fatty acid desaturation (e.g., stearoyl-CoA desaturase 1) and cholesterol synthesis (e.g., HMG-CoA reductase). Furthermore, the expression levels of genes that participate in glycogen metabolism, for example, glycogen phosphorylase, are measured. In addition, genes that participate in fatty acid storage, for example, lipoprotein lipase, are measured. Changes in the expression of hepatic transcription factors, such as sterol regulatory binding element protein 1, are also measured. The expression levels of genes related to gluconeogenesis (e.g., glucose-6-phosphatase and phosphoenolpyruvate carboxykinase 1), glucose uptake in both liver and fat (e.g., glucose transporter type 2 and glucose transporter type 4) and lipid homeostasis in fat (e.g., hormone sensitive lipase and lipoprotein lipase) are also measured.

Example 35

Antisense Inhibition of Rat Diacylglycerol Acyltransferase 2 in Primary Hepatocytes Dose Response In a further embodiment, oligonucleotides targeted to rat diacylglycerol acyltransferase 2 were selected for dose response studies in primary rat hepatocytes. The oligonucleotides tested were ISIS 217320, ISIS 217336, ISIS 217353, ISIS 217354, ISIS 217356, ISIS 217357 and ISIS 217376.

Primary rat hepatocytes were isolated from Sprague-Dawley rats (Charles River Laboratories, Wilmington, Mass.) and were cultured in Williams Medium E supplemented with 10% fetal bovine, 1% penicillin/streptomycin, 2 mM L-glutamine, and 0.01 M HEPES (Invitrogen Life Technologies, Carlsbad, Calif.). Cells were seeded into 96-well plates (Falcon-Primaria #3872) coated with 0.1 mg/ml collagen at a density of approximately 10,000 cells/well for use in oligonucleotide transfection experiments.

Cells were treated with 5, 10, 25, 50, 100 and 200 nM of antisense oligonucleotide, as described herein. Rat diacylglycerol acyltransferase 2 mRNA expression in oligonucleotide-treated cells was measured using quantitative real-time PCR. The data from the 25, 50, 100 and 200 nM treatments are averaged from 3 experiments and are shown as percent inhibition, relative to untreated control cells, in Table 24. The 5 and 10 nM treatments did not inhibit rat diacylglycerol acyltransferase 2 expression.

TABLE 24

Antisense inhibition of diacylglycerol acyltransferase 2 in rat primary hepatocytes: dose response

| ISIS # | SEQ ID NO | % Inhibition Dose of oligonucleotide (nM) | | | |
|---|---|---|---|---|---|
| | | 25 | 50 | 100 | 200 |
| 217320 | 29 | 0 | 42 | 45 | 27 |
| 217336 | 40 | 17 | 46 | 63 | 72 |
| 217353 | 50 | 6 | 60 | 76 | 73 |
| 217354 | 51 | 34 | 64 | 66 | 63 |
| 217356 | 122 | 0 | 47 | 65 | 69 |
| 217357 | 123 | 24 | 61 | 75 | 85 |
| 217376 | 142 | 0 | 43 | 70 | 81 |

As shown in Table 24, the oligonucleotides tested in this assay inhibited rat diacylglycerol acyltransferase 2 expression in primary hepatocytes. ISIS 217336, ISIS 217353, ISIS 217356, ISIS 217357 and ISIS 217376 inhibited target mRNA expression in a dose-dependent manner.

All publications cited in this specification are incorporated by reference herein. While the invention has been described with reference to a particularly preferred embodiment, it will be appreciated that modifications can be made without departing from the spirit of the invention. Such modifications are intended to fall within the scope of the appended claims.

What is claimed is:

1. An antisense compound 13 to 40 nucleobases in length targeted to a target segment of a nucleic acid molecule encoding diacylglycerol acyltransferase 2 (SEQ ID NO: 4), the target segment consisting of nucleotides 222-269 and wherein said compound has at least 95% complementarity with said target segment and is a chimeric oligonucleotide comprising at least one phosphorothioate internucleotide linkage and at least one 2'-O-methoxyethyl modified sugar moiety.

2. The antisense compound of claim 1 comprising 15 to 30 nucleobases in length.

3. The antisense compound of claim 1 having at least 99% complementarity with said target segment.

4. The antisense compound of claim 1, wherein the antisense compound is 20 nucleobases in length.

5. The antisense compound of claim 4, wherein all internucleotide linkages are phosphorothioates and at least one 2'-O-methoxyethyl nucleotide is at each of the 3' and 5' termini of said antisense compound.

6. The antisense compound of claim 5, wherein nucleotides 1-5 are 2'-O-methoxyethyl nucleotides, nucleotides 6-15 are 2'-deoxynucleotides, and nucleotides 16-20 are 2'-O-methoxyethyl nucleotides.

7. The antisense compound of claim 5, wherein nucleotides 1-2 are 2'-O-methoxyethyl nucleotides, nucleotides 3-18 are 2'-deoxynucleotides, and nucleotides 19-20 are 2'-O-methoxyethyl nucleotides.

8. An antisense compound 13 to 40 nucleobases in length targeted to at least an 8 nucleobase portion of nucleotides 222-269 of a nucleic acid molecule encoding diacylglycerol acyltransferase 2 (SEQ ID NO: 4), wherein said compound is a chimeric oligonucleotide comprising at least one phosphorothioate internucleotide linkage and at least one 2'-O-methoxyethyl modified sugar moiety, wherein the nucleobase sequence of the modified oligonucleotide is at least 95% complementary to SEQ ID NO:4.

9. A compound comprising a modified oligonucleotide consisting of 13-40 linked nucleosides having a nucleobase sequence comprising a portion having at least 8 contiguous nucleobases complementary within nucleotides 222-269 of a nucleic acid molecule encoding diacylglycerol acyltransferase 2 (SEQ ID NO: 4), wherein the nucleobase sequence of the modified oligonucleotide is at least 95% complementary to SEQ ID NO:4.

10. The compound of claim 9, wherein the nucleobase sequence of the modified oligonucleotide is 100% complementary to SEQ ID NO: 4.

11. A compound comprising a modified oligonucleotide consisting of 13-40 linked nucleosides having a nucleobase sequence comprising a portion having at least 8 contiguous nucleobases complementary within nucleotides 222-241, 229-248, 232-251, 234-253, 237-256, 249-268 or 250-269 of a nucleic acid molecule encoding diacylglycerol acyltransferase 2 (SEQ ID NO: 4), wherein the nucleobase sequence of the modified oligonucleotide is at least 95% complementary to SEQ ID NO:4.

12. A compound comprising a modified oligonucleotide consisting of 13-40 linked nucleosides having a nucleobase sequence comprising a portion having at least 8 contiguous nucleobases complementary within nucleotides 250-269 of a nucleic acid molecule encoding diacylglycerol acyltransferase 2 (SEQ ID NO: 4), wherein the nucleobase sequence of the modified oligonucleotide is at least 95% complementary to SEQ ID NO:4.

13. A compound comprising a modified oligonucleotide consisting of 13-40 linked nucleosides and having a nucleobase sequence having at least 95% complementarity to a nucleic acid molecule encoding diacylglycerol acyltransferase 2 (SEQ ID NO:4) and comprising at least 8 contiguous nucleobases of a nucleobase sequence selected from among the nucleobase sequences recited in SEQ ID NOs: 64, 279, 280, 345, 346, 347, 425 and 426.

14. A compound comprising a modified oligonucleotide consisting of 13-40 linked nucleo sides and having a nucleobase sequence having at least 95% complementarity to a nucleic acid molecule encoding diacylglycerol acyltransferase 2 (SEQ ID NO:4) and comprising at least 8 contiguous nucleobases of a nucleobase sequence recited in SEQ ID NO: 426.

15. The compound of claim 11, wherein the nucleobase sequence of the modified oligonucleotide is 100% complementary to SEQ ID NO: 4.

16. The compound of claim 12, wherein the nucleobase sequence of the modified oligonucleotide is 100% complementary to SEQ ID NO: 4.

17. The compound of claim 11, wherein the nucleobases are complementary within nucleotides 222-241 of a nucleic acid molecule encoding diacylglycerol acyltransferase 2 (SEQ ID NO: 4).

18. The compound of claim 11, wherein the nucleobases complementary within nucleotides 229-248 of a nucleic acid molecule encoding diacylglycerol acyltransferase 2 (SEQ ID NO: 4).

19. The compound of claim 11, wherein the nucleobases complementary within nucleotides 232-251 of a nucleic acid molecule encoding diacylglycerol acyltransferase 2 (SEQ ID NO: 4).

20. The compound of claim 11, wherein the nucleobases complementary within nucleotides 234-253 of a nucleic acid molecule encoding diacylglycerol acyltransferase 2 (SEQ ID NO: 4).

21. The compound of claim 11, wherein the nucleobases complementary within nucleotides 237-256 of a nucleic acid molecule encoding diacylglycerol acyltransferase 2 (SEQ ID NO: 4).

22. The compound of claim 11, wherein the nucleobases complementary within nucleotides 249-268 of a nucleic acid molecule encoding diacylglycerol acyltransferase 2 (SEQ ID NO: 4).

23. The compound of claim 13, wherein the nucleobase sequence is SEQ ID NO: 64.

24. The compound of claim 13, wherein the nucleobase sequence is SEQ ID NO: 279.

25. The compound of claim 13, wherein the nucleobase sequence is SEQ ID NO: 280.

26. The compound of claim 13, wherein the nucleobase sequence is SEQ ID NO: 345.

27. The compound of claim 13, wherein the nucleobase sequence is SEQ ID NO: 346.

28. The compound of claim 13, wherein the nucleobase sequence is SEQ ID NO: 347.

29. The compound of claim 13, wherein the nucleobase sequence is SEQ ID NO: 425.

30. The antisense compound of claim 1, wherein said compound comprises a modified oligonucleotide consisting of 13-40 linked nucleosides having a nucleobase sequence having at least 95% complementarity within nucleotides 246-265 of a nucleic acid molecule encoding diacylglycerol acyltransferase 2 (SEQ ID NO: 4).

31. The antisense compound of claim 1, wherein said compound comprises a modified oligonucleotide consisting of 13-40 linked nucleosides and having a nucleobase sequence having at least 95% complementarity to a nucleic acid molecule encoding diacylglycerol acyltransferase 2 (SEQ ID NO:4) and comprising at least 8 contiguous nucleobases of the nucleobase sequence recited in SEQ ID NO: 65.

* * * * *

UNITED STATES PATENT AND TRADEMARK OFFICE
CERTIFICATE OF CORRECTION

| | | |
|---|---|---|
| PATENT NO. | : 7,732,590 B2 | Page 1 of 1 |
| APPLICATION NO. | : 11/066725 | |
| DATED | : June 8, 2010 | |
| INVENTOR(S) | : Sanjay Bhanot et al. | |

It is certified that error appears in the above-identified patent and that said Letters Patent is hereby corrected as shown below:

Title page, item (63) after Aug. 18, 2004, insert the following:

--, which is a continuation-in-part of U.S. application No. 10/643,801, filed Aug. 18, 2003.--

Signed and Sealed this

Twenty-first Day of September, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,732,590 B2 | Page 1 of 1 |
| APPLICATION NO. | : 11/066725 | |
| DATED | : June 8, 2010 | |
| INVENTOR(S) | : Bhanot et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 57 days.

Signed and Sealed this

Fifteenth Day of March, 2011

David J. Kappos
*Director of the United States Patent and Trademark Office*